(12) United States Patent
Duchateau et al.

(10) Patent No.: US 11,692,169 B2
(45) Date of Patent: *Jul. 4, 2023

(54) CELLS FOR IMMUNOTHERAPY ENGINEERED FOR TARGETING ANTIGEN PRESENT BOTH ON IMMUNE CELLS AND PATHOLOGICAL CELLS

(71) Applicant: Cellectis, Paris (FR)

(72) Inventors: Philippe Duchateau, Draveil (FR); Laurent Poirot, Paris (FR)

(73) Assignee: CELLECTIS, Paris (FR)

( * ) Notice: Subject to any disclaimer, the term of this patent is extended or adjusted under 35 U.S.C. 154(b) by 409 days.

This patent is subject to a terminal disclaimer.

(21) Appl. No.: 16/939,466

(22) Filed: Jul. 27, 2020

(65) Prior Publication Data

US 2020/0407682 A1    Dec. 31, 2020

Related U.S. Application Data

(63) Continuation of application No. 15/118,801, filed as application No. PCT/EP2015/053162 on Feb. 13, 2015, now Pat. No. 10,836,998.

(30) Foreign Application Priority Data

Feb. 14, 2014 (DK) .............................. PA201470076

(51) Int. Cl.
| | |
|---|---|
| *C12N 5/0783* | (2010.01) |
| *A61K 35/17* | (2015.01) |
| *A61P 35/02* | (2006.01) |
| *A61P 35/00* | (2006.01) |

(52) U.S. Cl.
CPC ............ *C12N 5/0636* (2013.01); *A61K 35/17* (2013.01); *A61P 35/00* (2018.01); *A61P 35/02* (2018.01); *C12N 2501/599* (2013.01); *C12N 2510/00* (2013.01); *Y02A 50/30* (2018.01)

(58) Field of Classification Search
None
See application file for complete search history.

(56) References Cited

U.S. PATENT DOCUMENTS

| | | |
|---|---|---|
| 2007/0036773 A1 | 2/2007 | Cooper et al. |
| 2012/0060230 A1 | 3/2012 | Collingwood et al. |
| 2013/0315884 A1 | 11/2013 | Galetto et al. |
| 2013/0323214 A1 | 12/2013 | Gottschalk et al. |

FOREIGN PATENT DOCUMENTS

| | | |
|---|---|---|
| EP | 2039766 A1 | 3/2009 |
| WO | 2007014275 A2 | 2/2007 |
| WO | 2009083210 A1 | 7/2009 |
| WO | 2010132683 A1 | 11/2010 |
| WO | 2011109662 A1 | 9/2011 |
| WO | 20120145384 A1 | 10/2012 |
| WO | 2013074916 A1 | 5/2013 |
| WO | 2013176915 A1 | 11/2013 |
| WO | 2014191128 A1 | 12/2014 |

OTHER PUBLICATIONS

Hartman, W. et al., 2010, Leuk & Lymp., vol. 51: pp. 1315-1325.*
Mihara et al., "T-cell immunotherapy with a chimeric receptor against CD38 is effective in eliminating myeloma cells", Leukemia, Aug. 12, 2011; vol. 26, No. 2: pp. 365-367.
Torikai H., et al., "Toward eliminating HLA class I expression to generate universal cells from allogenic donors", Blood, Aug. 22, 2013; vol. 122, No. 8: pp. 1341-1349.
Provasi E., et al., "Editing T cell specificity towards leukemia by zinc finger nucleases and lentiviral gene transfer", Nature Medicine, Apr. 1, 2012; vol. 18, No. 5: pp. 807-817.
Dotti G., et al., "Fas knockdown mediated by siRNA in EBV-specific cytotoxic T-Lymphocytes (CTL) reduces their sensitivity to Fas/FasL-induced apoptosis", Molecular Therapy, May 2005; vol. 11, pp. 311-312.
Casucci M., et al., "CD44v6-targeted T cells mediate potent antitumor effects against acute myeloid leukemia and multiple myeloma", Blood, Nov. 14, 2013; vol. 122, No. 20: pp. 3461-3472.
Kellar D., et al., "CD56-specific T-cells can distinguish between allogenic and autologous CD56+ target", Molecular Therapy, May 1, 2011; vol. 19, Supplement 1, pp. 192-193.
Mamonkin M., et al. "A T-cell-directed chimeric antigen receptor for the selective treatment of T-cell malignancies", Blood, Aug. 20, 2015; vol. 126, No. 8: pp. 983-992.
Han C., et al. Desensitized chimeric antigen receptor T cells selectively recognize target cells with enhanced antigen expression: Nature Communications, 2018; vol. 468, No. 9, pp. 1-13.
Maus M., et al., "CARTs on the road for myeloma", Clinical Cancer Research, Aug. 1, 2014; vol. 20, No. 15: pp. 3899-3901.
Collins S., et al., "Elotuzumab directly enhances NK cell cytotoxicity against myeloma via CS1 ligation: evidence for augmented NK cell function complementing ADCC", Cancer Immunology Immunotherapy, Dec. 2013; vol. 62, No. 12, pp. 1841-1849.
Kershaw M. et al., "Gene-engineered T cells for cancer therapy", Nature Reviews, Aug. 2012; vol. 13, pp. 525-541.
Lloyd A., et al., "Beyond the antigen receptor: editing the genome of T-cells for cancer adoptive cellular therapies", Frontiers in Immunology, Aug. 5, 2013; vol. 4, Article 221, pp. 1-7.
Haga K., et al., "Permanent, lowered HLA Class I expression using lentivirus vectors with shRNA constructs: averting cytotoxicity by alloreactive T lymphocytes", Transplantation Proceedings, 2006; vol. 38, pp. 3184-3188.
Choo S., "The HLA system: genetics, immunology, clinical testing and clinical implications", Yonsei Medical Journal, 2007; vol. 48, No. 1, pp. 11-23.

(Continued)

*Primary Examiner* — Michael D Burkhart
(74) *Attorney, Agent, or Firm* — Arrigo, Lee, Guttman & Mouta-Bellum LLP

(57) ABSTRACT

Methods of developing genetically engineered immune cells for immunotherapy, which can be endowed with Chimeric Antigen Receptors targeting an antigen marker that is common to both the pathological cells and said immune cells (ex: CD38, CS1 or CD70) by the fact that the genes encoding said markers are inactivated in said immune cells by a rare cutting endonuclease such as TALEN, Cas9 or argonaute.

18 Claims, 31 Drawing Sheets

Figure 1:
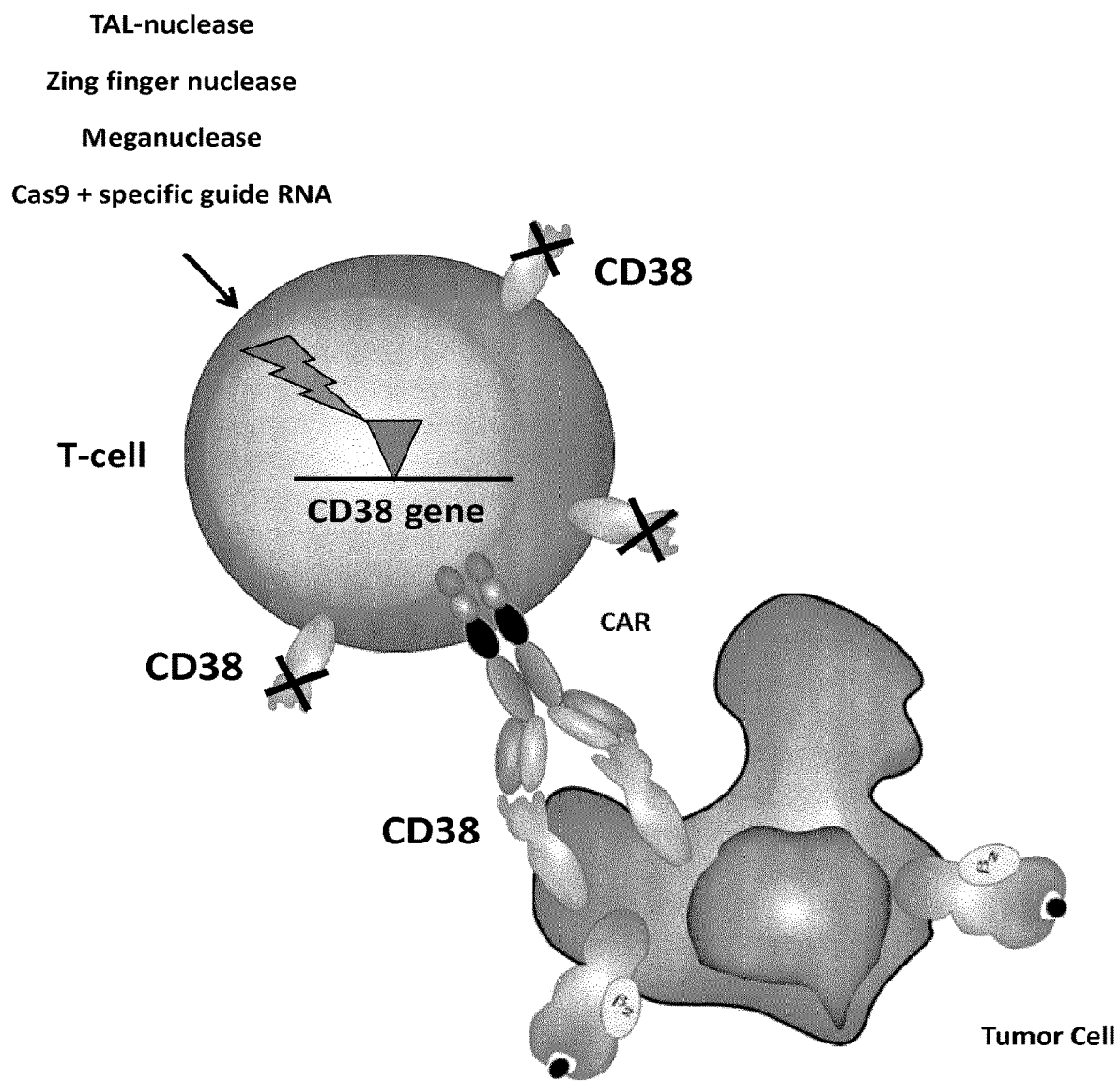

Specification includes a Sequence Listing.

(56) References Cited

OTHER PUBLICATIONS

Okamoto S., et al., "Improved expression and reactivity of transduced tumor-specific TCRs in human lymphocytes by specific silencing of endogenous TCR", Cancer Research, Dec. 1, 2009; vol. 69, No. 23, pp. 9003-9011.
Brenner M., et al., "Adoptive T cell therapy of cancer", Current Opinion in Immunology, 2010; vol. 22, pp. 251-257.
Pule M., et al., "Virus-specific T cells engineered to coexpress tumor-specific receptors: persistence and antitumor activity in individuals with neuroblastoma", Nov. 2008; vol. 14, No. 11, pp. 1264-1270.
Park J., et al., "Adoptive transfer of chimeric antigen receptor re-directed cytolytic T lymphocyte clones in patients with neuroblastoma", Apr. 2007; vol. 15, No. 4, pp. 825-833.
Lamers C., et al., "Treatment of metastatic renal cell carcinoma with autologous T-lymphocytes genetically retargeted against carbonic anhydrase IX: first clinical experience", May 1, 2006; vol. 24, No. 13, pp. e20-e22.
Kim S., et al., "Development of novel avenues to overcome challenges facing CAR T cells", Translational Research, May 30, 2017; vol. 187, pp. 22-31.
Sun S., et al., "Immunotherapy with CAR-modified T cells: toxicities and overcoming strategies", Journal of Immunology Research, Apr. 17, 2018; vol. 2018, pp. 1-10.
Wood A., et al., "Targeted genome editing across species using ZFNs and TALENs", Science, Jul. 15, 2011; vol. 333 No. 6040, pp. 1-4.
Szweykowska-Kulinska Z., et al., "RNA interference and its role in the regulation of eucaryotic expression", Acta Biochimica Polonica, 2003; vol. 50, No. 1, pp. 217-229.
Bhattacharyya J et al., "T-cell immunotherapy with a chimeric receptor against CD38 is effective in eradicating chemotherapy-resistant B-cell lymphoma cells overexpressing survivin induced by BMI-1", Blood Cancer Journal, Jun. 22, 2012; pp. 1-3.
Mihara K., et al., "Synergistic and persistent effect of T-cell immunotherapy with anti-CD19 or anti-CD38 chimeric receptor in conjunction with rituximab on B-cell non-Hodgkin lymphoma", British Journal of Haematology, 2010; vol. 151, pp. 37-46.
Blitz I., et al., "Biallelic Genome Modification in F0 Xenopus tropicalis Embryos Using the CRISPR/Cas System", Genesis, 2013; vol. 51 : pp. 827-834.
Taniguchi R., et al., "2B4 inhibits NK-cell fratricide", Blood, Sep. 15, 2007; vol. 110, No. 6, pp. 2020-2023.
Shaffer D. et al., "T cells redirected against CD70 for the immunotherapy of CD70-positive malignancies", American Society of Hematology, 2011; pp. 1-2 (abstract only).
Hsi E. et al., "CS1, a Potential New Therapeutic Antibody Target for the Treatment of Multiple Myeloma", Clinical Cancer Research, May 1, 2008; vol. 14, No. 9, pp. 2775-2783.
Vanseggelen H. et al., "T Cells Engineered With Chimeric Antigen Receptors Targeting NKG2D Ligands Display Lethal Toxicity in Mice", Molecular Therapy, Oct. 2015; vol. 23, No. 10, pp. 1600-1610.
Porteus M.H., "Mammalian Gene Targeting with Designed Zinc Finger Nucleases", Molecular Therapy, Feb. 2006; vol. 13, No. 2, pp. 438-446, c. 440-441.
Poirot et al., T-Cell Engineering For "off-The-shelf" Adoptive Immunotherapy, Blood (2013) 122(21):1661, Abstract.
Mihara et al., "Activated T-cell-mediated Immunotherapy With a Chimeric Receptor Against CD38 in B-cell Non-Hodgkin Lymphoma," J. Immunother., 32(7):737-743 (2009).
Miller et al., "A Tale nuclease architecture for efficient genome editing," Nature Biotechnology, 29(2):143-150 (2011).
European Patent Office, International Search Report and Written Opinion issued in International Patent Application No. PCT/EP2015/053162 dated Jun. 23, 2015.
Mannioui et al., "Treatment of B cells malignancies with anti-CD19 Car+, TCR-, CD52-, allogeneic T cells," Journal of ImmunoTherapy of Cancer, 2013, vol. 1, p. 34.
Mihara et al., "Activated T-cell-mediated Immunotherapy With a Chimeric Receptor Against CD38 in B-cell Non-Hodgkin Lymphoma," J. Immunotherapy, vol. 32, Sep. 2009, pp. 737-743.
Sadelain et al., "The Basic Principles of Chimeric Antigen Receptor Design," Cancer Discovery, Apr. 2013, pp. 1-12.
Torikai et al., "A foundation of universal T-cell based immunotherapy: T cells engineered to express a CD19-specific chimeric-antigen-receptor and eliminate expression of endogenous TCR," Blood, vol. 119, Jun. 2012, pp. 5696-5705.
Gomes-Silva et al.CD7-edited T cells expressing a CD7-specific CAR for the therapy of T-cell malignancies, Blood 130 (3): 285-296.
McHayleh et al., Chimeric Antigen Receptor T-Cells: The Future Is Now, Clin. Med. 2019, 8(2), 207.

\* cited by examiner

A

```
  1 ATGGCCAACT GCGAGTTCAG CCCGGTGTCC GGGGACAAAC CTCTGCTGCCG GCTCTCTAGG AGAGCCCAAC TCTGTCTTGG CGTCAGTATC CTGGTCCTGA
    TACCGGTTGA CGCTCAAGTC GGGCCACAGG CCCCTGTTTG GGACGACGGC CGAGAGATCC TCTCGGGTTG AGACAGAACC GCAGTCATAG GACCAGGACT
101 TCCTCGTCGT CGTGCTCGCC GTGGTCGTCC CGAGGTGGCC CCAGGTGGCC GTCGTAGCGG GTGGTGGGCC GGCCATGG GGCCTTTCCC GAGACCGTCC TGGGCGATG
    AGGAGCAGCA CGAGCAGCGG CACCAGCAGG GCTCCACCGG GGTCCACCGG CACCATCGCC CACCACCCGG CCGGTACC TCCGAAAGGG CTCTGGCAGG ACCGGCTAC
201 CGTCAGTAC ACTGAAATTC ATCCTGAGAT GAGGTGGGTT GGGGACTAAG GGGACAGCAG GGGCCCGCGC GCAGGGAAGC
    GCAGTCATG TGACTTTAAG TAGGACTCTA CTCCACCCAA CCCTGATTC CCCTGTCGTC CCCGGGGCCG CGTCCCTTCG
301 CGCCCGGATC GCC
    GCGGGCCTAG CGG
```

Figure 10 A

A
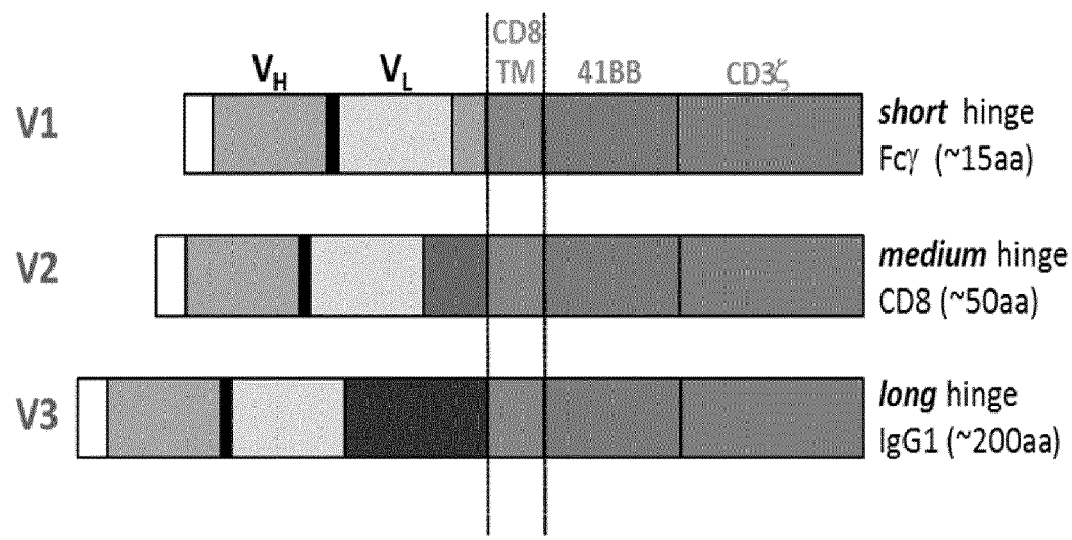
B
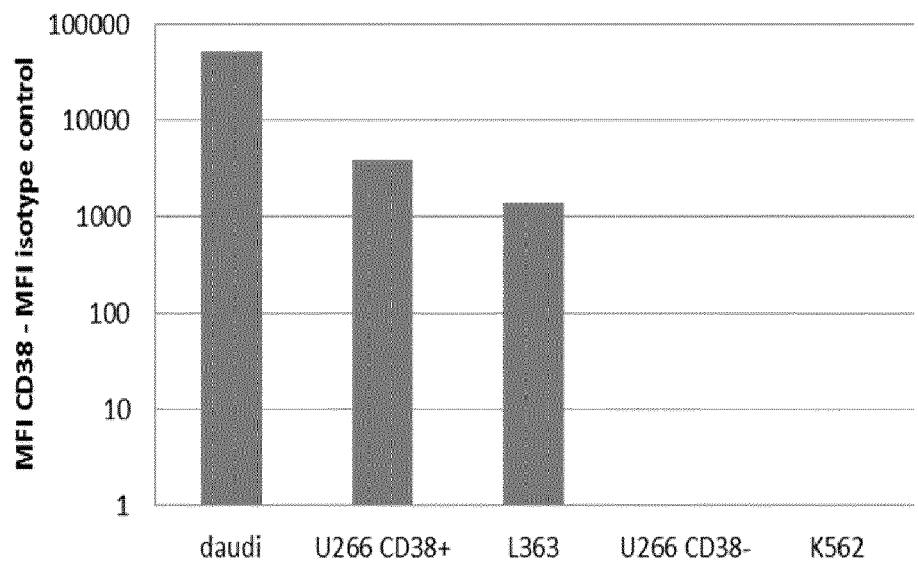
Figure 11

D0: T-cell purification and activation
D3: TALEn mRNA transfection
D6: CAR transduction
D12: FACS analysis
D14: Cytotoxicity Assay
D17: Re-activation
D20: FACS analysis T01: pCLS25985 / pCLS25986 pCLS25985: LEFT-NG-HD-HD-NI-NN-NI-NN-NI-NN-HD-NI-NI-NG-NI-NG-NG#-RIGHT
    pCLS25986: LEFT-NI-NN-NI-NG-NN-NI-NN-NN-NN-NG-NN-NI-NN-NN-HD-NG#-RIGHT

T02: pCLS25992 / pCLS26065 pCLS25992: LEFT-NN-NI-HD-NG-NG-HD-HD-NI-NN-NI-NN-NI-NN-HD-NI-NG#-RIGHT
    pCLS26065: LEFT-NN-NI-NN-NN-NN-NG-NN-NI-NN-NN-HD-NI-NG-NN-NG-NG#-RIGHT

T03: pCLS25987 / pCLS25988 pCLS25987: LEFT-NG-NN-NI-HD-NG-HD-NG-NI-NG-NG-NN-NG-HD-NG-NN-NG#-RIGHT
    pCLS25988: LEFT-NN-NG-NI-NG-NN-NN-NG-NN-NI-HD-NI-NI-NN-NI-NN-NG#-RIGHT

Figure 13

% of target cell viability

% of Specific cell lysis (CS1+)

FROM

CONT. 5
→

TO

CONT. 13
↓

Figure 16:
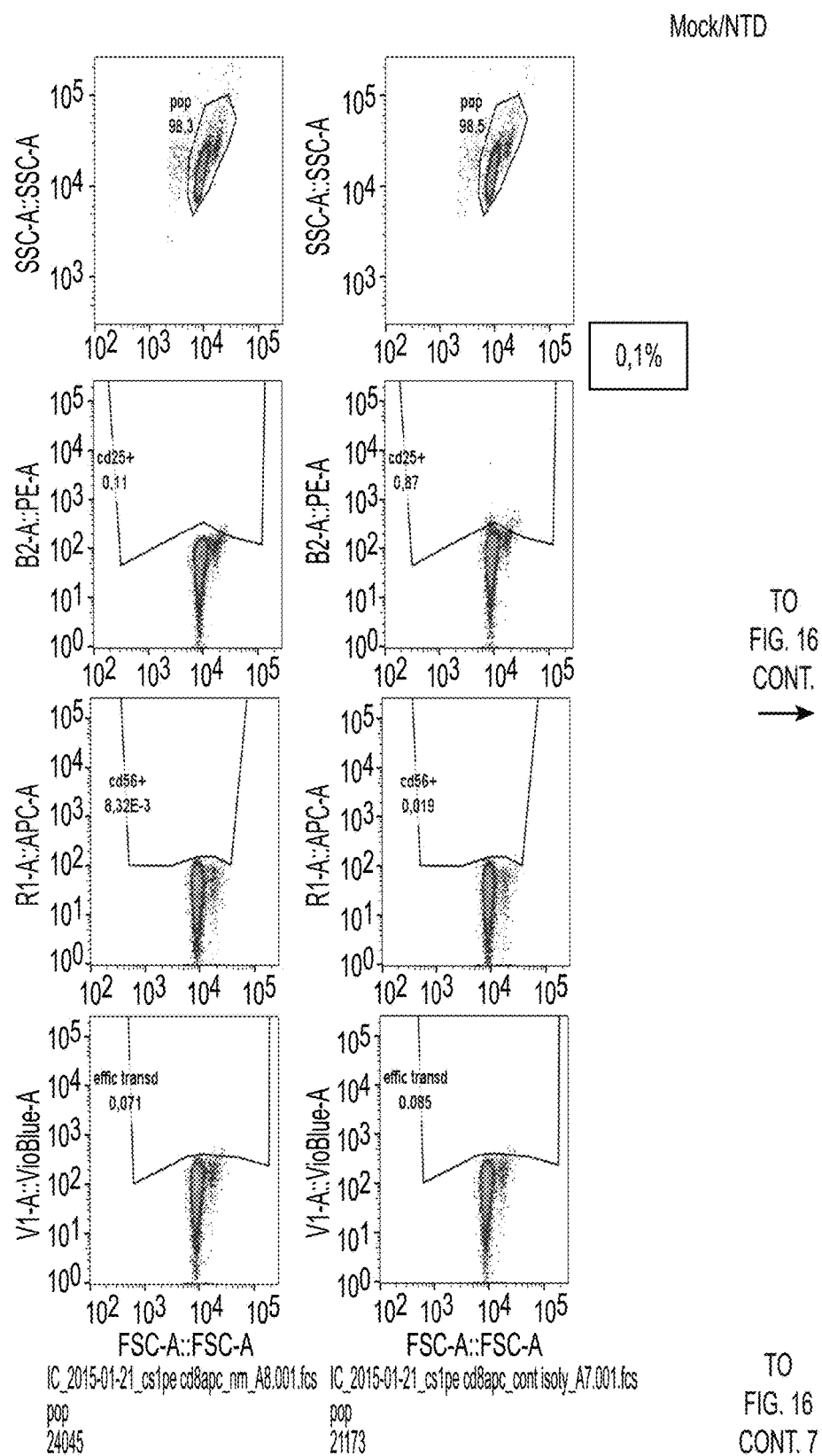
Figure 16:
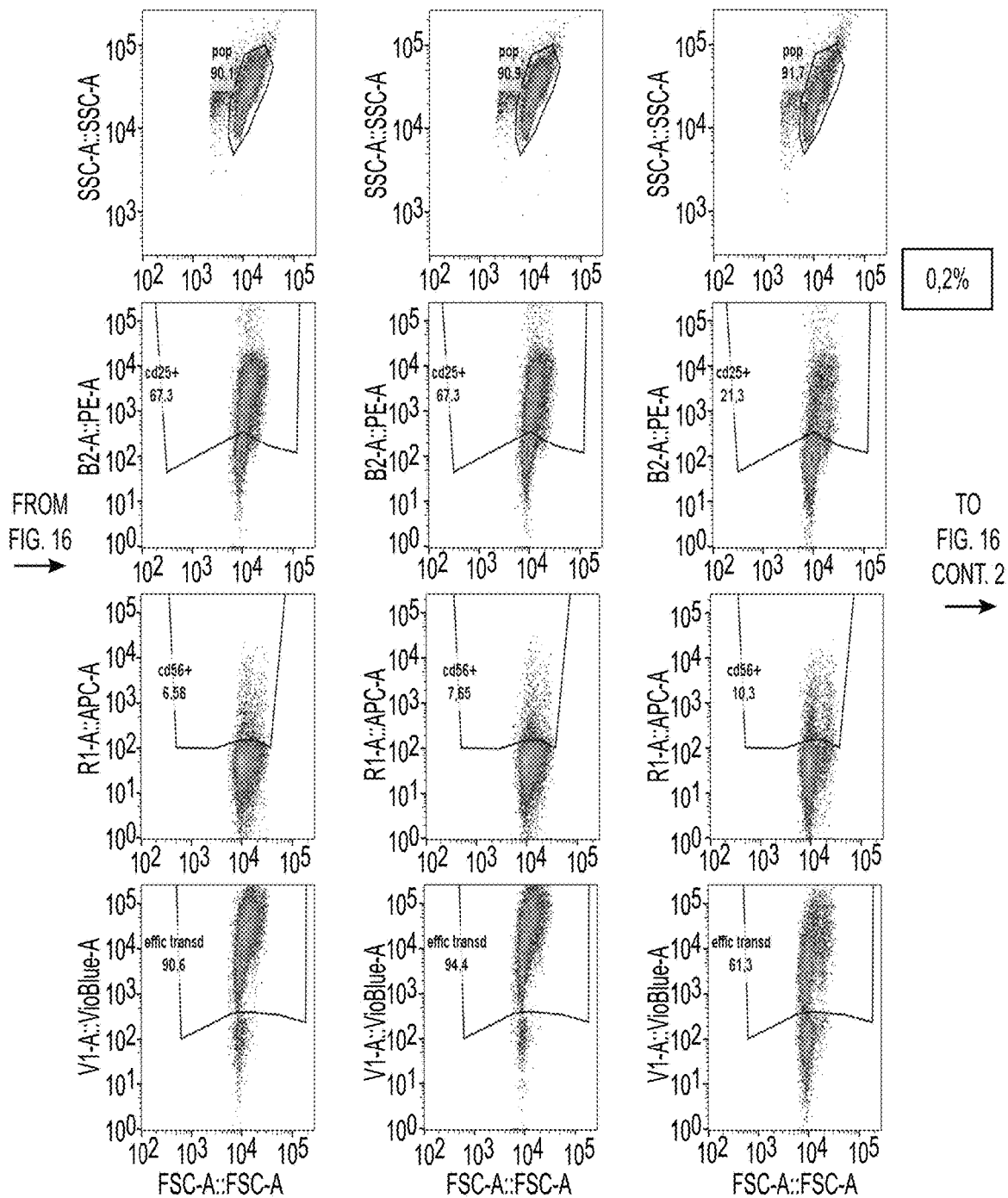
Figure 16:
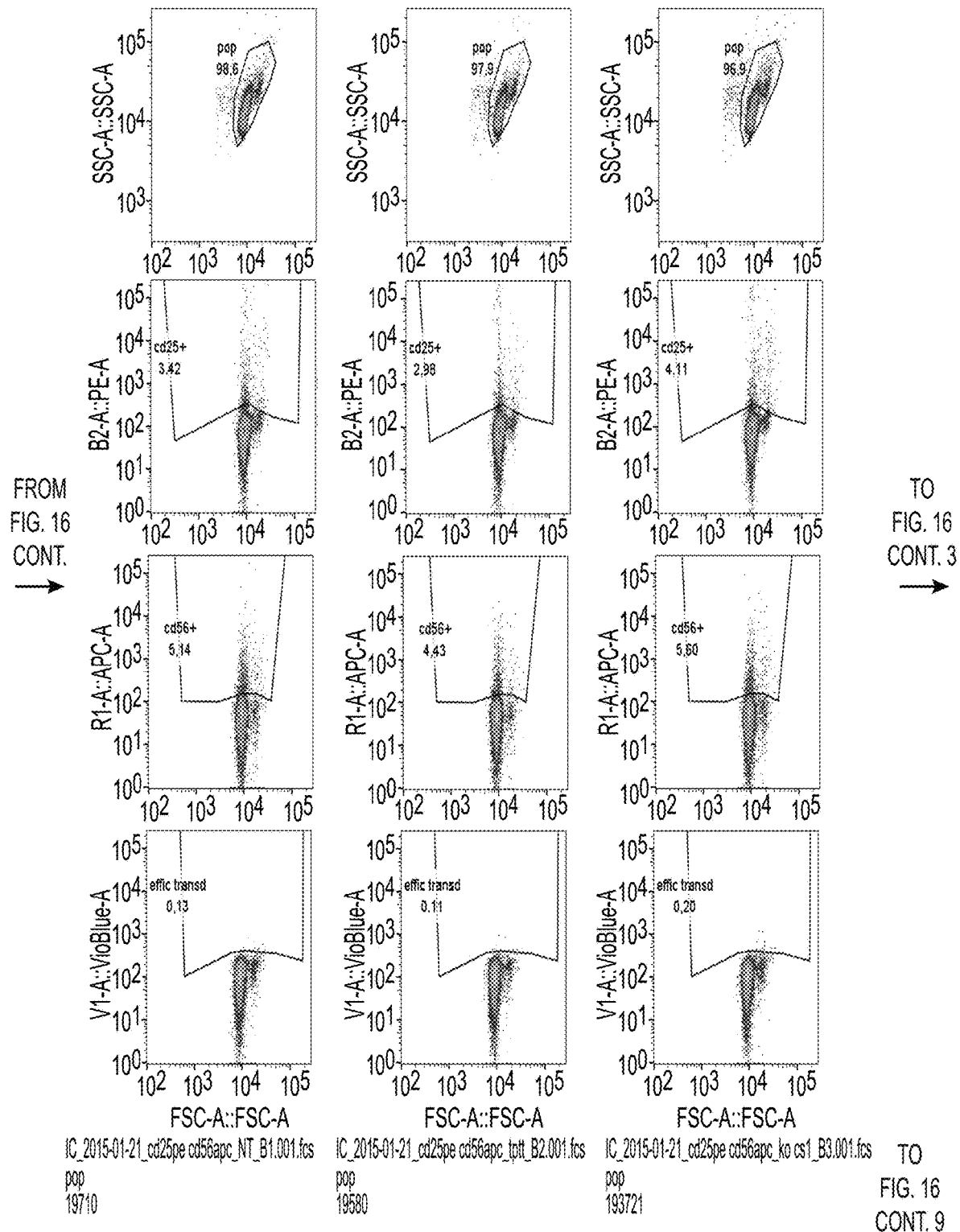
Figure 16:
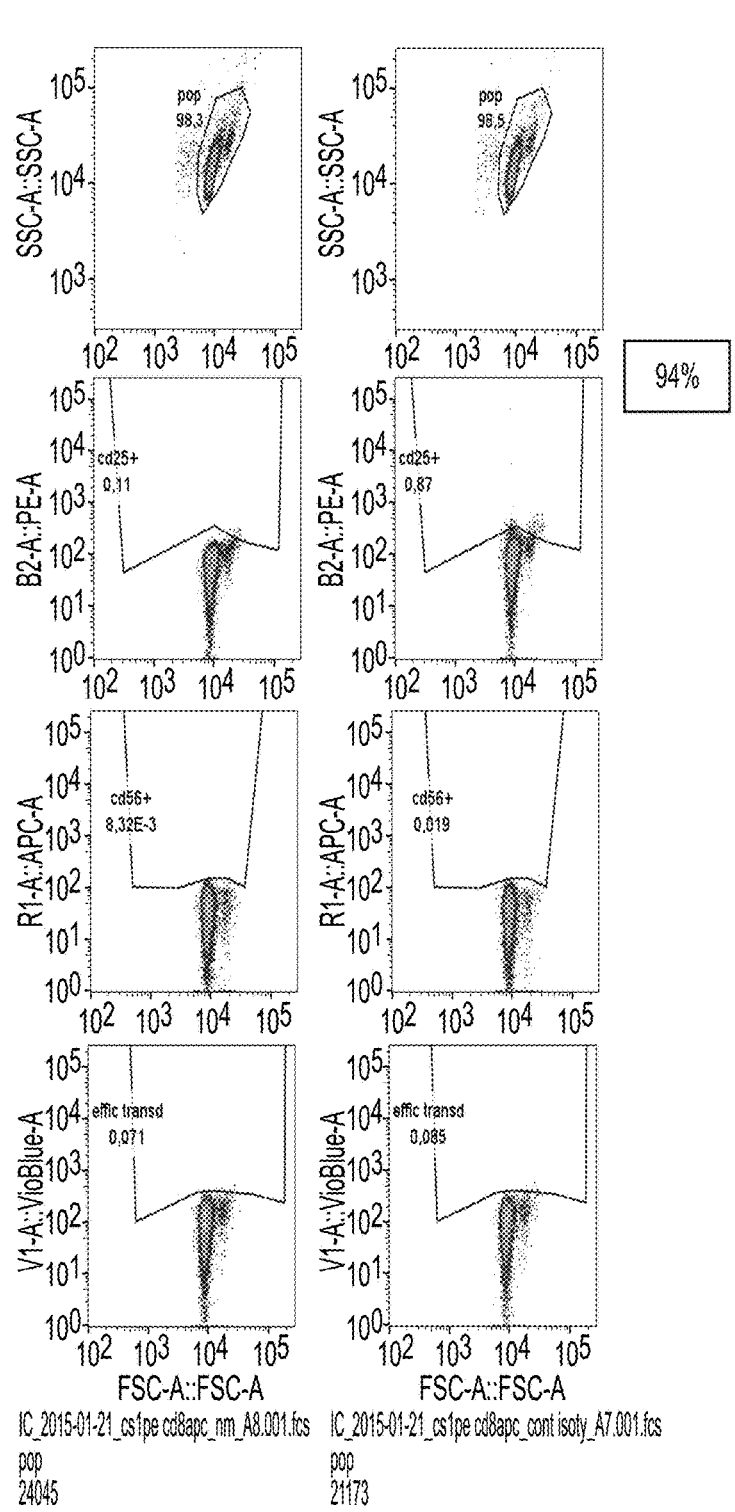
Figure 16:
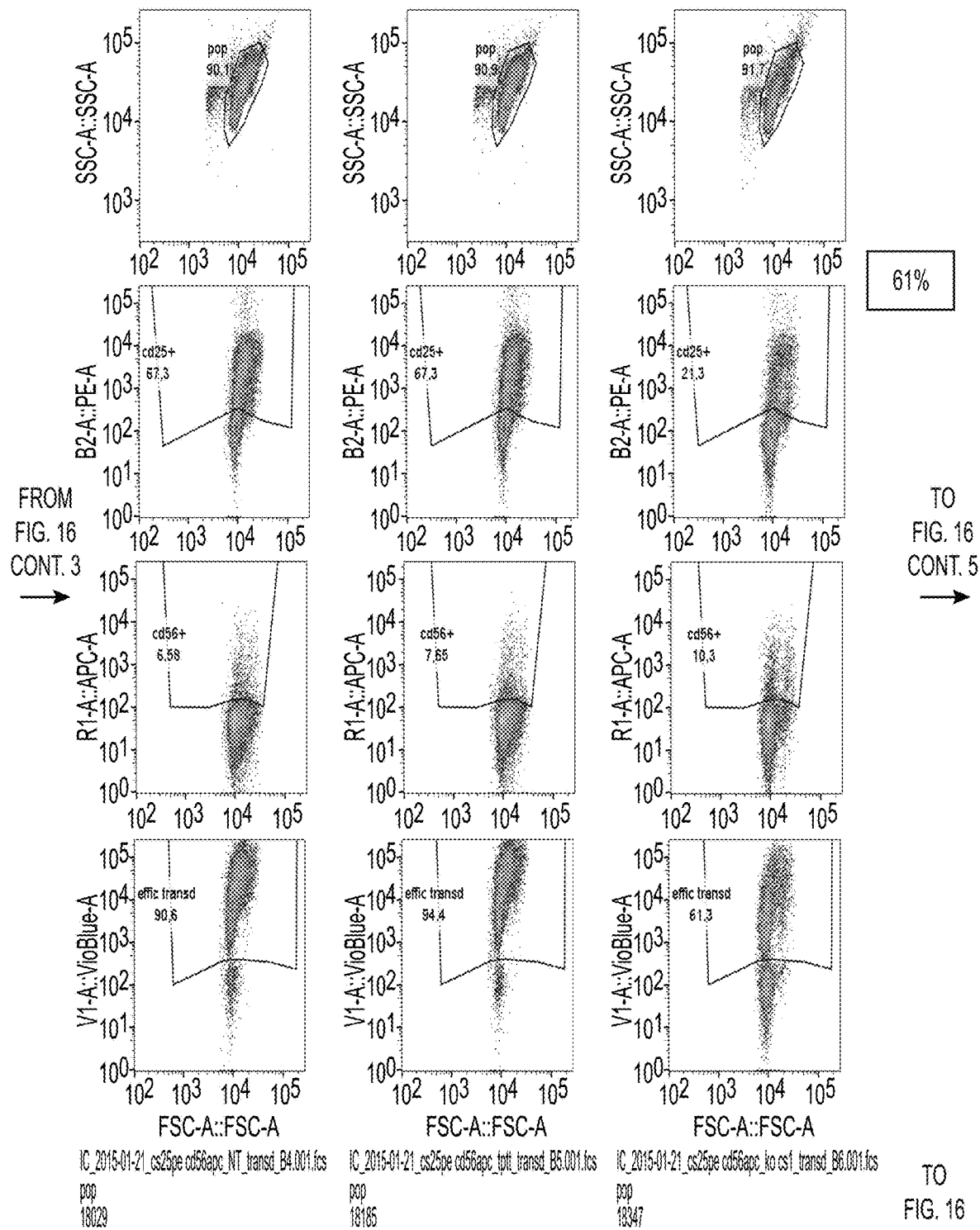
Figure 16:
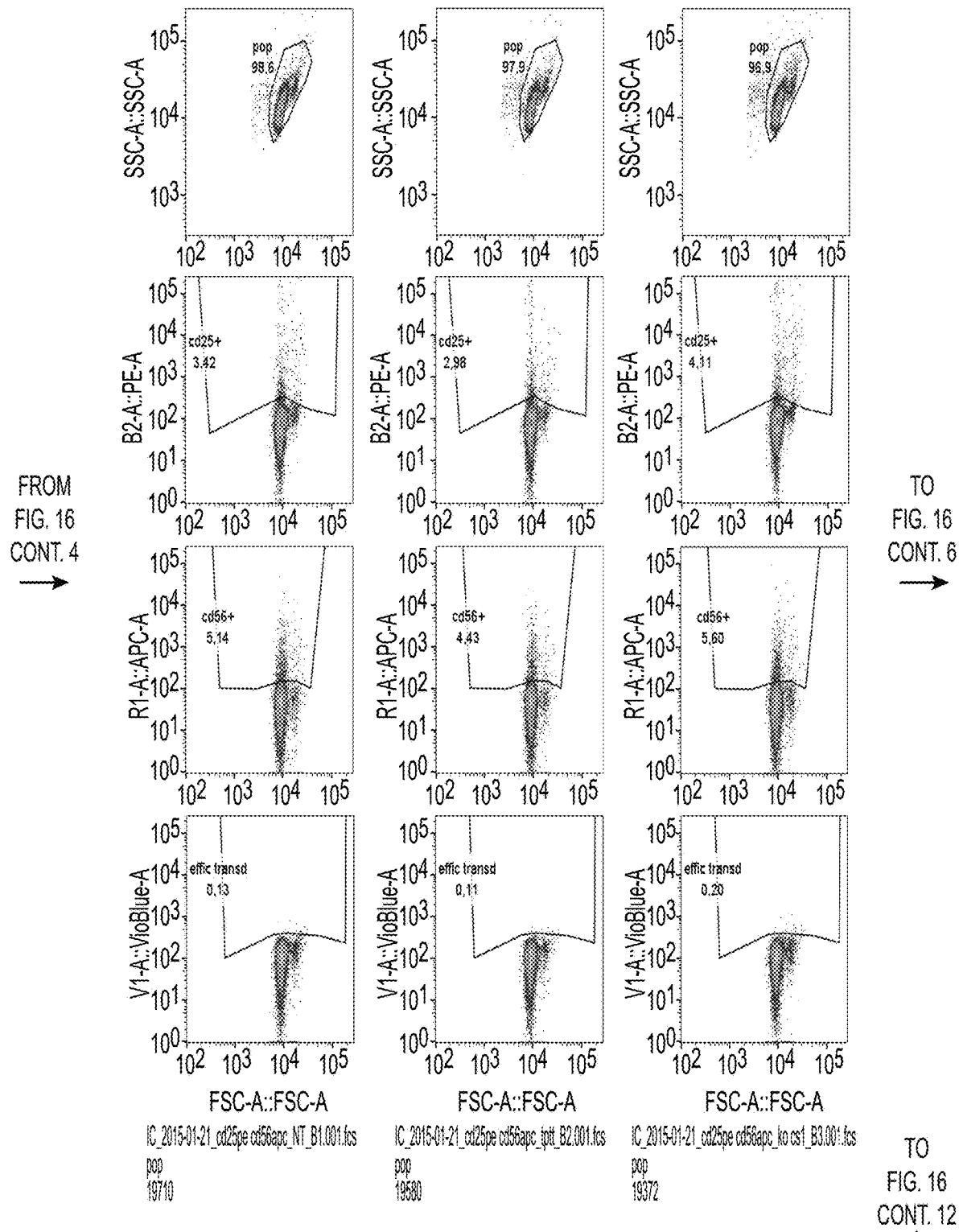
Figure 16:
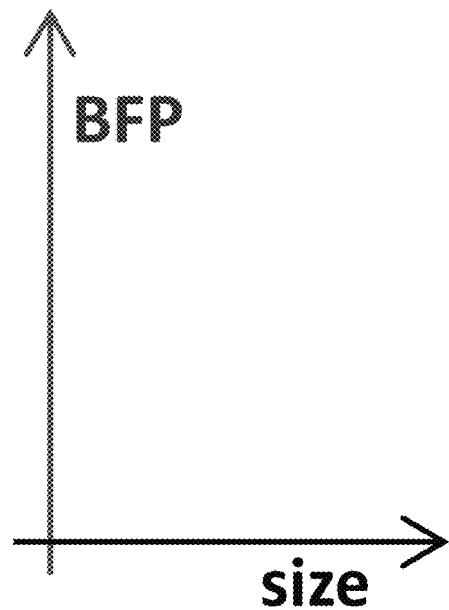
Figure 16:
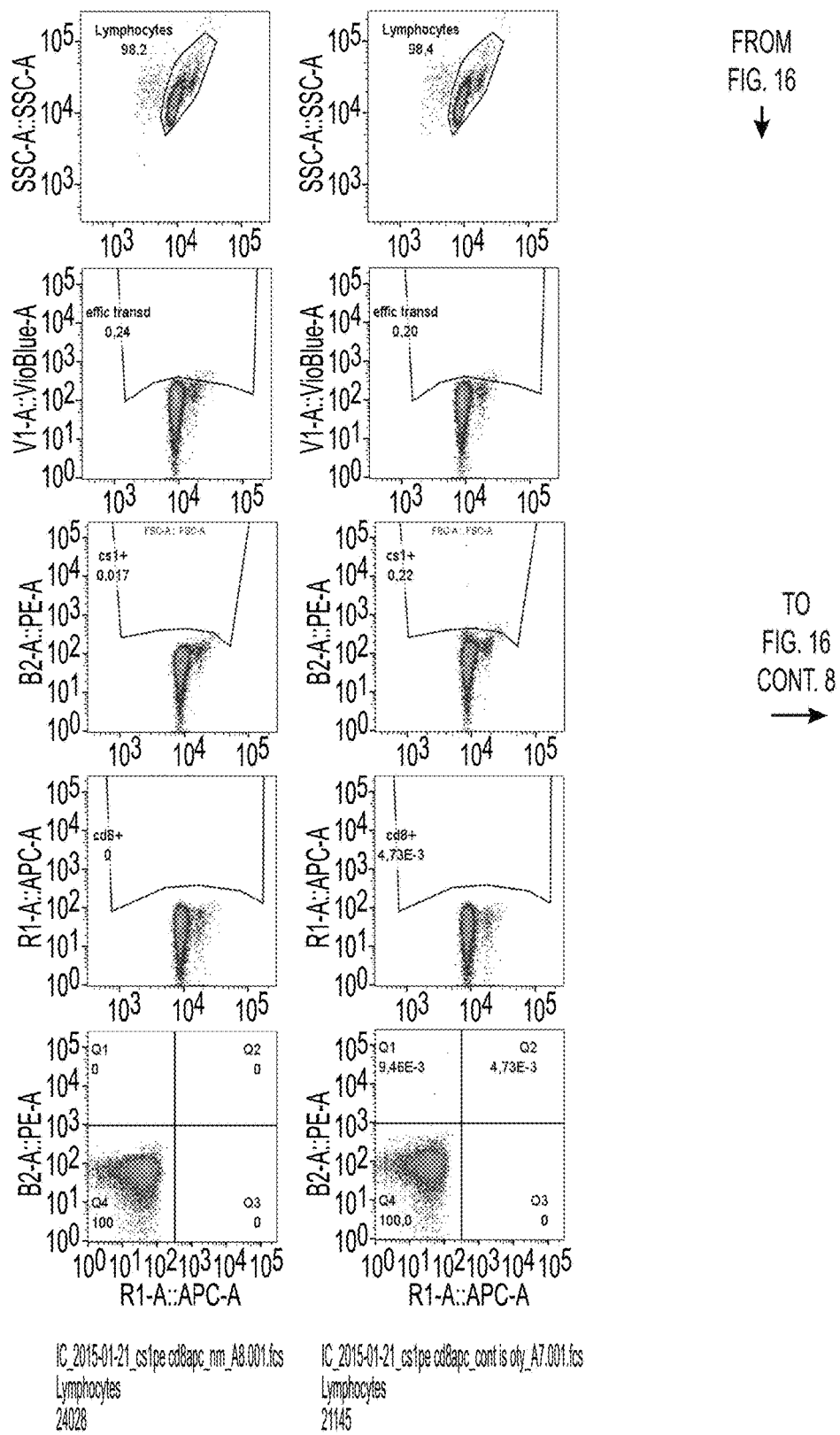
Figure 16:
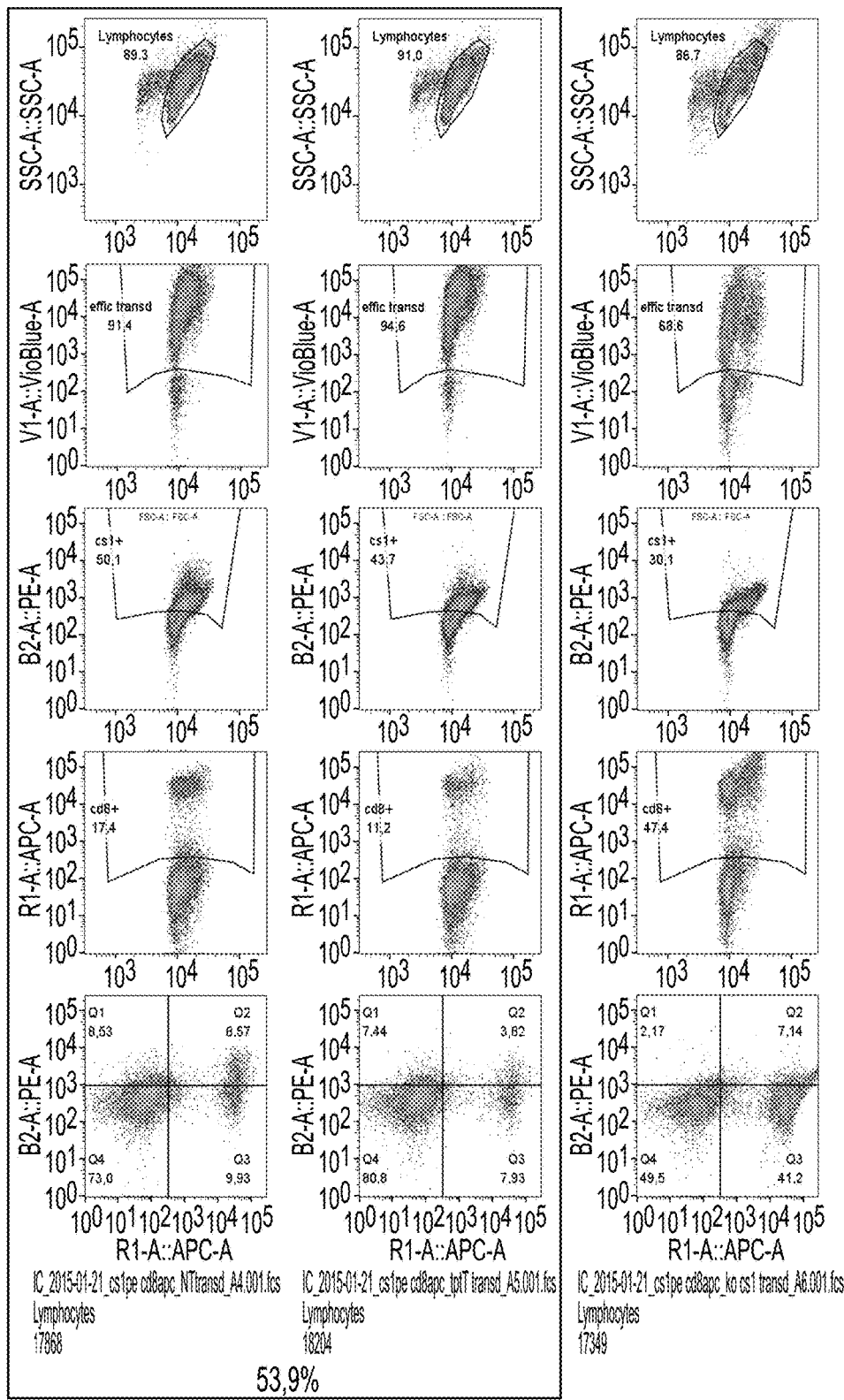
Figure 16:
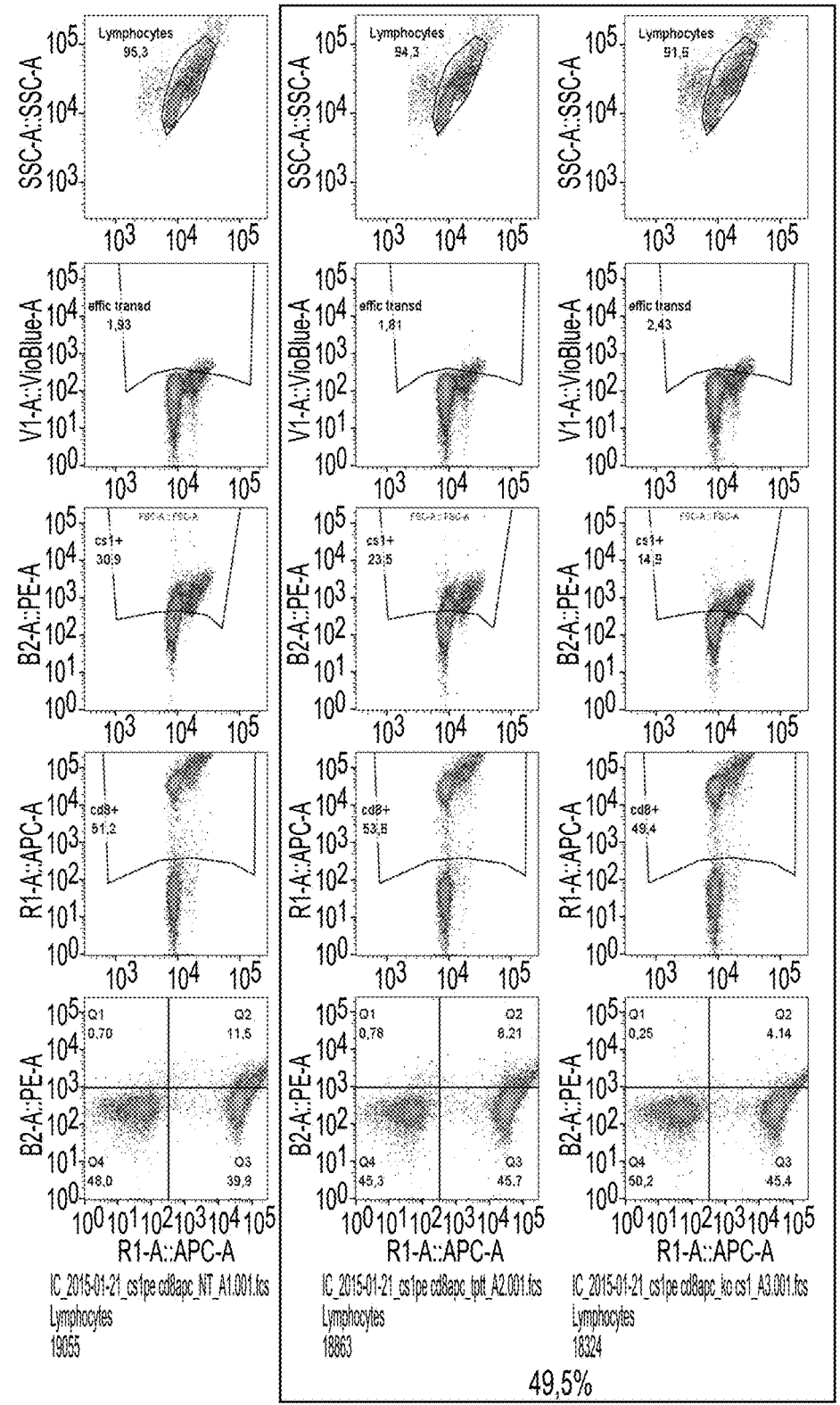
Figure 16:
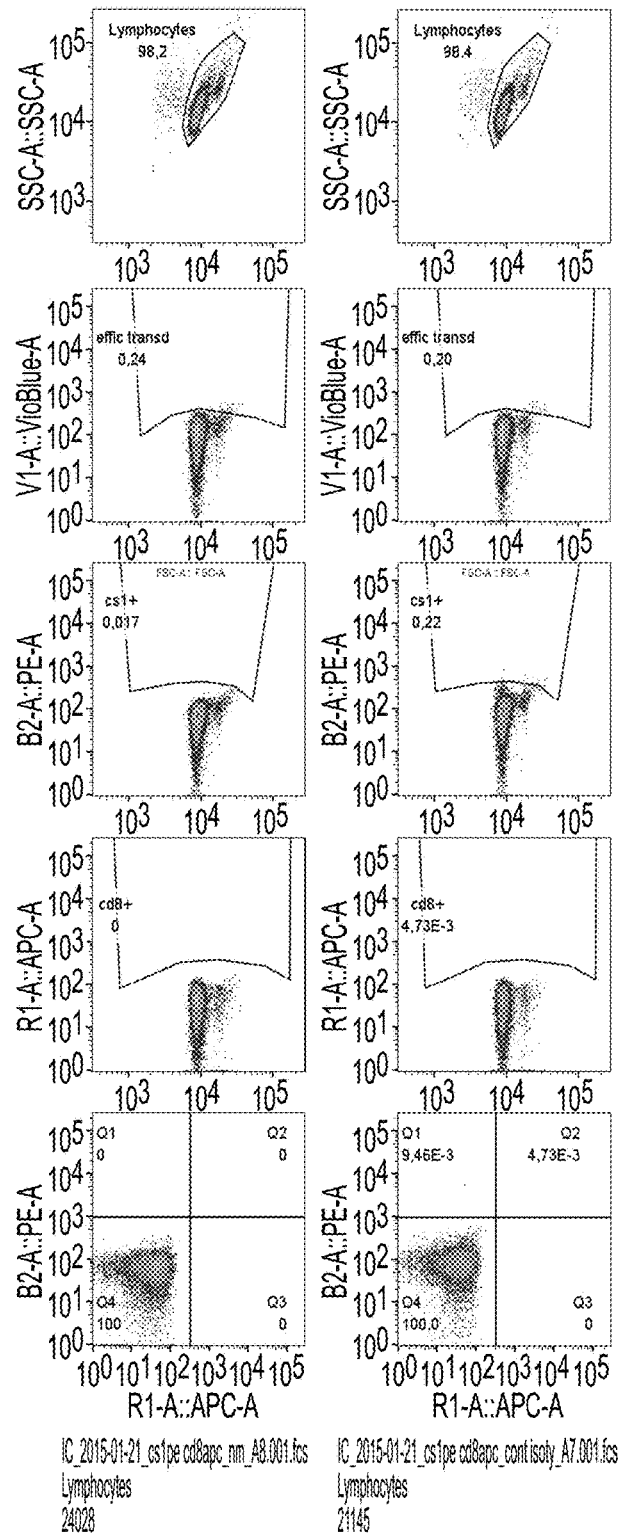
Figure 16:
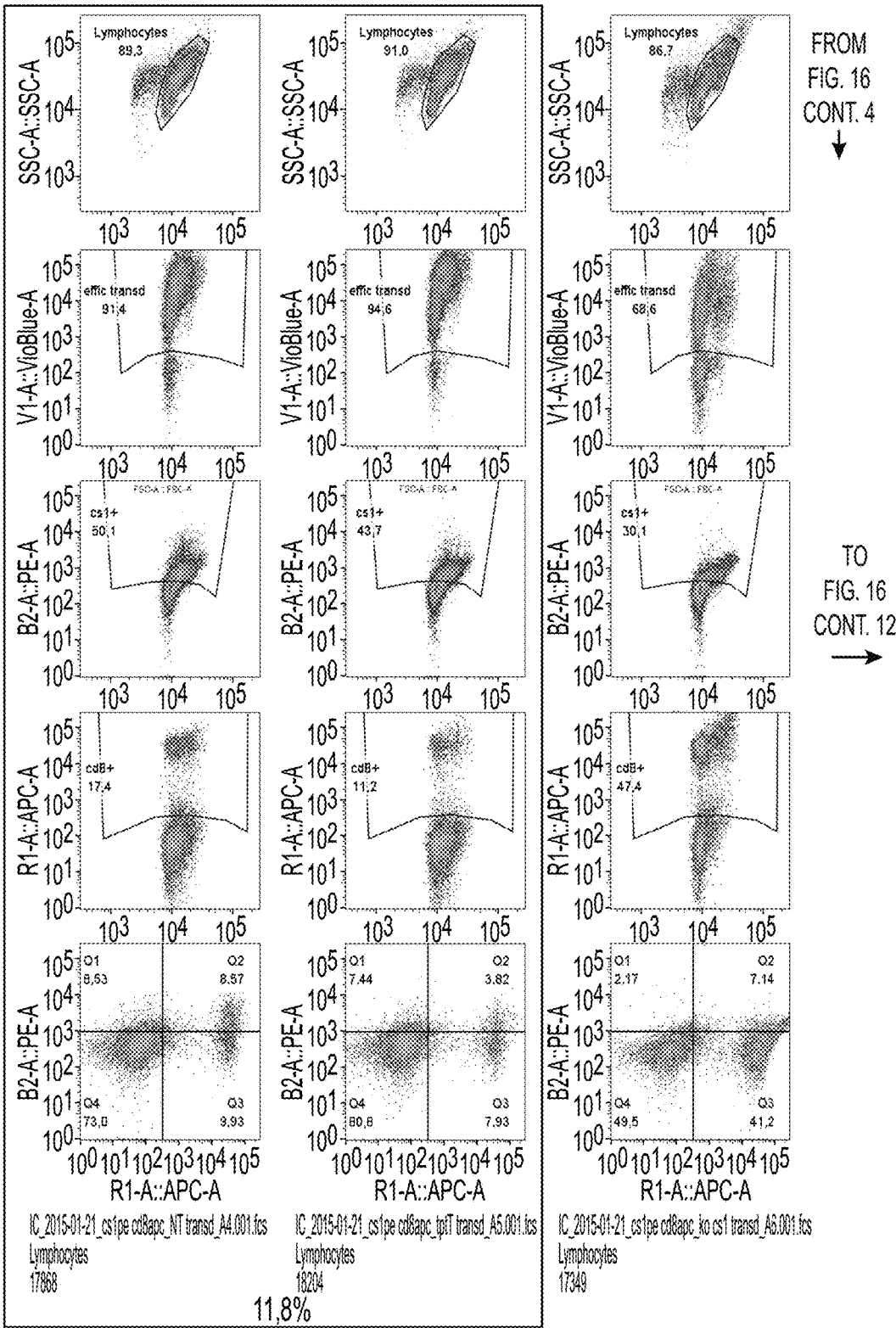
Figure 16:
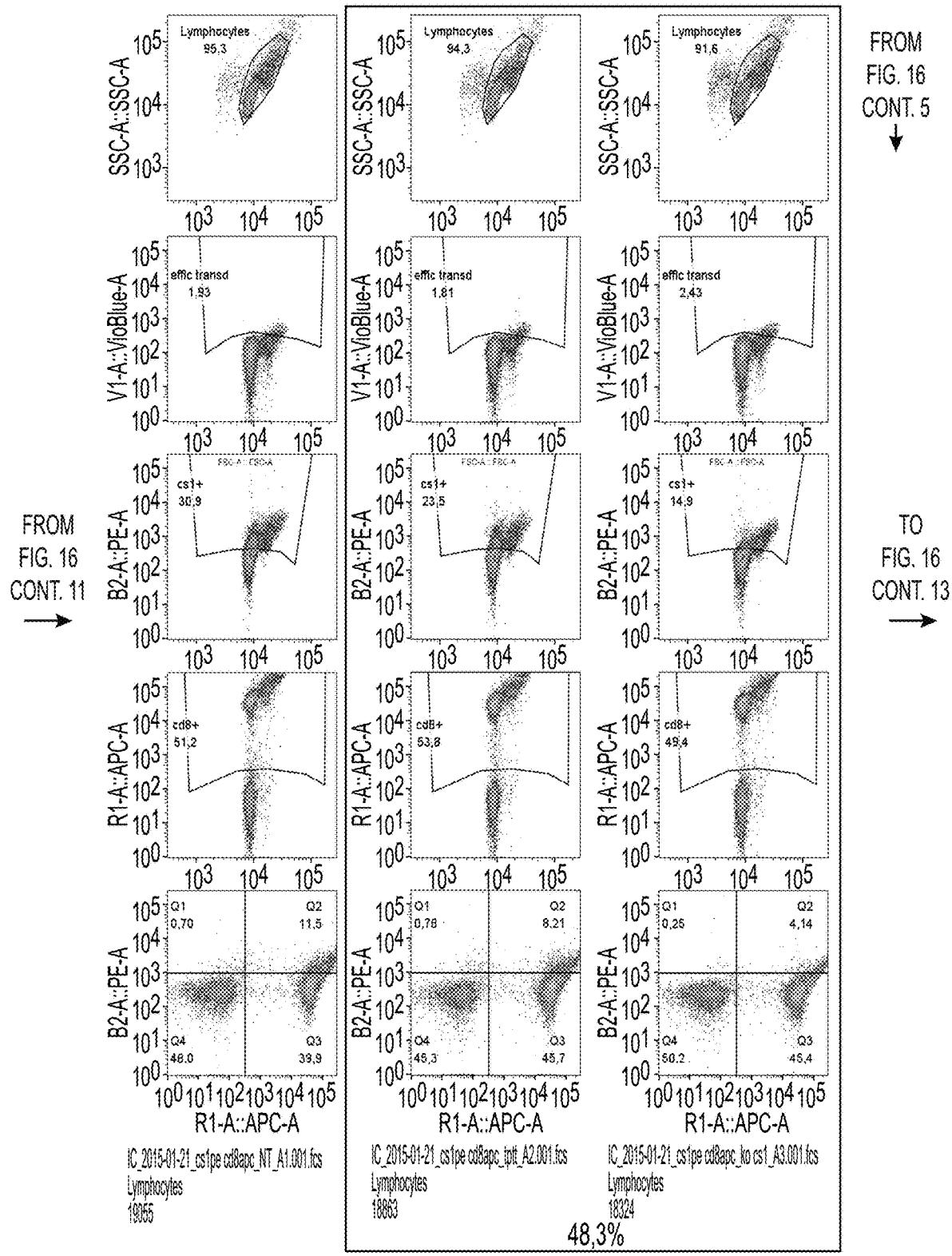

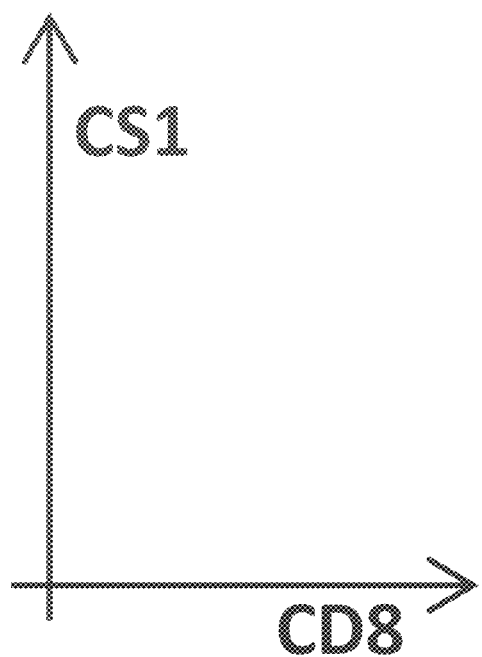
*FIG. 16* *CONT. 13*

CELLS FOR IMMUNOTHERAPY ENGINEERED FOR TARGETING ANTIGEN PRESENT BOTH ON IMMUNE CELLS AND PATHOLOGICAL CELLS

CROSS-REFERENCE TO RELATED APPLICATIONS

This application is a continuation of U.S. application Ser. No. 15/118,801, filed Aug. 12, 2016, which is a 371 of International Appln. PCT/EP2015/053162, filed Feb. 13, 2015, which claims the benefit of Danish Appln. PA201470076, filed Feb. 14, 2014, all of which are incorporated herein by reference.

SEQUENCE LISTING

The instant application contains a Sequence Listing which has been submitted electronically in ASCII format and is hereby incorporated by reference in its entirety. Said ASCII copy, created on Jul. 27, 2020, is named 15118801_Seq.txt and is 229,376 bytes in size.

FIELD OF THE INVENTION

The present invention relates to methods of developing genetically engineered, preferably non-alloreactive, immune cells for immunotherapy, which are endowed with Chimeric Antigen Receptors targeting an antigen marker that is common to both the pathological cells and the immune cells (ex: CD38).

The method comprises expressing a CAR directed against said antigen marker and inactivating the genes in the immune cells contributing to the presence of said antigen marker on the surface of said immune cells. This inactivation is typically performed by using transgenes encoding RNA-guided endonucleases (ex: Cas9/CRISPR), meganucleases, Zinc-finger nucleases or TAL nucleases. The engineered immune cells, preferably T-cells, direct their immune activity towards malignant, infected cells or defective immune cells, while avoiding their mutual destruction, auto-stimulation or aggregation. The invention opens the way to standard and affordable adoptive immunotherapy strategies using immune cells for treating cancer, infections and auto-immune diseases.

BACKGROUND OF THE INVENTION

Adoptive immunotherapy, which involves the transfer of autologous antigen-specific immune cells generated ex vivo, is a promising strategy to treat viral infections and cancer. The T cells used for adoptive immunotherapy, for instance, can be generated either by expansion of antigen-specific T-cells or redirection of T-cells through genetic engineering (Park, Rosenberg et al. 2011).

Novel specificities in T-cells have been successfully generated through the genetic transfer of transgenic T-cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity, however, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

The current protocol for treatment of patients using adoptive immunotherapy is based on autologous cell transfer. In this approach, T lymphocytes are recovered from patients, genetically modified or selected ex vivo, cultivated in vitro in order to amplify the number of cells if necessary and finally infused into the patient. In addition to lymphocyte infusion, the host may be manipulated in other ways that support the engraftment of the T cells or their participation in an immune response, for example pre-conditioning (with radiation or chemotherapy) and administration of lymphocyte growth factors (such as IL-2). Each patient receives an individually fabricated treatment, using the patient's own lymphocytes (i.e. an autologous therapy). Autologous therapies face substantial technical and logistic hurdles to practical application, their generation requires expensive dedicated facilities and expert personnel, they must be generated in a short time following a patient's diagnosis, and in many cases, pretreatment of the patient has resulted in degraded immune function, such that the patient's lymphocytes may be poorly functional and present in very low numbers. Because of these hurdles, each patient's autologous cell preparation is effectively a new product, resulting in substantial variations in efficacy and safety.

Ideally, one would like to use a standardized therapy in which allogeneic therapeutic cells could be pre-manufactured, characterized in detail, and available for immediate administration to patients. By allogeneic it is meant that the cells are obtained from individuals belonging to the same species but are genetically dissimilar. However, the use of allogeneic cells presently has many drawbacks. In immune-competent hosts allogeneic cells are rapidly rejected, a process termed host versus graft rejection (HvG), and this substantially limits the efficacy of the transferred cells. In immune-incompetent hosts, allogeneic cells are able to engraft, but their endogenous T-cell receptors (TCR) specificities may recognize the host tissue as foreign, resulting in graft versus host disease (GvHD), which can lead to serious tissue damage and death.

In order to provide allogeneic T-cells, the inventors previously disclosed a method to genetically engineer T-Cells, in which different effector genes, in particular those encoding T-cell receptors, were inactivated by using specific TAL-nucleases, better known under the trade mark TALEN™ (Cellectis, 8, rue de la Croix Jarry, 75013 PARIS). This method has proven to be highly efficiency in primary cells using RNA transfection as part of a platform allowing the mass production of allogeneic T-cells (WO 2013/176915).

CD38 (cluster of differentiation 38), also known as cyclic ADP ribose hydrolase is a glycoprotein found on the surface of many immune cells (white blood cells), in particular T-cells, including CD4+, CD8+, B lymphocytes and natural killer cells. CD38 also functions in cell adhesion, signal transduction and calcium signaling. Structural information about this protein can be found in the UniProtKB/Swiss-Prot database under reference P28907. In humans, the CD38 protein is encoded by the CD38 gene which located on chromosome 4. CD38 is a multifunctional ectoenzyme that catalyzes the synthesis and hydrolysis of cyclic ADP-ribose (cADPR) from NAD+ to ADP-ribose. These reaction products are deemed essential for the regulation of intracellular Ca2+. Also, loss of CD38 function was associated with impaired immune responses and metabolic disturbances (Malavasi F., et al. (2008). "Evolution and function of the ADP ribosyl cyclase/CD38 gene family in physiology and pathology". *Physiol. Rev.* 88(3): 841-86).

On another hand, CD38 protein is a marker of HIV infection, leukemias, myelomas, solid tumors, type II diabetes mellitus and bone metabolism, as well as some other genetically determined conditions. In particular, it has been used as a prognostic marker in leukemia (Ibrahim, S. et al. (2001) CD38 expression as an important prognostic factor in B-cell chronic lymphocytic leukemia. *Blood* 98:181-186).

Although, cells expressing CD38, as well as many other tumor antigen markers referred to in Table 1, such as CD70 and CS1 could be regarded as attractive targets for CARs, the fact that such antigen markers are also expressed at the surface of most T-cells, has hampered significantly the selection of these markers to perform immunotherapy.

The inventors here provide strategies for immunotherapy involving pathological cells expressing specific antigen markers also present at the surface of T-cells, like for instance malignant CD38 positive B-cells causing leukemia, CD70 and CS1.

SUMMARY OF THE INVENTION

The present invention discloses methods to engineer T-cells intended to target pathological cells, whereas said pathological cells express one or several antigen markers that are also present on the surface of T-cells. Examples of such antigen markers are found in Table 1. An example of such antigen marker is CD38. Other examples are CD70 and CS1. By antigen marker is meant the whole protein of an immune-reactive fragment thereof.

According to the invention, the T-cells are engineered in order to inactivate the expression of the genes encoding such antigen markers, or involved into the presentation of such antigen marker on the cell surface.

This inactivation is preferably performed by a genome modification, more particularly through the expression in the T-cell of a specific rare-cutting endonuclease able to target a genetic locus directly or indirectly involved in the production or presentation of said antigen marker at the surface of the T-cell. Different types of rare-cutting endonucleases can be used, such as Meganucleases, TAL-nucleases, zing-finger nucleases (ZEN), or RNA/DNA guided endonucleases like Cas9/CRISPR or Argonaute.

According to a preferred embodiment, the T-cells are endowed with at least one chimeric antigen receptors (CAR) allowing a specific binding of said cells bearing said targeted antigen marker.

According to another embodiment, the T-cells can be further engineered to make them allogeneic, especially by deleting genes involved into self-recognition, such as those, for instance, encoding components of T-cell receptors (TCR) or HLA complex.

The present invention encompasses the isolated cells or cell lines comprising the genetic modifications set forth in the detailed description, examples and figures, as well as any of the proteins, polypeptides or vectors useful to engineer said T-cells.

As a result of the invention, the engineered T-cells can be used as therapeutic products, ideally as an "off the shelf" product, in methods for treating or preventing cancer, infections or auto-immune disease.

Preferred immune cells according to the present invention are those resulting into the phenotypes:

[CAR targeting a antigen marker of Table1]$^+$[antigen marker of Table1]$^-$ such as the following ones:
[CAR CD38]$^+$[CD38]$^-$, preferably also [TCR] negative;
[CAR CD70]$^+$[CD70]$^-$, preferably also [TCR] negative;
[CAR CS1]$^+$[CS1]$^-$, preferably also [TCR] negative;
for their use as therapeutic products, preferably allogeneic ones.

BRIEF DESCRIPTION OF THE FIGURES AND TABLES

FIG. 1: Schematic representation of an engineered T-cell according to the present invention disrupted for CD38 and endowed with a chimeric antigen receptor (represented as a single-chain CAR) targeting a malignant cell bearing the antigen marker CD38.

Figure 2:
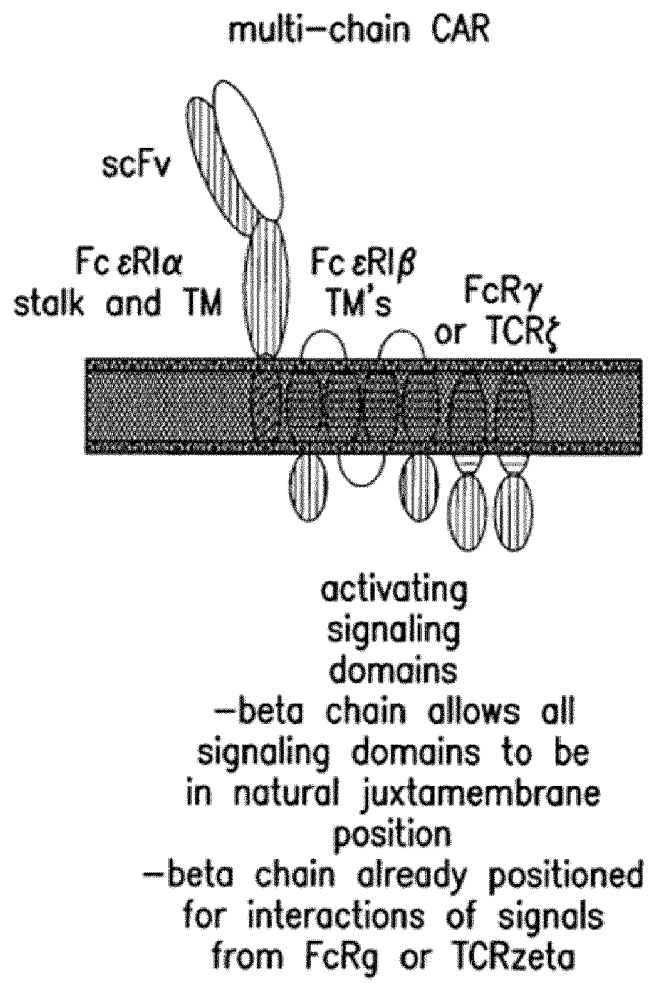

FIG. 2: Schematic representation of a multi-subunit chimeric antigen receptor.

Figures 3, 4:
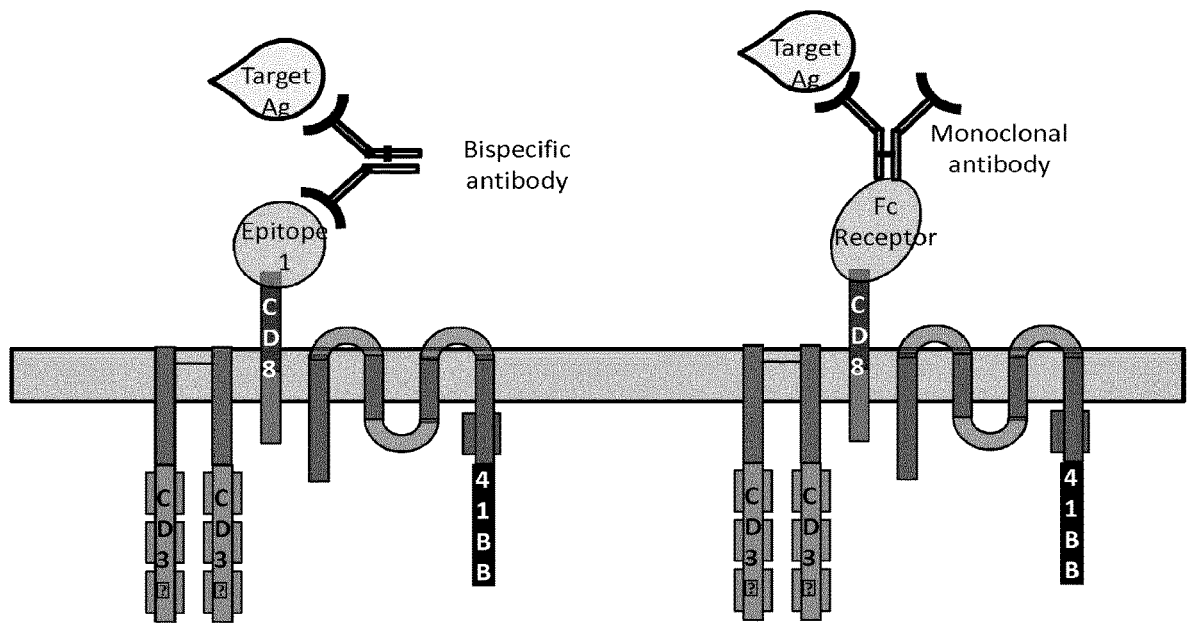

FIG. 3: Schematic representation of a therapeutic strategy according to the invention combining T-cells endowed with a multi-subunit CAR and circulating bi-specific antibody. In this particular aspect, the receptor present on the extracellular chain of the multi-subunit CAR is composed of an epitope which is recognized by a bi-specific antibody. The bi-specific antibody is intended to bind said epitope one the one hand and the antigen marker on the other hand to facilitate the binding of the T-cell to the pathological cell.

FIG. 4: Schematic representation of a therapeutic strategy according to the invention combining T-cells endowed with a multi-subunit CAR and circulating monoclonal antibody. In this particular aspect, the receptor present on the extracellular chain of the multi-subunit CAR is composed, for instance, of a Fc receptor intended to bind a monoclonal antibody that is directed against the antigen marker. The monoclonal antibody increases the chance of T-cells binding the pathological cells.

Figures 5, 6:
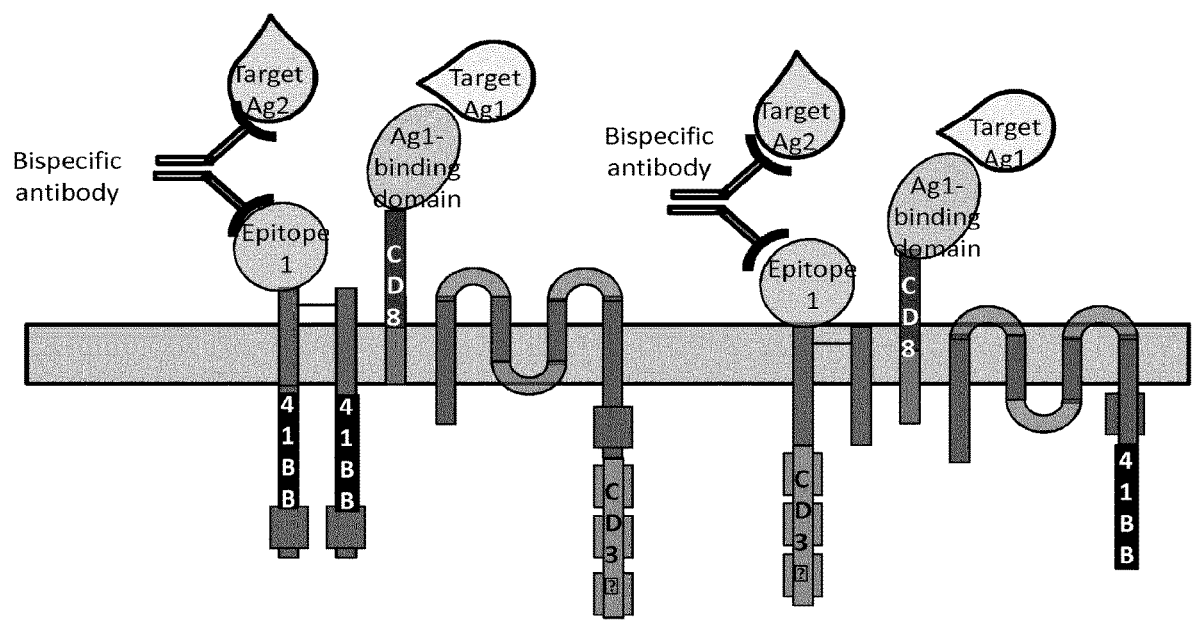

FIG. 5: Schematic representation of a therapeutic strategy according to the invention combining T-cells endowed with a multi-subunit CAR that comprises two extracellular cellular domains and one circulating bi-specific antibody. In this particular aspect, the extracellular cellular domains are located on distinct sub-units. These domains are respectively composed of an epitope that is recognized by a bi-specific antibody and of a receptor targeting an antigen. The receptor is directed against a first antigen marker, whereas the bi-specific antibody is intended to bind the epitope and a second antigen marker. This display aims to selectively target pathological cells bearing at their surface both the first and second antigen markers.

FIG. 6: display is similar to FIG. 5, but stimulation and co-stimulation domains (respectively 4-1BB and CD3zeta protein domains) have been exchanged to modulate the intensity of the activation of the T-cell resulting from the binding of the chimeric antigen receptor with the pathological cell.

Figures 7, 8:
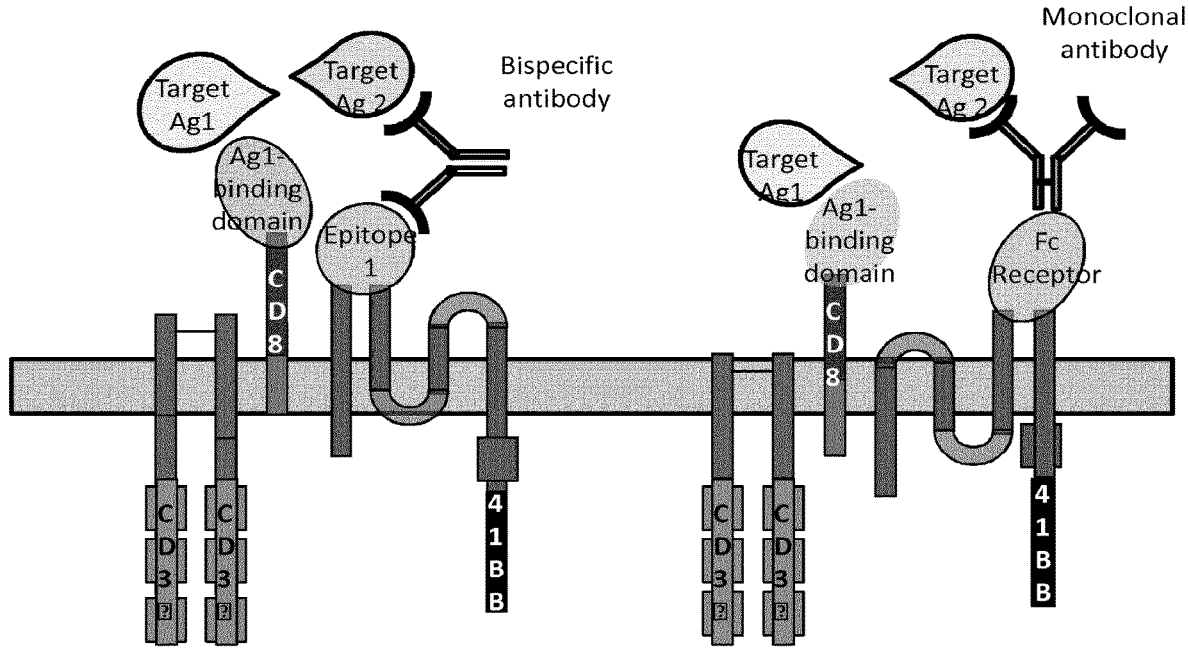

FIG. 7: display is similar to FIG. 5, but stimulation and co-stimulation domains (respectively 4-1BB and CD3zeta protein domains) have been exchanged and one CD3zeta domain has been added to increase the intensity of the activation of the T-cell resulting from the binding of the chimeric antigen receptor with the pathological cell.

FIG. 8: Schematic representation of a therapeutic strategy according to the invention combining T-cells endowed with a multi-subunit CAR that comprises two extracellular cellular domains and one circulating monoclonal antibody. In this particular aspect, the extracellular cellular domains are located on distinct sub-units. These domains are respectively composed of an antigen binding domain targeting an antigen marker and a Fc receptor intended to bind a monoclonal antibody that is directed against a second antigen marker. This display aims to selectively target pathological cells bearing at their surface both the first and second antigen markers.

Figure 9:
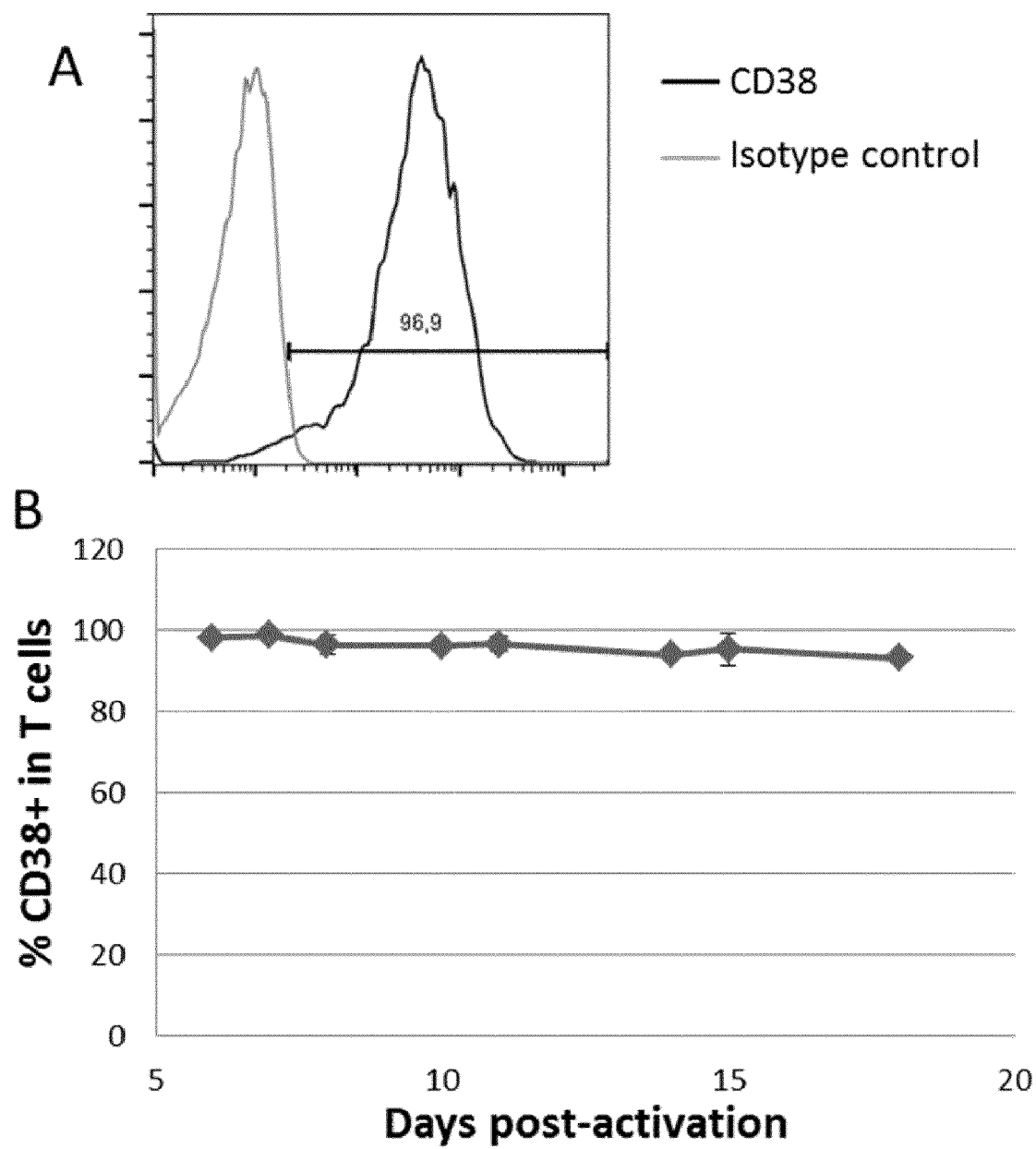

FIG. 9: CD38 expression by activated T cells. A. CD38 expression by T cells at day 6 after activation with CD3/CD28 coated beads+IL2. B. Longitudinal analysis of CD38 expression by T cells during 17 days after activation.

Figure 10:
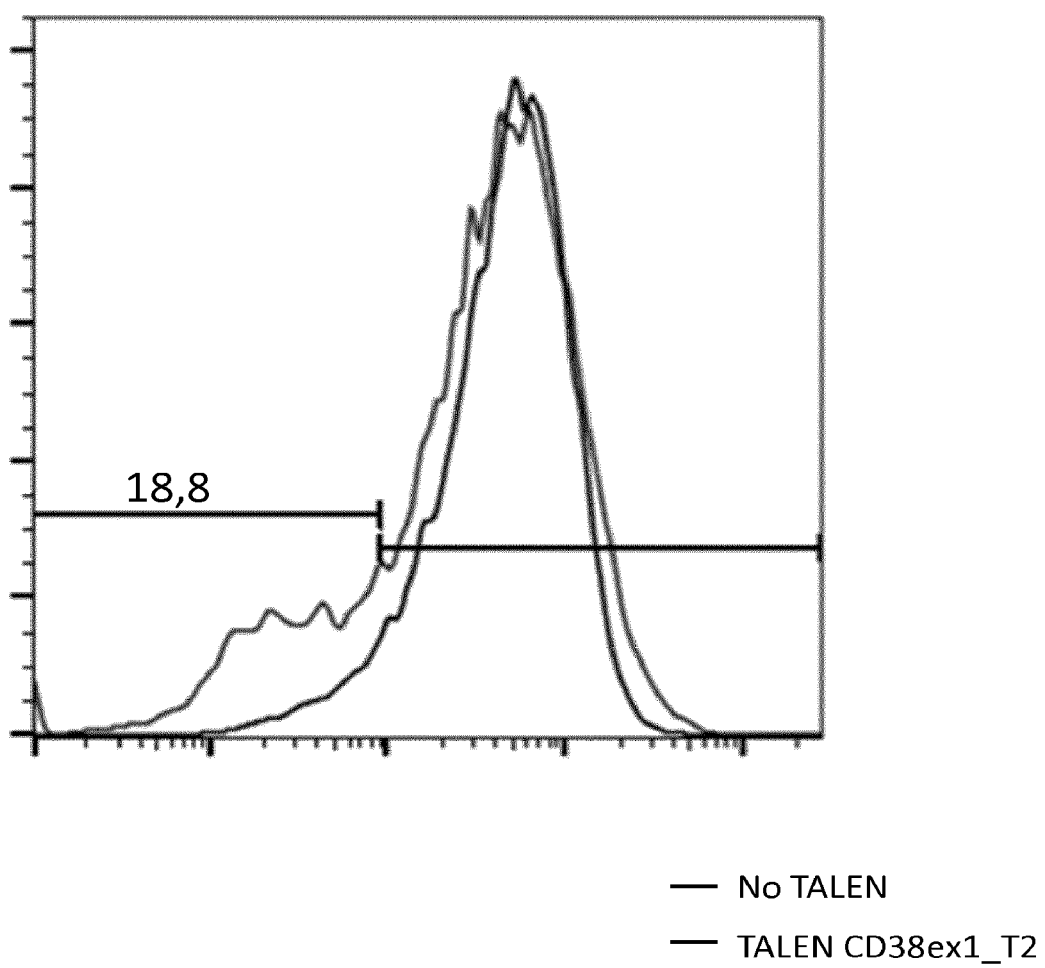

FIG. 10A: Knock-out (KO) on CD38 gene. Position on CD38 exon 1 sequence of the 3 different TALENs (T2, T4 and T5) designed to knock out CD38 in T cell.

FIG. 10B: Expression of CD38 in T cells after transfection with the TALEN CD38ex1_T2.

Figure 10C:
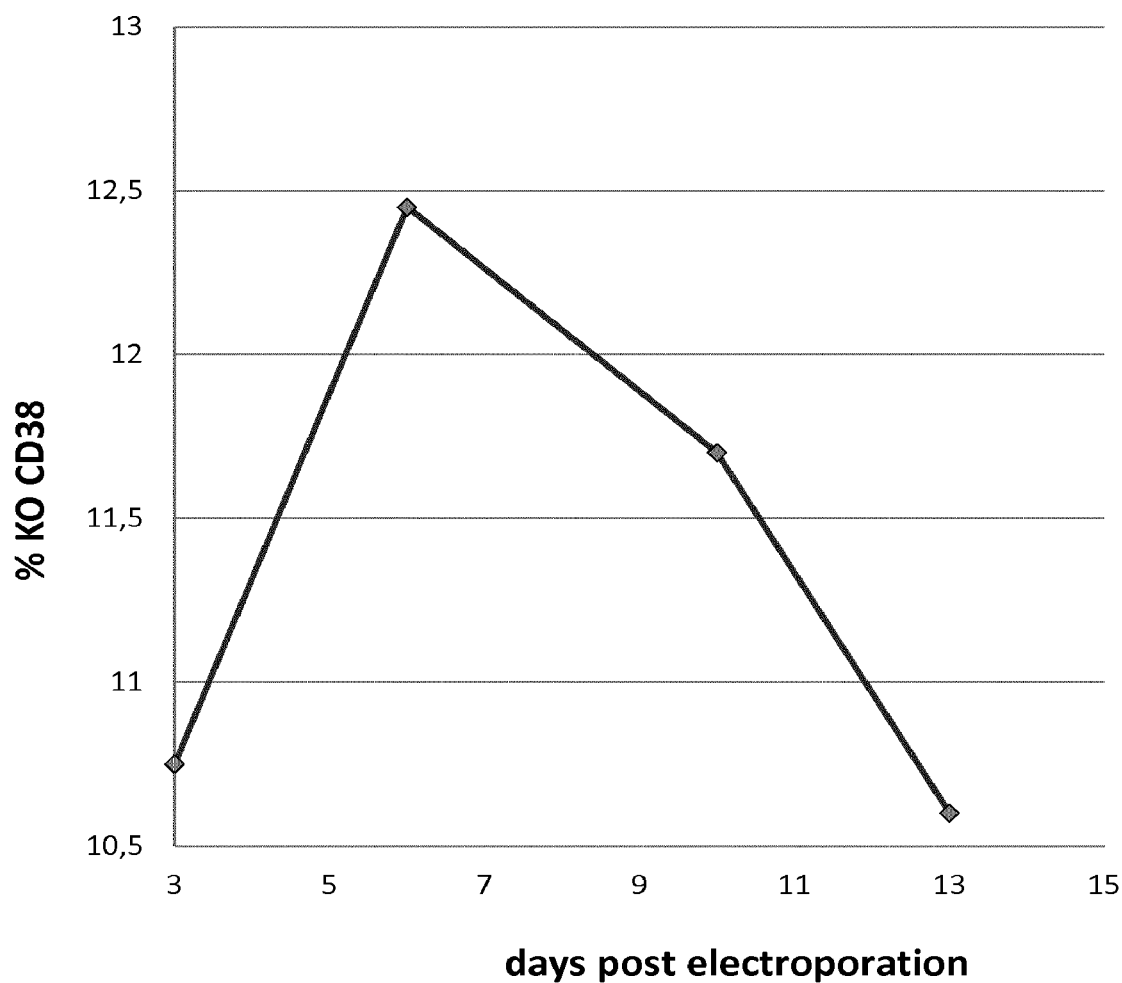

FIG. 10C: CD38 staining to control for the purification of CD38 KO T cells.

FIG. 11: CD38 CAR: A. Representation of the 3 versions of CARs designed. B. CD38 expression level by the target cell lines.

Figure 12:
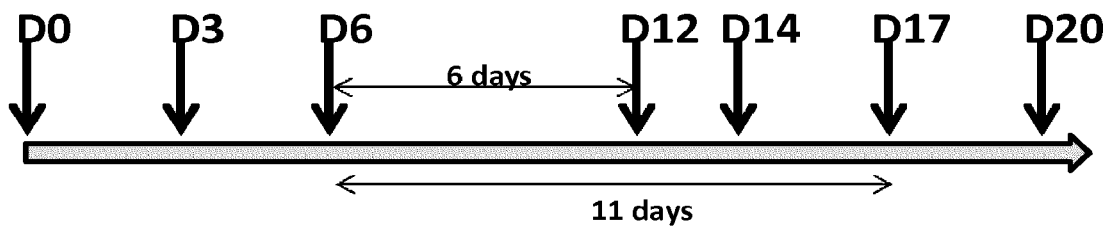
Figure 14A:
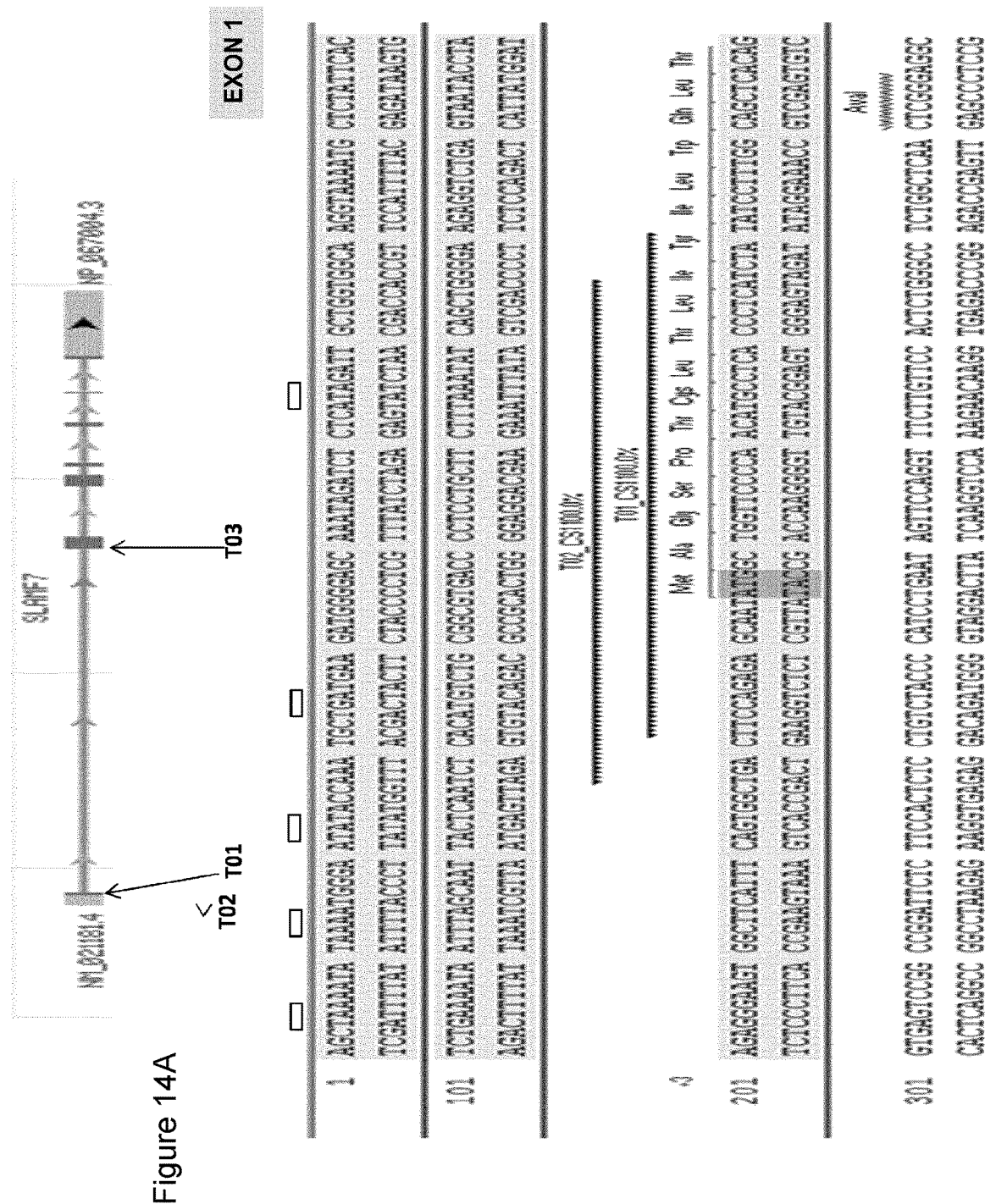

FIG. 12: Timing experiment for the engineering of the CAR CS1+ and KO CS1 T-cells and their subsequent testing;

FIG. 13: Constructs of T01, T02 and T03 with the TAL repeats used for the KO of CS1 gene;

FIG. 14A: Target location for the TALs T01 and T02 within the CS1 (SLAMF7) gene.

Figure 14B:
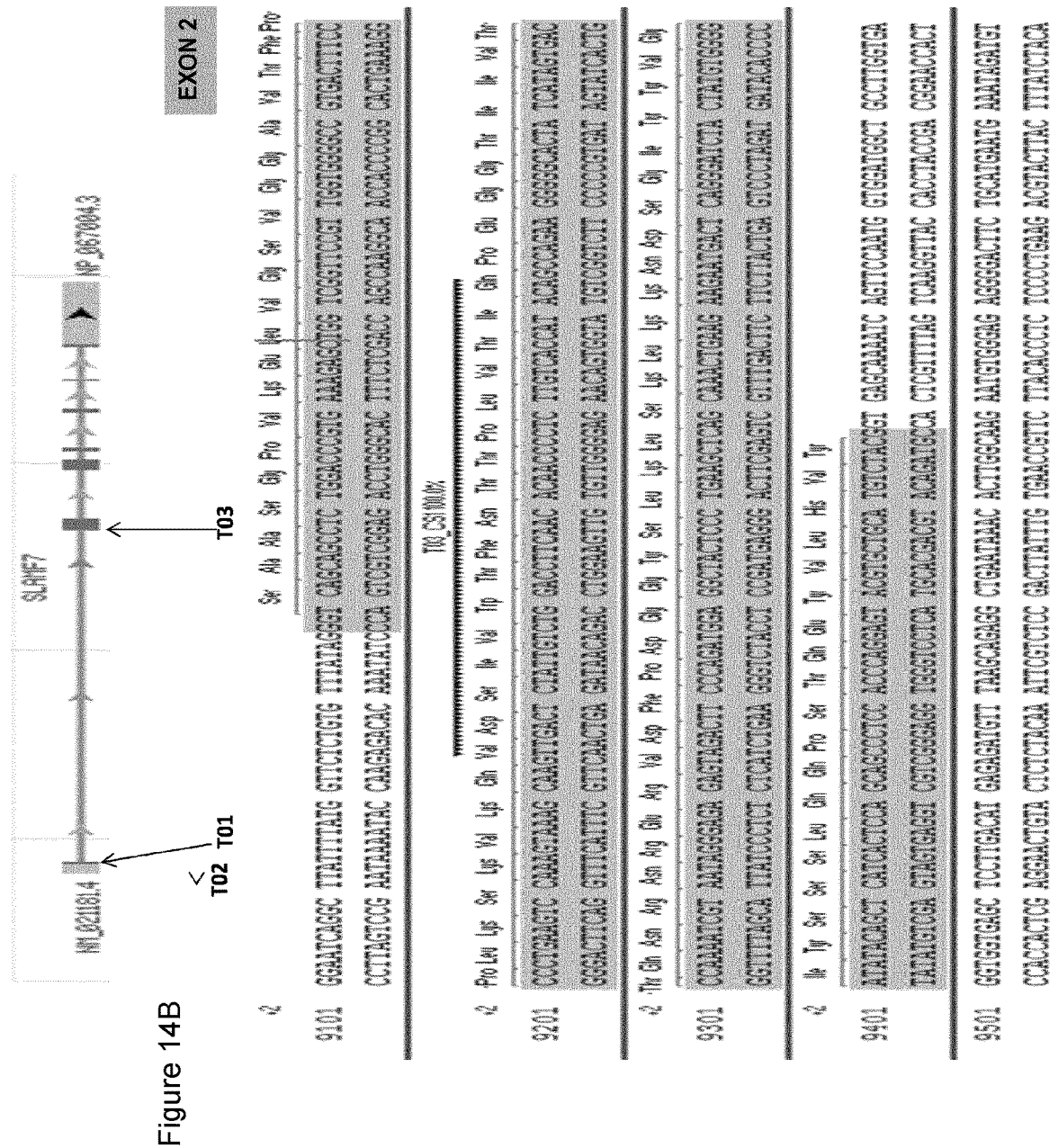

FIG. 14B: Target location for the TAL T03 within the CS1 (SLAMF7) gene.

Figure 15A:
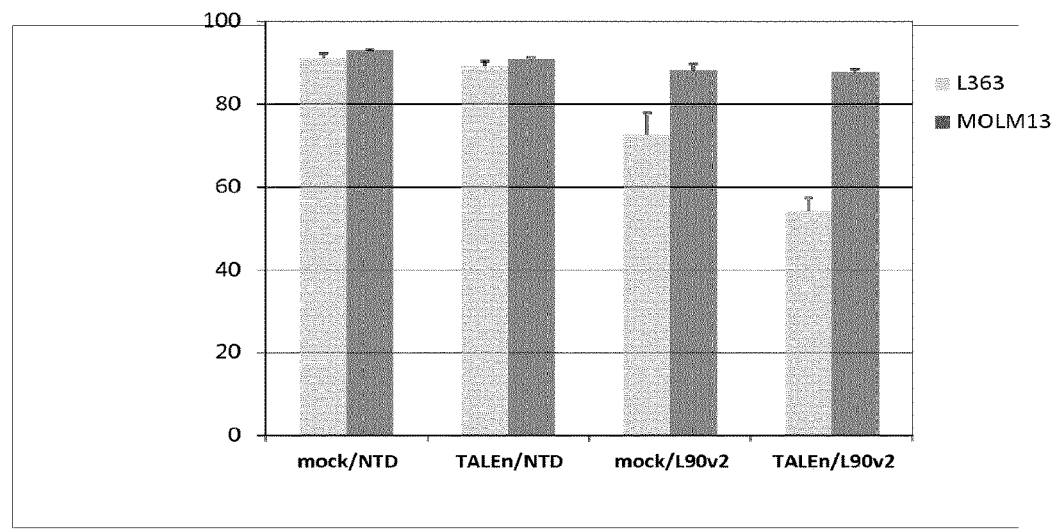

FIG. 15A: Measurement of percentage of target cell viability for TALEn or not TALEn transfected combined with CAR+ or not transduced cells: a reduced cell viability of CS1(+) cells shown when they were co-cultured with CAR+ T-cells, while no impact on CS1(−) cell viability was observed.

Figure 15B:
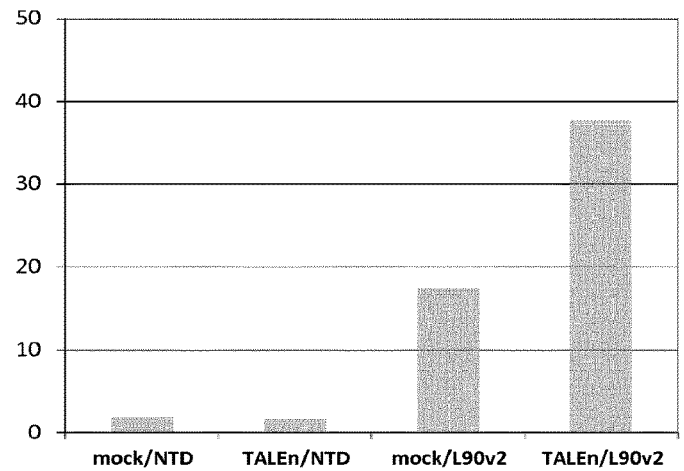

FIG. 15B: Measurement of percentage of specific cell lysis (CS1+) calculated using the flow cytometry data. It is shown that specific cell lysis is 2-times higher when T-cells have been transfected with TALEn targeting the CS1 gene prior to CAR transduction.

FIG. 16: Results of FACS analysis from cytoxic activity experiment, which show that transduction efficiencies are higher in mock transfected cells than in cells that have been transfected with TALEn targeting the CS1 gene (NTD: not transduced).

Figure 17:
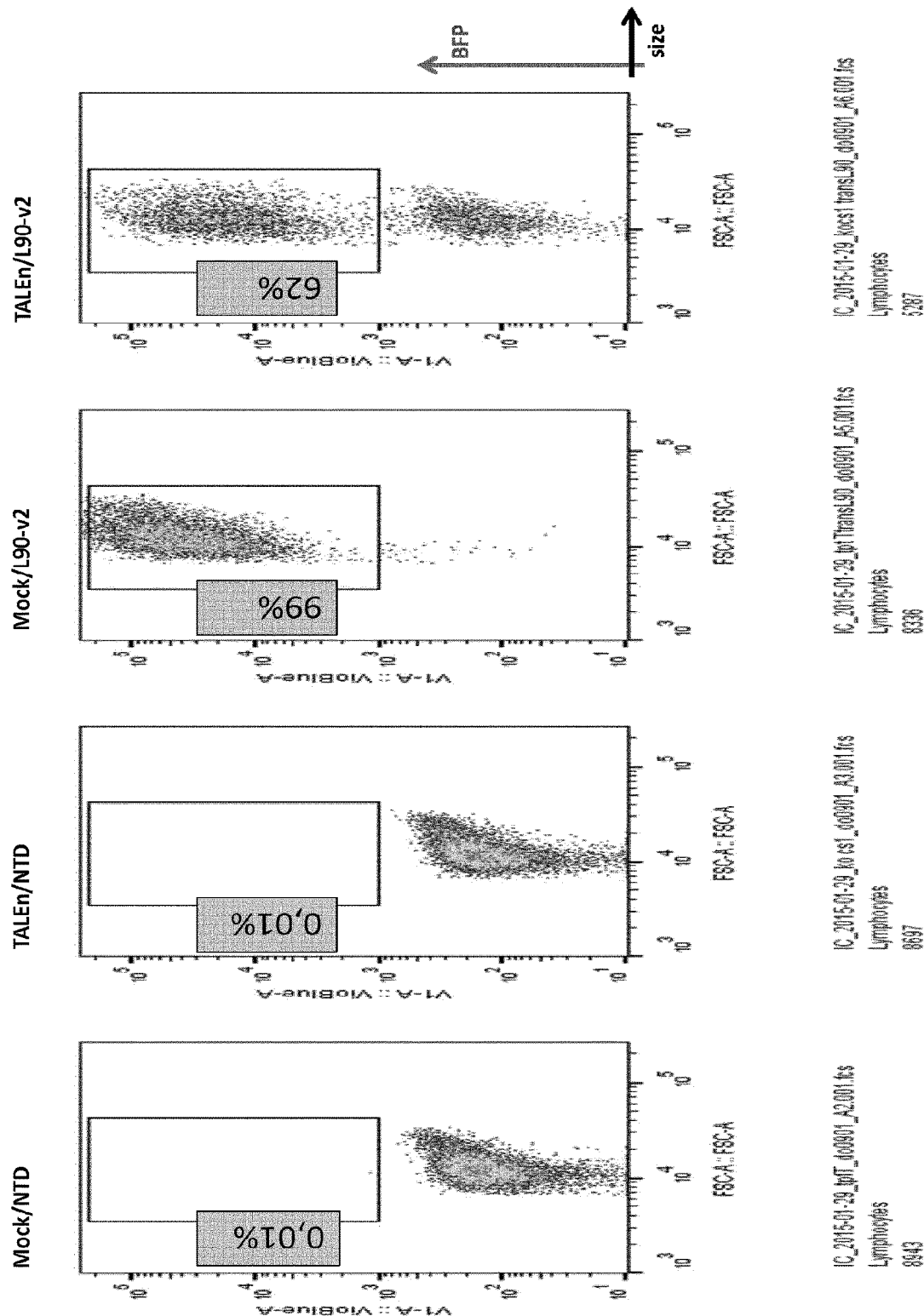
Figure 17:
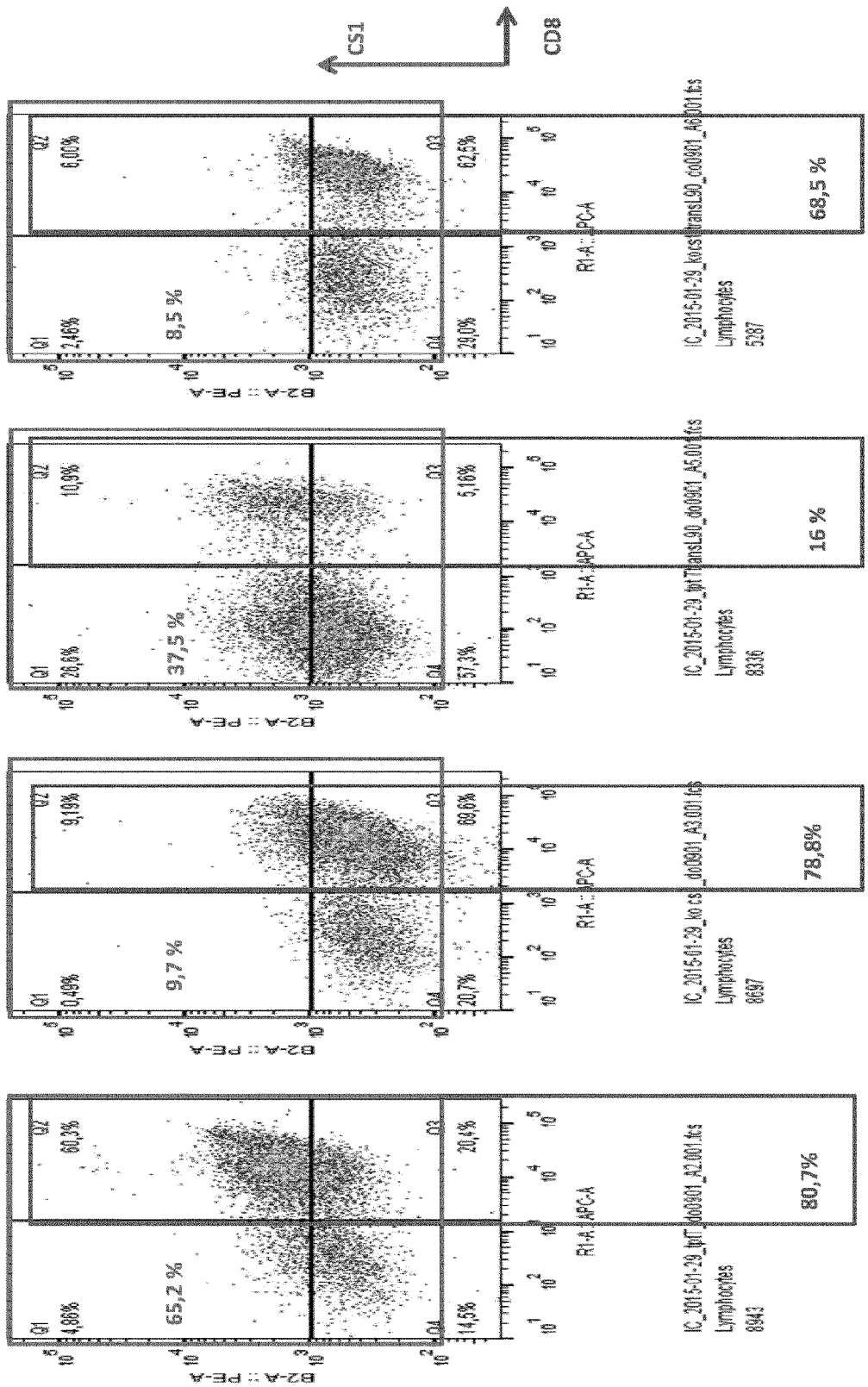

FIG. 17: Results from FACS analysis when the different samples are reactivated with CD3/CD28 beads at D11 after transduction, showing the transduction efficiencies and CD8/CS1 expression levels in each sample. An increase in CS1 levels upon re-activation is observed in mock transfected cells, while a low amount of cells are able to express CS1 in the TALEn transfected populations.

Table 1: Different cytopulse programs used for T-cells electroporation.

Table 2: appropriate target sequences for the guide RNA using Cas9 in T-cells

Table 3: List of genes encoding immune checkpoint proteins

Table 4: Cluster of differentiation (CD) antigen markers found to be expressed on the surface of T-cells, while being characteristic of different types of tumors.

Table 5 to 13: Main surface antigen markers expressed in T-cells, while being over-expressed in solid tumor cells from various types of cancer. The listed antigen markers were identified as explained in Example 1.

Table 5: colon tumor cells;
Table 6: breast tumor cells;
Table 7: digestive track tumor cells;
Table 8: kidney tumor cells;
Table 9: liver tumor cells;
Table 10: lung tumor cells;
Table 11: ovary tumor cells;
Table 12: pancreas tumor cells;
Table 13: prostate tumor cells;

Table 14: Main surface antigen markers expressed in T-cells, while being over-expressed in liquid tumor cells from various types of cancer (ALL, AML, CML, MDS, CLL, CTRL). The listed antigen markers were identified as explained in Example 1.

Table 15: Sequences of the tested CD38 target and TALENs for inactivation of the CD38 antigen;

Table 16: Sequences of two other CD38 targets and the corresponding TALENs for their inactivation;

Table 17: Sequences of VH and VL chains of the scFv anti-CD38 antibodies daratumumab and MOR202 and of specific CDRs for VH and VL chains Table 18: Polypeptide sequence of the 3 different structures of scFv daratumumab-based anti-CD38 CARs and of the individual components used;

Table 19: Sequences of VH and VL chains of the scFv anti-CS1 antibodies;

Table 20: Polypeptide sequence of anti-CS1 CARs based on the V1, V2 and V3 versions in FIG. 11A;

Table 21: Sequences of the CS1 target and TALENs for its inactivation;

Table 22: Sequences of the CD70 target and TALENs for its inactivation;

Table 23: Polynucleotide and nucleic acid sequences of VH and VL chains of the scFv anti-CD70 Ab4, Ab8 and 1F6 antibodies;

Table 24: Polypeptide sequence of anti-CD70 CARs based on the V1, V2 and V3 versions in FIG. 11A

DETAILED DESCRIPTION OF THE INVENTION

Unless specifically defined herein, all technical and scientific terms used have the same meaning as commonly understood by a skilled artisan in the fields of gene therapy, biochemistry, genetics, and molecular biology.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will prevail. Further, the materials, methods, and examples are illustrative only and are not intended to be limiting, unless otherwise specified.

The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, Current Protocols in Molecular Biology (Frederick M. AUSUBEL, 2000, Wiley and son Inc, Library of Congress, USA); Molecular Cloning: A Laboratory Manual, Third Edition, (Sambrook et al, 2001, Cold Spring Harbor, N.Y.: Cold Spring Harbor Laboratory Press); Oligonucleotide Synthesis (M. J. Gait ed., 1984); Mullis et al. U.S. Pat. No. 4,683,195; Nucleic Acid Hybridization (B. D. Harries & S. J. Higgins eds. 1984); Transcription And Translation (B. D. Hames & S. J. Higgins eds. 1984); Culture Of Animal Cells (R. I. Freshney, Alan R. Liss, Inc., 1987); Immobilized Cells And Enzymes (IRL Press, 1986); B. Perbal, A Practical Guide To Molecular Cloning (1984); the series, Methods In ENZYMOLOGY (J. Abelson and M. Simon, eds.-in-chief, Academic Press, Inc., New York), specifically, Vols. 154 and 155 (Wu et al. eds.) and Vol. 185, "Gene Expression Technology" (D. Goeddel, ed.); Gene Transfer Vectors For Mammalian Cells (J. H. Miller and M. P. Calos eds., 1987, Cold Spring Harbor Laboratory); Immunochemical Methods In Cell And Molecular Biology (Mayer and Walker, eds., Academic Press, London, 1987); Handbook Of Experimental Immunology, Volumes I-IV (D. M. Weir and C. C. Blackwell, eds., 1986); and Manipulating the Mouse Embryo, (Cold Spring Harbor Laboratory Press, Cold Spring Harbor, N.Y., 1986).

In a general aspect, the present invention relates to methods for new adoptive immunotherapy strategies in treating diseases linked with the development of pathological cells, such as cancer, infections and auto-immune diseases.

As a main objective of the invention is the possibility to target pathological cells that bear specific antigen markers in common with T-cells. By pathological cell is meant any types of cells present in a patient, which are deemed causing health deterioration.

In general, pathological cells are malignant or infected cells that need to be reduced or eliminated to obtain remission of a patient.

In a first embodiment, the method of the invention concerns a method of preparing appropriate immune cells, preferably T-cells for immunotherapy comprising the step of:
(a) Genetically inactivating or mutating a gene in an immune cell, which is involved in the expression or presentation of an antigen marker, said antigen marker being known to be present both on the surface of said T-cell and the pathological cell;
(b) Expressing into said immune cell a transgene encoding a chimeric antigen receptor directed against said antigen marker present at the surface of said pathological cell.

The immune cells according to the invention are endowed with a chimeric antigen receptor directed to an antigen marker that is commonly expressed by the pathological cells and immune cells, or known to be present on the surface of said T Cells. The expression "known to be present" means that the antigen marker is reported to be found on the surface of the immune cells grown in natural conditions in-vivo, especially in the blood, but not necessarily when they are cultured in-vitro. In any event, the method of the invention results into the absence of the antigen marker on the surface of the immune cell, thereby preventing the chimeric antigen receptor from reacting with the engineered T-cell surface. In this respect, the method may include a further step of purifying the resulting T-cells by excluding the cells presenting said marker antigen on their surface.

As shown in Table 4, this invention relates to an important number of antigen marker candidates reported to be expressed by tumor cells, but also by T-cells. Some of them, like CD38, have been used as specific markers in diagnostic methods for a while, especially with respect to Leukemia pathological cells, but not in therapy. Indeed, although these markers were identified in the art as quite specific markers, they could not be used as targets for immunotherapy because antibodies directed against these markers would have destroyed or interfered with patients' T-cells. The present inventors have established that CS1 and CD70 are also present on the surface of T-cells and that expressing CARs targeting CS1 and CD70 in such T cells leads to their depletion (see example 2).

According to a preferred embodiment of the invention, the gene mutation or inactivation of step a) of the above method is performed using a rare-cutting endonuclease.

By inactivating a gene it is intended that the gene of interest is not expressed in a functional protein form. In particular embodiments, the genetic modification of the method relies on the expression, in provided cells to engineer, of a rare-cutting endonuclease such that same catalyzes cleavage in one targeted gene thereby inactivating said targeted gene. The nucleic acid strand breaks caused by the endonuclease are commonly repaired through the distinct mechanisms of homologous recombination or non-homologous end joining (NHEJ). However, NHEJ is an imperfect repair process that often results in changes to the DNA sequence at the site of the cleavage. Mechanisms involve rejoining of what remains of the two DNA ends through direct re-ligation (Critchlow and Jackson 1998) or via the so-called microhomology-mediated end joining (Betts, Brenchley et al. 2003; Ma, Kim et al. 2003). Repair via non-homologous end joining (NHEJ) often results in small insertions or deletions and can be used for the creation of specific gene knockouts. Said modification may be a substitution, deletion, or addition of at least one nucleotide. Cells in which a cleavage-induced mutagenesis event, i.e. a mutagenesis event consecutive to an NHEJ event, has occurred can be identified and/or selected by well-known method in the art.

The term "rare-cutting endonuclease" refers to a wild type or variant enzyme capable of catalyzing the hydrolysis (cleavage) of bonds between nucleic acids within a DNA or RNA molecule, preferably a DNA molecule. Particularly, said nuclease can be an endonuclease, more preferably a rare-cutting endonuclease which is highly specific, recognizing nucleic acid target sites ranging from 10 to 45 base pairs (bp) in length, usually ranging from 10 to 35 base pairs in length, more usually from 12 to 20 base pairs. The endonuclease according to the present invention recognizes at specific polynucleotide sequences, further referred to as "target sequence" and cleaves nucleic acid inside these target sequences or into sequences adjacent thereto, depending on the molecular structure of said endonuclease. The rare-cutting endonuclease can recognize and generate a single- or double-strand break at specific polynucleotides sequences.

In a particular embodiment, said rare-cutting endonuclease according to the present invention is a RNA-guided endonuclease such as the Cas9/CRISPR complex. RNA guided endonucleases constitute a new generation of genome engineering tool where an endonuclease associates with a RNA molecule. In this system, the RNA molecule nucleotide sequence determines the target specificity and activates the endonuclease (Gasiunas, Barrangou et al. 2012; Jinek, Chylinski et al. 2012; Cong, Ran et al. 2013; Mali, Yang et al. 2013).

Cas 9

Cas9, also named Csn1 (COG3513) is a large protein that participates in both crRNA biogenesis and in the destruction of invading DNA. Cas9 has been described in different bacterial species such as S. thermophiles, Listeria innocua (Gasiunas, Barrangou et al. 2012; Jinek, Chylinski et al. 2012) and S. Pyogenes (Deltcheva, Chylinski et al. 2011). The large Cas9 protein (>1200 amino acids) contains two predicted nuclease domains, namely HNH (McrA-like) nuclease domain that is located in the middle of the protein and a splitted RuvC-like nuclease domain (RNase H fold) (Makarova, Grishin et al. (2006).

By "Cas9" is meant an engineered endonuclease or a homologue of Cas9 which is capable of processing target nucleic acid sequence. In particular embodiment, Cas9 can induce a cleavage in the nucleic acid target sequence which can correspond to either a double-stranded break or a single-stranded break. Cas9 variant can be a Cas9 endonuclease that does not naturally exist in nature and that is obtained by protein engineering or by random mutagenesis. Cas9 variants according to the invention can for example be obtained by mutations i.e. deletions from, or insertions or substitutions of at least one residue in the amino acid sequence of a S. pyogenes Cas9 endonuclease (COG3513). In the frame aspects of the present invention, such Cas9 variants remain functional, i.e. they retain the capacity of processing a target nucleic acid sequence. Cas9 variant can also be homologues of S. pyogenes Cas9 which can comprise deletions from, or insertions or substitutions of, at least one residue within the amino acid sequence of S. pyogenes Cas9. Any combination of deletion, insertion, and substitution may also be made to arrive at the final construct, provided that the final construct possesses the desired activity, in particular the capacity of binding a guide RNA or nucleic acid target sequence.

RuvC/RNaseH motif includes proteins that show wide spectra of nucleolytic functions, acting both on RNA and DNA (RNaseH, RuvC, DNA transposases and retroviral integrases and PIWI domain of Argonaut proteins). In the present invention the RuvC catalytic domain of the Cas9 protein can be characterized by the sequence motif: D-[I/L]-G-X-X-S-X-G-W-A, wherein X represents any one of the natural 20 amino acids and [I/L] represents isoleucine or leucine. In other terms, the present invention relates to Cas9 variant which comprises at least D-[I/L]-G-X-X-S-X-G-W-A sequence, wherein X represents any one of the natural 20 amino acids and [I/L] represents isoleucine or leucine.

HNH motif is characteristic of many nucleases that act on double-stranded DNA including colicins, restriction enzymes and homing endonucleases. The domain HNH (SMART ID: SM00507, SCOP nomenclature: HNH family) is associated with a range of DNA binding proteins, performing a variety of binding and cutting functions. The ones with known function are involved in a range of cellular processes including bacterial toxicity, horning functions in groups I and II introns and inteins, recombination, developmentally controlled DNA rearrangement, phage packaging, and restriction endonuclease activity (Dalgaard, Klar et al. 1997). These proteins are found in viruses, archaebacteria, eubacteria, and eukaryotes. Interestingly, as with the LAGLI-DADG and the GIY-YIG motifs, the HNH motif is often associated with endonuclease domains of self-propagating elements like inteins, Group I, and Group II introns (Dalgaard, Klar et al. 1997). The HNH domain can be characterized by the presence of a conserved Asp/His residue flanked by conserved His (amino-terminal) and His/Asp/Glu (carboxy-terminal) residues at some distance. A substantial number of these proteins can also have a CX2C motif on either side of the central Asp/His residue. Structurally, the HNH motif appears as a central hairpin of twisted β-strands, which are flanked on each side by an α helix (Kleanthous, Kuhlmann et al. 1999). The large HNH domain of Cas9 is represented by SEQ ID NO. 5. In the present invention, the HNH motif can be characterized by the sequence motif: Y-X-X-D-H-X-X-P-X-S-X-X-X-D-X-S, wherein X represents any one of the natural 20 amino acids. The present invention relates to a Cas9 variant which comprises at least Y-X-X-D-H-X-X-P-X-S-X-X-X-D-X-S sequence wherein X represents any one of the natural 20 amino acids.

This invention can be of particular interest to easily do targeted multiplex gene modifications and to create an inducible nuclease system by introduction of the guide RNA to the Cas9 cells. For the purpose of the present invention, the inventors have established that Cas9 protein can be divided into two separate split Cas9 RuvC and HNH domains which can process target nucleic acid sequence together or separately with the guide RNA.

Also the RuvC and HNH domains from different RNA guided endonucleases or Cas homologues may be assembled to improve nuclease efficiency or specificity. The domains from different species can be either split into two proteins or fused to each other to form a variant Cas protein. The Cas9 split system is deemed particularly suitable for an inducible method of genome targeting and to avoid the potential toxic effect of the Cas9 overexpression within the cell. Indeed, a first split Cas9 domain can be introduced into the cell, preferably by stably transforming said cell with a transgene encoding said split domain. Then, the complementary split part of Cas9 can be introduced into the cell, such that the two split parts reassemble into the cell to reconstitute a functional Cas9 protein at the desired time.

The reduction of the size of the split Cas9 compared to wild type Cas9 ease the vectorization and the delivery into the cell, for example, by using cell penetrating peptides. Re-arranging domains from different Cas proteins, allows to modulate the specificity and nuclease activity, for instance, by targeting PAM motifs that are slightly different from S. pyogenes Cas9

Split Cas9 System

The previous characterization of the RuvC and HNH domains has prompted the inventors to engineer Cas9 protein to create split Cas9 protein. Surprisingly, the inventors showed that these two split Cas9 could process together or separately the nucleic acid target. This observation allows developing a new Cas9 system using split Cas9 protein. Each split Cas9 domains can be prepared and used separately. Thus, this split system displays several advantages for vectorization and delivery of the RNA guided endonuclease in T-cells, allowing delivering a shorter and/or inactive protein, and is particularly suitable to induce genome engineering in T-cells at the desired time and thus limiting the potential toxicity of an integrated Cas9 nuclease.

By "Split Cas9" is meant here a reduced or truncated form of a Cas9 protein or Cas9 variant, which comprises either a RuvC or HNH domain, but not both of these domains. Such "Split Cas9" can be used independently with guide RNA or in a complementary fashion, like for instance, one Split Cas9 providing a RuvC domain and another providing the HNH domain. Different split RNA guided endonucleases may be used together having either RuvC and/or NHN domains.

Each Cas9 split domain can be derived from the same or from different Cas9 homologues. Many homologues of Cas9 have been identified in genome databases.

Said Cas9 split domains (RuvC and HNH domains) can be simultaneously or sequentially introduced into the cell such that said split Cas9 domain(s) process the target nucleic acid sequence in the cell. Said Cas9 split domains and guide RNA can be introduced into the cell by using cell penetrating peptides or other transfection methods as described elsewhere.

In another aspect of the invention, only one split Cas9 domain, referred to as compact Cas9 is introduced into said cell. Indeed, surprisingly the inventors showed that the split Cas9 domain comprising the RuvC motif as described above is capable of cleaving a target nucleic acid sequence independently of split domain comprising the HNH motif. Thus, they could establish that the guideRNA does not need the presence of the HNH domain to bind to the target nucleic acid sequence and is sufficiently stable to be bound by the RuvC split domain. In a preferred embodiment, said split Cas9 domain alone is capable of nicking said target nucleic acid sequence.

Each split domain can be fused to at least one active domain in the N-terminal and/or C-terminal end, said active domain can be selected from the group consisting of: nuclease (e.g. endonuclease or exonuclease), polymerase, kinase, phosphatase, methylase, demethylase, acetylase, desacetylase, topoisomerase, integrase, transposase, ligase, helicase, recombinase, transcriptional activator (e.g. VP64, VP16), transcriptional inhibitor (e. g; KRAB), DNA end processing enzyme (e.g. Trex2, Tdt), reporter molecule (e.g. fluorescent proteins, lacZ, luciferase).

HNH domain is responsible for nicking of one strand of the target double-stranded DNA and the RuvC-like RNaseH fold domain is involved in nicking of the other strand (comprising the PAM motif) of the double-stranded nucleic acid target (Jinek, Chylinski et al. 2012). However, in wild-type Cas9, these two domains result in blunt cleavage of the invasive DNA within the same target sequence (proto-spacer) in the immediate vicinity of the PAM (Jinek, Chylinski et al. 2012). Cas 9 can be a nickase and induces a nick event within different target sequences.

As non-limiting example, Cas9 or split Cas9 can comprise mutation(s) in the catalytic residues of either the HNH or RuvC-like domains, to induce a nick event within different target sequences. As non-limiting example, the catalytic residues of the Cas9 protein are those corresponding to amino acids D10, D31, H840, H868, N882 and N891 or aligned positions using CLUSTALW method on homologues of Cas Family members. Any of these residues can be replaced by any other amino acids, preferably by alanine residue. Mutation in the catalytic residues means either substitution by another amino acids, or deletion or addition of amino acids that induce the inactivation of at least one of the catalytic domain of cas9. (cf. In a particular embodiment, Cas9 or split Cas9 may comprise one or several of the above mutations. In another particular embodiment, split Cas9 comprises only one of the two RuvC and HNH catalytic domains. In the present invention, Cas9 from different species, Cas9 homologues, Cas9 engineered and functional variant thereof can be used. The invention envisions the use of any RNA guided endonuclease or split RNA guided endonucleases variants to perform nucleic acid cleavage in a genetic sequence of interest.

Preferably, the Cas9 variants according to the invention have an amino acid sequence sharing at least 70%, preferably at least 80%, more preferably at least 90%, and even more preferably 95% identity with Cas9 of S. *Pyogenes* (COG3513).

Meganucleases

Rare-cutting endonuclease can also be a homing endonuclease, also known under the name of meganuclease. Such homing endonucleases are well-known to the art (Stoddard 2005). Homing endonucleases are highly specific, recognizing DNA target sites ranging from 12 to 45 base pairs (bp) in length, usually ranging from 14 to 40 bp in length. The homing endonuclease according to the invention may for example correspond to a LAGLIDADG endonuclease, to a HNH endonuclease, or to a GIY-YIG endonuclease. Preferred homing endonuclease according to the present invention can be an I-CreI variant. A "variant" endonuclease, i.e. an endonuclease that does not naturally exist in nature and that is obtained by genetic engineering or by random mutagenesis can bind DNA sequences different from that recognized by wild-type endonucleases (see international application WO2006/097854).

Said rare-cutting endonuclease can be a modular DNA binding nuclease. By modular DNA binding nuclease is meant any fusion proteins comprising at least one catalytic domain of an endonuclease and at least one DNA binding domain or protein specifying a nucleic acid target sequence. The DNA binding domain is generally a RNA or DNA-binding domain formed by an independently folded polypeptide or protein domain that contains at least one motif that recognizes double- or single-stranded polynucleotides. Many such polypeptides have been described in the art having the ability to bind specific nucleic acid sequences. Such binding domains often comprise, as non-limiting examples, helix-turn helix domains, leucine zipper domains, winged helix domains, helix-loop-helix domains, HMG-box domains, Immunoglobin domains, B3 domain or engineered zinc finger domain.

Zinc-Finger Nucleases

Initially developed to cleave DNA in vitro, "Zinc Finger Nucleases" (ZFNs) are a fusion between the cleavage domain of the type IIS restriction enzyme, FokI, and a DNA recognition domain containing 3 or more C2H2 zinc finger motifs. The heterodimerization at a particular position in the DNA of two individual ZFNs in precise orientation and spacing leads to a double-strand break (DSB) in the DNA. The use of such chimeric endonucleases have been extensively reported in the art as reviewed by Urnov et al. (Genome editing with engineered zinc finger nucleases (2010) *Nature reviews Genetics* 11:636-646).

Standard ZFNs fuse the cleavage domain to the C-terminus of each zinc finger domain. In order to allow the two cleavage domains to dimerize and cleave DNA, the two individual ZFNs bind opposite strands of DNA with their C-termini a certain distance apart. The most commonly used linker sequences between the zinc finger domain and the cleavage domain requires the 5' edge of each binding site to be separated by 5 to 7 bp.

The most straightforward method to generate new zinc-finger arrays is to combine smaller zinc-finger "modules" of known specificity. The most common modular assembly process involves combining three separate zinc fingers that can each recognize a 3 base pair DNA sequence to generate a 3-finger array that can recognize a 9 base pair target site. Numerous selection methods have been used to generate zinc-finger arrays capable of targeting desired sequences. Initial selection efforts utilized phage display to select proteins that bound a given DNA target from a large pool of partially randomized zinc-finger arrays. More recent efforts have utilized yeast one-hybrid systems, bacterial one-hybrid and two-hybrid systems, and mammalian cells.

TAL-Nucleases

"TALE-nuclease" or "MBBBD-nuclease" refers to engineered proteins resulting from the fusion of a DNA binding domain typically derived from Transcription Activator Like Effector proteins (TALE) or Modular Base-per-Base Binding domain (MBBBD), with a catalytic domain having endonuclease activity. Such catalytic domain usually comes from enzymes, such as for instance I-TevI, ColE7, NucA and Fok-I. TALE-nuclease can be formed under monomeric or dimeric forms depending of the selected catalytic domain (WO2012138927). Such engineered TALE-nucleases are commercially available under the trade name TALEN™ (Cellectis, 8 rue de la Croix Jarry, 75013 Paris, France).

According to a preferred embodiment of the invention, the DNA binding domain is derived from a Transcription Activator like Effector (TALE), wherein sequence specificity is driven by a series of 33-35 amino acids repeats originating from *Xanthomonas* or *Ralstonia* bacterial proteins AvrBs3, PthXo1, AvrHah1, PthA, Tal1c as non-limiting examples.

These repeats differ essentially by two amino acids positions that specify an interaction with a base pair (Boch, Scholze et al. 2009; Moscou and Bogdanove 2009). Each base pair in the DNA target is contacted by a single repeat, with the specificity resulting from the two variant amino acids of the repeat (the so-called repeat variable dipeptide, RVD). TALE binding domains may further comprise an N-terminal translocation domain responsible for the requirement of a first thymine base (T0) of the targeted sequence and a C-terminal domain that containing a nuclear localization signals (NLS). A TALE nucleic acid binding domain generally corresponds to an engineered core TALE scaffold comprising a plurality of TALE repeat sequences, each repeat comprising a RVD specific to each nucleotides base of a TALE recognition site. In the present invention, each TALE repeat sequence of said core scaffold is made of 30 to 42 amino acids, more preferably 33 or 34 wherein two critical amino acids (the so-called repeat variable dipeptide, RVD) located at positions 12 and 13 mediates the recognition of one nucleotide of said TALE binding site sequence; equivalent two critical amino acids can be located at positions other than 12 and 13 specially in TALE repeat sequence taller than 33 or 34 amino acids long. Preferably, RVDs associated with recognition of the different nucleotides are HD for recognizing C, NG for recognizing T, NI for recognizing A, NN for recognizing G or A. In another embodiment, critical amino acids 12 and 13 can be mutated towards other amino acid residues in order to modulate their specificity towards nucleotides A, T, C and G and in particular to enhance this specificity. A TALE nucleic acid binding domain usually comprises between 8 and 30 TALE repeat sequences. More preferably, said core scaffold of the present invention comprises between 8 and 20 TALE repeat sequences; again more preferably 15 TALE repeat sequences. It can also comprise an additional single truncated TALE repeat sequence made of 20 amino acids located at the C-terminus of said set of TALE repeat sequences, i.e. an additional C-terminal half-TALE repeat sequence.

Other engineered DNA binding domains can be used as alternative sequences to form so-called modular base-per-base specific nucleic acid binding domains (MBBBD) as described in WO 2014/018601. Said MBBBD can be engineered, for instance, from newly identified proteins, namely EAV36_BURRH, E5AW43_BURRH, E5AW45_BURRH and E5AW46_BURRH proteins from the recently sequenced genome of the endosymbiont fungi *Burkholderia Rhizoxinica* (Lackner, Moebius et al. 2011). These nucleic acid binding polypeptides comprise modules of about 31 to 33 amino acids that are base specific. These modules display less than 40% sequence identity with *Xanthomonas* TALE common repeats and present more polypeptides sequence variability. The different domains from the above proteins (modules, N and C-terminals) from *Burkholderia* and *Xanthomonas* are useful to engineer new proteins or scaffolds having binding properties to specific nucleic acid sequences and may be combined to form chimeric TALE-MBBBD proteins.

As examples, the present invention encompasses a method for engineered T-cells in order to inactivate the expression of the genes encoding antigen markers such as CD38, CS1 and CD70 by using specific TALE-nucleases.

Particularly suitable for the realization of the invention, TALE-nucleases such as the ones in SEQ ID NO: 2-3; 5-6; 8-9, SEQ ID NO: 64-65; 67-68; 70-71 and SEQ ID NO: 73-74; 76-77; 79-80 for respectively CD38, CS1 and CD70 genes. These specific TALE-nucleases, their sequence target and the protocol used are presented more thoroughly in the following Examples 1-3.

Delivery Methods

The inventors have considered any means known in the art to allow delivery inside cells or subcellular compartments of said cells the polynucleotides expressing the endonucleases, their possible co-effectors (e.g. guide RNA or DNA associated with Cas9 or Argonaute nucleases) as well as the chimeric antigen receptors. These means include viral transduction, electroporation and also liposomal delivery means, polymeric carriers, chemical carriers, lipoplexes, polyplexes, dendrimers, nanoparticles, emulsion, natural endocytosis or phagocytose pathway as non-limiting examples.

As a preferred embodiment of the invention, polynucleotides encoding the endonucleases of the present invention are transfected under mRNA form in order to obtain transient expression and avoid chromosomal integration of foreign DNA, for example by electroporation. The inventors have determined different optimal conditions for mRNA electroporation in T-cell displayed in Table 1. The inventor used the cytoPulse technology which allows, by the use of pulsed electric fields, to transiently permeabilize living cells for delivery of material into the cells (U.S. Pat. No. 6,010,613 and WO 2004/083379). Pulse duration, intensity as well as the interval between pulses can be modified in order to reach the best conditions for high transfection efficiency with minimal mortality. Basically, the first high electric field pulses allow pore formation, while subsequent lower electric field pulses allow to moving the polynucleotide into the cell. In one aspect of the present invention, the inventor describe the steps that led to achievement of >95% transfection efficiency of mRNA in T cells, and the use of the electroporation protocol to transiently express different kind of proteins in T cells. In particular the invention relates to a method of transforming T cell comprising contacting said T cell with RNA and applying to T cell an agile pulse sequence consisting of:

(a) one electrical pulse with a voltage range from 2250 to 3000 V per centimeter, a pulse width of 0.1 ms and a pulse interval of 0.2 to 10 ms between the electrical pulses of step (a) and (b);

(b) one electrical pulse with a voltage range from 2250 to 3000 V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

In particular embodiment, the method of transforming T cell comprising contacting said T cell with RNA and applying to T cell an agile pulse sequence consisting of:

(a) one electrical pulse with a voltage of 2250, 2300, 2350, 2400, 2450, 2500, 2550, 2400, 2450, 2500, 2600, 2700, 2800, 2900 or 3000V per centimeter, a pulse width of 0.1 ms and a pulse interval of 0.2, 0.5, 1, 2, 3, 4, 5, 6, 7, 8, 9 or 10 ms between the electrical pulses of step (a) and (b);

(b) one electrical pulse with a voltage range from 2250, of 2250, 2300, 2350, 2400, 2450, 2500, 2550, 2400, 2450, 2500, 2600, 2700, 2800, 2900 or 3000V with a pulse width of 100 ms and a pulse interval of 100 ms between the electrical pulse of step (b) and the first electrical pulse of step (c); and (c) 4 electrical pulses with a voltage of 325 V with a pulse width of 0.2 ms and a pulse interval of 2 ms between each of 4 electrical pulses.

Any values included in the value range described above are disclosed in the present application. Electroporation medium can be any suitable medium known in the art. Preferably, the electroporation medium has conductivity in a range spanning 0.01 to 1.0 milliSiemens.

neered ex-vivo can be either re-implanted into a patient from where they originate, as part of an autologous treatment, or to be used as part of an allogeneic treatment. In this later case, it is preferable to further engineer the cells to make them non-alloreactive to ensure their proper engraftment. Accordingly, the method of the invention may include additional steps of procuring the T-cells from a donor and to inactivate genes thereof involved in MHC recognition and or being targets of immunosuppressive drugs such as described for instance in WO 2013/176915.

T cell receptors (TCR) are cell surface receptors that participate in the activation of T cells in response to the presentation of antigen. The TCR is generally made from two chains, alpha and beta, which assemble to form a heterodimer and associates with the CD3-transducing subunits to form the T-cell receptor complex present on the cell surface. Each alpha and beta chain of the TCR consists of an immunoglobulin-like N-terminal variable (V) and constant (C) region, a hydrophobic transmembrane domain, and a short cytoplasmic region. As for immunoglobulin molecules, the variable region of the alpha and beta chains are generated by V(D)J recombination, creating a large diversity of antigen specificities within the population of T cells. However, in contrast to immunoglobulins that recognize intact antigen, T cells are activated by processed peptide fragments in association with an MHC molecule, introducing an extra dimension to antigen recognition by T cells, known as MHC restriction. Recognition of MHC disparities between the donor and recipient through the T cell receptor leads to T cell proliferation and the potential development of

TABLE 1

Different cytopulse programs used to determine the minimal voltage required for electroporation in PBMC derived T-cells.

| Cyto-pulse program | Group 1 | | | | Group 2 | | | | Group 3 | | | |
|---|---|---|---|---|---|---|---|---|---|---|---|---|
| | Pulses | V | duration (ms) | Interval (ms) | Pulses | V | duration (ms) | Interval (ms) | Pulses | V | duration (ms) | Interval (ms) |
| 1 | 1 | 600 | 0.1 | 0.2 | 1 | 600 | 0.1 | 100 | 4 | 130 | 0.2 | 2 |
| 2 | 1 | 900 | 0.1 | 0.2 | 1 | 900 | 0.1 | 100 | 4 | 130 | 0.2 | 2 |
| 3 | 1 | 1200 | 0.1 | 0.2 | 1 | 1200 | 0.1 | 100 | 4 | 130 | 0.2 | 2 |
| 4 | 1 | 1200 | 0.1 | 10 | 1 | 900 | 0.1 | 100 | 4 | 130 | 0.2 | 2 |
| 5 | 1 | 900 | 0.1 | 20 | 1 | 600 | 0.1 | 100 | 4 | 130 | 0.2 | 2 |

Viral Transduction

According to the present invention, the use of retroviral vectors and more preferably of lentiviral vectors is particularly suited for expressing the chimeric antigen receptors into the T-cells. Methods for viral transduction are well known in the art (Walther et al. (2000) Viral Vectors for Gene Transfer. Drugs. 60(4:249-271). Integrative viral vectors allow the stable integration of the polynucleotides in the T-cells genome and to expressing the chimeric antigen receptors over a longer period of time.

Non Alloreactive T Cells

Although the method of the invention could be carried out in-vivo as part of a gene therapy, for instance, by using viral vectors targeting T-cells in blood circulation, which would include genetic sequences expressing a specific rare-cutting endonuclease along with other genetic sequences expressing a CAR, the method of the invention is more generally intended to be practiced ex-vivo on cultured T-cells obtainable from patients or donors. The engineered T-cells engi- GVHD. It has been shown that normal surface expression of the TCR depends on the coordinated synthesis and assembly of all seven components of the complex (Ashwell and Klusner 1990). The inactivation of TCRalpha or TCRbeta can result in the elimination of the TCR from the surface of T cells preventing recognition of alloantigen and thus GVHD.

Thus, still according to the invention, engraftment of the T-cells may be improved by inactivating at least one gene encoding a TCR component. TCR is rendered not functional in the cells by inactivating TCR alpha gene and/or TCR beta gene(s).

With respect to the use of Cas9/CRISPR system, the inventors have determined appropriate target sequences within the 3 exons encoding TCR, allowing a significant reduction of toxicity in living cells, while retaining cleavage efficiency. The preferred target sequences are noted in Table 2 (+ for lower ratio of TCR negative cells, ++ for intermediate ratio, +++ for higher ratio).

TABLE 2 appropriate target sequences for the guide RNA using Cas9 in T-cells

| Exon TCR | Position | Strand | Target genomic sequence | SEQ ID | efficiency |
|---|---|---|---|---|---|
| Ex1 | 78 | -1 | GAGAATCAAAATCGGTGAATAGG | 102 | +++ |
| Ex3 | 26 | 1 | TTCAAAACCTGTCAGTGATTGGG | 103 | +++ |
| Ex1 | 153 | 1 | TGTGCTAGACATGAGGTCTATGG | 104 | +++ |
| Ex3 | 74 | -1 | CGTCATGAGCAGATTAAACCCGG | 105 | +++ |
| Ex1 | 4 | -1 | TCAGGGTTCTGGATATCTGTGGG | 106 | +++ |
| Ex1 | 5 | -1 | GTCAGGGTTCTGGATATCTGTGG | 107 | +++ |
| Ex3 | 33 | -1 | TTCGGAACCCAATCACTGACAGG | 108 | +++ |
| Ex3 | 60 | -1 | TAAACCCGGCCACTTTCAGGAGG | 109 | +++ |
| Ex1 | 200 | -1 | AAAGTCAGATTTGTTGCTCCAGG | 110 | ++ |
| Ex1 | 102 | 1 | AACAAATGTGTCACAAAGTAAGG | 111 | ++ |
| Ex1 | 39 | -1 | TGGATTTAGAGTCTCTCAGCTGG | 112 | ++ |
| Ex1 | 59 | -1 | TAGGCAGACAGACTTGTCACTGG | 113 | ++ |
| Ex1 | 22 | -1 | AGCTGGTACACGGCAGGGTCAGG | 114 | ++ |
| Ex1 | 21 | -1 | GCTGGTACACGGCAGGGTCAGGG | 115 | ++ |
| Ex1 | 28 | -1 | TCTCTCAGCTGGTACACGGCAGG | 116 | ++ |
| Ex3 | 25 | 1 | TTTCAAAACCTGTCAGTGATTGG | 117 | ++ |
| Ex3 | 63 | -1 | GATTAAACCCGGCCACTTTCAGG | 118 | ++ |
| Ex2 | 17 | -1 | CTCGACCAGCTTGACATCACAGG | 119 | ++ |
| Ex1 | 32 | -1 | AGAGTCTCTCAGCTGGTACACGG | 120 | ++ |
| Ex1 | 27 | -1 | CTCTCAGCTGGTACACGGCAGGG | 121 | ++ |
| Ex2 | 12 | 1 | AAGTTCCTGTGATGTCAAGCTGG | 122 | ++ |
| Ex3 | 55 | 1 | ATCCTCCTCCTGAAAGTGGCCGG | 123 | ++ |
| Ex3 | 86 | 1 | TGCTCATGACGCTGCGGCTGTGG | 124 | ++ |
| Ex1 | 146 | 1 | ACAAAACTGTGCTAGACATGAGG | 125 | + |
| Ex1 | 86 | -1 | ATTTGTTTGAGAATCAAAATCGG | 126 | + |
| Ex2 | 3 | -1 | CATCACAGGAACTTTCTAAAAGG | 127 | + |
| Ex2 | 34 | 1 | GTCGAGAAAAGCTTTGAAACAGG | 128 | + |
| Ex3 | 51 | -1 | CCACTTTCAGGAGGAGGATTCGG | 129 | + |
| Ex3 | 18 | -1 | CTGACAGGTTTTGAAAGTTTAGG | 130 | + |
| Ex2 | 43 | 1 | AGCTTTGAAACAGGTAAGACAGG | 131 | + |
| Ex1 | 236 | -1 | TGGAATAATGCTGTTGTTGAAGG | 132 | + |
| Ex1 | 182 | 1 | AGAGCAACAGTGCTGTGGCCTGG | 133 | + |
| Ex3 | 103 | 1 | CTGTGGTCCAGCTGAGGTGAGGG | 134 | + |
| Ex3 | 97 | 1 | CTGCGGCTGTGGTCCAGCTGAGG | 135 | + |
| Ex3 | 104 | 1 | TGTGGTCCAGCTGAGGTGAGGGG | 136 | + |
| Ex1 | 267 | 1 | CTTCTTCCCCAGCCCAGGTAAGG | 137 | + |
| Ex1 | 15 | -1 | ACACGGCAGGGTCAGGGTTCTGG | 138 | + |
| Ex1 | 177 | 1 | CTTCAAGAGCAACAGTGCTGTGG | 139 | + |

TABLE 2-continued appropriate target sequences for the guide RNA using Cas9 in T-cells

| Exon TCR | Position | Strand | Target genomic sequence | SEQ ID | efficiency |
|---|---|---|---|---|---|
| Ex1 | 256 | -1 | CTGGGGAAGAAGGTGTCTTCTGG | 140 | + |
| Ex3 | 56 | 1 | TCCTCCTCCTGAAAGTGGCCGGG | 141 | + |
| Ex3 | 80 | 1 | TTAATCTGCTCATGACGCTGCGG | 142 | + |
| Ex3 | 57 | -1 | ACCCGGCCACTTTCAGGAGGAGG | 143 | + |
| Ex1 | 268 | 1 | TTCTTCCCCAGCCCAGGTAAGGG | 144 | + |
| Ex1 | 266 | -1 | CTTACCTGGGCTGGGGAAGAAGG | 145 | + |
| Ex1 | 262 | 1 | GACACCTTCTTCCCCAGCCCAGG | 146 | + |
| Ex3 | 102 | 1 | GCTGTGGTCCAGCTGAGGTGAGG | 147 | + |
| Ex3 | 51 | 1 | CCGAATCCTCCTCCTGAAAGTGG | 148 | + |

MHC antigens are also proteins that played a major role in transplantation reactions. Rejection is mediated by T cells reacting to the histocompatibility antigens on the surface of implanted tissues, and the largest group of these antigens is the major histocompatibility antigens (MHC). These proteins are expressed on the surface of all higher vertebrates and are called HLA antigens (for human leukocyte antigens) in human cells. Like TCR, the MHC proteins serve a vital role in T cell stimulation. Antigen presenting cells (often dendritic cells) display peptides that are the degradation products of foreign proteins on the cell surface on the MHC. In the presence of a co-stimulatory signal, the T cell becomes activated, and will act on a target cell that also displays that same peptide/MHC complex. For example, a stimulated T helper cell will target a macrophage displaying an antigen in conjunction with its MHC, or a cytotoxic T cell (CTL) will act on a virally infected cell displaying foreign viral peptides.

Thus, in order to provide less alloreactive T-cells, the method of the invention can further comprise the step of inactivating or mutating one HLA gene.

The class I HLA gene cluster in humans comprises three major loci, B, C and A, as well as several minor loci. The class II HLA cluster also comprises three major loci, DP, DQ and DR, and both the class I and class II gene clusters are polymorphic, in that there are several different alleles of both the class I and II genes within the population. There are also several accessory proteins that play a role in HLA functioning as well. The TapI and Tap2 subunits are parts of the TAP transporter complex that is essential in loading peptide antigens on to the class I HLA complexes, and the LMP2 and LMP7 proteosome subunits play roles in the proteolytic degradation of antigens into peptides for display on the HLA. Reduction in LMP7 has been shown to reduce the amount of MHC class I at the cell surface, perhaps through a lack of stabilization (Fehling et al. (1999) Science 265:1234-1237). In addition to TAP and LMP, there is the tapasin gene, whose product forms a bridge between the TAP complex and the HLA class I chains and enhances peptide loading. Reduction in tapasin results in cells with impaired MHC class I assembly, reduced cell surface expression of the MHC class I and impaired immune responses (Grandea et al. (2000) *Immunity* 13:213-222 and Garbi et al. (2000) *Nat. Immunol.* 1:234-238). Any of the above genes may be inactivated as part of the present invention as disclosed, for instance in WO 2012/012667.

Method of Engineering Drug-Resistant T-Cells:

To improve cancer therapy and selective engraftment of allogeneic T-cells, drug resistance can be conferred to the engineered T-cells to protect them from the toxic side effects of chemotherapy or immunosuppressive agents. Indeed, the inventors have observed that most patients were treated with chemotherapy and immune depleting agents as a standard of care, prior to receiving T-cell immunotherapy. Also they found that they could take advantage of these treatments to help the selection of the engineered T-cells, either by adding chemotherapy drugs in culture media for expansion of the cells ex-vivo prior to treatment, or by obtaining a selective expansion of the engineered T-cells in-vivo in patients under chemotherapy or immunosuppressive treatments.

Also the drug resistance of T-cells also permits their enrichment in or ex vivo, as T-cells which express the drug resistance gene, will survive and multiply relative to drug sensitive cells. In particular, the present invention relates to a method of engineering allogeneic and drug resistance T-cells resistant for immunotherapy comprising:

(a) Providing a T-cell;

(b) Selecting at least one drug;

(c) Modifying T-cell to confer drug resistance to said T-cell;

(d) Expanding said engineered T-cell in the presence of said drug, and optionally the preceding steps may be combined with the steps of the methods as previously described.

Drug resistance can be conferred to a T-cell by inactivating one or more gene(s) responsible for the cell's sensitivity to the drug (drug sensitizing gene(s)), such as the hypoxanthine-guanine phosphoribosyl transferase (HPRT) gene (Genbank: M26434.1). In particular HPRT can be inactivated in engineered T-cells to confer resistance to a cytostatic metabolite, the 6-thioguanine (6TG) which is converted by HPRT to cytotoxic thioguanine nucleotide and which is currently used to treat patients with cancer, in particular leukemias (Hacke, Treger et al. 2013). Another example if the inactivation of the CD3 normally expressed at the surface of the T-cell can confer resistance to anti-CD3 antibodies such as teplizumab.

Drug resistance can also be conferred to a T-cell by expressing a drug resistance gene. Said drug resistance gene refers to a nucleic acid sequence that encodes "resistance" to an agent, such as a chemotherapeutic agent (e.g. methotrexate). In other words, the expression of the drug resistance gene in a cell permits proliferation of the cells in the presence of the agent to a greater extent than the proliferation of a corresponding cell without the drug resistance gene. A drug resistance gene of the invention can encode resistance to anti-metabolite, methotrexate, vinblastine, cisplatin, alkylating agents, anthracyclines, cytotoxic antibiotics, anti-immunophilins, their analogs or derivatives, and the like.

Variant alleles of several genes such as dihydrofolate reductase (DHFR), inosine monophosphate dehydrogenase 2 (IMPDH2), calcineurin or methylguanine transferase (MGMT) have been identified to confer drug resistance to a cell. Said drug resistance gene can be expressed in the cell either by introducing a transgene encoding said gene into the cell or by integrating said drug resistance gene into the genome of the cell by homologous recombination. Several other drug resistance genes have been identified that can potentially be used to confer drug resistance to targeted cells (Takebe, Zhao et al. 2001; Sugimoto, Tsukahara et al. 2003; Zielske, Reese et al. 2003; Nivens, Felder et al. 2004; Bardenheuer, Lehmberg et al. 2005; Kushman, Kabler et al. 2007).

DHFR is an enzyme involved in regulating the amount of tetrahydrofolate in the cell and is essential to DNA synthesis. Folate analogs such as methotrexate (MTX) inhibit DHFR and are thus used as anti-neoplastic agents in clinic. Different mutant forms of DHFR which have increased resistance to inhibition by anti-folates used in therapy have been described. In a particular embodiment, the drug resistance gene according to the present invention can be a nucleic acid sequence encoding a mutant form of human wild type DHFR (GenBank: AAH71996.1) which comprises at least one mutation conferring resistance to an anti-folate treatment, such as methotrexate. In particular embodiment, mutant form of DHFR comprises at least one mutated amino acid at position G15, L22, F31 or F34, preferably at positions L22 or F31 ((Schweitzer, Dicker et al. 1990); International application WO 94/24277; U.S. Pat. No. 6,642,043).

As used herein, "antifolate agent" or "folate analogs" refers to a molecule directed to interfere with the folate metabolic pathway at some level. Examples of antifolate agents include, e.g., methotrexate (MTX); aminopterin; trimetrexate (Neutrexin™); edatrexate; N10-propargyl-5,8-dideazafolic acid (CB3717); ZD1694 (Tumodex), 5,8-dide-azaisofolic acid (IAHQ); 5,10-dideazatetrahydrofolic acid (DDATHF); 5-deazafolic acid; PT523 (N alpha-(4-amino-4-deoxypteroyl)-N delta-hemiphthaloyl-L-ornithine); 10-ethyl-10-deazaaminopterin (DDATHF, lomatrexol); piritrexim; 10-EDAM; ZD1694; GW1843; Pemetrexate and PDX (10-propargyl-10-deazaaminopterin).

Another example of drug resistance gene can also be a mutant or modified form of ionisine-5'-monophosphate dehydrogenase II (IMPDH2), a rate-limiting enzyme in the de novo synthesis of guanosine nucleotides. The mutant or modified form of IMPDH2 is a IMPDH inhibitor resistance gene. IMPDH inhibitors can be mycophenolic acid (MPA) or its prodrug mycophenolate mofetil (MMF). The mutant IMPDH2 can comprises at least one, preferably two mutations in the MAP binding site of the wild type human IMPDH2 (NP_000875.2) that lead to a significantly increased resistance to IMPDH inhibitor. The mutations are preferably at positions T333 and/or S351 (Yarn, Jensen et al. 2006; Sangiolo, Lesnikova et al. 2007; Jonnalagadda, Brown et al. 2013). In a particular embodiment, the threonine residue at position 333 is replaced with an isoleucine residue and the serine residue at position 351 is replaced with a tyrosine residue.

Another drug resistance gene is the mutant form of calcineurin. Calcineurin (PP2B) is an ubiquitously expressed serine/threonine protein phosphatase that is involved in many biological processes and which is central to T-cell activation. Calcineurin is a heterodimer composed of a catalytic subunit (CnA; three isoforms) and a regulatory subunit (CnB; two isoforms). After engagement of the T-cell receptor, calcineurin dephosphorylates the transcription factor NFAT, allowing it to translocate to the nucleus and active key target gene such as IL2. FK506 in complex with FKBP12, or cyclosporine A (CsA) in complex with CyPA block NFAT access to calcineurin's active site, preventing its dephosphorylation and thereby inhibiting T-cell activation (Brewin, Mancao et al. 2009). The drug resistance gene of the present invention can be a nucleic acid sequence encoding a mutant form of calcineurin resistant to calcineurin inhibitor such as FK506 and/or CsA. In a particular embodiment, said mutant form can comprise at least one mutated amino acid of the wild type calcineurin heterodimer a at positions: V314, Y341, M347, T351, W352, L354, K360, preferably double mutations at positions T351 and L354 or V314 and Y341. Correspondence of amino acid positions described herein is frequently expressed in terms of the positions of the amino acids of the form of wild-type human calcineurin heterodimer (GenBank: ACX34092.1).

In another particular embodiment, said mutant form can comprise at least one mutated amino acid of the wild type calcineurin heterodimer b at positions: V120, N123, L124 or K125, preferably double mutations at positions L124 and K125. Correspondence of amino acid positions described herein is frequently expressed in terms of the positions of the amino acids of the form of wild-type human calcineurin heterodimer b polypeptide (GenBank: ACX34095.1).

Another drug resistance gene is 0(6)-methylguanine methyltransferase (MGMT) encoding human alkyl guanine transferase (hAGT). AGT is a DNA repair protein that confers resistance to the cytotoxic effects of alkylating agents, such as nitrosoureas and temozolomide (TMZ). 6-benzylguanine (6-BG) is an inhibitor of AGT that potentiates nitrosourea toxicity and is co-administered with TMZ to potentiate the cytotoxic effects of this agent. Several mutant forms of MGMT that encode variants of AGT are highly resistant to inactivation by 6-BG, but retain their ability to repair DNA damage (Maze, Kurpad et al. 1999). In a particular embodiment, AGT mutant form can comprise a mutated amino acid of the wild type AGT position P140 (UniProtKB: P16455).

Another drug resistance gene can be multidrug resistance protein 1 (MDR1) gene. This gene encodes a membrane glycoprotein, known as P-glycoprotein (P-GP) involved in the transport of metabolic byproducts across the cell membrane. The P-Gp protein displays broad specificity towards several structurally unrelated chemotherapy agents. Thus, drug resistance can be conferred to cells by the expression of nucleic acid sequence that encodes MDR-1 (NP_000918).

Drug resistance gene can also be cytotoxic antibiotics, such as ble gene or mcrA gene. Ectopic expression of ble gene or mcrA in an immune cell gives a selective advantage when exposed to the chemotherapeutic agent, respectively the bleomycine or the mitomycin C.

The T-cells can also be made resistant to immunosuppressive agents. An immunosuppressive agent is an agent that suppresses immune function by one of several mechanisms of action. In other words, an immunosuppressive agent is a role played by a compound which is exhibited by a capability to diminish the extent and/or voracity of an immune response. As non-limiting example, an immunosuppressive agent can be a calcineurin inhibitor, a target of rapamycin, an interleukin-2 α-chain blocker, an inhibitor of inosine monophosphate dehydrogenase, an inhibitor of dihydrofolic acid reductase, a corticosteroid or an immunosuppressive antimetabolite. Classical cytotoxic immunosuppressants act by inhibiting DNA synthesis. Others may act through activation of T-cells or by inhibiting the activation of helper cells. The method according to the invention allows conferring immunosuppressive resistance to T cells for immunotherapy by inactivating the target of the immunosuppressive agent in T cells. As non-limiting examples, targets for immunosuppressive agent can be a receptor for an immunosuppressive agent such as: CD52, glucocorticoid receptor (GR), a FKBP family gene member and a cyclophilin family gene member.

In immunocompetent hosts, allogeneic cells are normally rapidly rejected by the host immune system. It has been demonstrated that, allogeneic leukocytes present in non-irradiated blood products will persist for no more than 5 to 6 days. Thus, to prevent rejection of allogeneic cells, the host's immune system must be effectively suppressed. Glucocorticoidsteroids are widely used therapeutically for immunosuppression. This class of steroid hormones binds to the glucocorticoid receptor (GR) present in the cytosol of T cells resulting in the translocation into the nucleus and the binding of specific DNA motifs that regulate the expression of a number of genes involved in the immunologic process. Treatment of T cells with glucocorticoid steroids results in reduced levels of cytokine production leading to T cell anergy and interfering in T cell activation. Alemtuzumab, also known as CAMPATH1-H, is a humanized monoclonal antibody targeting CD52, a 12 amino acid glycosylphosphatidyl-inositol- (GPI) linked glycoprotein (Waldmann and Hale, 2005). CD52 is expressed at high levels on T and B lymphocytes and lower levels on monocytes while being absent on granulocytes and bone marrow precursors. Treatment with Alemtuzumab, a humanized monoclonal antibody directed against CD52, has been shown to induce a rapid depletion of circulating lymphocytes and monocytes. It is frequently used in the treatment of T cell lymphomas and in certain cases as part of a conditioning regimen for transplantation. However, in the case of adoptive immunotherapy the use of immunosuppressive drugs will also have a detrimental effect on the introduced therapeutic T cells. Therefore, to effectively use an adoptive immunotherapy approach in these conditions, the introduced cells would need to be resistant to the immunosuppressive treatment.

As a preferred embodiment of the above steps, said gene of step (b), specific for an immunosuppressive treatment, is CD52, and the immunosuppressive treatment of step (d) comprises a humanized antibody targeting CD52 antigen. As another embodiment, said gene of step (b), specific for an immunosuppressive treatment, is a glucocorticoid receptor (GR) and the immunosuppressive treatment of step d) comprises a corticosteroid such as dexamethasone. As another embodiment, said target gene of step (b), specific for an immunosuppressive treatment, is a FKBP family gene member or a variant thereof and the immunosuppressive treatment of step (d) comprises FK506 also known as Tacrolimus or fujimycin. As another embodiment, said FKBP family gene member is FKBP12 or a variant thereof. As another embodiment, said gene of step (b), specific for an immunosuppressive treatment, is a cyclophilin family gene member or a variant thereof and the immunosuppressive treatment of step (d) comprises cyclosporine.

In a particular embodiment of the invention, the genetic modification step of the method relies on the inactivation of two genes selected from the group consisting of CD52 and GR, CD52 and TCR alpha, CDR52 and TCR beta, GR and TCR alpha, GR and TCR beta, TCR alpha and TCR beta. In another embodiment, the genetic modification step of the method relies on the inactivation of more than two genes. The genetic modification is preferably operated ex-vivo using at least two RNA guides targeting the different genes.

By inactivating a gene it is intended that the gene of interest is not expressed in a functional protein form.

Engineering Highly Active T Cells for Immunotherapy

According to the present invention, the T-cells can be selected from the group consisting of inflammatory T-lymphocytes, cytotoxic T-lymphocytes, regulatory T-lymphocytes or helper T-lymphocytes. In another embodiment, said cell can be derived from the group consisting of CD4+ T-lymphocytes and CD8+ T-lymphocytes. They can be extracted from blood or derived from stem cells. The stem cells can be adult stem cells, embryonic stem cells, more particularly non-human stem cells, cord blood stem cells, progenitor cells, bone marrow stem cells, induced pluripotent stem cells, totipotent stem cells or hematopoietic stem cells. Representative human cells are CD34+ cells. Prior to expansion and genetic modification of the cells of the invention, a source of cells can be obtained from a subject through a variety of non-limiting methods. T-cells can be obtained from a number of non-limiting sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available and known to those skilled in the art, may be used. In another embodiment, said cell can be derived from a healthy donor, from a patient diagnosed with cancer or from a patient diagnosed with an infection. In another embodiment, said cell is part of a mixed population of cells which present different phenotypic characteristics. In the scope of the present invention is also encompassed a cell line obtained from a transformed T-cell according to the method previously described.

As a further aspect of the invention, the T-cells according to the invention may be further engineered, preferably genetically engineered, to enhance their activity and/or activation, especially by modulating the expression of proteins involved in overall T-cell regulation, referred to as "immune-checkpoints".

Immune Check Points

It will be understood by those of ordinary skill in the art, that the term "immune checkpoints" means a group of molecules expressed by T cells. These molecules effectively serve as "brakes" to down-modulate or inhibit an immune response. Immune checkpoint molecules include, but are not limited to Programmed Death 1 (PD-1, also known as PDCD1 or CD279, accession number: NM_005018), Cytotoxic T-Lymphocyte Antigen 4 (CTLA-4, also known as CD152, GenBank accession number AF414120.1), LAG3 (also known as CD223, accession number: NM_002286.5), Tim3 (also known as HAVCR2, GenBank accession number: JX049979.1), BTLA (also known as CD272, accession number: NM_181780.3), BY55 (also known as CD160, GenBank accession number: CR541888.1), TIGIT (also known as IVSTM3, accession number: NM_173799), LAIR1 (also known as CD305, GenBank accession number: CR542051.1, {Meyaard, 1997 #122}), SIGLEC10 (GeneBank accession number: AY358337.1), 2B4 (also known as CD244, accession number: NM_001166664.1), PPP2CA, PPP2CB, PTPN6, PTPN22, CD96, CRTAM, SIGLEC7 {Nicoll, 1999 #123}, SIGLEC9 {Zhang, 2000 #124; Ikehara, 2004 #125}, TNFRSF10B, TNFRSF10A, CASP8, CASP10, CASP3, CASP6, CASP7, FADD, FAS, TGFBRII, TGFBRI, SMAD2, SMAD3, SMAD4, SMAD10, SKI, SKIL, TGIF1, IL10RA, IL10RB, HMOX2, IL6R, IL6ST, EIF2AK4, CSK, PAG1, SIT1, FOXP3, PRDM1, BATF {Quigley, 2010 #121}, GUCY1A2, GUCY1A3, GUCY1B2, GUCY1B3 which directly inhibit immune cells. For example, CTLA-4 is a cell-surface protein expressed on certain CD4 and CD8 T cells; when engaged by its ligands (B7-1 and B7-2) on antigen presenting cells, T-cell activation and effector function are inhibited. Thus the present invention relates to a method of engineering T-cells, especially for immunotherapy, comprising genetically modifying T-cells by inactivating at least one protein involved in the immune check-point, in particular PD1 and/or CTLA-4 or any immune-checkpoint proteins referred to in Table 3.

TABLE 3

List of genes encoding immune checkpoint proteins.

| Pathway | | Genes that can be inactivated In the pathway |
|---|---|---|
| Co-inhibitory receptors | CTLA4 (CD152) | CTLA4, PPP2CA, PPP2CB, PTPN6, PTPN22 |
| | PDCD1 (PD-1, CD279) | PDCD1 |
| | CD223 (lag3) | LAG3 |
| | HAVCR2 (tim3) | HAVCR2 |
| | BTLA(cd272) | BTLA |
| | CD160(by55) | CD160 |
| | IgSF family | TIGIT |
| | | CD96 |
| | | CRTAM |
| | LAIR1(cd305) | LAIR1 |
| | SIGLECs | SIGLEC7 |
| | | SIGLEC9 |
| | CD244(2b4) | CD244 |
| Death receptors | TRAIL | TNFRSF10B, TNFRSF10A, CASP8, CASP10, CASP3, CASP6, CASP7 |
| | FAS | FADD, FAS |
| Cytokine signalling | TGF-beta signaling | TGFBRII, TGFBRI, SMAD2, SMAD3, SMAD4, SMAD10, SKI, SKIL, TGIF1 |
| | IL10 signalling | IL10RA, IL10RB, HMOX2 |
| | IL6 signalling | IL6R, IL6ST |
| Arginine/ tryptophan starvation | | EIF2AK4 |
| Prevention of TCR signalling | | CSK, PAG1 |
| | | SIT1 |
| Induced Treg | induced Treg | FOXP3 |
| Transcription factors controlling exhaustion | transcription factors controlling exhaustion | PRDM1 (=blimp1, heterozygotes mice control chronic viral infection better than wt or conditional KO) BATF |
| Hypoxia mediated tolerance | iNOS induced guanylated cyclase | GUCY1A2, GUCY1A3, GUCY1B2, GUCY1B3 |

Engineered T-Cells Expressing Chimeric Antigen Receptors Against Pathological Cells The chimeric antigen receptors introduced into the T-cells according to the invention can adopt different design such as single-chain or multi-chain CARs. These different designs allow various strategies for improving specificity and binding efficiency towards the targeted pathological cells. Some of these strategies are illustrated in the figures of the present application. Single-chain CARs are the most classical version in the art. Multi-chain CAR architectures were developed by the applicant as allowing modulation of the activity of T-cells in terms of specificity and intensity. The multiple subunits can shelter additional co-stimulation domains or keep such domains at a distance, as well as other types of receptors, whereas classical single chain architecture can sometimes be regarded as too much sensitive and less permissive to multispecific interactions.

Single-Chain CAR

Adoptive immunotherapy, which involves the transfer of autologous antigen-specific T cells generated ex vivo, is a promising strategy to treat viral infections and cancer. The T cells used for adoptive immunotherapy can be generated either by expansion of antigen-specific T cells or redirection of T cells through genetic engineering (Park, Rosenberg et al. 2011). Transfer of viral antigen specific T cells is a well-established procedure used for the treatment of transplant associated viral infections and rare viral-related malignancies. Similarly, isolation and transfer of tumor specific T cells has been shown to be successful in treating melanoma.

Novel specificities in T cells have been successfully generated through the genetic transfer of transgenic T cell receptors or chimeric antigen receptors (CARs) (Jena, Dotti et al. 2010). CARs are synthetic receptors consisting of a targeting moiety that is associated with one or more signaling domains in a single fusion molecule. In general, the binding moiety of a CAR consists of an antigen-binding domain of a single-chain antibody (scFv), comprising the light and variable fragments of a monoclonal antibody joined by a flexible linker. Binding moieties based on receptor or ligand domains have also been used successfully. The signaling domains for first generation CARs are derived from the cytoplasmic region of the CD3zeta or the Fc receptor gamma chains. First generation CARs have been shown to successfully redirect T cell cytotoxicity. However, they failed to provide prolonged expansion and anti-tumor activity in vivo. Signaling domains from co-stimulatory molecules including CD28, OX-40 (CD134), and 4-1BB (CD137) have been added alone (second generation) or in combination (third generation) to enhance survival and increase proliferation of CAR modified T cells. CARs have successfully allowed T cells to be redirected against antigens expressed at the surface of tumor cells from various malignancies including lymphomas and solid tumors (Jena, Dotti et al. 2010).

In addition to the CAR targeting the antigen marker, which is common to the pathological cells and the T-cells, such as CD38, it is envisioned to express further CARs directed towards other antigen markers not necessarily expressed by the T-cells, so as to enhancing T-cells specificity.

Examples of chimeric antigen receptor that can be further expressed by the T-cells to create multi-specific cells, are antigen receptors directed against multiple myeloma or lymphoblastic leukemia antigen markers, such as TNFRSF17 (UNIPROT 002223), SLAMF7 (UNIPROT 09N025), GPRC5D (UNIPROT Q9NZD1), FKBP11 (UNIPROT Q9NYL4), KAMP3, ITGA8 (UNIPROT P53708), and FCRL5 (UNIPROT Q68SN8).

As further examples, the antigen of the target can be from any cluster of differentiation molecules (e.g. CD16, CD64, CD78, CD96, CLL1, CD116, CD117, CD71, CD45, CD71, CD123 and CD138), a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EG- FRvIII), CD19, CD20, CD30, CD40, disialoganglioside GD2, ductal-epithelial mucine, gp36, TAG-72, glycosphingolipids, glioma-associated antigen, β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, CD22, insulin growth factor (IGF1)-I, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the A1 domain of tenascin-C (TnC A1) and fibroblast associated protein (fap); a lineage-specific or tissue specific antigen such as CD3, CD4, CD8, CD24, CD25, CD33, CD34, CD133, CD138, CTLA-4, B7-1 (CD80), B7-2 (CD86), GM-CSF, cytokine receptors, endoglin, a major histocompatibility complex (MHC) molecule, BCMA (CD269, TNFRSF 17), or a virus-specific surface antigen such as an HIV-specific antigen (such as HIV gp120); an EBV-specific antigen, a CMV-specific antigen, a HPV-specific antigen, a Lasse Virus-specific antigen, an Influenza Virus-specific antigen as well as any derivate or variant of these surface markers. Antigens are not necessarily surface marker antigens but can be also endogenous small antigens presented by HLA class I at the surface of the cells.

As examples, the present invention encompasses single-chain CARs which target specifically cell surface marker, such as CD38, CS1 and/or CD70 as described in the examples, together with an inactivation of the genes encoding respectively CD38, CS1 and/or CD70 in the cells expressing said CARs.

As a specific example, the VH and VL chains of the scFv anti-CD38 share at least 80%, preferably 90% and more preferably 95% of identity with respectively SEQ ID NO:10 and 12 and SEQ ID NO: 11 and 13.

As a specific example, the antibody or epitope-binding on CD38 antigen, characterized in that said antibody or epitope-binding fragment thereof comprises at least one heavy chain and at least one light chain, wherein said heavy chain comprises three sequential complementarity-determining regions having amino acid sequences represented by SEQ ID NOS: 14-17, and wherein said light chain comprises three sequential complementarity-determining regions having amino acid sequences represented by SEQ ID NOS: 21-23.

As a another specific example, the antibody or epitope-binding on CD38 antigen, characterized in that said antibody or epitope-binding fragment thereof comprises at least one heavy chain and at least one light chain, wherein said heavy chain comprises three sequential complementarity-determining regions having amino acid sequences represented by SEQ ID NOS: 18-20, and wherein said light chain comprises three sequential complementarity-determining regions having amino acid sequences represented by SEQ ID NOS: 24-26.

As another specific example, the VH and VL chains of the scFv anti-CS1 share at least 80%, preferably 90% and more preferably 95% of identity with respectively SEQ ID NO:38-40-42-44-46 and SEQ ID NO: 39-41-42-45-46.

As still another specific example, the VH and VL chains of the scFv anti-CD70 share at least 80%, preferably 90% and more preferably 95% of identity at the polynucleotide or nucleic acid level with respectively SEQ ID NO:81-82; 85-86; 89-91 and SEQ ID NO: 83-84; 87-88; 91-92.

In an embodiment, the invention encompasses a polynucleotide encoding a single CAR anti-CD38 which shares at least 80%, preferably 90% and more preferably 95% of identity with SEQ ID NO: 35-37. In another embodiment, the invention encompassed a polynucleotide encoding a single CAR anti-CS1 which shares at least 80%, preferably 90% and more preferably 95% of identity with SEQ ID NO: 48-62.

In still another embodiment, the invention encompasses a polynucleotide encoding a single CAR anti-CD70 which shares at least 80%, preferably 90% and more preferably 95% of identity with SEQ ID NO: 93-101.

The present invention is more particularly drawn to immune cells that are endowed with a CAR presenting some identity with those described in the present application and that would bear rare-cutting endonuclease induced mutations in a gene encoding the cell marker targeted by said CAR (i.e. the CAR displays affinity with the product of said inactivated gene). By identity is meant at least 70%, preferably 80%, more preferably 90% and even more preferably 95% polynucleotide or polypeptide identity as determined by the software such as FASTA, or BLAST which are available as a part of the GCG sequence analysis package (University of Wisconsin, Madison, Wis.). BLASTP "Identities" shows the number and fraction of total residues in the high scoring sequence pairs which are identical. Amino acid sequences having these degrees of identity or similarity or any intermediate degree of identity of similarity to the amino acid sequences disclosed herein are contemplated and encompassed by this disclosure. The same applies with respect to polynucleotide sequences using BLASTN.

Multi-Subunit CAR

Chimeric antigen receptors from the prior art introduced in T-cells have been formed of single chain polypeptides that necessitate serial appending of signaling domains. However, by moving signaling domains from their natural juxtamembrane position may interfere with their function. To overcome this drawback, the applicant recently designed a multi-chain CAR derived from FcεRI to allow normal juxtamembrane position of all relevant signaling domains. In this new architecture, the high affinity IgE binding domain of FcεRI alpha chain is replaced by an extracellular ligand-binding domain such as scFv to redirect T-cell specificity against cell targets and the N and/or C-termini tails of FcεRI beta chain are used to place costimulatory signals in normal juxtamembrane positions.

Accordingly, the CAR expressed by the engineered T-cell according to the invention can be a multi-chain chimeric antigen receptor (CAR) particularly adapted to the production and expansion of engineered T-cells of the present invention. Such multi-chain CARs comprise at least two of the following components:
a) one polypeptide comprising the transmembrembrane domain of FcεRI alpha chain and an extracellular ligand-binding domain,
b) one polypeptide comprising a part of N- and C-terminal cytoplasmic tail and the transmembrane domain of FcεRI beta chain and/or
c) at least two polypeptides comprising each a part of intracytoplasmic tail and the transmembrane domain of FcεRI gamma chain, whereby different polypeptides multimerize together spontaneously to form dimeric, trimeric or tetrameric CAR.

According to such architectures, ligands binding domains and signaling domains are born on separate polypeptides.

The different polypeptides are anchored into the membrane in a close proximity allowing interactions with each other. In such architectures, the signaling and co-stimulatory domains can be in juxtamembrane positions (i.e. adjacent to the cell membrane on the internal side of it), which is deemed to allow improved function of co-stimulatory domains. The multi-subunit architecture also offers more flexibility and possibilities of designing CARs with more control on T-cell activation. For instance, it is possible to include several extracellular antigen recognition domains having different specificity to obtain a multi-specific CAR architecture. It is also possible to control the relative ratio between the different subunits into the multi-chain CAR. This type of architecture has been recently described by the applicant in PCT/US2013/058005 (WO2014/039523).

The assembly of the different chains as part of a single multi-chain CAR is made possible, for instance, by using the different alpha, beta and gamma chains of the high affinity receptor for IgE (FcεRI) (Metzger, Alcaraz et al. 1986) to which are fused the signaling and co-stimulatory domains. The gamma chain comprises a transmembrane region and cytoplasmic tail containing one immunoreceptor tyrosine-based activation motif (ITAM) (Cam bier 1995).

The multi-chain CAR can comprise several extracellular ligand-binding domains, to simultaneously bind different elements in target thereby augmenting immune cell activation and function. In one embodiment, the extracellular ligand-binding domains can be placed in tandem on the same transmembrane polypeptide, and optionally can be separated by a linker. In another embodiment, said different extracellular ligand-binding domains can be placed on different transmembrane polypeptides composing the multi-chain CAR. In another embodiment, the present invention relates to a population of multi-chain CARs comprising each one different extracellular ligand binding domains. In a particular, the present invention relates to a method of engineering immune cells comprising providing an immune cell and expressing at the surface of said cell a population of multi-chain CAR each one comprising different extracellular ligand binding domains. In another particular embodiment, the present invention relates to a method of engineering an immune cell comprising providing an immune cell and introducing into said cell polynucleotides encoding polypeptides composing a population of multi-chain CAR each one comprising different extracellular ligand binding domains. In a particular embodiment the method of engineering an immune cell comprises expressing at the surface of the cell at least a part of FcεRI beta and/or gamma chain fused to a signal-transducing domain and several part of FcεRI alpha chains fused to different extracellular ligand binding domains. In a more particular embodiment, said method comprises introducing into said cell at least one polynucleotide which encodes a part of FcεRI beta and/or gamma chain fused to a signal-transducing domain and several FcεRI alpha chains fused to different extracellular ligand binding domains. By population of multi-chain CARs, it is meant at least two, three, four, five, six or more multi-chain CARs each one comprising different extracellular ligand binding domains. The different extracellular ligand binding domains according to the present invention can preferably simultaneously bind different elements in target thereby augmenting immune cell activation and function.

The present invention also relates to an isolated immune cell which comprises a population of multi-chain CARs each one comprising different extracellular ligand binding domains.

The signal transducing domain or intracellular signaling domain of the multi-chain CAR of the invention is responsible for intracellular signaling following the binding of extracellular ligand binding domain to the target resulting in the activation of the immune cell and immune response. In other words, the signal transducing domain is responsible for the activation of at least one of the normal effector functions of the immune cell in which the multi-chain CAR is expressed. For example, the effector function of a T cell can be a cytolytic activity or helper activity including the secretion of cytokines.

In the present application, the term "signal transducing domain" refers to the portion of a protein which transduces the effector signal function signal and directs the cell to perform a specialized function.

Preferred examples of signal transducing domain for use in single or multi-chain CAR can be the cytoplasmic sequences of the Fc receptor or T cell receptor and co-receptors that act in concert to initiate signal transduction following antigen receptor engagement, as well as any derivate or variant of these sequences and any synthetic sequence that as the same functional capability. Signal transduction domain comprises two distinct classes of cytoplasmic signaling sequence, those that initiate antigen-dependent primary activation, and those that act in an antigen-independent manner to provide a secondary or co-stimulatory signal. Primary cytoplasmic signaling sequence can comprise signaling motifs which are known as immunoreceptor tyrosine-based activation motifs of ITAMs. ITAMs are well defined signaling motifs found in the intracytoplasmic tail of a variety of receptors that serve as binding sites for syk/zap70 class tyrosine kinases. Examples of ITAM used in the invention can include as non-limiting examples those derived from TCRzeta, FcRgamma, FcRbeta, FcRepsilon, CD3gamma, CD3delta, CD3epsilon, CD5, CD22, CD79a, CD79b and CD66d. In a preferred embodiment, the signaling transducing domain of the multi-chain CAR can comprise the CD3zeta signaling domain, or the intracytoplasmic domain of the FcεRI beta or gamma chains.

In particular embodiment the signal transduction domain of the multi-chain CAR of the present invention comprises a co-stimulatory signal molecule. A co-stimulatory molecule is a cell surface molecule other than an antigen receptor or their ligands that is required for an efficient immune response.

Ligand binding-domains can be any antigen receptor previously used, and referred to, with respect to single-chain CAR referred to in the literature, in particular scFv from monoclonal antibodies. Bispecific or multi-specific CARs as described in WO 2014/4011988 are incorporated by reference.

Similarly as described before with respect to single-chain CARs, the present invention encompasses immune cells endowed with multi-chain CARs which target specifically a cell surface marker such as CD38, CS1 or CD70. According to a preferred embodiment of the invention the CARs described above are expressed in immune cells, whereas inactivation of the endogenous genes encoding said surface marker(s) is induced by expression of a rare-cutting endonuclease.

Activation and Expansion of T Cells

The method according to the invention generally includes a further step of activating and/or expanding the T-cells. This can be done prior to or after genetic modification of the T cells, using the methods as described, for example, in U.S. Pat. Nos. 6,352,694; 6,534,055; 6,905,680; 6,692,964;

5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005. According to these methods, the T cells of the invention can be expanded by contact with a surface having attached thereto an agent that stimulates a CD3 TCR complex associated signal and a ligand that stimulates a co-stimulatory molecule on the surface of the T cells.

In particular, T cell populations may be stimulated in vitro such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4+ T cells or CD8+ T cells, an anti-CD3 antibody and an anti-CD28 antibody. For example, the agents providing each signal may be in solution or coupled to a surface. As those of ordinary skill in the art can readily appreciate, the ratio of particles to cells may depend on particle size relative to the target cell. In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. Cell surface proteins may be ligated by allowing paramagnetic beads to which anti-CD3 and anti-CD28 are attached (3×28 beads) to contact the T cells. In one embodiment the cells (for example, 4 to 10 T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. The mixture may be cultured for several hours (about 3 hours) to about 14 days or any hourly integer value in between. In another embodiment, the mixture may be cultured for 21 days. Conditions appropriate for T cell culture include an appropriate media (e.g., Minimal Essential Media or RPMI Media 1640 or, X-vivo 5, (Lonza)) that may contain factors necessary for proliferation and viability, including serum (e.g., fetal bovine or human serum), interleukin-2 (IL-2), insulin, IFN-g, 1L-4, 1L-7, GM-CSF, -10, -2, 1L-15, TGFp, and TNF- or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, A1M-V, DMEM, MEM, a-MEM, F-12, X-Vivo 1, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% CO2). T-cells that have been exposed to varied stimulation times may exhibit different characteristics.

In another particular embodiment, said cells can be expanded by co-culturing with tissue or cells. Said cells can also be expanded in vivo, for example in the subject's blood after administrating said cell into the subject.

Therapeutic Applications

The T-cells obtainable by the different methods described above are intended to be used as a medicament for treating, among others, cancer, infections or immune diseases in a patient in need thereof.

Said treatment can be ameliorating, curative or prophylactic. It may be either part of an autologous immunotherapy or part of an allogenic immunotherapy treatment. By autologous, it is meant that cells, cell line or population of cells used for treating patients are originating from said patient or from a Human Leucocyte Antigen (HLA) compatible donor. By allogeneic is meant that the cells or population of cells used for treating patients are not originating from said patient but from a donor.

The T-cells engineered according to one of the previous methods may be pooled, frozen, and administrated to one or several patients. When they are made non-alloreactive, they are available as an "off the shelf" therapeutic product, which means that they can be universally infused to patients in need thereof.

Said treatments are primarily intended to patients diagnosed with cancer, viral infection, autoimmune disorders or Graft versus Host Disease (GvHD). Cancers are preferably leukemias and lymphomas, which have liquid tumors, but may also concern solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

The present invention provides in Tables 4 to 14 with examples of antigen markers, which can be targeted with the engineered-cells of the invention for treating different types of cancer. Preferred antigen markers used for the immunotherapy of the present invention are more particularly CD38, CD319 (CS1) and CD70.

The present T-cells, when armed with specific CARs directed against patient's own immune cells, especially T-cells, allow the inhibition or regulation of said cells, which is a key step for treating auto-immune disease, such as rheumatoid polyarthritis, systemic lupus erythematosus, Sjogren's syndrome, scleroderma, fibromyalgia, myositis, ankylosing spondylitis, insulin dependent diabetes of type I, Hashimoto's thyroiditis, Addison's disease, Crohn's disease, Celiac's disease, amyotrophic lateral sclerosis (ALS) and multiple sclerosis (MS). Accordingly the present invention encompass a method for treating an immune disease by directing engineered T-cells as previously described against patient's own T-cells.

The above treatments can take place in combination with one or more therapies selected from the group of antibodies therapy, chemotherapy, cytokines therapy, dendritic cell therapy, gene therapy, hormone therapy, laser light therapy and radiation therapy.

The engineered T-cells as previously described, when they are made resistant to chemotherapy drugs and immunosuppressive drugs that are used as standards of care, especially methotrexate and the combination of fludarabine and Cyclophosphamide, are particularly suited for treating various forms of cancer. Indeed, the present invention preferably relies on cells or population of cells, In this aspect, it is expected that the chemotherapy and/or immunosuppressive treatment should help the selection and expansion of the engineered T-cells in-vivo.

In certain embodiments of the present invention, cells are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or nataliziimab treatment for MS patients or efaliztimab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAMPATH, anti-CD3 antibodies or other antibody therapies, cytoxin, fludaribine, cyclosporin, FK506, rapamycin, mycoplienolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1 1; Henderson et al., Immun. 73:316-321, 1991; Bierer et al., Citrr. Opin. mm n. 5:763-773, 93). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH, In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery. Said modified cells obtained by any one of the methods described here can be used in a particular aspect of the invention for treating patients in need thereof against Host versus Graft (HvG) rejection and Graft versus Host Disease (GvHD); therefore in the scope of the present invention is a method of treating patients in need thereof against Host versus Graft (HvG) rejection and Graft versus Host Disease (GvHD) comprising treating said patient by administering to said patient an effective amount of modified cells comprising inactivated TCR alpha and/or TCR beta genes.

According to one embodiment, said T cells of the invention can undergo robust in vivo T cell expansion upon administration to a patient, and can persist in the body fluids for an extended amount of time, preferably for a week, more preferably for 2 weeks, even more preferably for at least one month. Although the T-cells according to the invention are expected to persist during these periods, their life span into the patient's body are intended not to exceed a year, preferably 6 months, more preferably 2 months, and even more preferably one month.

The administration of the cells or population of cells according to the present invention may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous or intralymphatic injection, or intraperitoneally. In one embodiment, the cell compositions of the present invention are preferably administered by intravenous injection.

The administration of the cells or population of cells can consist of the administration of $10^4$-$10^9$ cells per kg body weight, preferably $10^5$ to $10^6$ cells/kg body weight including all integer values of cell numbers within those ranges. The cells or population of cells can be administrated in one or more doses. In another embodiment, said effective amount of cells are administrated as a single dose. In another embodiment, said effective amount of cells are administrated as more than one dose over a period time. Timing of administration is within the judgment of managing physician and depends on the clinical condition of the patient. The cells or population of cells may be obtained from any source, such as a blood bank or a donor. While individual needs vary, determination of optimal ranges of effective amounts of a given cell type for a particular disease or conditions within the skill of the art. An effective amount means an amount which provides a therapeutic or prophylactic benefit. The dosage administrated will be dependent upon the age, health and weight of the recipient, kind of concurrent treatment, if any, frequency of treatment and the nature of the effect desired.

In another embodiment, said effective amount of cells or composition comprising those cells are administrated parenterally. Said administration can be an intravenous administration. Said administration can be directly done by injection within a tumor.

Identification of Surface Antigen Marker Expressed on the Surface of T-Cells, while being Overexpressed in Solid Tumors Involved into Different Types of Cancer (Tables 5 to 13)

We used BioGPS microarray data from a panel of normal tissues (Human U133A/GNF1H Gene Atlas) cancer microarray data that also can be downloaded from BioGPS (Human Primary Tumors (U95)) uniprot data that contains the subcellular localization.

We drew the distribution of values coming from normal tissues and determined a threshold value of 5 for the relative expression.

We browsed all the genes assayed with microarrays (44.000 probes representing about 13 000 genes) and checked their localization in the membrane (protein not referred to as being a membrane protein were discarded). Expression in CD8+ T-cells was checked from the BioGPS database. The genes were listed according to the type of cancer where the corresponding expression was the highest (Tables 5 to 13).

Identification of Surface Antigen Marker Expressed on the Surface of T-Cells, while being Overexpressed in Different Liquid Blood Tumors (Table 14)

For that study, no RNA-seq data were available and thus we used microarray data that were obtained from a large study from the MILE consortium (Microarray Innovations in Leukemia), involving 11 laboratories (http://www.ngr-l.org.uk/wessex/downloads/tm08/TM08-S4-1_KenMill-s.pdf—Haferlach et al. 2010, http://www.ncbi.nlm.nih.gov/pubmed/20406941). This raw data include results for ALL (acute lymphoblastic leukemia), AML (acute myelogenous leukemia), CLL (chronic lymphoblastic leukemia) and CML (chronic myelogenous leukemia) and MDS (myelodysplastic syndrome). We also used uniprot data for subcellular localization as usual.

We first drew the overall distribution of values from all genes on all studied tissues. Then, to have an idea of the level necessary for expression, we took a list of genes which are expressed in some liquid tumors and for which therapeutic antibodies are available (CD52, CD 20, CD33, CD19, CD25, CD44, CD47, CD96, CD116, CD117, CD135, TIM-3). For each gene, we looked at the value obtained in the tumor in which it is expressed. Then, we computed the average for each tumor and gene pair for which the gene seems to give a cell membrane protein (cell membrane localization+description of at least one transmembrane domain in the protein). We discarded genes for which the expression in all the tissues was below this threshold of 0.15. We listed and ranked in Table 14, those genes which relative expression in T-cells was above 0.2. Thus, Table 4 provides putative antigen marker candidates for targeting liquid tumor cells as per the invention, in particular for treating ALL, AML, CLL, CML and MDS.

Example of Steps to Engineer T-Cells According to the Invention for Immunotherapy For a better understanding of the invention, it is provided below an example of the steps to follow to produce T-cells directed against leukemia CD38 positive cells:

1. Providing T-cells from a cell culture or from a blood sample from one individual patient or from blood bank and activating said T cells using anti-CD3/C28 activator beads (Dynabeads®). The beads provide both the primary and co-stimulatory signals that are required for activation and expansion of T cells.
2. Transducing said cells with a retroviral vector comprising a transgene encoding a Chimeric antigen receptor consisting of the fusion of CD3zeta activation domain, 4-1BB co-stimulation domain, a transmembrane domain and a hinge from CD28 fused to a sequence encoding the variable chain of an anti-CD38 antibody. For security improvement of the transformed T-cell, a suicide gene sensitive to rituximab may further be introduced as described in WO 2013/153391 into the lentiviral vector separated by T2A splitting sequences.
3. (Optionally) Engineering non alloreactive and/or resistant T cells:
   a) It is possible to Inactivate TCR alpha in said cells to eliminate the TCR from the surface of the cell and prevent recognition of host tissue as foreign by TCR of allogenic and thus to avoid GvHD by following the protocols set forth in WO 2013/176915.
   b) It is also possible to inactive one gene encoding target for an immunosuppressive agent or a chemotherapy drug to render said cells resistant to immunosuppressive or chemotherapy treatment to prevent graft rejection without affecting transplanted T cells. In this example, target of immunosuppressive agents is CD52 and immunosuppressive agent is a humanized monoclonal anti-CD52 antibody (ex: Alemtuzumab) as described in WO 2013/176915.
4. Gene Inactivation is performed by electoporating T-cells with mRNA encoding specific TAL-endonuclease (TALEN™—Cellectis, 8 rue de la Croix Jarry, France). Inactivated T cells are sorted using magnetic beads. For example, T cells still expressing the targeted gene (e.g. CD38, CD70 and CD70) can be removed by fixation on a solid surface, and inactivated cells are not exposed of the stress of being passed through a column. This gentle method increases the concentration of properly engineered T-cells.
5. Expansion in vitro of engineered T-cells prior to administration to a patient or in vivo following administration to a patient through stimulation of CD3 complex. Before administration step, patients can be subjected to an immunosuppressive treatment such as CAMPATH1-H, a humanized monoclonal anti-CD52 antibody.
6. Optionally exposed said cells with bispecific antibodies ex vivo prior to administration to a patient or in vivo following administration to a patient to bring the engineered cells into proximity to a target antigen.

Functional Analysis of the Engineered T-Cells Electroporated with a Monocistronic mRNA Encoding for an Anti-CD38 Single Chain Chimeric Antigen Receptor (CAR CD38):

To verify that genome engineering did not affect the ability of the engineered T-cells to present anti-tumor activity, especially when provided with a chimeric antigen receptor (CAR CD38), The engineered T-cells were incubated for 4 hours with Daudi cells expressing CD38 on their surface. The cell surface upregulation of CD107a, a marker of cytotoxic granule release by T lymphocytes (called degranulation) was measured by flow cytometry analysis (Betts, Brenchley et al. 2003).

24 hours post electroporation, cells were stained with a fixable viability dye eFluor-780 and a PE-conjugated goat anti mouse IgG F(ab')2 fragment specific to assess the cell surface expression of the CAR on the live cells. The vast majority of the live T-cells genetically disrupted for CD38, express the CAR on their surface. T cells were co-cultured with Daudi (CD38$^+$) cells for 6 hours and analyzed by flow cytometry to detect the expression of the degranulation marker CD107a at their surface (Betts, Brenchley et al. 2003).

The results showed that CD38 disrupted T-cells kept the same ability to degranulate in response to PMA/ionomycin (positive control) or CD38+ Daudi cells. CD107 upregulation is dependent on the presence of a CD38+. These data suggest that the genome engineering of the present T-cells had no negative impact on the ability of T cells to mount a controlled anti-tumor response.

TABLE 4

Cluster of differentiation (CD) antigen markers of various cancers found to be expressed on the surface of T-cells

| Antigen | Other Names | Structure | main Distribution | Function |
| --- | --- | --- | --- | --- |
| CD1a | T6 | IgSF, MHC-like | cortical thymocytes, Langerhans cells, DC | antigen presentation, with beta2m |
| CD1b | T6 | IgSF, MHC-like | cortical thymocytes, Langerhans cells, DC | antigen presentation, with beta2m |
| CD1c | T6 | IgSF, MHC-like | cortical thymocytes, Langerhans cells, DC, B subset | antigen presentation, with beta2m |
| CD1d | | IgSF, MHC-like | intestinal epith, B subset, monolow, DC | antigen presentation, with beta2m |
| CD3 gamma, CD3 delta | T3 | IgSF | T, thymocyte subset | with TCR, TCR surface expression/signal transduction |
| CD3 epsilon | T3 | IgSF | T, thymocyte subset | with TCR, TCR surface expression/signal transduction |

TABLE 4-continued

Cluster of differentiation (CD) antigen markers of various cancers found to be expressed on the surface of T-cells

| Antigen | Other Names | Structure | main Distribution | Function |
|---|---|---|---|---|
| CD4 | T4 | IgSF | thymocyte subset, T subset, mono, mac | MHC class II coreceptor, HIV receptor, T cell differentiation/activation |
| CD5 | T1, Tp67 | Scavenger R SF | thymocytes, T, B subset, B-CLL | CD72 receptor, TCR or BCR signaling, T-B interaction |
| CD7 | | IgSF | hematopoietic progenitors, thymocytes, T, NK | T costimulation |
| CD8a | T8, Leu-2 | IgSF | thymocyte subset, T subset, NK | MHC class I coreceptor, receptor for some mutated HIV-1, T cell differentiation/activation |
| CD8b | | IgSF | thymocyte subset, T subset | |
| CD9 | p24, MRP-1 | TM4SF | pre-B, eosinophils, basophils, platelets, Tact | cellular adhesion and migration |
| CD10 | CALLA, NEP, gp100 | type II TM | B precursors, T precursors, neutrophils | zinc-binding metalloproteinase, B cell development |
| CD11a | LFA-1, integrin alphaL | Integrin family | lymph, gran, mono, mac | CD11a/CD18 receptor for ICAM-1, -2, -3, intercellular adhesion, T costimulation |
| CD11b | Mac-1, integrin alphaM | Integrin family | myeloid cells, NK | binds CD54, ECM, iC3b |
| CD11c | p150, 95, CR4, integrin alphaX | Integrin family | DC, myeloid cells, NK, B, T subset | binds CD54, fibrinogen and iC3b |
| CD13 | Aminopeptidase N, APN | type II TM | myeloid cells | zinc-binding metalloproteinase, antigen processing, receptor for corona virus strains |
| CD14 | LPS-R | GPI-linked | mono, mac, Langerhans cells, granlow | receptor for LPS/LBP, recognition |
| CD15 | Lewis-x, Lex | CHO | neutrophils, eosinophils, mono | adhesion |
| CD16a | FcgammaRIIIA | IgSF | neutrophils, mac, NK | component of low affinity Fc receptor, phagocytosis and ADCC |
| CD16b | FcgammaRIIIB | IgSF | neutrophils | component of low affinity Fc receptor, phagocytosis and ADCC |
| CD20 | B1, Bp35 | TM4SF | B, T subset | B cell activation |
| CD21 | C3DR, CR2, EBV-R | CCRSF | B, FDC, T subset | complement C3d and EBV receptor, complex with CD19 and CD81, BCR coreceptor |
| CD22 | BL-CAM, Siglec-2 | IgSF, sialoadhesins | B | adhesion, B-mono, B-T interactions |
| CD23 | FcepsilonRII | C-type lectin | B, activated mac, eosinophils, FDC, platelets | CD19-CD21-CD81 receptor, IgE low affinity receptor, signal transduction |
| CD24 | BA-1 | GPI-linked | thymocytes, erythrocytes, peripheral lymph, myeloid | binds P-selectin |
| CD25 | Tac, p55 | type I TM | Tact, Bact, lymph progenitors | IL-2Ralpha, with IL-2Rbeta and gamma to form high affinity complex |
| CD31 | PECAM-1 | IgSF | mono, platelets, gran, endoth, lymph subset | CD38 receptor, adhesion |
| CD33 | p67, Siglec-3 | IgSF, sialoadhesins | myeloid progenitors, mono, gran, DC, mast cells, Tact | adhesion |
| CD37 | | TM4SF | B, Tlow, granlow | signal transduction |
| CD38 | T10 | | variable levels on majority of hematopoietic cells, high expression on plasma cells, B and Tact | ecto-ADP-ribosyl cyclase, cell activation |
| CD40 | | TNFRSF | B, mono, mac, FDC, endoth, T subset | CD154 receptor, B differentiation/costimulation, isotype-switching, rescues B cells from apoptosis |
| CD43 | Leukosialin, sialophorin | Sialomucin, type I TM | leukocytes, except resting B, plateletslow | inhibition of T cell interaction, CD54R, adhesion |
| CD44 | H-CAM, Pgp-1 | hyaladherin family | hematopoietic and non-hematopoietic cells, except platelets, hepatocytes, testis | binds hyaluronic acid, adhesion |
| CD45 | LCA, T200, B220 | | hematopoietic cells, multiple isoforms from alternative splicing | tyrosine phosphatase, enhanced TCR & BCR signals |
| CD45RA | | | B, T subset(naive), mono | exon A isoforms of CD45 |
| CD45RB | | | T subset, B, mono, mac, gran | exon B isoforms of CD45 |
| CD45RO | | | Tact, memory T, B subset, mono, mac, gran | isoform of CD45 lacking A, B, C exons |
| CD46 | MCP | CCRSF | nucleated cells | membrane cofactor protein, binds C3b & C4b allowing degradation by Factor I, measles virus receptor |
| CD47 | IAP | IgSF | hematopoietic cells, epith, endoth, fibroblasts, other tissues | leukocyte adhesion, migration, activation |
| CD48 | Blast-1 | IgSF | broad, all leukocytes | cell adhesion |
| CD52 | CAMPATH-1 | | thymocytes, T, B (not plasma cells), mono, mac | |
| CD53 | | TM4SF | leukocytes, DC, osteoblasts, osteoclasts | signal transduction |
| CD55 | DAF | GPI-linked | hematopoietic, endoth | binds C3b, complement regulation |
| CD56 | NCAM | IgSF | NK, T subset, neurons, some large granular lymphocyte leukemias, myeloid leukemias | adhesion |
| CD57 | HNK-1, Leu-7 | | NK subset, T subset | |
| CD58 | LFA-3 | IgSF | hematopoietic, non-hematopoietic cells | CD2 receptor, adhesion |
| CD59 | Protectin, MAC-inhibitor | GPI-linked | hematopoietic, non-hematopoietic cells | binds complement C8 and C9, blocks assembly of membrane attack complex |

TABLE 4-continued

Cluster of differentiation (CD) antigen markers of various cancers found to be expressed on the surface of T-cells

| Antigen | Other Names | Structure | main Distribution | Function |
|---|---|---|---|---|
| CD60a | GD3 | CHO | T subset, platelets, thymic epith, astrocytes | costimulation |
| CD63 | LIMP, LAMP-3 | TM4SF | activated platelets, mono, mac | lysosomal membrane protein, moves to cell surface after activation |
| CD68 | Macrosialin, gp110 | Sialomucin | intracellularly in mono, mac, neutrophils, basophils, large lymph, mast cells, DC, myeloid progenitors, liver | |
| CD69 | AIM | C-type lectin | Tact, B, NK and gran, thymocytes, platelets, Langerhans cells | signal transduction |
| CD70 | Ki-24 | TNFSF | Bact and Tact | CD27 ligand, T and B cell costimulation |
| CD74 | Ii, invariant chain | | B, mac, mono, Langerhans cells, DC, Tact | MHC class II traffic and function |
| CD79a | Iga | IgSF | B | component of BCR, BCR surface expression and signal transduction |
| CD79b | Igb | IgSF | B | component of BCR, BCR surface expression and signal transduction |
| CD81 | TAPA-1 | TM4SF | T, B, NK, thymocytes, DC, endoth, fibroblast, neuroblastomas, melanomas | complex with CD19 & CD21, signaling, T costimulation |
| CD82 | R2 | TM4SF | leukocytes | signal transduction |
| CD83 | HB15 | IgSF | Bact and Tact, DC, Langerhans cells | |
| CDw84 | | | mono, platelets, B, T subset, mac subset | |
| CD86 | B70, B7-2 | IgSF | mono, DC, Bact and Tact | binds to CD28, CD152, T costimulation |
| CD87 | UPA-R | GPI-linked | gran, mono, NK, Tact, endoth, fibroblasts | urokinase plasminogen activator receptor, inflammatory cell invasion, metastasis |
| CD90 | Thy-1 | IgSF, GPI-linked | CD34+ hematopoietic subset, neurons | hematopoietic stem cell and neuron differentiation |
| CD94 | KP43 | C-type lectin | NK, T subset | complex with NKG2, inhibits NK function |
| CD95 | Apo-1, Fas | TNFRSF | lymph (high upon activation), mono, neutrophils | FasL (CD178) receptor, apoptosis |
| CD96 | TACTILE | IgSF | NK, Tact | adhesion of activated T and NK |
| CD97 | | TM7SF | Bact and Tact, mono, gran | |
| CD98 | 4F2 | | T, B, NK, gran, all human cell lines | cellular activation |
| CD99 | MIC2, E2 | | leukocytes | T cell activation, adhesion |
| CD100 | | | hematopoietic cells except immature bone marrow cells, RBC and platelets | cell adhesion, cellular activation |
| CD103 | HML-1, alpha6, integrin alphaE | Integrin family | intraepithelial lymph, lymph subset, activated lymph | with integrin beta7, binds E-cadherin, lymph homing/retention |
| CD107a | LAMP-1 | | activated platelets, T, endoth, metastatic tumors | a lysosomal membrane protein |
| CD107b | LAMP-2 | | activated platelets, T, endoth, metastatic tumors | a lysosomal membrane protein |
| CD109 | | | Tact and platelets, CD34+ subset, endoth | |
| CD123 | IL-3R | CRSF | lymph subset, basophils, hematopoietic progenitors, mac, DC, megakaryocytes | IL-3Ralpha, with CDw131 |
| CD146 | MUC18, S-endo | IgSF | endoth, melanomas, FDC, Tact | adhesion |
| CD154 | CD40L, gp39, TRAP | TNFSF | Tact | CD40 ligand, B and DC costimulation |
| CD158a | p58.1 | IgSF, KIR family | NK subset, T subset | inhibition of NK cell cytolytic activity, MHC class-I specific NK receptor |
| CD158b | p58.2 | IgSF, KIR family | NK subset, T subset | inhibition of NK cell cytolytic activity, MHC class-I specific NK receptor |
| CD163 | 130 kD | Scavenger receptor SF | mono, mac | |
| CD164 | MGC-24 | epith, mono, lymphlow, bone marrow stromal cells, CD34+ erythroid progenitors | hematopoietic progenitor cell-stromal cell interaction | |
| CD168 | RHAMM | | mono, T subset, thymocyte subset, intracellularly in breast cancer cells | adhesion, tumor migration, metastasis |
| CD171 | L1 | IgSF | CNS, PNS, glial cells, mono, T subset, B, DC, several human tumor cells | kidney morphogenesis, lymph node architecture, T costimulation, neurohistogenesis, homotypic interaction, binds CD9, CD24, CD56, CD142, CD166, integrins |
| CD177 | NB1 | | neutrophil subset | |
| CD178 | FasL, CD95L | TNFSF | Tact, testis | CD95 ligand, apoptosis, immune privilege, soluble form in serum |
| CD180 | RP-105 | LRRF, TLR family | B subset, mono, DC | B cell activation, LPS signaling, with MD-1 |
| CD182 | CXCR2, IL-8RB | GPCR1 family | neutrophils, basophils, NK, T subset, mono | binding of IL-8 induces chemotaxis of neutrophils |
| CD185 | CXCR5, BLR1 | GPCR1 family | mature B and Burkitt Lymphoma cells | with chemokine BLC, possible regulatory function in Burkitt Lymphomagenesis and/or B differentiation, activation of mature B |

TABLE 4-continued

Cluster of differentiation (CD) antigen markers of various cancers found to be expressed on the surface of T-cells

| Antigen | Other Names | Structure | main Distribution | Function |
|---|---|---|---|---|
| CD191 | CCR1, MIP-1alphaR, RANTES-R | GPCR1 family | T, mono, stem cell subset | binds C-C type chemokines and transduces signal by increasing intracellular calcium ion levels |
| CD193 | CCR3, CKR3 | GPCR1 family | eosinophils, lower expression in neutrophils and mono, T subset | binds eotaxin, eotaxin-3, MCP-3, MCP-4, RANTES & MIP-1 delta, alternative coreceptor with CD4 for HIV-1 infectiongg |
| CD196 | CCR6, LARC receptor, DRY6 | GPCR1 family | T subset, B, DC subset | binds MIP-3alpha/LARC |
| CD197 | CCR7 | | T subset, DC Subset | 6Ckine and MIP-2beta receptor |
| CD200 | OX-2 | | thymocytes, endoth, B, Tact | inhibition of immune response |
| CD209 | DC-SIGN | | DC subset | ICAM-3 receptor, HIV-1 binding protein |
| CD227 | MUC1, EMA | Mucin family, type I TM | epith, stem cell subset, FDC, mono, B subset, some myelomas | adhesion, signaling, binds CD169, CD54, & selectins |
| CD231 | TALLA-1, A15 | TM4SF | T leukemias, neuroblastomas, brain neurons | marker for T cell acute lymphoblastic leukemia |
| CD246 | ALK, Ki-1 | | anaplastic T cell leukemias, small intestine, testis, brain, not on normal lymph | brain development, implicated in ALK lymphomas |
| CD254 | TRANCE, RANKL, OPGL | TNFSF | lymph node & BM stroma Tact | binds OPG and RANK, osteoclast differentiation, enhances DC to stimulate naïve-T proliferation |
| CD263 | TRAIL-R3, DcR1, LIT | | peripheral blood lymphocytes | receptor for TRAIL but lacks death domain |
| CD272 | BTLA | IgSF | Tact, B, remains on Th1 | HVEM receptor, inhibitory response |
| CD273 | B7DC, PD-L2, PDCD1L2 | IgSF | DC subset, mono, mac | PD-1 receptor, costimulation or suppression of T proliferation |
| CD276 | B7-H3 | B7 Family, ASV | in vitro cultured DC and mono, Tact, mammary tissue | costimulation, T activation |
| CD277 | BT3.1, butyrophilin SF3 A1, BTF5 | B7/BT family, ASV | T, B, NK, mono, DC, endoth, CD34+ cells, tumor cell lines | T activation |
| CD279 | PD1, SLEB2 | | Tact and Bact | B7-H1 & B7-DC receptor, autoimmune disease and peripheral tolerance |
| CD298 | Na+/K+-ATPase beta3 subunit | | broad | transport sodium & potassium ions across membrane |
| CD300a | CMRF35H, IRC1, IRp60 | IgSF, ASV | NK, mono, neutrophils, T and B subset and lymphocytic cell lines, AML | unknown |
| CD300c | CMRF35A, LIR | IgSF | mono, neutrophils, monocytic cell lines, B & T subsets | unknown |
| CD304 | BDCA4, neuropilin 1 | semaphorin family | neurons, CD4+/CD25+ Treg, DC, endothelial and tumor cells | interacts with VEGF165 & semaphorins, co-receptor with plexin, axonal guidance, angiogenesis, cell survival, migration |
| CD305 | LAIR1 | IgSF, ASV | NK, B, T, mono | inhibitory receptor on NK and T cells |
| CD314 | NKG2D, KLR | Type II lectin-like receptor | NK, CD8+ activated, NK1.1+ T, some myeloid cells | binds MHC class I, MICA, MICB, Rae1 & ULBP4, activates cytolysis and cytokine production, costimulation |
| CD317 | BST2, HM1.24 | Type II | B, T, NK, mono, DC, fibroblast cell line, myeloma | pre-B cell growth, overexpressed in multiple myeloma |
| CD319 | CS1, CRACC, SLAMF7 | SLAM receptor family | B Cells, Dendritic Cells, NK, NKT | multiple myeloma |

TABLE 5 antigen markers expressed on the surface of both colon tumor cells and T-cells

| Antigen | Protein Name | Relative expression in T-Cell | Relative Expression in colon cancer cells |
|---|---|---|---|
| EPCAM | Epithelial cell adhesion molecule | 2.97 | 13.99 |
| IFITM1 | Interferon-induced transmembrane protein 1 | 10.55 | 13.06 |
| CLDN4 | Claudin-4 | 2.87 | 11.62 |
| CDH17 | Cadherin-17 | 1.85 | 11.52 |
| CEACAM1 | Carcinoembryonic antigen-related cell adhesion molecule 1 | 3.33 | 10.84 |
| SLC26A3 | Chloride anion exchanger | 2.57 | 10.59 |
| ATP1A1 | Sodium/potassium-transporting ATPase subunit alpha-1 | 9.28 | 10.51 |
| SI | Isomaltase | 2.86 | 10.46 |
| ABCB1 | Multidrug resistance protein 1 | 6.09 | 10.24 |
| KCNQ1 | Potassium voltage-gated channel subfamily KQT member 1 | 3.36 | 9.99 |
| FCGRT | IgG receptor FcRn large subunit p51 | 4.8 | 9.98 |
| EPHB3 | Ephrin type-B receptor 3 | 5.23 | 9.74 |
| DSG2 | Desmoglein-2 | 3.04 | 8.5 |

TABLE 5-continued antigen markers expressed on the surface of both colon tumor cells and T-cells

| Antigen | Protein Name | Relative expression in T-Cell | Relative Expression in colon cancer cells |
|---|---|---|---|
| EPHB4 | Ephrin type-B receptor 4 | 6.5 | 8.44 |
| GUCY2C | Heat-stable enterotoxin receptor | 2.23 | 8.05 |
| EPHA2 | Ephrin type-A receptor 2 | 2.8 | 7.95 |
| LY6G6D | Lymphocyte antigen 6 complex locus protein G6f | 2.02 | 7.91 |
| CD97 | CD97 antigen subunit beta | 7.7 | 7.87 |
| SIGMAR1 | Sigma non-opioid intracellular receptor 1 | 4.58 | 7.85 |
| EREG | Epiregulin | 2.93 | 6.9 |
| FAIM2 | Protein lifeguard 2 | 2.94 | 6.82 |
| PIGR | Secretory component | 4.2 | 6.8 |
| SLC7A6 | Y + L amino acid transporter 2 | 8.06 | 6.55 |
| SCNN1D | Amiloride-sensitive sodium channel subunit delta | 1.77 | 5.74 |
| GPR35 | G-protein coupled receptor 35 | 1.98 | 5.5 |
| ABCG2 | ATP-binding cassette sub-family G member 2 | 1.79 | 5.35 |
| LPAR4 | Lysophosphatidic acid receptor 4 | 2.93 | 5.05 |
| GPR161 | G-protein coupled receptor 161 | 2.71 | 4.96 |
| CD1C | T-cell surface glycoprotein CD1c | 2.73 | 4.89 |
| SGCA | Alpha-sarcoglycan | 2.32 | 4.84 |
| CD22 | B-cell receptor CD22 | 4.12 | 4.75 |
| CD22 | B-cell receptor CD22 | 3.58 | 4.75 |
| CD22 | B-cell receptor CD22 | 2.73 | 4.75 |
| CD22 | B-cell receptor CD22 | 2.14 | 4.75 |
| SLC22A18 | Solute carrier family 22 member 18 | 2.32 | 4.62 |
| HTR7 | 5-hydroxytryptamine receptor 7 | 3.02 | 4.46 |
| LCT | Phlorizin hydrolase | 2.32 | 4.24 |
| CD33 | Myeloid cell surface antigen CD33 | 3.42 | 4.14 |
| PVR | Poliovirus receptor | 5.07 | 4.07 |
| PLXDC1 | Plexin domain-containing protein 1 | 5.85 | 3.99 |
| P2RY2 | P2Y purinoceptor 2 | 2.15 | 3.97 |
| CHRNB2 | Neuronal acetylcholine receptor subunit beta-2 | 6.31 | 3.88 |
| PTGDR | Prostaglandin D2 receptor | 4.08 | 3.65 |
| NCR1 | Natural cytotoxicity triggering receptor 1 | 2.63 | 3.33 |
| GYPA | Glycophorin-A | 3.18 | 3.31 |
| TNFRSF8 | Tumor necrosis factor receptor superfamily member 8 | 2 | 2.75 |
| KEL | Kell blood group glycoprotein | 1.93 | 2.48 |
| EDA | Ectodysplasin-A, secreted form | 2.7 | 2.42 |
| ACE | Angiotensin-converting enzyme, soluble form | 2.39 | 2.19 |
| DRD2 | D(2) dopamine receptor | 2.49 | 1.97 |
| CXCR3 | C-X-C chemokine receptor type 3 | 4.19 | 1.66 |
| MC2R | Adrenocorticotropic hormone receptor | 1.94 | 1.43 |

TABLE 6 antigen markers expressed on the surface of both breast tumor cells and T-cells

| Antigen | Protein Name | Relative expression in T-Cell | Relative Expression in colon cancer cells |
|---|---|---|---|
| ABCA8 | ATP-binding cassette sub-family A member 8 | 3.15 | 7.73 |
| ABCC10 | Multidrug resistance-associated protein 7 | 6.48 | 5.29 |
| ABCC6 | Multidrug resistance-associated protein 6 | 2.67 | 2.17 |
| ACCN2 | Acid-sensing ion channel 1 | 3.62 | 2.49 |
| ADAM12 | Disintegrin and metalloproteinase domain-containing protein 12 | 4.96 | 7.72 |
| ADCYAP1R1 | Pituitary adenylate cyclase-activating polypeptide type I receptor | 2.17 | 2.88 |
| ADRA1A | Alpha-1A adrenergic receptor | 3.31 | 4.85 |
| ADRA1B | Alpha-1B adrenergic receptor | 1.49 | 1.6 |
| ADRA1D | Alpha-1D adrenergic receptor | 2.39 | 3.38 |
| ADRA2A | Alpha-2A adrenergic receptor | 2.64 | 1.79 |
| ADRB3 | Beta-3 adrenergic receptor | 2.36 | 2.16 |
| AGER | Advanced glycosylation end product-specific receptor | 2.85 | 2.38 |
| AGTR2 | Type-2 angiotensin II receptor | 3.08 | 3.7 |
| ALK | ALK tyrosine kinase receptor | 4.97 | 4.27 |
| ANO3 | Anoctamin-3 | 2.39 | 3.69 |
| ANPEP | Aminopeptidase N | 3.26 | 10.78 |
| APLNR | Apelin receptor | 2.47 | 2.06 |
| AQP2 | Aquaporin-2 | 2.12 | 1.43 |
| ATP10A | Probable phospholipid-transporting ATPase VA | 3.96 | 6.02 |
| ATP2B2 | Plasma membrane calcium-transporting ATPase 4 | 2.75 | 4.81 |
| ATP2B3 | Plasma membrane calcium-transporting ATPase 3 | 3.7 | 4.14 |
| ATP4A | Potassium-transporting ATPase alpha chain 1 | 1.56 | 11.49 |
| ATP4B | Potassium-transporting ATPase subunit beta | 2.49 | 13.56 |
| ATP6V0A2 | V-type proton ATPase 116 kDa subunit a isoform 2 | 2.51 | 2.57 |
| ATRN | Attractin | 4.09 | 9.44 |
| AVPR1A | Vasopressin V1a receptor | 2.52 | 4.03 |
| AVPR1B | Vasopressin V1b receptor | 2.97 | 3.32 |
| AVPR2 | Vasopressin V2 receptor | 2.68 | 2.93 |
| BAI1 | Brain-specific angiogenesis inhibitor 1 | 2.73 | 0.33 |
| BAI2 | Brain-specific angiogenesis inhibitor 2 | 2.34 | 4.14 |
| BAI3 | Brain-specific angiogenesis inhibitor 3 | 2.73 | 4.76 |
| BDKRB1 | B1 bradykinin receptor | 2.07 | 3.28 |
| BRS3 | Bombesin receptor subtype-3 | 2.74 | 4.12 |
| BTF3 | Butyrophilin subfamily 3 member A2 | 11.29 | 13.02 |
| C18orf1 | Low-density lipoprotein receptor class A domain-containing protein 4 | 3.18 | 8.45 |
| C3AR1 | C3a anaphylatoxin chemotactic receptor | 3.04 | 5.15 |
| C6orf105 | Androgen-dependent TFPI-regulating protein | 2.34 | 3.84 |
| CASR | Extracellular calcium-sensing receptor | 2.52 | 5 |
| CCBP2 | Atypical chemokine receptor 2 | 1.72 | 3.29 |
| CCKAR | Cholecystokinin receptor type A | 2.46 | 3 |
| CCKBR | Gastrin/cholecystokinin type B receptor | 2.25 | 5.66 |
| CCR2 | C-C chemokine receptor type 2 | 5.94 | 3.56 |
| CCR3 | C-C chemokine receptor type 3 | 1.89 | 4.17 |
| CCR6 | C-C chemokine receptor-like 2 | 3.33 | 5.23 |
| CCR8 | C-C chemokine receptor type 8 | 2.28 | 3.93 |
| CCR9 | C-C chemokine receptor type 9 | 1.68 | 1.98 |
| CD1A | T-cell surface glycoprotein CD1a | 1.98 | 4.88 |
| CD1B | T-cell surface glycoprotein CD1b | 2.35 | 4.94 |

TABLE 6-continued antigen markers expressed on the surface of both breast tumor cells and T-cells

| Antigen | Protein Name | Relative expression in T-Cell | Relative Expression in colon cancer cells |
|---|---|---|---|
| CD1D | Antigen-presenting glycoprotein CD1d | 2.82 | 4.96 |
| CD300C | CMRF35-like molecule 6 | 2.04 | 5.04 |
| CD4 | T-cell surface glycoprotein CD4 | 2.84 | 6.17 |
| CD40LG | CD40 ligand, soluble form | 2.1 | 3.49 |
| CD5 | T-cell surface glycoprotein CD5 | 3.14 | 1.01 |
| CD63 | CD63 antigen | 8.6 | 13.18 |
| CD84 | SLAM family member 5 | 4.7 | 3.17 |
| CDH15 | Cadherin-15 | 2.07 | 3.55 |
| CDH19 | Protocadherin-16 | 2.82 | 8.4 |
| CDH22 | Cadherin-22 | 3 | 4.9 |
| CDH8 | Cadherin-8 | 3.63 | 5.87 |
| CDON | Cell adhesion molecule-related/down-regulated by oncogenes | 2.35 | 3.61 |
| CHRNA4 | Neuronal acetylcholine receptor subunit alpha-4 | 2.14 | 3.33 |
| CHRNA5 | Neuronal acetylcholine receptor subunit alpha-5 | 2.2 | 4.88 |
| CHRNA6 | Neuronal acetylcholine receptor subunit alpha-6 | 2.26 | 4.93 |
| CHRNB3 | Neuronal acetylcholine receptor subunit beta-3 | 1.85 | 3.91 |
| CHRNE | Acetylcholine receptor subunit epsilon | 2.56 | 2.83 |
| CLDN3 | Claudin-3 | 2.91 | 13.56 |
| CLDN7 | Claudin-7 | 1.89 | 12.87 |
| CLDN8 | Claudin-8 | 2.46 | 10.67 |
| CLDN9 | Claudin-9 | 1.74 | 1.69 |
| CLEC4M | C-type lectin domain family 4 member M | 2.7 | 3.32 |
| CMKLR1 | Chemokine-like receptor 1 | 2.62 | 5 |
| CNNM2 | Metal transporter CNNM2 | 2.47 | 5.32 |
| CNR2 | Cannabinoid receptor 2 | 2.38 | 3.66 |
| CRHR1 | Corticotropin-releasing factor receptor 1 | 2.15 | 10.71 |
| CRHR2 | Corticotropin-releasing factor receptor 2 | 2.32 | 6.44 |
| CSF1 | Processed macrophage colony-stimulating factor 1 | 5.63 | 7.61 |
| CSF1R | Macrophage colony-stimulating factor 1 receptor | 2.2 | 4.02 |
| CSF3R | Granulocyte colony-stimulating factor receptor | 1.85 | 2.8 |
| CX3CL1 | Processed fractalkine | 2.35 | 9.31 |
| CXCR5 | C-X-C chemokine receptor type 5 | 2.07 | 6.06 |
| DAGLA | Sn1-specific diacylglycerol lipase alpha | 2.6 | 2.11 |
| DRD1 | D(1A) dopamine receptor | 2.67 | 5.71 |
| DRD3 | D(3) dopamine receptor | 2.72 | 4.99 |
| DRD4 | D(4) dopamine receptor | 1.49 | 0.89 |
| DRD5 | D(1B) dopamine receptor | 2.26 | 4.91 |
| DSC2 | Desmocollin-2 | 2.26 | 11.12 |
| DSCAM | Down syndrome cell adhesion molecule | 2.54 | 3.76 |
| DSG1 | Desmoglein-1 | 2.62 | 7.71 |
| EMR2 | EGF-like module-containing mucin-like hormone receptor-like 2 | 2.25 | 3.38 |
| EPHA5 | Ephrin type-A receptor 5 | 2.42 | 7.48 |
| EPHA7 | Ephrin type-A receptor 7 | 2.61 | 4.87 |
| ERBB3 | Receptor tyrosine-protein kinase erbB-3 | 2.39 | 12.76 |
| F2RL2 | Proteinase-activated receptor 3 | 3.2 | 5.16 |
| FAM168B | Myelin-associated neurite-outgrowth inhibitor | 8.34 | 11.16 |
| FAP | Seprase | 1.87 | 10.15 |
| FAS | Tumor necrosis factor receptor superfamily member 6 | 5.68 | 7.24 |
| FASLG | FasL intracellular domain | 2.23 | 2.66 |
| FCAR | Immunoglobulin alpha Fc receptor | 2.8 | 3.85 |
| FCER1A | High affinity immunoglobulin epsilon receptor subunit alpha | 2.54 | 4.59 |
| FCGR2A | Low affinity immunoglobulin gamma Fc region receptor II-a | 2.77 | 8.81 |
| FCGR2B | Low affinity immunoglobulin gamma Fc region receptor II-b | 2.46 | 5.35 |
| FGFR2 | Fibroblast growth factor receptor 2 | 4.01 | 9.83 |
| FGFR4 | Fibroblast growth factor receptor 4 | 2.56 | 7.42 |
| FLT3LG | Fms-related tyrosine kinase 3 ligand | 7.86 | 4.37 |
| FPR1 | fMet-Leu-Phe receptor | 3.38 | 5.92 |
| FPR3 | N-formyl peptide receptor 3 | 1.91 | 2.61 |
| FSHR | Follicle-stimulating hormone receptor | 1.89 | 3.78 |
| FZD5 | Frizzled-5 | 2.82 | 5.2 |
| FZD5 | Frizzled-5 | 1.81 | 5.2 |
| FZD9 | Frizzled-9 | 2.66 | 3.16 |
| GABRA1 | Gamma-aminobutyric acid receptor subunit alpha-1 | 2.2 | 6.26 |
| GABRA5 | Gamma-aminobutyric acid receptor subunit alpha-5 | 2.49 | 3.24 |
| GABRA6 | Gamma-aminobutyric acid receptor subunit alpha-6 | 2.54 | 2.98 |
| GABRB1 | Gamma-aminobutyric acid receptor subunit beta-1 | 1.89 | 2.37 |
| GABRB2 | Gamma-aminobutyric acid receptor subunit beta-2 | 2.26 | 3.89 |
| GABRG3 | Gamma-aminobutyric acid receptor subunit gamma-3 | 2.23 | 2.85 |
| GABRP | Gamma-aminobutyric acid receptor subunit pi | 2.93 | 12.34 |
| GABRR1 | Gamma-aminobutyric acid receptor subunit rho-1 | 2.35 | 3.47 |
| GABRR2 | Gamma-aminobutyric acid receptor subunit rho-2 | 4.16 | 5.43 |
| GALR2 | Galanin receptor type 2 | 1.85 | 0.46 |
| GALR3 | Galanin receptor type 3 | 0.68 | 0.48 |
| GCGR | Glucagon receptor | 1.38 | 3.4 |
| GHRHR | Growth hormone-releasing hormone receptor | 1.61 | 3.49 |
| GJA5 | Gap junction alpha-5 protein | 1.72 | 2.05 |
| GJA8 | Gap junction alpha-8 protein | 2.39 | 6.51 |
| GJC1 | Gap junction delta-3 protein | 1.94 | 3.89 |
| GLP1R | Glucagon-like peptide 1 receptor | 5.72 | 3.41 |
| GLRA1 | Glycine receptor subunit alpha-1 | 2.15 | 3.87 |
| GLRA3 | Glycine receptor subunit alpha-3 | 3.19 | 3.1 |
| GNRHR | Gonadotropin-releasing hormone receptor | 2.72 | 4.1 |
| GPNMB | Transmembrane glycoprotein NMB | 2.14 | 13.94 |
| GPR1 | G-protein coupled receptor 1 | 3.83 | 4.1 |
| GPR135 | Probable G-protein coupled receptor 135 | 4.15 | 1.91 |
| GPR143 | G-protein coupled receptor 143 | 1.93 | 3.65 |
| GPR15 | G-protein coupled receptor 15 | 1.81 | 4.41 |
| GPR17 | Uracil nucleotide/cysteinyl leukotriene receptor | 1.93 | 1.74 |
| GPR171 | Probable G-protein coupled receptor 171 | 7.73 | 6.32 |

TABLE 6-continued antigen markers expressed on the surface of both breast tumor cells and T-cells

| Antigen | Protein Name | Relative expression in T-Cell | Relative Expression in colon cancer cells |
|---|---|---|---|
| GPR18 | N-arachidonyl glycine receptor | 7.05 | 3.52 |
| GPR182 | G-protein coupled receptor 182 | 1.66 | 1.29 |
| GPR19 | Probable G-protein coupled receptor 19 | 1.89 | 5.26 |
| GPR20 | G-protein coupled receptor 20 | 2.02 | 2.53 |
| GPR3 | G-protein coupled receptor 3 | 3.01 | 5.36 |
| GPR31 | 12-(S)-hydroxy-5,8,10,14-eicosatetraenoic acid receptor | 1.63 | 1.64 |
| GPR37L1 | Prosaposin receptor GPR37L1 | 2.23 | 4 |
| GPR39 | G-protein coupled receptor 39 | 1.81 | 1.36 |
| GPR44 | Prostaglandin D2 receptor 2 | 2 | 2.32 |
| GPR45 | Probable G-protein coupled receptor 45 | 2.78 | 5.31 |
| GPR6 | G-protein coupled receptor 6 | 2.56 | 3.38 |
| GPR65 | Psychosine receptor | 6.59 | 4.5 |
| GPR68 | Ovarian cancer G-protein coupled receptor 1 | 2.12 | 1.09 |
| GPR98 | G-protein coupled receptor 98 | 1.89 | 4.7 |
| GRIA1 | Glutamate receptor 1 | 4.17 | 4.77 |
| GRIA3 | Glutamate receptor 3 | 2.51 | 6.83 |
| GRIK2 | Glutamate receptor ionotropic, kainate 5 | 2.56 | 4.94 |
| GRIK3 | Glutamate receptor ionotropic, kainate 3 | 2.05 | 3.58 |
| GRIN1 | Glutamate receptor ionotropic, NMDA 1 | 4.52 | 1.49 |
| GRIN2B | Glutamate receptor ionotropic, NMDA 2B | 2.22 | 3.56 |
| GRIN2C | Glutamate receptor ionotropic, NMDA 2C | 2.56 | 3.37 |
| GRM1 | Metabotropic glutamate receptor 1 | 3.21 | 3.69 |
| GRM2 | Metabotropic glutamate receptor 2 | 2.04 | 0.44 |
| GRM3 | Metabotropic glutamate receptor 3 | 2.39 | 3.41 |
| GRM4 | Metabotropic glutamate receptor 4 | 5.2 | 3.78 |
| GRM5 | Metabotropic glutamate receptor 5 | 2.26 | 5.28 |
| GRM7 | Metabotropic glutamate receptor 7 | 2.86 | 3.07 |
| GYPB | Glycophorin-B | 2.43 | 4.02 |
| HBP1 | Glycosylphosphatidylinositol-anchored high density lipoprotein-binding protein 1 | 7.32 | 9.27 |
| HCRTR2 | Orexin receptor type 2 | 2.32 | 2.42 |
| HTR1B | 5-hydroxytryptamine receptor 1B | 2.82 | 3.51 |
| HTR1D | 5-hydroxytryptamine receptor 1D | 2.29 | 2.33 |
| HTR1E | 5-hydroxytryptamine receptor 1E | 1.72 | 2.4 |
| HTR2A | 5-hydroxytryptamine receptor 2A | 2.1 | 3.67 |
| HTR2C | 5-hydroxytryptamine receptor 2C | 2.49 | 5.18 |
| HTR4 | 5-hydroxytryptamine receptor 4 | 3.86 | 4.25 |
| ICAM4 | Intercellular adhesion molecule 4 | 2.51 | 2.16 |
| ICOS | Inducible T-cell costimulator | 3.91 | 3.86 |
| IL6R | Interleukin-6 receptor subunit alpha | 4.24 | 3.08 |
| IL6R | Interleukin-6 receptor subunit alpha | 2.64 | 3.08 |
| IL6ST | Interleukin-6 receptor subunit beta | 9.43 | 12.67 |
| IL9R | Interleukin-9 receptor | 2.71 | 2.86 |
| ITGB3 | Integrin beta-3 | 4.16 | 3.69 |
| KCNA3 | Potassium voltage-gated channel subfamily A member 3 | 2.09 | 4.9 |
| KCND2 | Potassium voltage-gated channel subfamily D member 2 | 2.67 | 4.25 |
| KCNH1 | Potassium voltage-gated channel subfamily H member 1 | 2.31 | 4.48 |
| KCNJ4 | Inward rectifier potassium channel 4 | 2.43 | 3.49 |
| KCNMA1 | Calcium-activated potassium channel subunit alpha-1 | 2.35 | 7.17 |
| KCNS1 | Potassium voltage-gated channel subfamily S member 1 | 5.66 | 6.49 |
| KCNV2 | Potassium voltage-gated channel subfamily V member 2 | 2.38 | 4.06 |
| KIR2DL4 | Killer cell immunoglobulin-like receptor 2DL4 | 1.68 | 3.31 |
| KIR3DL1 | Killer cell immunoglobulin-like receptor 3DL1 | 2.56 | 2.73 |
| KIR3DL3 | Killer cell immunoglobulin-like receptor 3DL3 | 1.7 | 3.06 |
| KLRG1 | Killer cell lectin-like receptor subfamily G member 1 | 8.3 | 5.76 |
| LAMP1 | Lysosome-associated membrane glycoprotein 1 | 10.9 | 13.6 |
| LHCGR | Lutropin-choriogonadotropic hormone receptor | 2.23 | 4.92 |
| LNPEP | Leucyl-cystinyl aminopeptidase, pregnancy serum form | 2.68 | 5.05 |
| LPAR2 | Lysophosphatidic acid receptor 2 | 5.5 | 4.23 |
| LRIG2 | Leucine-rich repeats and immunoglobulin-like domains protein 2 | 3.35 | 5.48 |
| LRRTM2 | Leucine-rich repeat transmembrane neuronal protein 2 | 2.42 | 4.24 |
| LTB4R | Leukotriene B4 receptor 1 | 4.96 | 2.26 |
| MAS1 | Proto-oncogene Mas | 1.91 | 3.11 |
| MC1R | Melanocyte-stimulating hormone receptor | 2.94 | 0.96 |
| MC5R | Melanocortin receptor 5 | 2.28 | 1.63 |
| MEP1B | Meprin A subunit beta | 2.61 | 3.87 |
| MFSD5 | Molybdate-anion transporter | 1.98 | 4.72 |
| MOG | Myelin-oligodendrocyte glycoprotein | 3.08 | 4.74 |
| MTNR1B | Melatonin receptor type 1B | 1.61 | 1.67 |
| MUC1 | Mucin-1 subunit beta | 2.73 | 13.68 |
| MUSK | Muscle, skeletal receptor tyrosine-protein kinase | 2.39 | 4.75 |
| NCAM2 | Neural cell adhesion molecule 2 | 2.12 | 4.49 |
| NCR2 | Natural cytotoxicity triggering receptor 2 | 4.79 | 7.09 |
| NCR3 | Natural cytotoxicity triggering receptor 3 | 4.55 | 2.74 |
| NIPA2 | Magnesium transporter NIPA2 | 6.77 | 3.9 |
| NLGN1 | Neuroligin-1 | 2.62 | 7.71 |
| NLGN4Y | Neuroligin-4, Y-linked | 2.52 | 5.26 |
| NMBR | Neuromedin-B receptor | 1.68 | 2.47 |
| NPHS1 | Nephrin | 2.74 | 4.33 |
| NPY2R | Neuropeptide Y receptor type 2 | 2.68 | 4.43 |
| NPY5R | Neuropeptide Y receptor type 5 | 2.38 | 5.05 |
| NTSR2 | Neurotensin receptor type 2 | 1.72 | 3 |
| OPRD1 | Delta-type opioid receptor | 2.26 | 2.14 |
| OPRL1 | Nociceptin receptor | 2.31 | 1.51 |
| OPRM1 | Mu-type opioid receptor | 3.18 | 4.01 |
| OR10H3 | Olfactory receptor 10H3 | 1.63 | 4.02 |
| OR1E1 | Olfactory receptor 1E1 | 3.04 | 4.77 |
| OR2F1 | Olfactory receptor 2F1 | 2.64 | 5.73 |
| OR2F2 | Olfactory receptor 2F2 | 2.19 | 2.3 |

TABLE 6-continued antigen markers expressed on the surface of both breast tumor cells and T-cells

| Antigen | Protein Name | Relative expression in T-Cell | Relative Expression in colon cancer cells |
|---|---|---|---|
| OR2H1 | Olfactory receptor 2H1 | 3.39 | 3.82 |
| OR2H2 | Olfactory receptor 2H2 | 3.79 | 6.37 |
| OR2J2 | Olfactory receptor 2J2 | 2.41 | 2.16 |
| OR2J2 | Olfactory receptor 2J2 | 1.93 | 2.16 |
| OR5I1 | Olfactory receptor 5I1 | 1.85 | 2.8 |
| OR7E24 | Olfactory receptor 7E24 | 2.5 | 3.47 |
| P2RX7 | P2X purinoceptor 7 | 2.36 | 2.15 |
| PANX1 | Pannexin-1 | 2.14 | 4.38 |
| PCDHA9 | Protocadherin alpha-9 | 2.82 | 3.56 |
| PCDHB11 | Protocadherin beta-11 | 1.91 | 5.23 |
| PCDHGA8 | Protocadherin gamma-A8 | 3.13 | 4.48 |
| PLA2R1 | Soluble secretory phospholipase A2 receptor | 2.91 | 5.16 |
| PLXNA3 | Plexin-A3 | 2.42 | 3.25 |
| POP1 | Blood vessel epicardial substance | 1.74 | 2.59 |
| PPYR1 | Neuropeptide Y receptor type 4 | 2.2 | 2.75 |
| PTGER1 | Prostaglandin E2 receptor EP1 subtype | 1.96 | 0.94 |
| PTGFR | Prostaglandin F2-alpha receptor | 2.75 | 4.89 |
| PTGIR | Prostacyclin receptor | 2.78 | 2.12 |
| PTPRJ | Receptor-type tyrosine-protein phosphatase eta | 2.63 | 4.6 |
| PTPRR | Receptor-type tyrosine-protein phosphatase R | 2.47 | 9.99 |
| PVRL1 | Poliovirus receptor-related protein 1 | 2.52 | 4.51 |
| PVRL2 | Poliovirus receptor-related protein 2 | 3.84 | 10.05 |
| ROS1 | Proto-oncogene tyrosine-protein kinase ROS | 2.93 | 3.38 |
| S1PR2 | Sphingosine 1-phosphate receptor 2 | 1.74 | 1.17 |
| S1PR4 | Sphingosine 1-phosphate receptor 4 | 4 | 0.21 |
| SCNN1B | Amiloride-sensitive sodium channel subunit beta | 1.89 | 3.16 |
| SCNN1G | Amiloride-sensitive sodium channel subunit gamma | 2.23 | 2.61 |
| SEMA4D | Semaphorin-4D | 10.66 | 1.56 |
| SEMA6A | Semaphorin-6A | 4.55 | 7.81 |
| SEMA6C | Semaphorin-6C | 5.02 | 3.73 |
| SGCB | Beta-sarcoglycan | 2.69 | 3.45 |
| SGCB | Beta-sarcoglycan | 2.04 | 3.45 |
| SLC12A3 | Solute carrier family 12 member 3 | 2.26 | 3.36 |
| SLC14A1 | Urea transporter 1 | 2.97 | 6.21 |
| SLC14A2 | Urea transporter 2 | 2.85 | 4.4 |
| SLC16A1 | Monocarboxylate transporter 1 | 3.46 | 8.84 |
| SLC16A2 | Monocarboxylate transporter 8 | 1.77 | 5.17 |
| SLC16A6 | Monocarboxylate transporter 7 | 2.41 | 11.66 |
| SLC22A1 | Solute carrier family 22 member 1 | 2.95 | 11.61 |
| SLC22A6 | Solute carrier family 22 member 6 | 2.26 | 2.53 |
| SLC5A12 | Sodium-coupled monocarboxylate transporter 2 | 2.98 | 4.45 |
| SLC6A1 | Sodium- and chloride-dependent GABA transporter 1 | 2.45 | 4.3 |
| SLC6A4 | Sodium-dependent serotonin transporter | 2.17 | 2.66 |
| SLC6A6 | Sodium- and chloride-dependent taurine transporter | 2.54 | 4.13 |
| SLC7A7 | Y + L amino acid transporter 1 | 2.22 | 9.78 |
| SLC8A1 | Sodium/calcium exchanger 1 | 2.07 | 2.36 |
| SLC9A1 | Sodium/hydrogen exchanger 1 | 3.15 | 5.54 |
| SLC9A3 | Sodium/hydrogen exchanger 3 | 2.12 | 3.15 |
| SLCO1A2 | Solute carrier organic anion transporter family member 1A2 | 3.87 | 4.98 |
| SLCO2B1 | Solute carrier organic anion transporter family member 2B1 | 4.43 | 8.92 |
| SORT1 | Sortilin | 2.93 | 4.6 |
| SSTR2 | Somatostatin receptor type 2 | 3.08 | 4.47 |
| SSTR3 | Somatostatin receptor type 3 | 2.23 | 1.5 |
| SSTR4 | Somatostatin receptor type 4 | 1.83 | 1.53 |
| SSTR5 | Somatostatin receptor type 5 | 2.57 | 1.47 |
| TACR1 | Substance-P receptor | 2.66 | 3.2 |
| TACR3 | Neuromedin-K receptor | 2.32 | 5.7 |
| TLR6 | Toll-like receptor 6 | 2.2 | 4.58 |
| TMPRSS6 | Transmembrane protease serine 6 | 4.02 | 3.69 |
| TNFSF11 | Tumor necrosis factor ligand superfamily member 11, | 2.57 | 5.18 |
| TNFSF14 | Tumor necrosis factor ligand superfamily member 14, soluble form | 3.34 | 2.83 |
| TPO | Thyroid peroxidase | 1.96 | 1.89 |
| TRAT1 | T-cell receptor-associated transmembrane adapter 1 | 7.51 | 5.29 |
| TRHR | Thyrotropin-releasing hormone receptor | 2 | 4.18 |
| TRPM1 | Transient receptor potential cation channel subfamily M member 1 | 2.43 | 5.22 |
| TSHR | Thyrotropin receptor | 2.9 | 4.87 |
| TSHR | Thyrotropin receptor | 2.12 | 4.87 |
| UNC93A | Protein unc-93 homolog A | 2.64 | 4.94 |
| VIPR2 | Vasoactive intestinal polypeptide receptor 2 | 2.58 | 3.37 |
| ZP2 | Processed zona pellucida sperm-binding protein 2 | 1.94 | 3.55 |

TABLE 7 antigen markers expressed on the surface of both digestive tumor cells and T-cells

| Antigen | Protein Name | Relative expression in T-Cell | Relative Expression in colon cancer cells |
|---|---|---|---|
| ACVR1B | Activin receptor type-1B | 5.16 | 10.48 |
| AMIGO2 | Amphoterin-induced protein 2 | 6.73 | 8.2 |
| ATP1B1 | Sodium/potassium-transporting ATPase subunit beta-1 | 2.64 | 12.31 |
| ATP8B1 | Probable phospholipid-transporting ATPase IC | 8.22 | 2.17 |
| CCR7 | C-C chemokine receptor type 7 | 10.25 | 11.52 |
| CD164 | Sialomucin core protein 24 | 10.27 | 12.12 |
| CD180 | CD180 antigen | 2.5 | 6.47 |
| CD40 | Tumor necrosis factor receptor superfamily member 5 | 5.02 | 6 |
| CD53 | Leukocyte surface antigen CD53 | 10.79 | 11.3 |
| CD79A | B-cell antigen receptor complex-associated protein alpha chain | 3.74 | 9.17 |
| CD79B | B-cell antigen receptor complex-associated protein beta chain | 3.6 | 6.66 |
| CD8B | T-cell surface glycoprotein CD8 beta chain | 8.43 | 2.62 |
| CELSR1 | Cadherin EGF LAG seven-pass G-type receptor 1 | 2.72 | 8.68 |
| CLCN5 | H(+)/Cl(−) exchange transporter 5 | 2.71 | 4.97 |
| CLDN18 | Claudin-18 | 3.05 | 14.51 |

TABLE 7-continued antigen markers expressed on the surface of both digestive tumor cells and T-cells

| Antigen | Protein Name | Relative expression in T-Cell | Relative Expression in colon cancer cells |
|---|---|---|---|
| CLIC1 | Chloride intracellular channel protein 1 | 9.94 | 13.83 |
| COL13A1 | Collagen alpha-1(XIII) chain | 2.96 | 6.24 |
| DIO3 | Type III iodothyronine deiodinase | 2.04 | 2.9 |
| EDNRA | Endothelin-1 receptor | 2.9 | 8.96 |
| EMR1 | EGF-like module-containing mucin-like hormone receptor-like 1 | 1.83 | 7.29 |
| ENPP1 | Nucleotide pyrophosphatase | 2.57 | 9.66 |
| EPHB1 | Ephrin type-B receptor 1 | 2.02 | 6.33 |
| EPHB1 | Ephrin type-B receptor 1 | 1.81 | 6.33 |
| F2R | Proteinase-activated receptor 1 | 3.04 | 9.78 |
| F2RL1 | Proteinase-activated receptor 2, alternate cleaved 2 | 3.31 | 9.47 |
| FCER2 | Low affinity immunoglobulin epsilon Fc receptor soluble form | 2.49 | 8.77 |
| GABBR1 | Gamma-aminobutyric acid type 6 receptor subunit 1 | 5.1 | 8.52 |
| GABRA3 | Gamma-aminobutyric acid receptor subunit alpha-3 | 2.12 | 3.84 |
| GPR183 | G-protein coupled receptor 183 | 4.79 | 10.22 |
| GPR37 | Prosaposin receptor GPR37 | 3.1 | 8.23 |
| GPRC5A | Retinoic acid-induced protein 3 | 1.87 | 13.69 |
| GRPR | Gastrin-releasing peptide receptor | 2.04 | 3.35 |
| GYPC | Glycophorin-C | 9.22 | 7.58 |
| IL1R2 | Interleukin-1 receptor type 2, soluble form | 2.82 | 12.83 |
| KIAA0319 | Dyslexia-associated protein KIAA0319 | 2.43 | 5.61 |
| LAMP2 | Lysosome-associated membrane glycoprotein 2 | 4.05 | 11.29 |
| LRP8 | Low-density lipoprotein receptor-related protein 8 | 4.24 | 8.84 |
| LSR | Lipolysis-stimulated lipoprotein receptor | 4.99 | 11.48 |
| MICB | MHC class I polypeptide-related sequence B | 5.27 | 9.89 |
| MMP16 | Matrix metalloproteinase-16 | 3.19 | 6.18 |
| MS4A1 | B-lymphocyte antigen CD20 | 2.15 | 8.02 |
| MYOF | Myoferlin | 2.41 | 11.56 |
| NAT1 | Sodium-coupled neutral amino acid transporter 3 | 3.49 | 12.09 |
| NFASC | Neurofascin | 3.78 | 8.28 |
| NPY1R | Neuropeptide Y receptor type 1 | 2.32 | 6.93 |
| OR2B6 | Olfactory receptor 2B6 | 2.78 | 4.24 |
| P2RY10 | Putative P2Y purinoceptor 10 | 3.39 | 6.62 |
| PCDH1 | Protocadherin-1 | 4.45 | 10.07 |
| PROM1 | Prominin-1 | 2.52 | 11.77 |
| PSEN1 | Presenilin-1 CTF12 | 2.94 | 8.83 |
| PTGER2 | Prostaglandin E2 receptor EP2 subtype | 6.33 | 6.74 |
| PTGER4 | Prostaglandin E2 receptor EP4 subtype | 8.62 | 5.12 |
| PTPRK | Receptor-type tyrosine-protein phosphatase kappa | 2.14 | 10.9 |
| RET | Extracellular cell-membrane anchored RET cadherin 120 kDa fragment | 2.38 | 12.3 |
| SERINC3 | Serine incorporator 3 | 7.93 | 12.01 |
| SIT1 | Sodium- and chloride-dependent transporter XTRP3 | 5.92 | 4.82 |
| SLAMF1 | Signaling lymphocytic activation molecule | 4.4 | 9.03 |
| SLC29A1 | Equilibrative nucleoside transporter 1 | 2.07 | 6.12 |
| SLC39A6 | Zinc transporter ZIP6 | 6.69 | 15.23 |
| SLC7A5 | Large neutral amino acids transporter small subunit 1 | 3.79 | 10.98 |
| STX4 | Syntaxin-4 | 5.68 | 7.67 |
| TGFBR3 | Transforming growth factor beta receptor type 3 | 7.55 | 7.29 |
| TGOLN2 | Trans-Golgi network integral membrane protein 2 | 9.59 | 11.3 |
| TLR1 | Toll-like receptor 1 | 2.34 | 4.57 |
| TMED10 | Transmembrane emp24 domain-containing protein 10 | 9.34 | 12.24 |
| TMEM97 | Transmembrane protein 97 | 2.75 | 9.02 |
| TNF | Tumor necrosis factor, soluble form | 1.63 | 3.18 |
| TNFRSF17 | Tumor necrosis factor receptor superfamily member 17 | 1.89 | 10.47 |
| TNFRSF1B | Tumor necrosis factor-binding protein 2 | 5.51 | 9.4 |
| VDAC1 | Voltage-dependent anion-selective channel protein 1 | 6.52 | 11.5 |

TABLE 8 antigen markers expressed on the surface of both kidney tumor cells and T-cells

| Antigen | Protein Name | Relative expression in T-Cell | Relative Expression in colon cancer cells |
|---|---|---|---|
| ADORA3 | Adenosine receptor A3 | 1.89 | 4.56 |
| ATP11A | Probable phospholipid-transporting ATPase IH | 3.62 | 8.8 |
| BSG | Basigin | 4.77 | 11.34 |
| BTN3A2 | Butyrophilin subfamily 3 member A2 | 10.86 | 8.19 |
| C10orf72 | V-set and transmembrane domain-containing protein 4 | 2.04 | 6.85 |
| CADM3 | Cell adhesion molecule 3 | 3.57 | 6.39 |
| CD8A | T-cell surface glycoprotein CD8 alpha chain | 10.35 | 6.6 |
| CDH16 | Cadherin-16 | 2.17 | 7.09 |
| CDH4 | Cadherin-4 | 2.15 | 3.6 |
| CDH5 | Cadherin-5 | 2.5 | 9.55 |
| CHL1 | Processed neural cell adhesion molecule L1-like protein | 2.69 | 10.43 |
| CHRNB1 | Acetylcholine receptor subunit beta | 2.12 | 3.6 |
| CLIC4 | Chloride intracellular channel protein 4 | 3.34 | 13.12 |
| CNR1 | Cannabinoid receptor 1 | 2.26 | 5.64 |
| CRIM1 | Processed cysteine-rich motor neuron 1 protein | 3.57 | 12.39 |
| CSPG4 | Chondroitin sulfate proteoglycan 4 | 3.33 | 6.59 |
| CYBB | Cytochrome b-245 heavy chain | 2.86 | 8.07 |
| EDNRB | Endothelin B receptor | 3.04 | 8.97 |
| FLT1 | Vascular endothelial growth factor receptor 1 | 2.75 | 8.5 |
| FZD1 | Frizzled-1 | 2.72 | 7.59 |
| GJC2 | Gap junction gamma-2 protein | 2.09 | 2.94 |
| GLRB | Glycine receptor subunit beta | 2.51 | 7.15 |
| GPER | G-protein coupled estrogen receptor 1 | 2.34 | 8.64 |
| GPM6A | Neuronal membrane glycoprotein M6-a | 2.95 | 6.88 |
| GPR162 | Probable G-protein coupled receptor 162 | 2.75 | 2.81 |

TABLE 8-continued antigen markers expressed on the surface of both kidney tumor cells and T-cells

| Antigen | Protein Name | Relative expression in T-Cell | Relative Expression in colon cancer cells |
|---|---|---|---|
| GPR4 | G-protein coupled receptor 4 | 2.93 | 8.09 |
| GRM8 | Metabotropic glutamate receptor 8 | 3.43 | 8.25 |
| HLA-DPB1 | HLA class II histocompatibility antigen, DP beta 1 chain | 9.93 | 13.99 |
| HTR6 | 5-hydroxytryptamine receptor 6 | 4.83 | 10.07 |
| INSR | Insulin receptor subunit beta | 3.44 | 8.95 |
| ITM2B | Bri23 peptide | 11.16 | 12.19 |
| KCNJ1 | ATP-sensitive inward rectifier potassium channel 1 | 2.5 | 4.17 |
| KDR | Vascular endothelial growth factor receptor 2 | 2.99 | 9.95 |
| KL | Klotho peptide | 2.83 | 7.59 |
| LAIR1 | Leukocyte-associated immunoglobulin-like receptor 1 | 5.64 | 4.25 |
| MFAP3 | Microfibril-associated glycoprotein 3 | 3.7 | 7.3 |
| MFAP3L | Microfibrillar-associated protein 3-like | 3.44 | 8.7 |
| MICA | MHC class I polypeptide-related sequence A | 4.07 | 2.01 |
| NCAM1 | Neural cell adhesion molecule 1 | 2.45 | 7.31 |
| NOTCH3 | Notch 3 intracellular domain | 3.21 | 12.41 |
| NOTCH4 | Notch 4 intracellular domain | 5.89 | 8.84 |
| OLR1 | Oxidized low-density lipoprotein receptor 1, soluble form | 2.84 | 8.41 |
| P2RY14 | P2Y purinoceptor 14 | 2.63 | 4.63 |
| PCDH17 | Protocadherin-17 | 1.7 | 7.36 |
| PDGFRB | Platelet-derived growth factor receptor beta | 2.68 | 10.48 |
| PECAM1 | Platelet endothelial cell adhesion molecule | 7.7 | 10.85 |
| PLXND1 | Plexin-D1 | 5.02 | 11.68 |
| PPAP2B | Lipid phosphate phosphohydrolase 3 | 4.17 | 12.46 |
| PTAFR | Platelet-activating factor receptor | 3.01 | 4.81 |
| PTGER3 | Prostaglandin E2 receptor EP3 subtype | 4.76 | 10.26 |
| PTH1R | Parathyroid hormone/parathyroid hormone-related peptide receptor | 2.35 | 7.31 |
| RAMP3 | Receptor activity-modifying 3protein | 1.79 | 8.84 |
| ROR2 | Tyrosine-protein kinase transmembrane receptor ROR2 | 3.2 | 5.98 |
| S1PR1 | Sphingosine 1-phosphate receptor 1 | 5.17 | 6.51 |
| SCARB1 | Scavenger receptor class B member 1 | 3.01 | 10.4 |
| SLC13A3 | Solute carrier family 13 member 3 | 3.32 | 7.89 |
| SLC16A4 | Monocarboxylate transporter 5 | 2.88 | 12.54 |
| SLC17A3 | Sodium-dependent phosphate transport protein 4 | 1.58 | 11.55 |
| SLC28A1 | Sodium/nucleoside cotransporter 1 | 4.76 | 6.3 |
| SLC2A5 | Solute carrier family 2, facilitated glucose transporter member 5 | 2.74 | 8.5 |
| SLC39A14 | Zinc transporter ZIP14 | 2.66 | 11.63 |
| SLC6A13 | Sodium- and chloride-dependent GABA transporter 2 | 2.75 | 7.44 |
| SLC7A8 | Large neutral amino acids transporter small subunit 2 | 5.03 | 10.46 |
| SLCO2A1 | Solute carrier organic anion transporter family member 2A1 | 3.46 | 8.06 |
| TBXA2R | Thromboxane A2 receptor | 4.01 | 3.64 |
| TGFBR2 | TGF-beta receptor type-2 | 10.41 | 10.94 |
| THSD7A | Thrombospondin type-1 domain-containing protein 7A | 3.05 | 8 |
| TIE1 | Tyrosine-protein kinase receptor Tie-1 | 2.04 | 4.41 |
| TNFRSF1A | Tumor necrosis factor-binding protein 1 | 6.84 | 10.52 |
| TNFSF12 | Tumor necrosis factor ligand superfamily member 12, secreted form | 4.35 | 4.1 |
| VAMP5 | Vesicle-associated membrane protein 5 | 3.49 | 6.18 |

TABLE 9 antigen markers expressed on the surface of both liver tumor cells and T-cells

| Antigen | Protein Name | Relative expression in T-Cell | Relative Expression in colon cancer cells |
|---|---|---|---|
| ABCB4 | Multidrug resistance protein 3 | 2.02 | 3.7 |
| ADAM10 | Disintegrin and metalloproteinase domain-containing protein 10 | 9.42 | 9.41 |
| ATR | Anthrax toxin receptor 1 | 6.98 | 9.9 |
| BST2 | Bone marrow stromal antigen 2 | 7.38 | 12.45 |
| BTN3A3 | Butyrophilin subfamily 3 member A3 | 9.72 | 7.48 |
| C9 | Complement component C9b | 2.41 | 10.52 |
| CHRND | Acetylcholine receptor subunit delta | 2.43 | 4.05 |
| CLDN14 | Claudin-14 | 2.79 | 2.4 |
| EPOR | Erythropoietin receptor | 4.67 | 10.55 |
| ERBB2 | Receptor tyrosine-protein kinase erbB-2 | 2.36 | 14.12 |
| F2RL3 | Proteinase-activated receptor 4 | 2.17 | 2.61 |
| GJB1 | Gap junction beta-1 protein | 2.96 | 9.4 |
| GPR126 | G-protein coupled receptor 126 | 2.23 | 11.32 |
| IL1R1 | Interleukin-1 receptor type 1, soluble form | 2.88 | 12.57 |
| ITGB1 | Integrin beta-1 | 8.76 | 13.48 |
| NAALADL1 | N-acetylated-alpha-linked acidic dipeptidase-like protein | 3.03 | 1.46 |
| OR7A5 | Olfactory receptor 7A5 | 1.51 | 3.83 |
| SGCD | Delta-sarcoglycan | 3.99 | 7.21 |
| SIGLEC6 | Sialic acid-binding Ig-like lectin 6 | 3.57 | 3.49 |
| SLC38A3 | Sodium-coupled neutral amino acid transporter 3 | 1.89 | 8.91 |
| TFR2 | Transferrin receptor protein 2 | 2.74 | 10.47 |

TABLE 10 antigen markers expressed on the surface of both lung tumor cells and T-cells

| Antigen | Protein Name | Relative expression in T-Cell | Relative Expression in colon cancer cells |
|---|---|---|---|
| ABCB6 | ATP-binding cassette sub-family B member 6, mitochondrial | 2.88 | 9.82 |
| ABCC1 | Multidrug resistance-associated protein 1 | 7.05 | 8.16 |

TABLE 10-continued antigen markers expressed on the surface of both lung tumor cells and T-cells

| Antigen | Protein Name | Relative expression in T-Cell | Relative Expression in colon cancer cells |
|---|---|---|---|
| ACCN1 | Acid-sensing ion channel 2 | 2.25 | 0.8 |
| ADAM23 | Disintegrin and metalloproteinase domain-containing protein 23 | 2.51 | 4.73 |
| ADORA1 | Adenosine receptor A1 | 4.49 | 8.22 |
| ADORA2B | Adenosine receptor A2b | 1.66 | 7.5 |
| AJAP1 | Adherens junction-associated protein 1 | 1.85 | 6.24 |
| APLP1 | C30 | 2.22 | 6.02 |
| AQP3 | Aquaporin-3 | 8.38 | 13.88 |
| ATP10D | Probable phospholipid-transporting ATPase VD | 2.43 | 7.4 |
| ATP1A3 | Sodium/potassium-transporting ATPase subunit alpha-3 | 3.01 | 3.13 |
| ATP1B2 | Sodium/potassium-transporting ATPase subunit beta-2 | 3.21 | 3.8 |
| ATP1B3 | Sodium/potassium-transporting ATPase subunit beta-3 | 8.6 | 14.26 |
| AXL | Tyrosine-protein kinase receptor UFO | 2.51 | 9.58 |
| BEST1 | Bestrophin-1 | 2.49 | 4.44 |
| BTC | Betacellulin | 2.86 | 4.59 |
| BTN3A1 | Butyrophilin subfamily 3 member A1 | 10.66 | 11.63 |
| CALCR | Calcitonin receptor | 2.95 | 8.62 |
| CALCRL | Calcitonin gene-related peptide type 1 receptor | 2.12 | 7.67 |
| CCR1 | C-C chemokine receptor type 1 | 2.63 | 9.77 |
| CD163 | Soluble CD163 | 2.66 | 8.76 |
| CD300A | CMRF35-like molecule 8 | 7.96 | 4.23 |
| CD300A | CMRF35-like molecule 8 | 2.29 | 4.23 |
| CD68 | Macrosialin | 4.02 | 8.92 |
| CD74 | HLA class II histocompatibility antigen gamma chain | 9.1 | 13.44 |
| CD86 | T-lymphocyte activation antigen CD86 | 2.93 | 5.04 |
| CHRNA3 | Neuronal acetylcholine receptor subunit alpha-3 | 2.54 | 4.62 |
| CHRNA3 | Neuronal acetylcholine receptor subunit alpha-3 | 2 | 4.62 |
| CKAP4 | Cytoskeleton-associated protein 4 | 6.15 | 11.94 |
| CLCA2 | Calcium-activated chloride channel regulator 2, 35 kDa form | 2.99 | 9.81 |
| CLDN5 | Claudin-5 | 3.66 | 7.73 |
| CLSTN1 | CTF1-alpha | 8.26 | 12.51 |
| CNIH3 | Protein cornichon homolog 3 | 2.7 | 6.09 |
| COMT | Catechol O-methyltransferase | 7.78 | 12.13 |
| CSPG5 | Chondroitin sulfate proteoglycan 5 | 2.84 | 5.69 |
| CXCR6 | C-X-C chemokine receptor type 6 | 3.16 | 3.91 |
| CXCR7 | Atypical chemokine receptor 3 | 2.5 | 8.95 |
| DCHS1 | Protocadherin-16 | 4.29 | 2.28 |
| DSC3 | Desmocollin-2 | 2.82 | 8.95 |
| DSG3 | Desmoglein-3 | 2.23 | 10.73 |
| EGFR | Epidermal growth factor receptor | 3.8 | 10.92 |
| FAT2 | Protocadherin Fat 2 | 2.25 | 9.29 |
| FCER1G | High affinity immunoglobulin epsilon receptor subunit gamma | 3.13 | 8.96 |
| FCGR1A | High affinity immunoglobulin gamma Fc receptor I | 2.09 | 9.65 |
| FLT4 | Vascular endothelial growth factor receptor 3 | 3.19 | 3.36 |
| FPR2 | N-formyl peptide receptor 2 | 2.9 | 7.14 |
| FURIN | Furin | 6.42 | 7.5 |
| FZD6 | Frizzled-6 | 2.64 | 10.45 |
| GABBR2 | Gamma-aminobutyric acid type B receptor subunit 2 | 3.79 | 9.19 |
| GABRB3 | Gamma-aminobutyric acid receptor subunit beta-3 | 2.46 | 8.83 |
| GABRD | Gamma-aminobutyric acid receptor subunit delta | 1.72 | 1.67 |
| GABRE | Gamma-aminobutyric acid receptor subunit epsilon | 1.85 | 9.18 |
| GIPR | Gastric inhibitory polypeptide receptor | 3.43 | 5.37 |
| GJA1 | Gap junction alpha-1 protein | 2.84 | 12.65 |
| GJB3 | Gap junction beta-3 protein | 3.72 | 3.79 |
| GJB5 | Gap junction beta-5 protein | 1.77 | 6.69 |
| GLRA2 | Glycine receptor subunit alpha-2 | 2.26 | 6.15 |
| GPR109B | Hydroxycarboxylic acid receptor 3 | 1.77 | 2.91 |
| GPR12 | G-protein coupled receptor 12 | 2 | 1.76 |
| GPR176 | Probable G-protein coupled receptor 176 | 2.05 | 3.86 |
| GPR50 | Melatonin-related receptor | 2.26 | 3.16 |
| GRIK1 | Glutamate receptor ionotropic, kainate 1 | 4.66 | 5.65 |
| GRIN2D | Glutamate receptor ionotropic, NMDA 2D | 2.17 | 2.32 |
| HCRTR1 | Orexin receptor type 1 | 2.34 | 3.56 |
| HLA-DPA1 | HLA class II histocompatibility antigen, DP alpha 1 chain | 8.31 | 12.86 |
| HLA-DQA1 | HLA class II histocompatibility antigen, DQ alpha 1 chain | 2.35 | 11.44 |
| HLA-DQB1 | HLA class II histocompatibility antigen, DQ beta 1 chain | 7.4 | 12.71 |
| HLA-DRA | HLA class II histocompatibility antigen, DR alpha chain | 6.42 | 14.18 |
| HLA-DRB4 | HLA class II histocompatibility antigen, DR beta 4 chain | 2.72 | 11.24 |
| IGSF9B | Protein turtle homolog B | 3.92 | 2.81 |
| IL1RAP | Interleukin-1 receptor accessory protein | 3.99 | 11.4 |
| IL1RL1 | Interleukin-1 receptor-like 1 | 2.55 | 5.15 |
| IL4R | Soluble interleukin-4 receptor subunit alpha | 4.15 | 9.56 |
| IL7R | Interleukin-7 receptor subunit alpha | 11.62 | 11.26 |
| ITGA6 | Integrin alpha-6 light chain | 7.99 | 12.76 |
| JPH3 | Junctophilin-3 | 2.34 | 2.5 |
| KCNS3 | Potassium voltage-gated channel subfamily S member 3 | 2.45 | 8.91 |
| KIT | Mast/stem cell growth factor receptor Kit | 2.85 | 8.67 |
| KITLG | Soluble KIT ligand | 2.58 | 7.27 |
| LILRB3 | Leukocyte immunoglobulin-like receptor subfamily B member 3 | 5.65 | 8.03 |
| LILRB4 | Leukocyte immunoglobulin-like receptor subfamily B member 4 | 3.12 | 10.44 |
| LPAR1 | Lysophosphatidic acid receptor 1 | 4.12 | 5.47 |
| LPHN3 | Latrophilin-3 | 2.85 | 6.43 |
| MMP24 | Processed matrix metalloproteinase-24 | 5.19 | 5.73 |
| MPZ | Myelin protein P0 | 2.56 | 3.63 |
| MUC4 | Mucin-4 beta chain | 3.04 | 10.34 |
| NCKAP1L | Nck-associated protein 1-like | 6.69 | 7.51 |
| NKG7 | Protein NKG7 | 10.92 | 3.66 |
| NOTCH2 | Notch 2 intracellular domain | 6.62 | 6.22 |
| NRCAM | Neuronal cell adhesion molecule | 2.78 | 8.16 |
| NRG2 | Neuregulin-2 | 3.55 | 9.22 |
| NRXN1 | Neurexin-1 | 2.56 | 5.33 |
| NTRK2 | BDNF/NT-3 growth factors receptor | 2.56 | 10.7 |

TABLE 10-continued antigen markers expressed on the surface of both lung tumor cells and T-cells

| Antigen | Protein Name | Relative expression in T-Cell | Relative Expression in colon cancer cells |
|---|---|---|---|
| NTSR1 | Neurotensin receptor type 1 | 1.74 | 9.74 |
| P2RY1 | P2Y purinoceptor 1 | 2.34 | 7.62 |
| P2RY6 | P2Y purinoceptor 6 | 4.27 | 5.79 |
| PCDH8 | Protocadherin-8 | 2.67 | 9.29 |
| PCDHA3 | Protocadherin alpha-3 | 2.14 | 3.54 |
| PIK3IP1 | Phosphoinositide-3-kinase-interacting protein 1 | 8.68 | 3.47 |
| PLXNA2 | Plexin-A2 | 2.88 | 7.3 |
| PRR4 | Processed poliovirus receptor-related protein 4 | 3.24 | 8.02 |
| PTPRE | Receptor-type tyrosine-protein phosphatase epsilon | 6.03 | 7.92 |
| PTPRO | Receptor-type tyrosine-protein phosphatase U | 10.46 | 9.01 |
| PTPRU | Receptor-type tyrosine-protein phosphatase U | 3.72 | 6.18 |
| RABAC1 | Prenylated Rab acceptor protein 1 | 7.54 | 8.82 |
| SCTR | Secretin receptor | 2.2 | 2.48 |
| SECTM1 | Secreted and transmembrane protein 1 | 2.42 | 6.9 |
| SGCE | Epsilon-sarcoglycan | 2.15 | 9.65 |
| SGCG | Gamma-sarcoglycan | 2.56 | 5.74 |
| SLC16A3 | Monocarboxylate transporter 4 | 5.89 | 12.72 |
| SLC16A7 | Monocarboxylate transporter 2 | 5.39 | 6.97 |
| SLC20A2 | Sodium-dependent phosphate transporter 2 | 2.51 | 12.69 |
| SLC26A4 | Pendrin | 3.57 | 9.39 |
| SLC2A1 | Solute carrier family 2, facilitated glucose transporter member 1 | 5.1 | 5.83 |
| SLC4A7 | Sodium bicarbonate cotransporter 3 | 4.89 | 8.7 |
| SLCO3A1 | Solute carrier organic anion transporter family member 3A1 | 4.87 | 7.91 |
| SYNE2 | Nesprin-2 | 9.43 | 10.43 |
| TACR2 | Substance-K receptor | 2.23 | 6.68 |
| TFRC | Transferrin receptor protein 1, serum form | 7.32 | 14.31 |
| TMEFF1 | Tomoregulin-1 | 3.22 | 5.05 |
| TMPRSS11D | Transmembrane protease serine 11D catalytic chain | 2.35 | 8.32 |

TABLE 11 antigen markers expressed on the surface of both ovary tumor cells and T-cells;

| Antigen | Protein Name | Relative expression in T-Cell | Relative Expression in colon cancer cells |
|---|---|---|---|
| ACVR2B | Activin receptor type-2B | 2.1 | 4.26 |
| ADAM28 | Disintegrin and metalloproteinase domain-containing protein 28 | 2.83 | 9.22 |
| ADRA2C | Alpha-2C adrenergic receptor | 4.6 | 5.13 |
| ATP2B1 | Plasma membrane calcium-transporting ATPase 1 | 5.3 | 11.49 |
| ATP2B4 | Plasma membrane calcium-transporting ATPase 4 | 8.21 | 10.1 |
| ATP7A | Copper-transporting ATPase 1 | 3.91 | 7.31 |
| CD200 | OX-2 membrane glycoprotein | 2.83 | 10.51 |
| CD47 | Leukocyte surface antigen CD47 | 9.88 | 10.42 |
| CDH12 | Cadherin-12 | 2.31 | 5.91 |
| CDH18 | Cadherin-18 | 2.28 | 4.79 |
| CDH2 | Cadherin-2 | 3.72 | 11.97 |
| CDH6 | Cadherin-6 | 2.77 | 8.68 |
| CDIPT | CDP-diacylglycerol--inositol 3-phosphatidyltransferase | 8.88 | 10.73 |
| CELSR2 | Cadherin EGF LAG seven-pass G-type receptor 2 | 2.66 | 8.38 |
| CHRNA1 | Acetylcholine receptor subunit alpha | 2.42 | 5.71 |
| CLSTN3 | Calsyntenin-3 | 3.87 | 4.54 |
| CX3CR1 | CX3C chemokine receptor 1 | 9 | 11.42 |
| DDR1 | Epithelial discoidin domain-containing receptor 1 | 3.83 | 12.36 |
| EPHA1 | Ephrin type-A receptor 1 | 2.02 | 5.96 |
| EPHA4 | Ephrin type-A receptor 4 | 2.39 | 8.56 |
| ERBB4 | ERBB4 intracellular domain | 2.29 | 9.76 |
| FGFR1 | Fibroblast growth factor receptor 1 | 5.42 | 11.4 |
| FGFR3 | Fibroblast growth factor receptor 3 | 2.95 | 11.35 |
| FZD2 | Frizzled-2 | 1.91 | 8.06 |
| FZD7 | Frizzled-7 | 2.55 | 10.24 |
| GJA4 | Gap junction alpha-4 protein | 2.04 | 6.7 |
| GPR125 | Probable G-protein coupled receptor 125 | 2.35 | 7.88 |
| GPR56 | GPR56 C-terminal fragment | 8.6 | 11.27 |
| GPR64 | G-protein coupled receptor 64 | 2.04 | 8.57 |
| GPRC5B | G-protein coupled receptor family C group 5 member B | 1.96 | 10.29 |
| GRIA2 | Glutamate receptor 2 | 1.96 | 11.78 |
| GRIK5 | Glutamate receptor ionotropic, kainate 5 | 5.79 | 3.36 |
| GRIN2A | Glutamate receptor ionotropic, NMDA 2A | 1.68 | 2.96 |
| HEG1 | Protein HEG homolog 1 | 4.8 | 10.1 |
| HRH1 | Histamine H1 receptor | 2.31 | 6.26 |
| HTR3A | 5-hydroxytryptamine receptor 3A | 2.1 | 9.35 |
| IFITM2 | Interferon-induced transmembrane protein 2 | 10.27 | 11.36 |
| IFITM3 | Interferon-induced transmembrane protein 3 | 8.55 | 13.48 |
| KCNH2 | Potassium voltage-gated channel subfamily H member 2 | 2.09 | 5.36 |
| KCNJ12 | ATP-sensitive inward rectifier potassium channel 12 | 2.29 | 2.21 |
| L1CAM | Neural cell adhesion molecule L1 | 2.61 | 8.73 |
| LGR5 | Leucine-rich repeat-containing G-protein coupled receptor 5 | 2.45 | 12.12 |
| LPHN1 | Latrophilin-1 | 4.5 | 5.56 |
| LPHN1 | Latrophilin-1 | 1.63 | 5.56 |
| LPHN2 | Latrophilin-2 | 1.93 | 7.14 |
| MGA | Glucoamylase | 5.15 | 5.65 |
| NEO1 | Neogenin | 1.85 | 10.31 |
| NPTN | Neuroplastin | 8.46 | 13.14 |
| NRG1 | Neuregulin-1 | 2.61 | 6.53 |
| NTRK1 | High affinity nerve growth factor receptor | 2.09 | 2.49 |
| PCDH7 | Protocadherin-7 | 2.89 | 8.52 |
| PCDH9 | Protocadherin-9 | 2.99 | 6.15 |
| PDGFRA | Platelet-derived growth factor receptor alpha | 3.69 | 8.44 |
| PDGFRA | Platelet-derived growth factor receptor alpha | 2.26 | 8.44 |
| PLXNB1 | Plexin-B1 | 2.26 | 6.71 |
| PLXNB2 | Plexin-B2 | 3.1 | 10.68 |
| PODXL | Podocalyxin | 2.73 | 11.41 |
| PRSS8 | Prostasin heavy chain | 2.07 | 10.77 |
| PTH2R | Parathyroid hormone 2 receptor | 1.85 | 8.67 |
| PVRL3 | Poliovirus receptor-related protein 3 | 2.56 | 10.15 |
| SCNN1A | Amiloride-sensitive sodium channel subunit alpha | 5.97 | 10.63 |

TABLE 11-continued antigen markers expressed on the surface of both ovary tumor cells and T-cells;

| Antigen | Protein Name | Relative expression in T-Cell | Relative Expression in colon cancer cells |
|---|---|---|---|
| SLC29A2 | Equilibrative nucleoside transporter 2 | 2.93 | 1.89 |
| SSPN | Sarcospan | 3.49 | 9.16 |
| STAR | Heat-stable enterotoxin receptor | 2.36 | 7.13 |
| TGFA | Transforming growth factor alpha | 2.64 | 1.71 |
| TMED1 | Transmembrane emp24 domain-containing protein 1 | 4.79 | 9.3 |
| TMEM59 | Transmembrane protein 59 | 8.83 | 12.74 |
| TNFRSF25 | Tumor necrosis factor receptor superfamily member 25 | 7.53 | 4.27 |
| TYRO3 | Tyrosine-protein kinase receptor TYRO3 | 4.11 | 10.27 |
| UPK2 | Uroplakin-2 | 2.29 | 7.49 |

TABLE 12 antigen markers expressed on the surface of both pancreas tumor cells and T-cells

| Antigen | Protein Name | Relative expression in T-Cell | Relative Expression in colon cancer cells |
|---|---|---|---|
| ADAM9 | Disintegrin and metalloproteinase domain-containing protein 9 | 3.49 | 10.99 |
| B4GALT1 | Processed beta-1,4-galactosyltransferase 1 | 7.44 | 8.99 |
| BDKRB2 | B2 bradykinin receptor | 2.52 | 4.44 |
| CA9 | Carbonic anhydrase 9 | 3.34 | 11.9 |
| CACNA1C | Voltage-dependent L-type calcium channel subunit alpha-1C | 2.36 | 4.54 |
| CD58 | Lymphocyte function-associated antigen 3 | 6.51 | 8.16 |
| CDH11 | Cadherin-11 | 2.85 | 10.38 |
| CDH3 | Cadherin-3 | 1.96 | 10.91 |
| CFTR | Cystic fibrosis transmembrane conductance regulator | 3.12 | 11.45 |
| CHRNB4 | Neuronal acetylcholine receptor subunit beta-4 | 2.38 | 0.66 |
| CLDN10 | Claudin-10 | 2.36 | 11.5 |
| CXCR4 | C-X-C chemokine receptor type 4 | 11.74 | 10.98 |
| DAG1 | Beta-dystroglycan | 5.65 | 10.98 |
| DDR2 | Discoidin domain-containing receptor 2 | 2.34 | 8 |
| DMPK | Myotonin-protein kinase | 3.7 | 4.21 |
| FAT1 | Protocadherin Fat 1, nuclear form | 3.3 | 12.45 |
| HTR2B | 5-hydroxytryptamine receptor 2B | 2.22 | 7.73 |
| LDLR | Low-density lipoprotein receptor | 2.93 | 12.14 |
| NCKAP1 | Nck-associated protein 1 | 3.34 | 11.99 |
| PMP22 | Peripheral myelin protein 22 | 2.09 | 10.66 |
| PNPLA2 | Patatin-like phospholipase domain-containing protein 2 | 5.46 | 3.45 |
| PNPLA2 | Patatin-like phospholipase domain-containing protein 2 | 2.35 | 3.45 |
| TEK | Angiopoietin-1 receptor | 3.87 | 8.52 |
| TGFBR1 | TGF-beta receptor type-1 | 2.17 | 4.3 |

TABLE 13 antigen markers expressed on the surface of both prostate tumor cells and T-cells

| Antigen | Protein Name | Relative expression in T-Cell | Relative Expression in colon cancer cells |
|---|---|---|---|
| ACCN3 | Acid-sensing ion channel 3 | 2.47 | 2.03 |
| ADRB1 | Beta-1 adrenergic receptor | 2.85 | 5.09 |
| ADRB2 | Beta-2 adrenergic receptor | 5.74 | 9.43 |
| AGTR1 | Type-1 angiotensin II receptor | 2.81 | 11.62 |
| APLP2 | Amyloid-like protein 2 | 7.06 | 13.06 |
| ATP1A2 | Sodium/potassium-transporting ATPase subunit alpha-2 | 3.07 | 7.55 |
| ATP8A1 | Probable phospholipid-transporting ATPase IA | 7.23 | 9.16 |
| CADM1 | Cell adhesion molecule 1 | 4.42 | 12.28 |
| CHRM3 | Muscarinic acetylcholine receptor M3 | 1.85 | 9.23 |
| CHRNA2 | Neuronal acetylcholine receptor subunit alpha-2 | 2.83 | 5.34 |
| CXADR | Coxsackievirus and adenovirus receptor | 3.31 | 12.74 |
| DPP4 | Dipeptidyl peptidase 4 soluble form | 6.42 | 11.22 |
| ECE1 | Endothelin-converting enzyme 1 | 7.14 | 4.7 |
| ENPP4 | Bis(5'-adenosyl)-triphosphatase ENPP4 | 6.57 | 7.49 |
| EPHA3 | Ephrin type-A receptor 3 | 2.84 | 7.85 |
| ERG | Potassium voltage-gated channel subfamily H member 2 | 2.72 | 11.3 |
| FAM38A | Piezo-type mechanosensitive ion channel component 1 | 8.4 | 9.57 |
| FOLH1 | Glutamate carboxypeptidase 2 | 2.96 | 13.18 |
| GABRA2 | Gamma-aminobutyric acid receptor subunit alpha-2 | 3 | 6.42 |
| GHR | Growth hormone-binding protein | 2.52 | 6.84 |
| GPM6B | Neuronal membrane glycoprotein M6-b | 3.22 | 6.56 |
| GPR116 | Probable G-protein coupled receptor 116 | 3.69 | 10.09 |
| HBEGF | Heparin-binding EGF-like growth factor | 2.87 | 8.12 |
| JAM3 | Junctional adhesion molecule C | 4.29 | 7.26 |
| KCND3 | Potassium voltage-gated channel subfamily D member 3 | 3.09 | 9.77 |
| LIFR | Leukemia inhibitory factor receptor | 2.71 | 6.8 |
| LRBA | Lipopolysaccharide-responsive and beige-like anchor protein | 5.35 | 9.26 |
| MME | Neprilysin | 2.62 | 8.05 |
| NOV | Plexin-A1 | 2.43 | 10.41 |
| NRP1 | Neuropilin-1 | 3.17 | 7.85 |
| OPRK1 | Kappa-type opioid receptor | 2.07 | 4.92 |
| PLXNB3 | Plexin-B3 | 2.57 | 3.59 |
| PPAP2A | Lipid phosphate phosphohydrolase 1 | 3.6 | 11.55 |
| SCAMP5 | Secretory carrier-associated membrane protein 5 | 3.03 | 8.43 |
| SLC23A2 | Solute carrier family 23 member 2 | 3.55 | 7.04 |
| SLC2A4 | Solute carrier family 2, facilitated glucose transporter member 4 | 2.67 | 5.96 |
| SLC36A1 | Proton-coupled amino acid transporter 1 | 3.38 | 9.28 |
| SLC4A4 | Electrogenic sodium bicarbonate cotransporter 1 | 3.14 | 11.29 |
| STIM1 | Stromal interaction molecule 1 | 3.68 | 6.51 |
| TMPRSS2 | Transmembrane protease serine 2 catalytic chain | 2.67 | 9.63 |
| TRPV6 | Transient receptor potential cation channel subfamily V member 6 | 4.84 | 8.09 |

TABLE 13-continued antigen markers expressed on the surface of both prostate tumor cells and T-cells

| Antigen | Protein Name | Relative expression in T-Cell | Relative Expression in colon cancer cells |
|---|---|---|---|
| VIPR1 | Vasoactive intestinal polypeptide receptor 1 | 4.41 | 7.73 |
| YIPF3 | Protein YIPF3, 36 kDa form III | 4 | 4.3 |

TABLE 14 antigen markers expressed on the surface of T-cells and overexpressed in liquid tumor cells (ALL, AML, CML, MDS, CLL, CTRL)

| Antigen | Protein Name | Relative expression on T cell |
|---|---|---|
| CD63 | CD63 antigen | 0.83 |
| CXCR4 | C-X-C chemokine receptor type 4 | 0.82 |
| IFITM2 | Interferon-induced transmembrane protein 2 | 0.82 |
| ITM2B | Bri23 peptide | 0.81 |
| BTF3 | Butyrophilin subfamily 3 member A2 | 0.8 |
| HLA-DRB1 | HLA class II histocompatibility antigen, DRB1-12 beta chain | 0.79 |
| HLA-DRA | HLA class II histocompatibility antigen, DR alpha chain | 0.78 |
| IFITM3 | Interferon-induced transmembrane protein 3 | 0.78 |
| NKG7 | Protein NKG7 | 0.78 |
| FCER1G | High affinity immunoglobulin epsilon receptor subunit gamma | 0.78 |
| IFITM1 | Interferon-induced transmembrane protein 1 | 0.76 |
| NPTN | Neuroplastin | 0.76 |
| GYPC | Glycophorin-C | 0.76 |
| GPR160 | Probable G-protein coupled receptor 160 | 0.76 |
| HLA-DPB1 | HLA class II histocompatibility antigen, DP beta 1 chain | 0.75 |
| BRI3 | CT-BRI3 | 0.75 |
| SLC38A2 | Sodium-coupled neutral amino acid transporter 2 | 0.74 |
| C5AR1 | C5a anaphylatoxin chemotactic receptor 1 | 0.74 |
| CDIPT | CDP-diacylglycerol--inositol 3-phosphatidyltransferase | 0.73 |
| TNFSF13B | Tumor necrosis factor ligand superfamily member 13b, soluble form | 0.73 |
| CSF3R | Granulocyte colony-stimulating factor receptor | 0.73 |
| HLA-DPA1 | HLA class II histocompatibility antigen, DP alpha 1 chain | 0.71 |
| CD164 | Sialomucin core protein 24 | 0.71 |
| CD97 | CD97 antigen subunit beta | 0.7 |
| C3AR1 | C3a anaphylatoxin chemotactic receptor 1 | 0.69 |
| P2RY8 | P2Y purinoceptor 8 | 0.68 |
| BSG | Basigin | 0.68 |
| APLP2 | Amyloid-like protein 2 | 0.67 |
| TFRC | Transferrin receptor protein 1, serum form | 0.67 |
| MGAM | Glucoamylase | 0.67 |
| GYPA | Glycophorin-A | 0.67 |
| TMED10 | Transmembrane emp24 domain-containing protein 10 | 0.66 |
| FCGRT | IgG receptor FcRn large subunit p51 | 0.66 |
| CKAP4 | Cytoskeleton-associated protein 4 | 0.66 |
| DYSF | Dysferlin | 0.66 |
| SPPL2A | Signal peptide peptidase-like 2A | 0.65 |
| LAMP2 | Lysosome-associated membrane glycoprotein 2 | 0.65 |
| SLC7A5 | Large neutral amino acids transporter small subunit 1 | 0.65 |
| TNFRSF1B | Tumor necrosis factor-binding protein 2 | 0.64 |
| TREM1 | Triggering receptor expressed on myeloid cells 1 | 0.64 |
| GPR183 | G-protein coupled receptor 183 | 0.63 |
| SERINC3 | Serine incorporator 3 | 0.63 |
| CD58 | Lymphocyte function-associated antigen 3 | 0.63 |
| GYPB | Glycophorin-B | 0.63 |
| RABAC1 | Prenylated Rab acceptor protein 1 | 0.62 |
| KCNH2 | Potassium voltage-gated channel subfamily H member 2 | 0.62 |
| FPR1 | fMet-Leu-Phe receptor | 0.62 |
| P2RY13 | P2Y purinoceptor 13 | 0.62 |
| CLEC5A | C-type lectin domain family 5 member A | 0.62 |
| SLC7A7 | Y + L amino acid transporter 1 | 0.61 |
| MICB | MHC class I polypeptide-related sequence B | 0.61 |
| CD300LF | CMRF35-like molecule 1 | 0.61 |
| GJB6 | Gap junction beta-6 protein | 0.61 |
| ATP1A1 | Sodium/potassium-transporting ATPase subunit alpha-1 | 0.6 |
| PTGER4 | Prostaglandin E2 receptor EP4 subtype | 0.6 |
| CD8A | T-cell surface glycoprotein CD8 alpha chain | 0.6 |
| PTGER2 | Prostaglandin E2 receptor EP2 subtype | 0.6 |
| GPR97 | Probable G-protein coupled receptor 97 | 0.6 |
| IMP3 | Signal peptide peptidase-like 2A | 0.59 |
| LAMP1 | Lysosome-associated membrane glycoprotein 1 | 0.59 |
| LILRB3 | Leukocyte immunoglobulin-like receptor subfamily B member 3 | 0.59 |
| GPR109B | Hydroxycarboxylic acid receptor 3 | 0.58 |
| SAT2 | Sodium-coupled neutral amino acid transporter 2 | 0.58 |
| GPR65 | Psychosine receptor | 0.58 |
| AMICA1 | Junctional adhesion molecule-like | 0.58 |
| PAG1 | Phosphoprotein associated with glycosphingolipid-enriched microdomains 1 | 0.58 |
| ENPP4 | Bis(5'-adenosyl)-triphosphatase ENPP4 | 0.57 |
| SLC40A1 | Solute carrier family 40 member 1 | 0.57 |
| OLR1 | Oxidized low-density lipoprotein receptor 1, soluble form | 0.57 |
| LRRC33 | Negative regulator of reactive oxygen species | 0.56 |
| IL7R | Interleukin-7 receptor subunit alpha | 0.56 |
| LAIR1 | Leukocyte-associated immunoglobulin-like receptor 1 | 0.56 |
| ITM2C | CT-BRI3 | 0.56 |
| GPR84 | G-protein coupled receptor 84 | 0.56 |
| SLC12A7 | Solute carrier family 12 member 7 | 0.55 |
| PTAFR | Platelet-activating factor receptor | 0.55 |
| CD33 | Myeloid cell surface antigen CD33 | 0.55 |
| SLC22A16 | Solute carrier family 22 member 16 | 0.55 |
| CCR7 | C-C chemokine receptor type 7 | 0.54 |
| TLR1 | Toll-like receptor 1 | 0.54 |
| TGOLN2 | Trans-Golgi network integral membrane protein 2 | 0.54 |
| YIPF3 | Protein YIPF3, 36 kDa form III | 0.54 |
| BST2 | Bone marrow stromal antigen 2 | 0.54 |
| MAGT1 | Magnesium transporter protein 1 | 0.54 |
| TMEM173 | Stimulator of interferon genes protein | 0.54 |
| ERMAP | Erythroid membrane-associated protein | 0.54 |
| CEACAM1 | Carcinoembryonic antigen-related cell adhesion molecule 1 | 0.54 |
| NIPA2 | Magnesium transporter NIPA2 | 0.53 |
| PECAM1 | Platelet endothelial cell adhesion molecule | 0.53 |
| CD1D | Antigen-presenting glycoprotein CD1d | 0.53 |
| TMEM59 | Transmembrane protein 59 | 0.53 |
| NCKAP1L | Nck-associated protein 1-like | 0.53 |
| FAS | Tumor necrosis factor receptor superfamily member 6 | 0.53 |
| IL6R | Interleukin-6 receptor subunit alpha | 0.53 |
| TNFRSF1A | Tumor necrosis factor-binding protein 1 | 0.53 |
| KEL | Kell blood group glycoprotein | 0.53 |
| TMEM149 | IGF-like family receptor 1 | 0.52 |
| SLC3A2 | 4F2 cell-surface antigen heavy chain | 0.52 |
| ORAI1 | Calcium release-activated calcium channel protein 1 | 0.52 |

TABLE 14-continued antigen markers expressed on the surface of T-cells and overexpressed in liquid tumor cells (ALL, AML, CML, MDS, CLL, CTRL)

| Antigen | Protein Name | Relative expression on T cell |
|---|---|---|
| XKR8 | XK-related protein 8, processed form | 0.52 |
| C9orf46 | Plasminogen receptor (KT) | 0.52 |
| TMEM127 | Transmembrane protein 127 | 0.52 |
| SLC2A1 | Solute carrier family 2, facilitated glucose transporter member 1 | 0.52 |
| FCGR1B | High affinity immunoglobulin gamma Fc receptor IB | 0.52 |
| CXCR2 | C-X-C chemokine receptor type 2 | 0.52 |
| IL4R | Soluble interleukin-4 receptor subunit alpha | 0.51 |
| HSD17B7 | 3-keto-steroid reductase | 0.51 |
| SEMA4D | Semaphorin-4D | 0.51 |
| ZDHHC5 | Palmitoyltransferase ZDHHC5 | 0.51 |
| ADRB2 | Beta-2 adrenergic receptor | 0.51 |
| S1PR4 | Sphingosine 1-phosphate receptor 4 | 0.51 |
| PILRA | Paired immunoglobulin-like type 2 receptor alpha | 0.51 |
| LTB4R | Leukotriene B4 receptor 1 | 0.51 |
| SORT1 | Sortilin | 0.51 |
| SLCO4C1 | Solute carrier organic anion transporter family member 4C1 | 0.51 |
| ANO10 | Anoctamin-10 | 0.51 |
| CLSTN1 | CTF1-alpha | 0.5 |
| RHBDF2 | Inactive rhomboid protein 2 | 0.5 |
| CCR1 | C-C chemokine receptor type 1 | 0.5 |
| EPCAM | Epithelial cell adhesion molecule | 0.49 |
| PNPLA2 | Patatin-like phospholipase domain-containing protein 2 | 0.49 |
| SLC12A6 | Solute carrier family 12 member 6 | 0.49 |
| SLC30A1 | Zinc transporter 1 | 0.49 |
| GPR27 | Probable G-protein coupled receptor 27 | 0.49 |
| EPOR | Erythropoietin receptor | 0.48 |
| CD79A | B-cell antigen receptor complex-associated protein alpha chain | 0.48 |
| HLA-DQB1 | HLA class II histocompatibility antigen, DQ beta 1 chain | 0.48 |
| HBP1 | Glycosylphosphatidylinositol-anchored high density lipoprotein-binding protein 1 | 0.48 |
| ABCA7 | ATP-binding cassette sub-family A member 7 | 0.48 |
| RAG1AP1 | Sugar transporter SWEET1 | 0.48 |
| CD47 | Leukocyte surface antigen CD47 | 0.48 |
| CXCL16 | C-X-C motif chemokine 16 | 0.48 |
| SLC14A1 | Urea transporter 1 | 0.47 |
| TGFBR2 | TGF-beta receptor type-2 | 0.47 |
| LRBA | Lipopolysaccharide-responsive and beige-like anchor protein | 0.47 |
| MFSD5 | Molybdate-anion transporter | 0.47 |
| RELT | Tumor necrosis factor receptor superfamily member 19L | 0.47 |
| ATP2B4 | Plasma membrane calcium-transporting ATPase 4 | 0.47 |
| FURIN | Furin | 0.47 |
| GAPT | Protein GAPT | 0.47 |
| NFAM1 | NFAT activation molecule 1 | 0.47 |
| ATP2B1 | Plasma membrane calcium-transporting ATPase 1 | 0.46 |
| SLC26A11 | Sodium-independent sulfate anion transporter | 0.46 |
| STX4 | Syntaxin-4 | 0.46 |
| NAT1 | Sodium-coupled neutral amino acid transporter 3 | 0.46 |
| STIM1 | Stromal interaction molecule 1 | 0.46 |
| SLC39A4 | Zinc transporter ZIP4 | 0.46 |
| ESYT2 | Extended synaptotagmin-2 | 0.46 |
| TM7SF3 | Transmembrane 7 superfamily member 3 | 0.46 |
| SEMA4A | Semaphorin-4A | 0.46 |
| CYBB | Cytochrome b-245 heavy chain | 0.46 |
| FCAR | Immunoglobulin alpha Fc receptor | 0.46 |
| GABBR1 | Gamma-aminobutyric acid type B receptor subunit 1 | 0.45 |
| CD53 | Leukocyte surface antigen CD53 | 0.45 |
| SIGLEC10 | Sialic acid-binding Ig-like lectin 10 | 0.45 |
| S1PR1 | Sphingosine 1-phosphate receptor 1 | 0.45 |
| BTN3A2 | Butyrophilin subfamily 3 member A2 | 0.45 |
| NOTCH2 | Notch 2 intracellular domain | 0.45 |
| PIK3IP1 | Phosphoinositide-3-kinase-interacting protein 1 | 0.45 |
| FAM168B | Myelin-associated neurite-outgrowth inhibitor | 0.45 |
| LPAR2 | Lysophosphatidic acid receptor 2 | 0.45 |
| ATP1B3 | Sodium/potassium-transporting ATPase subunit beta-3 | 0.45 |
| FLVCR1 | Feline leukemia virus subgroup C receptor-related protein 1 | 0.45 |
| SECTM1 | Secreted and transmembrane protein 1 | 0.45 |
| SLC38A5 | Sodium-coupled neutral amino acid transporter 5 | 0.45 |
| GPR18 | N-arachidonyl glycine receptor | 0.44 |
| LMBR1L | Protein LMBR1L | 0.44 |
| ABCC1 | Multidrug resistance-associated protein 1 | 0.44 |
| SLC22A18 | Solute carrier family 22 member 18 | 0.44 |
| CSF1R | Macrophage colony-stimulating factor 1 receptor | 0.44 |
| EMR1 | EGF-like module-containing mucin-like hormone receptor-like 1 | 0.44 |
| FPR2 | N-formyl peptide receptor 2 | 0.44 |
| KIT | Mast/stem cell growth factor receptor Kit | 0.44 |
| MS4A1 | B-lymphocyte antigen CD20 | 0.43 |
| MICA | MHC class I polypeptide-related sequence A | 0.43 |
| GPR172A | Solute carrier family 52, riboflavin transporter, member 2 | 0.43 |
| F11R | Junctional adhesion molecule A | 0.43 |
| ADAM10 | Disintegrin and metalloproteinase domain-containing protein 10 | 0.43 |
| FAM38A | Piezo-type mechanosensitive ion channel component 1 | 0.43 |
| CD68 | Macrosialin | 0.43 |
| SLC26A6 | Solute carrier family 26 member 6 | 0.43 |
| MCOLN1 | Mucolipin-1 | 0.43 |
| SLCO3A1 | Solute carrier organic anion transporter family member 3A1 | 0.43 |
| PPAP2B | Lipid phosphate phosphohydrolase 3 | 0.43 |
| ICAM4 | Intercellular adhesion molecule 4 | 0.43 |
| CXCR1 | C-X-C chemokine receptor type 1 | 0.43 |
| CD300A | CMRF35-like molecule 8 | 0.43 |
| RELL1 | RELT-like protein 1 | 0.43 |
| TAPBPL | Tapasin-related protein | 0.42 |
| FCGR2C | Low affinity immunoglobulin gamma Fc region receptor II-c | 0.42 |
| SLC16A6 | Monocarboxylate transporter 7 | 0.42 |
| TMED1 | Transmembrane emp24 domain-containing protein 1 | 0.42 |
| CD86 | T-lymphocyte activation antigen CD86 | 0.42 |
| SLC16A3 | Monocarboxylate transporter 4 | 0.42 |
| SLC2A5 | Solute carrier family 2, facilitated glucose transporter member 5 | 0.42 |
| SLC29A1 | Equilibrative nucleoside transporter 1 | 0.42 |
| SLC16A14 | Monocarboxylate transporter 14 | 0.42 |
| P2RY2 | P2Y purinoceptor 2 | 0.42 |
| SUCNR1 | Succinate receptor 1 | 0.42 |
| BTN3A1 | Butyrophilin subfamily 3 member A1 | 0.41 |
| LAT2 | Linker for activation of T-cells family member 2 | 0.41 |
| PLXND1 | Plexin-D1 | 0.41 |
| ECE1 | Endothelin-converting enzyme 1 | 0.41 |
| TGFBR1 | TGF-beta receptor type-1 | 0.41 |
| CCRL2 | C-C chemokine receptor-like 2 | 0.41 |
| TFR2 | Transferrin receptor protein 2 | 0.41 |
| SLC44A1 | Choline transporter-like protein 1 | 0.41 |
| ITGA6 | Integrin alpha-6 light chain | 0.41 |
| PMP22 | Peripheral myelin protein 22 | 0.41 |
| LAX1 | Lymphocyte transmembrane adapter 1 | 0.4 |
| AMIGO2 | Amphoterin-induced protein 2 | 0.4 |
| SLC38A1 | Sodium-coupled neutral amino acid transporter 1 | 0.4 |
| SLC41A1 | Solute carrier family 41 member 1 | 0.4 |
| C2orf89 | Metalloprotease TIKI1 | 0.4 |
| ABCC10 | Multidrug resistance-associated protein 7 | 0.4 |

TABLE 14-continued antigen markers expressed on the surface of T-cells and overexpressed in liquid tumor cells (ALL, AML, CML, MDS, CLL, CTRL)

| Antigen | Protein Name | Relative expression on T cell |
|---|---|---|
| CLDN15 | Claudin-15 | 0.4 |
| SLC39A6 | Zinc transporter ZIP6 | 0.4 |
| SLC16A5 | Monocarboxylate transporter 6 | 0.4 |
| TTYH3 | Protein tweety homolog 3 | 0.4 |
| ATP7A | Copper-transporting ATPase 1 | 0.4 |
| COMT | Catechol O-methyltransferase | 0.4 |
| SLC17A5 | Sialin | 0.4 |
| TMIGD2 | Transmembrane and immunoglobulin domain-containing protein 2 | 0.4 |
| CLEC7A | C-type lectin domain family 7 member A | 0.4 |
| SLC31A1 | High affinity copper uptake protein 1 | 0.4 |
| LRRC4 | Leucine-rich repeat-containing protein 4 | 0.4 |
| P2RY10 | Putative P2Y purinoceptor 10 | 0.39 |
| ATP10D | Probable phospholipid-transporting ATPase VD | 0.39 |
| BTN3A3 | Butyrophilin subfamily 3 member A3 | 0.39 |
| LIME1 | Lck-interacting transmembrane adapter 1 | 0.39 |
| TNF | Tumor necrosis factor, soluble form | 0.39 |
| PAQR8 | Membrane progestin receptor beta | 0.39 |
| OXER1 | Oxoeicosanoid receptor 1 | 0.39 |
| TRAT1 | T-cell receptor-associated transmembrane adapter 1 | 0.39 |
| GPBAR1 | G-protein coupled bile acid receptor 1 | 0.39 |
| SLC36A1 | Proton-coupled amino acid transporter 1 | 0.39 |
| PTPRE | Receptor-type tyrosine-protein phosphatase epsilon | 0.39 |
| PROM1 | Prominin-1 | 0.39 |
| CD74 | HLA class II histocompatibility antigen gamma chain | 0.38 |
| CNST | Consortin | 0.38 |
| TMEM49 | Vacuole membrane protein 1 | 0.38 |
| CLIC4 | Chloride intracellular channel protein 4 | 0.38 |
| NAALADL1 | N-acetylated-alpha-linked acidic dipeptidase-like protein | 0.38 |
| ANTXR2 | Anthrax toxin receptor 2 | 0.38 |
| FGFR1 | Fibroblast growth factor receptor 1 | 0.38 |
| IL1RAP | Interleukin-1 receptor accessory protein | 0.38 |
| ATP1B2 | Sodium/potassium-transporting ATPase subunit beta-2 | 0.38 |
| ABCG2 | ATP-binding cassette sub-family G member 2 | 0.38 |
| CLEC12A | C-type lectin domain family 12 member A | 0.38 |
| HLA-DQA1 | HLA class II histocompatibility antigen, DQ alpha 1 chain | 0.37 |
| B4GALT1 | Processed beta-1,4-galactosyltransferase 1 | 0.37 |
| CNNM3 | Metal transporter CNNM3 | 0.37 |
| ATP1B1 | Sodium/potassium-transporting ATPase subunit beta-1 | 0.37 |
| SLC39A1 | Zinc transporter ZIP1 | 0.37 |
| ATRN | Attractin | 0.37 |
| CYSLTR1 | Cysteinyl leukotriene receptor 1 | 0.37 |
| TRPV2 | Transient receptor potential cation channel subfamily V member 2 | 0.37 |
| SLC27A1 | Long-chain fatty acid transport protein 1 | 0.37 |
| GPR171 | Probable G-protein coupled receptor 171 | 0.37 |
| DAGLB | Sn1-specific diacylglycerol lipase beta | 0.37 |
| KCNQ1 | Potassium voltage-gated channel subfamily KQT member 1 | 0.37 |
| FZD6 | Frizzled-6 | 0.37 |
| CSF2RA | Granulocyte-macrophage colony-stimulating factor receptor subunit alpha | 0.37 |
| PTH2R | Parathyroid hormone 2 receptor | 0.37 |
| MARCH1 | E3 ubiquitin-protein ligase MARCH1 | 0.36 |
| BACE2 | Beta-secretase 2 | 0.36 |
| CD5 | T-cell surface glycoprotein CD5 | 0.36 |
| TMEM219 | Insulin-like growth factor-binding protein 3 receptor | 0.36 |
| XPR1 | Xenotropic and polytropic retrovirus receptor 1 | 0.36 |
| CD1C | T-cell surface glycoprotein CD1c | 0.36 |
| CNNM2 | Metal transporter CNNM2 | 0.36 |
| TMEM88 | Transmembrane protein 88 | 0.36 |
| ICOS | Inducible T-cell costimulator | 0.36 |
| KLRG1 | Killer cell lectin-like receptor subfamily G member 1 | 0.36 |
| LRP8 | Low-density lipoprotein receptor-related protein 8 | 0.36 |
| F2R | Proteinase-activated receptor 1 | 0.36 |
| HM13 | Minor histocompatibility antigen H13 | 0.36 |
| EMR2 | EGF-like module-containing mucin-like hormone receptor-like 2 | 0.36 |
| TREML1 | Trem-like transcript 1 protein | 0.36 |
| C17orf60 | Allergin-1 | 0.36 |
| GPR146 | Probable G-protein coupled receptor 146 | 0.36 |
| SLAMF6 | SLAM family member 6 | 0.35 |
| SLC7A6 | Y + L amino acid transporter 2 | 0.35 |
| RELL2 | RELT-like protein 2 | 0.35 |
| LGR6 | Leucine-rich repeat-containing G-protein coupled receptor 6 | 0.35 |
| PANX1 | Pannexin-1 | 0.35 |
| C18orf1 | Low-density lipoprotein receptor class A domain-containing protein 4 | 0.35 |
| SLMAP | Sarcolemmal membrane-associated protein | 0.35 |
| CCR5 | C-C chemokine receptor type 5 | 0.35 |
| MUC1 | Mucin-1 subunit beta | 0.35 |
| EMR3 | EGF-like module-containing mucin-like hormone receptor-like 3 subunit beta | 0.35 |
| COL23A1 | Collagen alpha-1(XXII) chain | 0.35 |
| OR2W3 | Olfactory receptor 2W3 | 0.35 |
| LNPEP | Leucyl-cystinyl aminopeptidase, pregnancy serum form | 0.34 |
| PRR7 | Proline-rich protein 7 | 0.34 |
| NOTCH1 | Notch 1 intracellular domain | 0.34 |
| RFT1 | Solute carrier family 52, riboflavin transporter, member 1 | 0.34 |
| TNFRSF25 | Tumor necrosis factor receptor superfamily member 25 | 0.34 |
| ANO6 | Anoctamin-6 | 0.34 |
| AQP3 | Aquaporin-3 | 0.34 |
| ADAM9 | Disintegrin and metalloproteinase domain-containing protein 9 | 0.34 |
| INSR | Insulin receptor subunit beta | 0.34 |
| FZD5 | Frizzled-5 | 0.34 |
| ERG | Potassium voltage-gated channel subfamily H member 2 | 0.34 |
| MME | Neprilysin | 0.34 |
| FCGR2B | Low affinity immunoglobulin gamma Fc region receptor II-b | 0.33 |
| LSR | Lipolysis-stimulated lipoprotein receptor | 0.33 |
| DDR1 | Epithelial discoidin domain-containing receptor 1 | 0.33 |
| CNR2 | Cannabinoid receptor 2 | 0.33 |
| ATR | Anthrax toxin receptor 1 | 0.33 |
| P2RY14 | P2Y purinoceptor 14 | 0.33 |
| VEZT | Vezatin | 0.33 |
| ALG10B | Putative Dol-P-Glc:Glc(2)Man(9)GlcNAc(2)-PP-Dol alpha-1,2-glucosyltransferase | 0.33 |
| PAQR7 | Membrane progestin receptor alpha | 0.33 |
| FLT3LG | Fms-related tyrosine kinase 3 ligand | 0.33 |
| CD40LG | CD40 ligand, soluble form | 0.33 |
| FCGR2A | Low affinity immunoglobulin gamma Fc region receptor II-a | 0.33 |
| CLDN12 | Claudin-12 | 0.33 |
| GP6 | Platelet glycoprotein VI | 0.33 |
| EPHB4 | Ephrin type-B receptor 4 | 0.33 |
| SEMA4C | Semaphorin-4C | 0.33 |
| CD300C | CMRF35-like molecule 6 | 0.33 |
| PEAR1 | Platelet endothelial aggregation receptor 1 | 0.33 |
| FFAR2 | Free fatty acid receptor 2 | 0.33 |
| SLC2A6 | Solute carrier family 2, facilitated glucose transporter member 6 | 0.32 |
| TMEM150A | Transmembrane protein 150A | 0.32 |
| ANO8 | Anoctamin-8 | 0.32 |
| CD200R1 | Cell surface glycoprotein CD200 receptor 1 | 0.32 |
| FCER1A | High affinity immunoglobulin epsilon receptor subunit alpha | 0.32 |

TABLE 14-continued antigen markers expressed on the surface of T-cells and overexpressed in liquid tumor cells (ALL, AML, CML, MDS, CLL, CTRL)

| Antigen | Protein Name | Relative expression on T cell |
|---|---|---|
| BEST1 | Bestrophin-1 | 0.32 |
| CLDN5 | Claudin-5 | 0.32 |
| SLC47A1 | Multidrug and toxin extrusion protein 1 | 0.32 |
| SLC5A10 | Sodium/glucose cotransporter 5 | 0.32 |
| CD40 | Tumor necrosis factor receptor superfamily member 5 | 0.31 |
| ANO9 | Anoctamin-9 | 0.31 |
| CLEC2D | C-type lectin domain family 2 member D | 0.31 |
| VIPR1 | Vasoactive intestinal polypeptide receptor 1 | 0.31 |
| SLC16A7 | Monocarboxylate transporter 2 | 0.31 |
| UTS2R | Urotensin-2 receptor | 0.31 |
| CLSTN3 | Calsyntenin-3 | 0.31 |
| GPR35 | G-protein coupled receptor 35 | 0.31 |
| SYT15 | Synaptotagmin-15 | 0.31 |
| FAM57A | Protein FAM57A | 0.31 |
| CD8B | T-cell surface glycoprotein CD8 beta chain | 0.31 |
| IL17RC | Interleukin-17 receptor C | 0.31 |
| GLDN | Gliomedin | 0.31 |
| FZD2 | Frizzled-2 | 0.31 |
| KCNA3 | Potassium voltage-gated channel subfamily A member 3 | 0.3 |
| MGA | Glucoamylase | 0.3 |
| GPR1 | G-protein coupled receptor 1 | 0.3 |
| IL6ST | Interleukin-6 receptor subunit beta | 0.3 |
| PCDHGB5 | Protocadherin gamma-B5 | 0.3 |
| OR1I1 | Olfactory receptor 1I1 | 0.3 |
| PTH1R | Parathyroid hormone/parathyroid hormone-related peptide receptor | 0.3 |
| NLGN2 | Neuroligin-2 | 0.3 |
| MMP24 | Processed matrix metalloproteinase-24 | 0.3 |
| CDH22 | Cadherin-22 | 0.3 |
| TNFRSF8 | Tumor necrosis factor receptor superfamily member 8 | 0.3 |
| CHRNG | Acetylcholine receptor subunit gamma | 0.3 |
| PSEN1 | Presenilin-1 CTF12 | 0.3 |
| GPR114 | Probable G-protein coupled receptor 114 | 0.3 |
| PLXNB2 | Plexin-B2 | 0.3 |
| CHRNA2 | Neuronal acetylcholine receptor subunit alpha-2 | 0.3 |
| GPR34 | Probable G-protein coupled receptor 34 | 0.3 |
| LPAR6 | Lysophosphatidic acid receptor 6 | 0.3 |
| ATP8A1 | Probable phospholipid-transporting ATPase IA | 0.3 |
| FZD1 | Frizzled-1 | 0.3 |
| CCR2 | C-C chemokine receptor type 2 | 0.3 |
| P2RY1 | P2Y purinoceptor 1 | 0.3 |
| SLC16A9 | Monocarboxylate transporter 9 | 0.3 |
| C20orf103 | Lysosome-associated membrane glycoprotein 5 | 0.3 |
| ADORA2B | Adenosine receptor A2b | 0.3 |
| CLEC12B | C-type lectin domain family 12 member B | 0.3 |
| FCRL3 | Fc receptor-like protein 3 | 0.29 |
| CD180 | CD180 antigen | 0.29 |
| TIGIT | T-cell immunoreceptor with Ig and ITIM domains | 0.29 |
| PPAP2A | Lipid phosphate phosphohydrolase 1 | 0.29 |
| ATP11C | Probable phospholipid-transporting ATPase IG | 0.29 |
| TNFRSF17 | Tumor necrosis factor receptor superfamily member 17 | 0.29 |
| TNFSF12 | Tumor necrosis factor ligand superfamily member 12, secreted form | 0.29 |
| TBXA2R | Thromboxane A2 receptor | 0.29 |
| OR3A3 | Olfactory receptor 3A3 | 0.29 |
| GPR153 | Probable G-protein coupled receptor 153 | 0.29 |
| ATP11A | Probable phospholipid-transporting ATPase IH | 0.29 |
| LRFN1 | Leucine-rich repeat and fibronectin type III domain-containing protein 1 | 0.29 |
| OR51B2 | Olfactory receptor 51B2 | 0.29 |
| KCNS1 | Potassium voltage-gated channel subfamily S member 1 | 0.29 |
| OR12D2 | Olfactory receptor 12D2 | 0.29 |
| GRM4 | Metabotropic glutamate receptor 4 | 0.29 |
| NEO1 | Neogenin | 0.29 |
| DRD5 | D(1B) dopamine receptor | 0.29 |
| PLXDC1 | Plexin domain-containing protein 1 | 0.29 |
| GPR157 | Probable G-protein coupled receptor 157 | 0.29 |
| CD300LB | CMRF35-like molecule 7 | 0.29 |
| MARVELD1 | MARVEL domain-containing protein 1 | 0.29 |
| MFAP3 | Microfibril-associated glycoprotein 3 | 0.29 |
| CHRNB1 | Acetylcholine receptor subunit beta | 0.29 |
| PVRL2 | Poliovirus receptor-related protein 2 | 0.29 |
| F2RL1 | Proteinase-activated receptor 2, alternate cleaved 2 | 0.29 |
| GPR124 | G-protein coupled receptor 124 | 0.29 |
| BACE1 | Beta-secretase 1 | 0.29 |
| C6orf105 | Androgen-dependent TFPI-regulating protein | 0.28 |
| CXCR3 | C-X-C chemokine receptor type 3 | 0.28 |
| IGSF8 | Immunoglobulin superfamily member 8 | 0.28 |
| ATP8B1 | Probable phospholipid-transporting ATPase IC | 0.28 |
| TP53I13 | Tumor protein p53-inducible protein 13 | 0.28 |
| MC1R | Melanocyte-stimulating hormone receptor | 0.28 |
| CD84 | SLAM family member 5 | 0.28 |
| CALHM1 | Calcium homeostasis modulator protein 1 | 0.28 |
| CHRNA6 | Neuronal acetylcholine receptor subunit alpha-6 | 0.28 |
| CDH10 | Cadherin-10 | 0.28 |
| SLC16A1 | Monocarboxylate transporter 1 | 0.28 |
| GPRC5D | G-protein coupled receptor family C group 5 member D | 0.28 |
| AGER | Advanced glycosylation end product-specific receptor | 0.28 |
| FASLG | FasL intracellular domain | 0.28 |
| GPR56 | GPR56 C-terminal fragment | 0.28 |
| SIGLEC1 | Sialoadhesin | 0.28 |
| KIR2DL5A | Killer cell immunoglobulin-like receptor 2DL5A | 0.28 |
| PLB1 | Lysophospholipase | 0.28 |
| CD200 | OX-2 membrane glycoprotein | 0.27 |
| ADAM28 | Disintegrin and metalloproteinase domain-containing protein 28 | 0.27 |
| SIT1 | Sodium- and chloride-dependent transporter XTRP3 | 0.27 |
| SLC23A2 | Solute carrier family 23 member 2 | 0.27 |
| CCR10 | C-C chemokine receptor type 10 | 0.27 |
| PRR4 | Processed poliovirus receptor-related protein 4 | 0.27 |
| GJD2 | Gap junction delta-2 protein | 0.27 |
| SLC2A8 | Solute carrier family 2, facilitated glucose transporter member 8 | 0.27 |
| CD209 | CD209 antigen | 0.27 |
| CD274 | Programmed cell death 1 ligand 1 | 0.27 |
| PROM2 | Prominin-2 | 0.27 |
| ATP6V0A2 | V-type proton ATPase 116 kDa subunit a isoform 2 | 0.27 |
| MPZ | Myelin protein P0 | 0.27 |
| TNFRSF18 | Tumor necrosis factor receptor superfamily member 18 | 0.27 |
| MFSD2A | Major facilitator superfamily domain-containing protein 2A | 0.27 |
| HEG1 | Protein HEG homolog 1 | 0.27 |
| OXTR | Oxytocin receptor | 0.27 |
| CD99L2 | CD99 antigen-like protein 2 | 0.27 |
| LILRB4 | Leukocyte immunoglobulin-like receptor subfamily B member 4 | 0.27 |
| SMAGP | Small cell adhesion glycoprotein | 0.27 |
| OR51I2 | Olfactory receptor 51I2 | 0.27 |
| LY6G6D | Lymphocyte antigen 6 complex locus protein G6f | 0.27 |
| KCNQ4 | Potassium voltage-gated channel subfamily KQT member 4 | 0.27 |
| HRH2 | Histamine H2 receptor | 0.27 |
| SLC39A2 | Zinc transporter ZIP2 | 0.27 |
| CLDN10 | Claudin-10 | 0.27 |

TABLE 14-continued antigen markers expressed on the surface of T-cells and overexpressed in liquid tumor cells (ALL, AML, CML, MDS, CLL, CTRL)

| Antigen | Protein Name | Relative expression on T cell |
|---|---|---|
| GPM6B | Neuronal membrane glycoprotein M6-b | 0.27 |
| STEAP4 | Metalloreductase STEAP4 | 0.27 |
| APOLD1 | Apolipoprotein L domain-containing protein 1 | 0.27 |
| S1PR3 | Sphingosine 1-phosphate receptor 3 | 0.27 |
| SGMS2 | Phosphatidylcholine:ceramide cholinephosphotransferase 2 | 0.27 |
| KIR2DS5 | Killer cell immunoglobulin-like receptor 2DS5 | 0.27 |
| STAR | Heat-stable enterotoxin receptor | 0.27 |
| NIPA1 | Magnesium transporter NIPA1 | 0.26 |
| CNNM4 | Metal transporter CNNM4 | 0.26 |
| SLAMF1 | Signaling lymphocytic activation molecule | 0.26 |
| KIAA1919 | Sodium-dependent glucose transporter 1 | 0.26 |
| TLR6 | Toll-like receptor 6 | 0.26 |
| CRB3 | Protein crumbs homolog 3 | 0.26 |
| SLC12A9 | Solute carrier family 12 member 9 | 0.26 |
| GPR68 | Ovarian cancer G-protein coupled receptor 1 | 0.26 |
| OR51J1 | Olfactory receptor 51J1 | 0.26 |
| TREML2 | Trem-like transcript 2 protein | 0.26 |
| GPR176 | Probable G-protein coupled receptor 176 | 0.26 |
| FLVCR2 | Feline leukemia virus subgroup C receptor-related protein 2 | 0.26 |
| LPAR1 | Lysophosphatidic acid receptor 1 | 0.26 |
| PANX2 | Pannexin-2 | 0.26 |
| SLC6A6 | Sodium- and chloride-dependent taurine transporter | 0.26 |
| PROKR2 | Prokineticin receptor 2 | 0.26 |
| CLDN9 | Claudin-9 | 0.26 |
| MYOF | Myoferlin | 0.26 |
| LY6G6F | Lymphocyte antigen 6 complex locus protein G6f | 0.26 |
| ESAM | Endothelial cell-selective adhesion molecule | 0.26 |
| NCR3 | Natural cytotoxicity triggering receptor 3 | 0.25 |
| HLA-DQB2 | HLA class II histocompatibility antigen, DQ beta 2 chain | 0.25 |
| SLC4A5 | Electrogenic sodium bicarbonate cotransporter 4 | 0.25 |
| P2RY4 | P2Y purinoceptor 4 | 0.25 |
| ABCB1 | Multidrug resistance protein 1 | 0.25 |
| SLC9A1 | Sodium/hydrogen exchanger 1 | 0.25 |
| CELSR2 | Cadherin EGF LAG seven-pass G-type receptor 2 | 0.25 |
| SYT8 | Synaptotagmin-8 | 0.25 |
| PCDHA9 | Protocadherin alpha-9 | 0.25 |
| TMEM204 | Transmembrane protein 204 | 0.25 |
| PTPRJ | Receptor-type tyrosine-protein phosphatase eta | 0.25 |
| GRPR | Gastrin-releasing peptide receptor | 0.25 |
| SEMA6B | Semaphorin-6B | 0.25 |
| CLCN5 | H(+)/Cl(−) exchange transporter 5 | 0.25 |
| GLRA2 | Glycine receptor subunit alpha-2 | 0.25 |
| PLVAP | Plasmalemma vesicle-associated protein | 0.25 |
| ACVR1B | Activin receptor type-1B | 0.25 |
| JAM3 | Junctional adhesion molecule C | 0.25 |
| LDLRAD33 | Low-density lipoprotein receptor class A domain-containing protein | 0.25 |
| XG | Glycoprotein Xg | 0.25 |
| SLC2A11 | Solute carrier family 2, facilitated glucose transporter member 11 | 0.24 |
| PCDH9 | Protocadherin-9 | 0.24 |
| VAMP5 | Vesicle-associated membrane protein 5 | 0.24 |
| CDHR2 | Cadherin-related family member 2 | 0.24 |
| DRD2 | D(2) dopamine receptor | 0.24 |
| LRIG2 | Leucine-rich repeats and immunoglobulin-like domains protein 2 | 0.24 |
| RAMP3 | Receptor activity-modifying protein 3 | 0.24 |
| SLC39A14 | Zinc transporter ZIP14 | 0.24 |
| STRA6 | Stimulated by retinoic acid gene 6 protein homolog | 0.24 |
| ADRA2C | Alpha-2C adrenergic receptor | 0.24 |
| CLDN19 | Claudin-19 | 0.24 |
| CX3CR1 | CX3C chemokine receptor 1 | 0.24 |
| CD79B | B-cell antigen receptor complex-associated protein beta chain | 0.24 |
| KIR2DL2 | Killer cell immunoglobulin-like receptor 2DL2 | 0.24 |
| CXCR7 | Atypical chemokine receptor 3 | 0.24 |
| OR5L2 | Olfactory receptor 5L2 | 0.24 |
| LRRC52 | Leucine-rich repeat-containing protein 52 | 0.24 |
| JPH1 | Junctophilin-1 | 0.24 |
| ADORA1 | Adenosine receptor A1 | 0.24 |
| GPRC5C | G-protein coupled receptor family C group 5 member C | 0.24 |
| RET | Extracellular cell-membrane anchored RET cadherin 120 kDa fragment | 0.24 |
| PVR | Poliovirus receptor | 0.24 |
| ITGB3 | Integrin beta-3 | 0.24 |
| PTGIR | Prostacyclin receptor | 0.24 |
| LPHN1 | Latrophilin-1 | 0.24 |
| OR10J1 | Olfactory receptor 10J1 | 0.24 |
| MFAP3L | Microfibrillar-associated protein 3-like | 0.24 |
| GPNMB | Transmembrane glycoprotein NMB | 0.24 |
| CELSR3 | Cadherin EGF LAG seven-pass G-type receptor 3 | 0.23 |
| CCR6 | C-C chemokine receptor-like 2 | 0.23 |
| DMPK | Myotonin-protein kinase | 0.23 |
| UPK3B | Uroplakin-3b | 0.23 |
| OR1D2 | Olfactory receptor 1D2 | 0.23 |
| OR7D2 | Olfactory receptor 7D2 | 0.23 |
| ITGB1 | Integrin beta-1 | 0.23 |
| HRH3 | Histamine H3 receptor | 0.23 |
| GRIN2C | Glutamate receptor ionotropic, NMDA 2C | 0.23 |
| KIR3DL1 | Killer cell immunoglobulin-like receptor 3DL1 | 0.23 |
| EPHB2 | Ephrin type-B receptor 2 | 0.23 |
| OR2S2 | Olfactory receptor 2S2 | 0.23 |
| KIR2DL4 | Killer cell immunoglobulin-like receptor 2DL4 | 0.23 |
| CNNM1 | Metal transporter CNNM1 | 0.23 |
| MARVELD2 | MARVEL domain-containing protein 2 | 0.23 |
| CXCR6 | C-X-C chemokine receptor type 6 | 0.23 |
| NOV | Plexin-A1 | 0.23 |
| ABCB6 | ATP-binding cassette sub-family B member 6, mitochondrial | 0.23 |
| PVRL1 | Poliovirus receptor-related protein 1 | 0.23 |
| SLC46A2 | Thymic stromal cotransporter homolog | 0.23 |
| ADORA3 | Adenosine receptor A3 | 0.23 |
| GPR125 | Probable G-protein coupled receptor 125 | 0.23 |
| CD22 | B-cell receptor CD22 | 0.22 |
| FZD3 | Frizzled-3 | 0.22 |
| LPAR5 | Lysophosphatidic acid receptor 5 | 0.22 |
| TMEM8B | Transmembrane protein 8B | 0.22 |
| PLXNA1 | Plexin-A1 | 0.22 |
| NPFFR1 | Neuropeptide FF receptor 1 | 0.22 |
| SEZ6L2 | Seizure 6-like protein 2 | 0.22 |
| LRRTM2 | Leucine-rich repeat transmembrane neuronal protein 2 | 0.22 |
| SLC16A11 | Monocarboxylate transporter 11 | 0.22 |
| GRIK5 | Glutamate receptor ionotropic, kainate 5 | 0.22 |
| SYT6 | Synaptotagmin-6 | 0.22 |
| TMEM102 | Transmembrane protein 102 | 0.22 |
| OR8B8 | Olfactory receptor 8B8 | 0.22 |
| GJB1 | Gap junction beta-1 protein | 0.22 |
| GRM6 | Metabotropic glutamate receptor 6 | 0.22 |
| C20orf54 | Solute carrier family 52, riboflavin transporter, member 3 | 0.22 |
| OR52D1 | Olfactory receptor 52D1 | 0.22 |
| SLC46A1 | Proton-coupled folate transporter | 0.22 |
| DSC2 | Desmocollin-2 | 0.22 |
| FAT1 | Protocadherin Fat 1, nuclear form | 0.22 |
| GCGR | Glucagon receptor | 0.22 |
| POP1 | Blood vessel epicardial substance | 0.22 |
| CXADR | Coxsackievirus and adenovirus receptor | 0.22 |
| ABCC6 | Multidrug resistance-associated protein 6 | 0.22 |
| GJA1 | Gap junction alpha-1 protein | 0.22 |

TABLE 14-continued antigen markers expressed on the surface of T-cells and overexpressed in liquid tumor cells (ALL, AML, CML, MDS, CLL, CTRL)

| Antigen | Protein Name | Relative expression on T cell |
|---|---|---|
| CXCR5 | C-X-C chemokine receptor type 5 | 0.21 |
| ABCB4 | Multidrug resistance protein 3 | 0.21 |
| CTLA4 | Cytotoxic T-lymphocyte protein 4 | 0.21 |
| TRPV1 | Transient receptor potential cation channel subfamily V member 1 | 0.21 |
| MRGPRX4 | Mas-related G-protein coupled receptor member X4 | 0.21 |
| SIGLEC6 | Sialic acid-binding Ig-like lectin 6 | 0.21 |
| IL9R | Interleukin-9 receptor | 0.21 |
| CHRNB2 | Neuronal acetylcholine receptor subunit beta-2 | 0.21 |
| PDGFRB | Platelet-derived growth factor receptor beta | 0.21 |
| TMPRSS11D | Transmembrane protease serine 11D catalytic chain | 0.21 |
| CDH24 | Cadherin-24 | 0.21 |
| PRRT2 | Proline-rich transmembrane protein 2 | 0.21 |
| GALR3 | Galanin receptor type 3 | 0.21 |
| OR51I1 | Olfactory receptor 51I1 | 0.21 |
| PTPRU | Receptor-type tyrosine-protein phosphatase U | 0.21 |
| LPAR4 | Lysophosphatidic acid receptor 4 | 0.21 |
| ZNRF3 | E3 ubiquitin-protein ligase ZNRF3 | 0.21 |
| P2RY6 | P2Y purinoceptor 6 | 0.21 |
| AGTR1 | Type-1 angiotensin II receptor | 0.21 |
| GPR182 | G-protein coupled receptor 182 | 0.21 |
| PODXL | Podocalyxin | 0.21 |
| BDKRB1 | B1 bradykinin receptor | 0.21 |
| DCHS1 | Protocadherin-16 | 0.21 |
| GRIN3B | Glutamate receptor ionotropic, NMDA 3B | 0.21 |
| PTGDR | Prostaglandin D2 receptor | 0.21 |
| PVRL4 | Processed poliovirus receptor-related protein 4 | 0.21 |
| GPR77 | C5a anaphylatoxin chemotactic receptor 2 | 0.21 |
| PARM1 | Prostate androgen-regulated mucin-like protein 1 | 0.21 |
| OR10H1 | Olfactory receptor 10H1 | 0.21 |
| OR10D3 | Putative olfactory receptor 10D3 | 0.21 |
| TNFSF14 | Tumor necrosis factor ligand superfamily member 14, soluble form | 0.21 |
| FCRL5 | Fc receptor-like protein 5 | 0.2 |
| RNF43 | E3 ubiquitin-protein ligase RNF43 | 0.2 |
| AMIGO1 | Amphoterin-induced protein 1 | 0.2 |
| OR1F1 | Olfactory receptor 1F1 | 0.2 |
| SLCO4A1 | Solute carrier organic anion transporter family member 4A1 | 0.2 |
| TTYH2 | Protein tweety homolog 2 | 0.2 |
| GABRR2 | Gamma-aminobutyric acid receptor subunit rho-2 | 0.2 |
| GJD3 | Gap junction delta-3 protein | 0.2 |
| GRID1 | Glutamate receptor ionotropic, delta-1 | 0.2 |
| CLDN1 | Claudin-1 | 0.2 |
| SLC6A13 | Sodium- and chloride-dependent GABA transporter 2 | 0.2 |
| SLC30A8 | Zinc transporter 8 | 0.2 |
| KIR2DL3 | Killer cell immunoglobulin-like receptor 2DL3 | 0.2 |
| GPR78 | G-protein coupled receptor 78 | 0.2 |
| UPK2 | Uroplakin-2 | 0.2 |
| CLDN14 | Claudin-14 | 0.2 |
| EDA | Ectodysplasin-A, secreted form | 0.2 |
| PTGER1 | Prostaglandin E2 receptor EP1 subtype | 0.2 |
| TRPV5 | Transient receptor potential cation channel subfamily V member 5 | 0.2 |
| PRIMA1 | Proline-rich membrane anchor 1 | 0.2 |
| GJA9 | Gap junction alpha-9 protein | 0.2 |
| SLC7A3 | Cationic amino acid transporter 3 | 0.2 |
| SSTR2 | Somatostatin receptor type 2 | 0.2 |
| CD1A | T-cell surface glycoprotein CD1a | 0.2 |
| SLC7A8 | Large neutral amino acids transporter small subunit 2 | 0.2 |
| CLIC6 | Chloride intracellular channel protein 6 | 0.2 |
| EPHA8 | Ephrin type-A receptor 8 | 0.2 |
| SLC20A2 | Sodium-dependent transporter 2 | 0.2 |
| SCNN1A | Amiloride-sensitive sodium channel subunit alpha | 0.2 |
| OR51B6 | Olfactory receptor 51B6 | 0.2 |
| OR14J1 | Olfactory receptor 14J1 | 0.2 |
| OR10C1 | Olfactory receptor 10C1 | 0.2 |
| OPRL1 | Nociceptin receptor | 0.2 |
| CCR9 | C-C chemokine receptor type 9 | 0.2 |
| JPH4 | Junctophilin-4 | 0.2 |
| HTR1E | 5-hydroxytryptamine receptor 1E | 0.2 |
| MC3R | Melanocortin receptor 3 | 0.2 |
| CD163L1 | Scavenger receptor cysteine-rich type 1 protein M160 | 0.2 |
| SEZ6 | Seizure receptor 6 homolog | 0.2 |
| PRSS8 | Prostasin heavy chain | 0.2 |
| CDH26 | Cadherin-like protein 26 | 0.2 |
| ODZ1 | Teneurin C-terminal-associated peptide | 0.2 |
| FGFR3 | Fibroblast growth factor receptor 3 | 0.2 |

Example 1—Knock Out (KO) on CD38 Gene & Expression of Anti-CD38 CAR

Presentation of the CD38 Target—Cyclic ADP Ribose Hydrolase

CD38 is a glycoprotein found on the surface of many immune cells, including multiple myeloma (MM) cells that express a high level of CD38 in a large majority of patients. CD38 is a validated target for MM as many studies have shown efficient killing of CD38+MM cells from patients and CD38+MM cell lines using anti-CD38 mAbs by CDC and ADCC (Ellis, J. H. K. et al, Journal of Immunology, 1995, 155 (2), 925-937). Daratumumab is a therapeutic human CD38 monoclonal antibody which induces killing of multiple myeloma and other hematological tumors (De Weers, M. et al, *J Immunol* 2011 186:1840-1848). In some studies, it has been shown that CD38 is also highly expressed by activated T cells (Sandoval-Montes C J et al, 2005, Leukoc Biol. 77(4):513-21).

Expression of CD38 by T-Cells

The CD38 expression by T cells after CD3/CD28 beads and IL-2 stimulation was analyzed by FACS every 3-4 days during 17 days. It was observed that more than 90% T cells express between day 6 and day 17 after activation (FIG. 10B).

Thus, in order to avoid killing of activated T cells by anti-CD38 CAR+ T cells CD38 surface expression in T cells needs to be prevented. This may be accomplished by the inactivation of the CD38 gene using TALE-nucleases. TALEN is a trademark owned by the applicant (Cellectis, 8 rue de la Croix Jarry, 75013 PARIS) designating customized format of TAL nucleases.

Strategy for the CD38 Knock-Out (KO)

Heterodimeric TALE-nuclease targeting two 17-pb long sequences separated by a 13-pb spacer within the CD38 gene were designed and produced. Each half target is recognized by repeats of the half TALE-nucleases listed in the following Table 15 and FIG. 10A.

The repeats sequence of the left TALEN for the CD38ex1_T2 target was NN-NI-NN-NN-NG-NN-NN-NN-NG-NG-NN-NN-HD-NN-NI-NG, and the one for the right TALEN was NN-NG-HD-HD-HD-HD-NN-HD-NI-NN-NG-NN-HD-HD-HD-NG.

TABLE 15

Sequences of the tested CD38 target and TALENs for inactivation of the CD38 antigen

| Name | TALEN L/R | SEQ ID # | Nucleic acid sequence or polypeptide sequence |
|---|---|---|---|
| CD38 target | N/A | 1 | TGAGGTGGGTTGGCGACtaaggcgcaccggTGGGCACTGCGGGACA |
| CD38ex 1_T2-L1 TALEN | L | 2 | MGDPKKKRKVIDYPYDVPDYAIDIADLRTLGYSQQQQEKIKPKVRSTV AQHHEALVGHGFTHAHIVALSQHPAALGTVAVKYQDMIAALPEATHE AIVGVGKQWSGARALEALLTVAGELRGPPLQLDTGQLLKIAKRGGVTA VEAVHAWRNALTGAPLNLTPQQVVAIASNNGGKQALETVQRLLPVL CQAHGLTPEQVVAIASNIGGKQALETVQALLPVLCQAHGLTPQQVVAI ASNNGGKQALETVQRLLPVLCQAHGLTPQQVVAIASNNGGKQALET VQRLLPVLCQAHGLTPQQVVAIASNGGGKQALETVQRLLPVLCQAHG LTPQQVVAIASNNGGKQALETVQRLLPVLCQAHGLTPQQVVAIASNN GGKQALETVQRLLPVLCQAHGLTPQQVVAIASNNGGKQALETVQRLL PVLCQAHGLTPQQVVAIASNGGGKQALETVQRLLPVLCQAHGLTPQ QVVAIASNGGGKQALETVQRLLPVLCQAHGLTPQQVVAIASNNGGK QALETVQRLLPVLCQAHGLTPQQVVAIASNNGGKQALETVQRLLPVL CQAHGLTPEQVVAISHDGGKQALETVQRLLPVLCQAHGLTPQQVV AIASNNGGKQALETVQRLLPVLCQAHGLTPEQVVAIASNIGGKQALET VQALLPVLCQAHGLTPQQVVAIASNGGGRPALESIVAQLSRPDPALAA LTNDHLVALACLGGRPALDAVKKGLGDPISRSQLVKSELEEKKSELRHK LKYVPHEYIELIEIARNSTQDRILEMKVMEFFMKVYGYRGKHLGGSRKP DGAIYTVGSPIDYGVIVDTKAYSGGYNLPIGQADEMQRYVEENQTRN KHINPNEWWKVYPSSVTEFKFLFVSGHFKGNYKAQLTRLNHITNCNG AVLSVEELLIGGEMIKAGTLTLEEVRRKFNNGEINFAAD |
| CD38ex 1_T2-R1 TALEN | R | 3 | MGDPKKKRKVIDKETAAAKFERQHMDSIDIADLRTLGYSQQQQEKIKP KVRSTVAQHHEALVGHGFTHAHIVALSQHPAALGTVAVKYQDMIAAL PEATHEAIVGVGKQWSGARALEALLTVAGELRGPPLQLDTGQLLKIAK RGGVTAVEAVHAWRNALTGAPLNLTPQQVVAIASNNGGKQALETV QRLLPVLCQAHGLTPQQVVAIASNGGGKQALETVQRLLPVLCQAHGL TPEQVVAIASHDGGKQALETVQRLLPVLCQAHGLTPEQVVAIASHDG GKQALETVQRLLPVLCQAHGLTPEQVVAIASHDGGKQALETVQRLLP VLCQAHGLTPEQVVAIASHDGGKQALETVQRLLPVLCQAHGLTPQQV VAIASNNGGKQALETVQRLLPVLCQAHGLTPEQVVAIASHDGGKQAL ETVQRLLPVLCQAHGLTPEQVVAIASNIGGKQALETVQALLPVLCQAH GLTPQQVVAIASNNGGKQALETVQRLLPVLCQAHGLTPQQVVAIASN GGGKQALETVQRLLPVLCQAHGLTPQQVVAIASNNGGKQALETVQR LLPVLCQAHGLTPEQVVAIASHDGGKQALETVQRLLPVLCQAHGLTPE QVVAIASHDGGKQALETVQRLLPVLCQAHGLTPEQVVAIASHDGGKQ ALETVQRLLPVLCQAHGLTPQQVVAIASNGGGRPALESIVAQLSRPDP ALAALTNDHLVALACLGGRPALDAVKKGLGDPISRSQLVKSELEEKKSE LRHKLKYVPHEYIELIEIARNSTQDRILEMKVMEFFMKVYGYRGKHLGG SRKPDGAIYTVGSPIDYGVIVDTKAYSGGYNLPIGQADEMQRYVEENQ TRNKHINPNEWWKVYPSSVTEFKFLFVSGHFKGNYKAQLTRLNHITNC NGAVLSVEELLIGGEMIKAGTLTLEEVRRKFNNGEINFAAD |

Each TALE-nuclease construct was subcloned using restriction enzyme digestion in a mammalian expression vector under the control of the T7 promoter. mRNA encoding TALE-nuclease cleaving CD38 were synthesized from plasmids carrying the coding sequence downstream from the T7 promoter.

Purified T cells activated during 72 hours with anti CD3/CD28 coated beads and recombinant IL-2 were transfected by electroporation (Cytopulse) with each of the 2 mRNAs (10 μg each) encoding both half CD38ex1_T2 TALE-nucleases. To investigate, the CD38 KO, the percentage of CD38 negative T cells was assessed by flow cytometry at day 3, 6, 10 and 13 after TALEN mRNA transfection. It was observed that 15% of transfected T cells were CD38 deficient (FIG. 10C) and this deficiency was stable during 13 days after transfection.

In addition two alternative TALE-nucleases targeting the CD38 gene have been designed. Each half target is recognized by repeats of the half TALE-nucleases listed in the following Table 16 and FIG. 10A. The repeats sequence of the left TALEN for the CD38ex1_T4 target was NG-NN-HD-NN-NI-NN-NG-NG-HD-NI-NN-HD-HD-HD-NN-NN-NG, and the one for the right TALEN was NG-NN-HD-NG-NN-HD-HD-NN-NN-HD-NG-HD-NG-HD-NG-NI. The repeats sequence of the left TALEN for the CD38ex1_T5 target was NG-NN-NI-NG-HD-HD-NG-HD-NN-NG-HD-NN-NG-NN-NN-NG, and the one for the right TALEN was HD-NN-NI-NN-NN-NG-NN-NN-HD-NN-HD-HD-NI-NN-HD-NI.

TABLE 16

Sequences of two other CD38 targets and the corresponding
TALENs for their inactivation

| Name | TALEN L/R | SEQ ID # | Nucleic acid sequence or repeats sequence |
|---|---|---|---|
| CD38ex 1_T4 target | N/A | 4 | TGCGAGTTCAGCCCGGtgtccggggacaaacccTGCTGCCGGCTCTCTA |
| CD38ex 1_T4-L TALEN | L | 5 | MGDPKKKRKVIDYPYDVPDYAIDIADLRTLGYSQQQQEKIKPKVRSTVA QHHEALVGHGFTHAHIVALSQHPAALGTVAVKYQDMIAALPEATHEA IVGVGKQWSGARALEALLTVAGELRGPPLQLDTGQLLKIAKRGGVTAV EAVHAWRNALTGAPLNLTPQQVVAIASNGGGKQALETVQRLLPVLCQ AHGLTPEQVVAIASNNGGKQALETVQALLPVLCQAHGLTPQQVVAIA SHDGGKQALETVQRLLPVLCQAHGLTPQQVVAIASNNGGKQALETVQ RLLPVLCQAHGLTPQQVVAIASNIGGKQALETVQRLLPVLCQAHGLTP QQVVAIASNNGGKQALETVQRLLPVLCQAHGLTPQQVVAIASNGGGK QALETVQRLLPVLCQAHGLTPQQVVAIASNGGGKQALETVQRLLPVLC QAHGLTPQQVVAIASHDGGKQALETVQRLLPVLCQAHGLTPQQVVAI ASNIGGKQALETVQRLLPVLCQAHGLTPQQVVAIASNNGGKQALETV QRLLPVLCQAHGLTPQQVVAIASHDGGKQALETVQRLLPVLCQAHGL TPEQVVAIASHDGGKQALETVQRLLPVLCQAHGLTPQQVVAIASHDG GKQALETVQRLLPVLCQAHGLTPEQVVAIASNNGGKQALETVQALLPV LCQAHGLTPQQVVAIASNNGGKQALETVQRLLPVLCQAHGLTPEQVV AIASNGGGRPALESIVAQLSRPDPALAALTNDHLVALACLGGRPALDAV KKGLGDPISRSQLVKSELEEKKSELRHKLKYVPHEYIELIEIARNSTQDRIL EMKVMEFFMKVYGYRGKHLGGSRKPDGAIYTVGSPIDYGVIVDTKAYS GGYNLPIGQADEMQRYVEENQTRNKHINPNEWWKVYPSSVTEFKFLF VSGHFKGNYKAQLTRLNHITNCNGAVLSVEELLIGGEMIKAGTLTLEEV RRKFNNGEINFAAD |
| CD38ex 1_T4-R TALEN | R | 6 | MGDPKKKRKVIDKETAAAKFERQHMDSIDIADLRTLGYSQQQQEKIKP KVRSTVAQHHEALVGHGFTHAHIVALSQHPAALGTVAVKYQDMIAAL PEATHEAIVGVGKQWSGARALEALLTVAGELRGPPLQLDTGQLLKIAK RGGVTAVEAVHAWRNALTGAPLNLTPQQVVAIASNGGGKQALETVQ RLLPVLCQAHGLTPQQVVAIASNNGGKQALETVQRLLPVLCQAHGLTP EQVVAIASHDGGKQALETVQRLLPVLCQAHGLTPEQVVAIASNGGGK QALETVQRLLPVLCQAHGLTPEQVVAIASNNGGKQALETVQRLLPVLC QAHGLTPEQVVAIASHDGGKQALETVQRLLPVLCQAHGLTPQQVVAI ASHDGGKQALETVQRLLPVLCQAHGLTPEQVVAIASNNGGKQALETV QRLLPVLCQAHGLTPEQVVAIASNNGGKQALETVQALLPVLCQAHGLT PQQVVAIASHDGGKQALETVQRLLPVLCQAHGLTPQQVVAIASNGGG KQALETVQRLLPVLCQAHGLTPQQVVAIASHDGGKQALETVQRLLPVL CQAHGLTPEQVVAIASNGGGKQALETVQRLLPVLCQAHGLTPEQVVAI ASHDGGKQALETVQRLLPVLCQAHGLTPEQVVAIASNGGGKQALETV QRLLPVLCQAHGLTPQQVVAIASNIGGRPALESIVAQLSRPDPALAALT NDHLVALACLGGRPALDAVKKG LGDPISRSQLVKSELEEKKSELRHKLKY VPHEYIELIEIARNSTQDRILEMKVMEFFMKVYGYRGKHLGGSRKPDG AIYTVGSPIDYGVIVDTKAYSGGYNLPIGQADEMQRYVEENQTRNKHI NPNEWWKVYPSSVTEFKFLFVSGHFKGNYKAQLTRLNHITNCNGAVLS VEELLIGGEMIKAGTLTLEEVRRKFNNGEINFAAD |
| CD38ex 1_T5 target | N/A | 7 | TGATCCTCGTCGTGGTgctcgcggtggtcgtccCGAGGTGGCGCCAGCA |
| CD38ex 1_T5-L TALEN | L | 8 | MGDPKKKRKVIDYPYDVPDYAIDIADLRTLGYSQQQQEKIKPKVRSTVA QHHEALVGHGFTHAHIVALSQHPAALGTVAVKYQDMIAALPEATHEA IVGVGKQWSGARALEALLTVAGELRGPPLQLDTGQLLKIAKRGGVTAV EAVHAWRNALTGAPLNLTPQQVVAIASNGGGKQALETVQRLLPVLCQ AHGLTPEQVVAIASNNGGKQALETVQALLPVLCQAHGLTPQQVVAIA SNIGGKQALETVQRLLPVLCQAHGLTPQQVVAIASNGGGKQALETVQ RLLPVLCQAHGLTPQQVVAIASHDGGKQALETVQRLLPVLCQAHGLTP QQVVAIASHDGGKQALETVQRLLPVLCQAHGLTPQQVVAIASNGGGK QALETVQRLLPVLCQAHGLTPQQVVAIASHDGGKQALETVQRLLPVLC QAHGLTPQQVVAIASNNGGKQALETVQRLLPVLCQAHGLTPQQVVAI ASNGGGKQALETVQRLLPVLCQAHGLTPQQVVAIASHDGGKQALETV QRLLPVLCQAHGLTPQQVVAIASNNGGKQALETVQRLLPVLCQAHGL TPEQVVAIASNGGGKQALETVQRLLPVLCQAHGLTPQQVVAIASNNG GKQALETVQRLLPVLCQAHGLTPEQVVAIASNNGGKQALETVQALLPV LCQAHGLTPQQVVAIASNGGGRPALESIVAQLSRPDPALAALTNDHLV ALACLGGRPALDAVKKGLGDPISRSQLVKSELEEKKSELRHKLKYVPHEY IELIEIARNSTQDRILEMKVMEFFMKVYGYRGKHLGGSRKPDGAIYTVG SPIDYGVIVDTKAYSGGYNLPIGQADEMQRYVEENQTRNKHINPNEW WKVYPSSVTEFKFLFVSGHFKGNYKAQLTRLNHITNCNGAVLSVEELLI GGEMIKAGTLTLEEVRRKFNNGEINFAAD |

TABLE 16-continued

Sequences of two other CD38 targets and the corresponding
TALENs for their inactivation

| Name | TALEN L/R | SEQ ID # | Nucleic acid sequence or repeats sequence |
|---|---|---|---|
| CD38ex 1_T5-R TALEN | R | 9 | MGDPKKKRKVIDKETAAAKFERQHMDSIDIADLRTLGYSQQQQEKIKP KVRSTVAQHHEALVGHGFTHAHIVALSQHPAALGTVAVKYQDMIAAL PEATHEAIVGVGKQWSGARALEALLTVAGELRGPPLQLDTGQLLKIAK RGGVTAVEAVHAWRNALTGAPLNLTPQQVVAIASHDGGKQALETVQ RLLPVLCQAHGLTPQQVVAIASNNGGKQALETVQRLLPVLCQAHGLTP EQVVAIASNIGGKQALETVQRLLPVLCQAHGLTPEQVVAIASNNGGKQ ALETVQRLLPVLCQAHGLTPEQVVAIASNNGGKQALETVQRLLPVLCQ AHGLTPEQVVAIASNGGGKQALETVQRLLPVLCQAHGLTPQQVVAIAS NNGGKQALETVQRLLPVLCQAHGLTPEQVVAIASNNGGKQALETVQR LLPVLCQAHGLTPEQVVAIASHDGGKQALETVQALLPVLCQAHGLTPQ QVVAIASNNGGKQALETVQRLLPVLCQAHGLTPQQVVAIASHDGGKQ ALETVQRLLPVLCQAHGLTPQQVVAIASHDGGKQALETVQRLLPVLCQ AHGLTPEQVVAIASNIGGKQALETVQRLLPVLCQAHGLTPEQVVAIAS NNGGKQALETVQRLLPVLCQAHGLTPEQVVAIASHDGGKQALETVQR LLPVLCQAHGLTPQQVVAIASNIGGRPALESIVAQLSRPDPALAALTND HLVALACLGGRPALDAVKKGLGDPISRSQLVKSELEEKKSELRHKLKYVP HEYIELIEIARNSTQDRILEMKVMEFFMKVYGYRGKHLGGSRKPDGAIY TVGSPIDYGVIVDTKAYSGGYNLPIGQADEMQRYVEENQTRNKHINPN EWWKVYPSSVTEFKFLFVSGHFKGNYKAQLTRLNHITNCNGAVLSVEE LLIGGEMIKAGTLTLEEVRRKFNNGEINFAAD |

Strategy for the Expression of the CAR Anti-CD38

Structure and Composition of CARs Anti-CD38

In Table 17 are presented VH and VL chain of scFv anti-CD38. SEQ ID NO:10-11 correspond to the humanized anti-CD38 antibody daratumumab (Genmab) and SEQ ID NO: 12-13 to the MOR202 (or MOR03087) such as described in the U.S. Pat. No. 8,263,746B patent.

SEQ ID NO:14-20 and SEQ ID NO:21-26 correspond to the CDR sequence for respectively the VH chain (HCDR) and the VL chain (LCDR) such as described in the WO 2008/047242 application.

TABLE 17

Sequences of VH and VL chains of the scFv anti-CD38 antibodies
daratumumab, MOR202 and of specific CDRs for VH and VL chains.

| Name | VH or VL chain | SEQ ID # | Polypeptide or nucleic acid sequence |
|---|---|---|---|
| Daratumumab | VH | 10 | EVQLLESGGGLVQPGGSLRLSCAVSGFTFNSFAMSWVRQAPGK GLEWVSAISGSGGGTYYADSVKGRFTISRDNSKNTLYLQMNSLR AEDTAVYFCAKDKILWFGEPVFDYWGQGTLVTVSSASTKGPSV FPLAPSSKSTSGGTAALGCLVKDYFPEPVTVSWNSGALTSGVHT FPAVLQSSGLYSLSSVVTVPSSSLGTQTYICNVNHKPSNTKVDKR VEPKSCDKTHTCPPCPAPELLGGPSVFLFPPKPKDTLMISRTPEV TCVVVDVSHEDPEVKFNWYVDGVEVHNAKTKPREEQYNSTYR VVSVLTVLHQDWLNGKEYKCKVSNKALPAPIEKTISKAKGQPRE PQVYTLPPSREEMTKNQVSLTCLVKGFYPSDIAVEWESNGQPE NNYKTTPPVLDSDGSFFLYSKLTVDKSRWQQGNVFSCSVMHEA LHNHYTQKSLSLSPGK |
| | VL | 11 | EIVLTQSPATLSLSPGERATLSCRASQSVSSYLAWYQQKPGQAP RLLIYDASNRATGIPARFSGSGSGTDFTLTISSLEPEDFAVYYCQQ RSNWPPTFGQGTKVEIKRTVAAPSVFIFPPSDEQLKSGTASVVCL LNNFYPREAKVQWKVDNALQSGNSQESVTEQDSKDSTYSLSST LTLSKADYEKHKVYACEVTHQGLSSPVTKSFNRGEC |
| MOR202 (or MOR03087) | VH | 12 | QVQLVESGGGLVQPGGSLRLSCAASGFTFSSYYMNWVRQAPG KGLEWVSGISGDPSNTYYADSVKGRFTISRDNSKNTLYLQMNSL RAEDTAVYYCARDLPLVYTGFAYWGQGTLVTVSS |
| | VL | 13 | DIELTQPPSVSVAPGQTARISCSGDNLRHYYVYWYQQKPGQAP VLVIYGDSKRPSGIPERFSGSNSGNTATLTISGTQAEDEADYYCQ TYTGGASLVFGGGTKLTVLGQ |
| HCDR1-1 | VH | 14 | GFTFSSYYMN |
| HCDR1-2 | VH | 15 | SYYMN |
| HCDR2 | VH | 16 | GISGDPSNTYYADSVKG |
| HCDR3 | VH | 17 | DLPLVYTGFAY |
| HCDR4 | VH | 18 | DYWMQ |
| HCDR5 | VH | 19 | TIYPGDGDTGYAQKFK |

TABLE 17-continued

Sequences of VH and VL chains of the scFv anti-CD38 antibodies daratumumab, MOR202 and of specific CDRs for VH and VL chains.

| Name | VH or VL chain | SEQ ID # | Polypeptide or nucleic acid sequence |
|---|---|---|---|
| HCDR6 | VH | 20 | GDYYGSNSLDY |
| LCDR1 | VL | 21 | SGDNLRHYYVY |
| LCDR2 | VL | 22 | GDSKRPS |
| LCDR3 | VL | 23 | QTYTGGASL |
| LCDR4 | VL | 24 | KASQDVSTVVA |
| LCDR5 | VL | 25 | SASYRYI |
| LCDR6 | VL | 26 | QQHSPPYT |

For the daratumumbab scFv 3 different CARs constructs (GMB005-V1&V2&V3) have been designed such as presented in FIG. 11A and their sequence displayed in the following Table 18. All three constructs share the same components, in terms of signal peptide (CD8a), GS linker (between the scFv VH and VL chains), transmembrane domain (TM), 4-1BB costimulatory domain, and CD3ζ activation domain (sequences displayed in the following Table 18). Their differences come from the choice of the hinge (Table 18):

V1: FcRIIa hinge
V2: CD8a hinge
V3: IgG1 hinge

TABLE 18

Polypeptide sequence of the 3 different structures of scFv daratumumab-based anti-CD38 CARs and of the individual components used

| Name of CAR | SEQ ID # | |
|---|---|---|
| CD8α-Signal peptide (SP) | 27 | MALPVTALLLPLALLLHAARP |
| GS linker | 28 | GGGGSGGGGSGGGGS |
| FCRIIα hinge | 29 | GLAVSTISSFFPPGYQ |
| CD8α hinge | 30 | TTTPAPRPPTPAPTIASQPLSLRPEACRPAAGGAVHTRGLDFACDIYIWAPLAGTCGVLL LSLVITLYC |
| IgG1 hinge | 31 | EPKSPDKTHTCPPCPAPPVAGPSVFLFPPKPKDTLMIARTPEVTCVVVDVSHEDPEVKF NWYVDGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQPENNY KTTPPVLDSDGSFFLYSKLTVDKSRWQQGNVFSCSVMHEALHNHYTQKSLSLSPGK |
| TM domain | 32 | IYIWAPLAGTCGVLLLSLVITLYC |
| 4-1 BB co-stimulatory domain | 33 | KRGRKKLLYIFKQPFMRPVQTTQEEDGCSCRFPEEEEGGCEL |
| CD3ζ activation domain | 34 | RVKFSRSADAPAYQQGQNQLYNELNLGRREEYDVLDKRRGRDPEMGGKPRRKNPQE GLYN ELQKDKMAEAYSEIGMKGERRRGKGHDGLYQGLSTATKDTYDALHMQALPPR |
| GMB005-V1 CAR | 35 | PLALLLHAARPEVQLLESGGGLVQPGGSLRLSCAVSGFTFNSFAMSWVRQAPG KGLEWVSAISGSGGGTYYADSVKGRFTISRDNSKNTLYLQMNSLRAEDTAVYF CAKDKILWFGEPVFDYWGQGTLVTVSSASGGGGSGGGGSGGGGSEIVLTQSP ATLSLSPGERATLSCRASQSVSSYLAWYQQKPGQAPRLLIYDASNRATGIPARFS GSGSGTDFTLTISSLEPEDFAVYYCQQRSNWPPTFGQGTKVEIKGLAVSTISSFF PPGYQIYIWAPLAGTCGVLLLSLVITLYCKRGRKKLLYIFKQPFMRPVQTTQEED GCSCRFPEEEEGGCELRVKFSRSADAPAYQQGQNQLYNELNLGRREEYDVLDK RRGRDPEMGGKPRRKNPQEGLYNELQKDKMAEAYSEIGMKGERRRGKGHD GLYQGLSTATKDTYDA |
| GMB005-V2 CAR | 36 | PLALLLHAARPEVQLLESGGGLVQPGGSLRLSCAVSGFTFNSFAMSWVRQAPG KGLEWVSAISGSGGGTYYADSVKGRFTISRDNSKNTLYLQMNSLRAEDTAVYF CAKDKILWFGEPVFDYWGQGTLVTVSSASGGGGSGGGGSGGGGSEIVLTQSP ATLSLSPGERATLSCRASQSVSSYLAWYQQKPGQAPRLLIYDASNRATGIPARFS |

TABLE 18-continued

Polypeptide sequence of the 3 different structures of scFv daratumumab-based anti-CD38 CARs and of the individual components used

| Name of CAR | SEQ ID # | |
|---|---|---|
| | | GSGSGTDFTLTISSLEPEDFAVYYCQQRSNWPPTFGQGTKVEIKTTTPAPRPPT PAPTIASQPLSLRPEACRPAAGGAVHTRGLDFACDIYIWAPLAGTCGVLLLSLVI TLYCKRGRKKLLYIFKQPFMRPVQTTQEEDGCSCRFPEEEEGGCELRVKFSRSA DAPAYQQGQNQLYNELNLGRREEYDVLDKRRGRDPEMGGKPRRKNPQEGLY NELQKDKMAEAYSEIGMKGERRRGKGHDGLYQGLSTATKDTYDA |
| GMB005-V3 CAR | 37 | PLALLLHAARPEVQLLESGGGLVQPGGSLRLSCAVSGFTFNSFAMSWVRQAPG KGLEWVSAISGSGGGTYYADSVKGRFTISRDNSKNTLYLQMNSLRAEDTAVYF CAKDKILWFGEPVFDYWGQGTLVTVSSASGGGGSGGGGSGGGGSEIVLTQSP ATLSLSPGERATLSCRASQSVSSYLAWYQQKPGQAPRLLIYDASNRATGIPARFS GSGSGTDFTLTISSLEPEDFAVYYCQQRSNWPPTFGQGTKVEIKEPKSPDKTHT CPPCPAPPVAGPSVFLFPPKPKDTLMIARTPEVTCVVVDVSHEDPEVKFNWYV DGVEVHNAKTKPREEQYNSTYRVVSVLTVLHQDWLNGKEYKCKVSNKALPAPI EKTISKAKGQPREPQVYTLPPSRDELTKNQVSLTCLVKGFYPSDIAVEWESNGQ PENNYKTTPPVLDSDGSFFLYSKLTVDKSRWQQGNVFSCSVMHEALHNHYTQ KSLSLSPGKIYIWAPLAGTCGVLLLSLVITLYCKRGRKKLLYIFKQPFMRPVQTTQ EEDGCSCRFPEEEEGGCELRVKFSRSADAPAYQQGQNQLYNELNLGRREEYDV LDKRRGRDPEMGGKPRRKNPQEGLYNELQKDKMAEAYSEIGMKGERRRGKG HDGLYQGLSTATKDTYDA |

Screening

CD38 TALENs will be transfected at day 4 after activation. 3 days after the CD38 deficient cells will be sorted by negative selection and transfected 3 days after with anti-CD38 CAR mRNAs. The CAR molecules generated will then be screened for expression and degranulation activity toward target cell lines expression CD38 upon CAR mRNA transient transfection. Target cell lines expressing different expression levels of CD38 (FIG. 11B) will be used for activity testing:

- U266 CD38+ and U266 CD38− obtained by magnetic separation using anti-CD38 microbeads
- L363, a multiple myeloma cell line expressing intermediate levels of CD38
- Daudi, a cell line derived from Burkitt lymphoma expressing high levels of CD38
- K562, a cell line CD38 negative cell line derived from chronic myelogenous leukemia.

This first screening will be followed by a second screening step in which a number of selected candidates will be tested for their ability to induce degranulation, IFNγ release and specific cytotoxic activity towards the selected target cell lines. Candidate selection will then be narrowed and some candidates selected for lentivirus vector production and CAR activity will be assessed in CD38 KO T-cells stably expressing the CARs.

Example 2 Activity of Anti-CS1 CAR in the Context of CS1 KO

Presentation of CS1 Target

Multiple myeloma (MM) is a B-cell malignancy characterized by the aberrant clonal expansion of plasma cells (PCs) within the bone marrow, with an estimated 21,700 new cases and 10,710 deaths from MM identified in the United States in 2012 (Siegel R, et al. Cancer J Clin 2012 62:10-29). In 2013, it has been estimated that 22,350 individuals will be newly diagnosed with MM in the United States and 10,710 people will die from it, accounting for 20% of the deaths from all hematologic malignancies. Despite the use of proteasome inhibitors and immune-modulating drugs, which have improved overall survival (Palumbo A, et al. Leukemia 2009 23:449-456), MM remains an incurable malignancy (Podar K, et al. Leukemia 2009 23:10-24) for which novel therapeutic approaches are urgently needed.

The cell surface glycoprotein CS1 (also referred in the literature as SLAMF7, CD319 or CRACC—NCBI Reference Sequence: NP_067004.3) is highly and ubiquitously expressed on the surface of myeloma cells (Hsi E D, et al. Clin Cancer Res 2008 14:2775-84). CS1 is expressed at very low levels in the majority of immune effector cells, including natural killer (NK) cells, some subsets of T cells, and normal B cells, and is almost undetectable on myeloid cells (Hsi E D, et al. Clin Cancer Res 2008 14:2775-84). Notably, CS1 is negligibly expressed in human hematopoietic stem cells (Hsi E D, et al. Clin Cancer Res 2008 14:2775-84), which can be used for stem cell transplantation to treat hematologic malignancies, including MM. The functions of CS1 in MM remain incompletely understood, and it has been documented that CS1 may play a role in myeloma cell adhesion, clonogenic growth, and tumorigenicity (Benson D M Jr, et al. J Clin Oncol 2012 30:2013-5; Tai Y T, et al. Blood 2009 113:4309-18).

Structure of the CAR Anti-CS1

The same structures V1, V2 and V3 are designed such as in the Example 1 for the anti-CD38 antigen target single-chain CAR, with the same components in terms of hinge, transmembrane domain, co-activation and transduction domains (such as depicted in the FIG. 11A and sequences shown in Table 18).

In Table 19 are presented the VH and VL chains of scFv anti-CS1. SEQ ID NO:38-40-42-44-46 and SEQ ID NO:39-41-43-45-47 correspond to respectively the VH chain and the VL chain of the murine scFv Luc63, Luc90, Luc34, LucX1 and LucX2.

In Table 20 are presented anti-CS1 CARs with the above scFv; these CARs being based on the versions V1, V2 and V3 of FIG. 11A, wherein respectively the short FcERγ hinge, the medium hinge CD8α hinge and the long IgG1 hinge are used. The underlined parts correspond to the scFv VH and VL chains bound by a linker.

TABLE 19

Sequences of VH and VL chains of the scFv anti-CS1 antibodies

| Name | VH or VL chain | SEQ ID NO: | Polypeptide sequence |
|---|---|---|---|
| Luc63 | VH | 38 | EVKLLESGGGLVQPGGSLKLSCAASGFDFSRYWMSWVRQAPGKGLEWIG EINPDSSTINYTPSLKDKFIISRDNAKNTLYLQMSKVRSEDTALYYCARPDGN YWYFDVWGAGTTVTVSS |
|  | VL | 39 | DIVMTQSHKFMSTSVGDRVSITCKASQDVGIAVAWYQQKPGQSPKLLIY WASTRHTGVPDRFTGSGSGTDFTLTISNVQSEDLADYFCQQYSSYPYTFGG GTKLEIK |
| Luc90 | VH | 40 | QVQLQQPGAELVRPGASVKLSCKASGYSFTTYWMNWVKQRPGQGLEWI GMIHPSDSETRLNQKFKDKATLTVDKSSSTAYMQLSSPTSEDSAVYYCARS TMIATRAMDYWGQGTSVTVSS |
|  | VL | 41 | DIVMTQSQKSMSTSVGDRVSITCKASQDVITGVAWYQQKPGQSPKLLIYS ASYRYTGVPDRFTGSGSGTDFTFTISNVQAEDLAVYYCQQHYSTPLTFGAG TKLELK |
| Luc34 | VH | 42 | QVQLQQSGAELARPGASVKLSCKASGYTFTSYWMQWVKQRPGQGLEWI GAIYPGDGDTRYTQKFKGKATLTADKSSSTAYMQLSSLASEDSAVYYCARG KVYYGSNPFAYWGQGTLVTVSA |
|  | VL | 43 | DIQMTQSSSYLSVSLGGRVTITCKASDHINNWLAWYQQKPGNAPRLLISG ATSLETGVPSRFSGSGSGKDYTLSITSLQTEDVATYYCQQYWSTPWTFGGG TKLEIK |
| LucX1 | VH | 44 | QVQLQQSGPELVKPGASVKISCKASGYAFSSSWMNWVKQRPGQGLEWI GRIYPG DGDTKYNGKFKGKATLTADKSSSTAYMQLSSLTSVDSAVYFCARS TMIATGAMDYWGQGTSVTVSS |
|  | VL | 45 | ETTVTQSPASLSMAIGEKVTIRCITSTDIDDDMNWYQQKPGEPPKLLISEGN TLRPGVPSRFSSSGYGTDFVFTIENMLSEDVADYCLQSDNLPLTFGGGTKL EIK |
| LucX2 | VH | 46 | QVQLQQSGPELVKPGASVKISCKASGYAFSSSWMNWVKQRPGQGLEW1 GRIYPGDGDTKYNGKFKGKATLTADKSSSTAYMQLSSLTSVDSAVYFCARS TMIATGAMDYWGQGTSVTVSS |
|  | VL | 47 | DIVMTQSHKFMSTSVGDRVSITCKASQDVSTAVAWYQQKPGQSPKLLIYS ASYRYTGVPDRFTGSGSGTDFTFTISSVQAEDLAVYYCQQHYSTPPYTFGG GTKLEIK |

TABLE 20

Polypeptide sequence of anti-CS1 CARs based on the V1, V2 and V3 versions in FIG. 11A

| Name of CAR | SEQ ID # | Polypeptide sequence |
|---|---|---|
| Luc63-V1 CAR | 48 | MALPVTALLLPLALLLHAARP<u>EVKLLESGGGLVQPGGSLKLSCAASGFDFSRYWMSWVRQAPGKGL EWIGEINPDSSTINYTPSLKDKFIISRDNAKNTLYLQMSKVRSEDTALYYCARPDGNYWYFDVWGAG TTVTVSS</u>GGGGSGGGGSGGGGS<u>DIVMTQSHKFMSTSVGDRVSITCKASQDVGIAVAWYQQKPGQ SPKLLIYWASTRHTGVPDRFTGSGSGTDFTLTISNVQSEDLADYFCQQYSSYPYTFGGGTKLEIK</u>GLAV STISSFFPPGYQKRGRKKLLYIFKQPFMRPVQTTQEEDGCSCRFPEEEEGGCELRVKFSRSADAPAYQ QGQNQLYNELNLGRREEYDVLDKRRGRDPEMGGKPRRKNPQEGLYNELQKDKMAEAYSEIGMKG ERRRGKGHDGLYQGLSTATKDTYDALHMQALPPR |
| Luc63-V2 CAR | 49 | MALPVTALLLPLALLLHAARP<u>EVKLLESGGGLVQPGGSLKLSCAASGFDFSRYWMSWVRQAPGKGL EWIGEINPDSSTINYTPSLKDKFIISRDNAKNTLYLQMSKVRSEDTALYYCARPDGNYWYFDVWGAG TTVTVSS</u>GGGGSGGGGSGGGGS<u>DIVMTQSHKFMSTSVGDRVSITCKASQDVGIAVAWYQQKPGQ SPKLLIYWASTRHTGVPDRFTGSGSGTDFTLTISNVQSEDLADYFCQQYSSYPYTFGGGTKLEIK</u>TTTP APRPPTPAPTIASQPLSLRPEACRPAAGGAVHTRGLDFACDIYIWAPLAGTCGVLLLSLVITLYCKRGR KKLLYIFKQPFMRPVQTTEEDGCSCRFPEEEEGGCELRVKFSRSADAPAYQQGQNQLYNELNLGR REEYDVLDKRRGRDPEMGGKPRRKNPQEGLYNELQKDKMAEAYSEIGMKGERRRGKGHDGLYQG LSTATKDTYDALHMQALPPR |
| Luc63-V3 CAR | 50 | MALPVTALLLPLALLLHAARP<u>EVKLLESGGGLVQPGGSLKLSCAASGFDFSRYWMSWVRQAPGKGL EWIGEINPDSSTINYTPSLKDKFIISRDNAKNTLYLQMSKVRSEDTALYYCARPDGNYWYFDVWGAG TTVTVSS</u>GGGGSGGGGSGGGGS<u>DIVMTQSHKFMSTSVGDRVSITCKASQDVGIAVAWYQQKPGQ SPKLLIYWASTRHTGVPDRFTGSGSGTDFTLTISNVQSEDLADYFCQQYSSYPYTFGGGTKLEIK</u>EPKS PDKTHTCPPCPAPPVAGPSVFLFPPKPKDTLMIARTPEVTCVVVDVSHEDPEVKFNWYVDGVEVHN AKTKPREEQYNSTYRVVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFFLYSKLTVDKSRWQQG NVFSCSVMHEALHNHYTQKSLSLSPGKKRGRKKLLYIFKQPFMRPVQTTQEEDGCSCRFPEEEEGGC ELRVKFSRSADAPAYQQGQNQLYNELNLGRREEYDVLDKRRGRDPEMGGKPRRKNPQEGLYNELQ KDKMAEAYSEIGMKGERRRGKGHDGLYQGLSTATKDTYDALHMQALPPR |

TABLE 20-continued

Polypeptide sequence of anti-CS1 CARs based on the V1, V2 and V3 versions in FIG. 11A

| Name of CAR | SEQ ID # | Polypeptide sequence |
|---|---|---|
| Luc90-V1 CAR | 51 | MALPVTALLLPLALLLHAARP<u>QVQLQQPGAELVRPGASVKLSCKASGYSFTTYWMNWVKQRPGQ GLEWIGMIHPSDSETRLNQKFKDKATLTVDKSSTAYMQLSSPTSEDSAVYYCARSTMIATRAMDY WGQGTSVTVSS</u>GGGGSGGGGSGGGGS<u>DIVMTQSQKSMSTSVGDRVSITCKASQDVITGVAWYQ QKPGQSPKLLIYSASYRYTGVPDRFTGSGSGTDFTFTISNVQAEDLAVYYCQQHYSTPLTFGAGTKLEL K</u>GLAVSTISSFFPPGYQKRGRKKLLYIFKQPFMRPVQTTQEEDGCSCRFPEEEEGGCELRVKFSRSAD APAYQQGQNQLYNELNLGRREEYDVLDKRRGRDPEMGGKPRRKNPQEGLYNELQKDKMAEAYSE IGMKGERRRGKGHDGLYQGLSTATKDTYDALHMQALPPR |
| Luc90-V2 CAR | 52 | MALPVTALLLPLALLLHAARP<u>QVQLQQPGAELVRPGASVKLSCKASGYSFTTYWMNWVKQRPGQ GLEWIGMIHPSDSETRLNQKFKDKATLTVDKSSTAYMQLSSPTSEDSAVYYCARSTMIATRAMDY WGQGTSVTVSS</u>GGGGSGGGGSGGGGS<u>DIVMTQSQKSMSTSVGDRVSITCKASQDVITGVAWYQ QKPGQSPKLLIYSASYRYTGVPDRFTGSGSGTDFTFTISNVQAEDLAVYYCQQHYSTPLTFGAGTKLEL K</u>TTTPAPRPPTPAPTIASQPLSLRPEACRPAAGGAVHTRGLDFACDIYIWAPLAGTCGVLLLSLVITLYC KRGRKKLLYIFKQPFMRPVQTTQEEDGCSCRFPEEEEGGCELRVKFSRSADAPAYQQGQNQLYNEL NLGRREEYDVLDKRRGRDPEMGGKPRRKNPQEGLYNELQKDKMAEAYSEIGMKGERRRGKGHDG LYQGLSTATKDTYDALHMQALPPR |
| Luc90-V3 CAR | 53 | MALPVTALLLPLALLLHAARP<u>QVQLQQPGAELVRPGASVKLSCKASGYSFTTYWMNWVKQRPGQ GLEWIGMIHPSDSETRLNQKFKDKATLTVDKSSTAYMQLSSPTSEDSAVYYCARSTMIATRAMDY WGQGTSVTVSS</u>GGGGSGGGGSGGGGS<u>DIVMTQSQKSMSTSVGDRVSITCKASQDVITGVAWYQ QKPGQSPKLLIYSASYRYTGVPDRFTGSGSGTDFTFTISNVQAEDLAVYYCQQHYSTPLTFGAGTKLEL K</u>EPKSPDKTHTCPPCPAPPVAGPSVFLFPPKPKDTLMIARTPEVTCVVVDVSHEDPEVKFNWYVDG VEVHNAKTKPREEQYNSTYRVVSVLTVLHQDWLNGKEYKCKVSNKALPAPIEKTISKAKGQPREPQV YTLPPSRDELTKNQVSLTCLVKGFYPSDIAVEWESNGQPENNYKTTPPVLDSDGSFFLYSKLTVDKSR WQQGNVFSCSVMHEALHNHYTQKSLSLSPGKKRGRKKLLYIFKQPFMRPVQTTQEEDGCSCRFPEE EEGGCELRVKFSRSADAPAYQQGQNQLYNELNLGRREEYDVLDKRRGRDPEMGGKPRRKNPQEGL YNELQKDKMAEAYSEIGMKGERRRGKGHDGLYQGLSTATKDTYDALHMQALPPR |
| Luc34-V1 CAR | 54 | MALPVTALLLPLALLLHAARP<u>QVQLQQSGAELARPGASVKLSCKASGYTFTSYWMQWVKQRPGQG LEWIGAIYPGDGDTRYTQKFKGKATLTADKSSSTAYMQLSSLASEDSAVYYCARGKVYYGSNPFAYW GQGTLVTVSA</u>GGGGSGGGGSGGGGS<u>DIQMTQSSSYLSVSLGGRVTITCKASDHINNWLAWYQQK PGNAPRLLISGATSLETGVPSRFSGSGSGKDYTLSITSLQTEDVATYYCQQYWSTPWTFGGGTKLEIK G</u>LAVSTISSFFPPGYQKRG RKKLLYI FKQPFM RPVQTTQE EDGCSCRFPEE EEGGCE LRVKFSRSADA PAYQQGQNQLYNELNLGRREEYDVLDKRRGRDPEMGGKPRRKNPQEGLYNELQKDKMAEAYSEI GMKGERRRGKGHDGLYQGLSTATKDTYDALHMQALPPR |
| Luc34-V2 CAR | 55 | MALPVTALLLPLALLLHAARP<u>QVQLQQSGAELARPGASVKLSCKASGYTFTSYWMQWVKQRPGQG LEWIGAIYPGDGDTRYTQKFKGKATLTADKSSSTAYMQLSSLASEDSAVYYCARGKVYYGSNPFAYW GQGTLVTVSA</u>GGGGSGGGGSGGGGS<u>DIQMTQSSSYLSVSLGGRVTITCKASDHINNWLAWYQQK PGNAPRLLISGATSLETGVPSRFSGSGSGKDYTLSITSLQTEDVATYYCQQYWSTPWTFGGGTKLEIK</u> TTTPAPRPPTPAPTIASQPLSLRPEACRPAAGGAVHTRGLDFACDIYIWAPLAGTCGVLLLSLVITLYCK RGRKKLLYIFKQPFMRPVQTTQEEDGCSCRFPEEEEGGCELRVKFSRSADAPAYQQGQNQLYNELN LGRREEYDVLDKRRGRDPEMGGKPRRKNPQEGLYNELQKDKMAEAYSEIGMKGERRRGKGHDGL YQGLSTATKDTYDALHMQALPPR |
| Luc34-V3 CAR | 56 | MALPVTALLLPLALLLHAARP<u>QVQLQQSGAELARPGASVKLSCKASGYTFTSYWMQWVKQRPGQG LEWIGAIYPGDGDTRYTQKFKGKATLTADKSSSTAYMQLSSLASEDSAVYYCARGKVYYGSNPFAYW GQGTLVTVSA</u>GGGGSGGGGSGGGGS<u>DIQMTQSSSYLSVSLGGRVTITCKASDHINNWLAWYQQK PGNAPRLLISGATSLETGVPSRFSGSGSGKDYTLSITSLQTEDVATYYCQQYWSTPWTFGGGTKLEIK</u> EPKSPDKTHTCPPCPAPPVAGPSVFLFPPKPKDTLMIARTPEVTCVVVDVSHEDPEVKFNWYVDGVE VHNAKTKPREEQYNSTYRVVSVLTVLHQDWLNGKEYKCKVSNKALPAPIEKTISKAKGQPREPQVYT LPPSRDELTKNQVSLTCLVKGFYPSDIAVEWESNGQPENNYKTTPPVLDSDGSFFLYSKLTVDKSRW QQGNVFSCSVMHEALHNHYTQKSLSLSPGKKRGRKKLLYIFKQPFMRPVQTTQEEDGCSCRFPEEE EGGCELRVKFSRSADAPAYQQGQNQLYNELNLGRREEYDVLDKRRGRDPEMGGKPRRKNPQEGLY NELQKDKMAEAYSEIGMKGERRRGKGHDGLYQGLSTATKDTYDALHMQALPPR |
| LucX1-V1 CAR | 57 | MALPVTALLLPLALLLHAARP<u>QVQLQQSGPELVKPGASVKISCKASGYAFSSSWMNWVKQRPGQG LEWIGRIYPGDGDTKYNGKFKGKATLTADKSSSTAYMQLSSLTSVDSAVYFCARSTMIATGAMDYW GQGTSVTVSS</u>GGGGSGGGGSGGGGS<u>ETTVTQSPASLSMAIGEKVTIRCITSTDIDDDMNWYQQKP GEPPKLLISEGNTLRPGVPSRFSSSGYGTDFVFTIENMLSEDVADYYCLQSDNLPLTFGGGTKLEIKG</u>L AVSTISSFFPPGYQKRGRKKLLYIFKQPFMRPVQTTQEEDGCSCRFPEEEEGGCELRVKFSRSADAPA YQQGQNQLYNELNLGRREEYDVLDKRRGRDPEMGGKPRRKNPQEGLYNELQKDKMAEAYSEIGM KGERRRGKGHDGLYQGLSTATKDTYDALHMQALPPR |
| LucX1-V2 CAR | 58 | MALPVTALLLPLALLLHAARP<u>QVQLQQSGAELARPGASVKLSCKASGYTFTSYWMQWVKQRPGQG LEWIGAIYPGDGDTRYTQKFKGKATLTADKSSSTAYMQLSSLASEDSAVYYCARGKVYYGSNPFAYW GQGTLVTVSA</u>GGGGSGGGGSGGGGS<u>DIQMTQSSSYLSVSLGGRVTITCKASDHINNWLAWYQQK PGNAPRLLISGATSLETGVPSRFSGSGSGKDYTLSITSLQTEDVATYYCQQYWSTPWTFGGGTKLEIK</u> TTTPAPRPPTPAPTIASQPLSLRPEACRPAAGGAVHTRGLDFACDIYIWAPLAGTCGVLLLSLVITLYCK RGRKKLLYIFKQPFMRPVQTTQEEDGCSCRFPEEEEGGCELRVKFSRSADAPAYQQGQNQLYNELN LGRREEYDVLDKRRGRDPEMGGKPRRKNPQEGLYNELQKDKMAEAYSEIGMKGERRRGKGHDGL YQGLSTATKDTYDALHMQALPPR |

TABLE 20-continued

Polypeptide sequence of anti-CS1 CARs based on the V1, V2 and V3 versions in FIG. 11A

| Name of CAR | SEQ ID # | Polypeptide sequence |
|---|---|---|
| LucX1-V3 CAR | 59 | MALPVTALLLPLALLLHAARPQVQLQQSGPELVKPGASVKISCKASGYAFSSSWMNWVKQRPGQG<br>LEWIGRIYPGDGDTKYNGKFKGKATLTADKSSSTAYMQLSSLTSVDSAVYFCARSTMIATGAMDYW<br>GQGTSVTVSSGGGGSGGGGSGGGGSETTVTQSPASLSMAIGEKVTIRCITSTDIDDDMNWYQQKP<br>GEPPKLLISEGNTLRPGVPSRFSSSGYGTDFVFTIENMLSEDVADYYCLQSDNLPLTFGGGTKLEIKEPK<br>SPDKTHTCPPCPAPPVAGPSVFLFPPKPKDTLMIARTPEVTCVVVDVSHEDPEVKFNWYVDGVEVH<br>NAKTKPREEQYNSTYRVVSVLTVLHQDWLNGKEYKCKVSNKALPAPIEKTISKAKGQPREPQVYTLP<br>PSRDELTKNQVSLTCLVKGFYPSDIAVEWESNGQPENNYKTTPPVLDSDGSFFLYSKLTVDKSRWQQ<br>GNVFSCSVMHEALHNHYTQKSLSLSPGKKRGRKKLLYIFKQPFMRPVQTTQEEDGCSCRFPEEEEGG<br>CELRVKFSRSADAPAYQQGQNQLYNELNLGRREEYDVLDKRRGRDPEMGGKPRRKNPQEGLYNEL<br>QKDKMAEAYSEIGMKGERRRGKGHDGLYQGLSTATKDTYDALHMQALPPR |
| LucX2-V1 CAR | 60 | MALPVTALLLPLALLLHAARPQVQLQQSGPELVKPGASVKISCKASGYAFSSSWMNWVKQRPGQG<br>LEWIGRIYPGDGDTKYNGKFKGKATLTADKSSSTAYMQLSSLTSVDSAVYFCARSTMIATGAMDYW<br>GQGTSVTVSSGGGGSGGGGSGGGGSDIVMTQSHKFMSTSVGDRVSITCKASQDVSTAVAWYQQ<br>KPGQSPKLLIYSASYRYTGVPDRFTGSGSGTDFTFTISSVQAEDLAVYYCQQHYSTPPYTFGGGTKLEI<br>KGLAVSTISSFFPPGYQKRGRKKLLYIFKQPFMRPVQTTQEEDGCSCRFPEEEEGGCELRVKFSRSAD<br>APAYQQGQNQLYNELNLGRREEYDVLDKRRGRDPEMGGKPRRKNPQEGLYNELQKDKMAEAYSE<br>IGMKGERRRGKGHDGLYQGLSTATKDTYDALHMQALPPR |
| LucX2-V2 CAR | 61 | MALPVTALLLPLALLLHAARPQVQLQQSGPELVKPGASVKISCKASGYAFSSSWMNWVKQRPGQG<br>LEWIGRIYPGDGDTKYNGKFKGKATLTADKSSSTAYMQLSSLTSVDSAVYFCARSTMIATGAMDYW<br>GQGTSVTVSSGGGGSGGGGSGGGGSDIVMTQSHKFMSTSVGDRVSITCKASQDVSTAVAWYQQ<br>KPGQSPKLLIYSASYRYTGVPDRFTGSGSGTDFTFTISSVQAEDLAVYYCQQHYSTPPYTFGGGTKLEI<br>KTTTPAPRPPTPAPTIASQPLSLRPEACRPAAGGAVHTRGLDFACDIYIWAPLAGTCGVLLLSLVITLYC<br>KRGRKKLLYIFKQPFMRPVQTTQEEDGCSCRFPEEEEGGCELRVKFSRSADAPAYQQGQNQLYNEL<br>NLGRREEYDVLDKRRGRDPEMGGKPRRKNPQEGLYNELQKDKMAEAYSEIGMKGERRRGKGHDG<br>LYQGLSTATKDTYDALHMQALPPR |
| LucX2-V3 CAR | 62 | MALPVTALLLPLALLLHAARPQVQLQQSGPELVKPGASVKISCKASGYAFSSSWMNWVKQRPGQG<br>LEWIGRIYPGDGDTKYNGKFKGKATLTADKSSSTAYMQLSSLTSVDSAVYFCARSTMIATGAMDYW<br>GQGTSVTVSSGGGGSGGGGSGGGGSDIVMTQSHKFMSTSVGDRVSITCKASQDVSTAVAWYQQ<br>KPGQSPKLLIYSASYRYTGVPDRFTGSGSGTDFTFTISSVQAEDLAVYYCQQHYSTPPYTFGGGTKLEI<br>KEPKSPDKTHTCPPCPAPPVAGPSVFLFPPKPKDTLMIARTPEVTCVVVDVSHEDPEVKFNWYVDG<br>VEVHNAKTKPREEQYNSTYRVVSVLTVLHQDWLNGKEYKCKVSNKALPAPIEKTISKAKGQPREPQV<br>YTLPPSRDELTKNQVSLTCLVKGFYPSDIAVEWESNGQPENNYKTTPPVLDSDGSFFLYSKLTVDKSR<br>WQQGNVFSCSVMHEALHNHYTQKSLSLSPGKKRGRKKLLYIFKQPFMRPVQTTQEEDGCSCRFPEE<br>EEGGCELRVKFSRSADAPAYQQGQNQLYNELNLGRREEYDVLDKRRGRDPEMGGKPRRKNPQEGL<br>YNELQKDKMAEAYSEIGMKGERRRGKGHDGLYQGLSTATKDTYDALHMQALPPR |

Strategy for CAR CS1+ and KO CS1 Engineering

CS1 is expressed at high levels in plasmacytoid cells from patients with Multiple Myeloma, making this an interesting target for CAR development. T-cells, especially the CD8 subset, express low levels of CS1, which is a drawback for T-cell CAR development, since they could be killed when expressing an anti-CS1 CAR.

In this example we assessed the activity of the Luc90-v2 CAR (sequence shown in Table 20) in human T-cells that were either mock transfected, or transfected with a TALEN targeting the CS1 (SLAM F7) gene, to see if the CAR activity was enhanced when the CS1 gene was disrupted in CAR+ T-cells. The course of the experiment is shown in the FIG. 12.

T-cells were purified from buffy-coat samples and activated using CD3/CD28-coated beads. Cells were co-transfected 72 h after activation with 10 μg of mRNA encoding the T01_left TAL and 10 μg of the mRNA encoding the T01_right TAL. Sequences of the TALs are shown in the following Table 21 and the plasmid constructs (T01, T02 and T03) with the TAL repeats shown in FIG. 13.

FIG. 14 shows the target location for the TALs T01, T02 and T03 within the CS1 (SLAMF7) gene: T01 and T02 target the exon 1 (FIG. 14A), whereas T03 targets the exon 2 (FIG. 14B).

TABLE 21

Sequences of the CS1 target and TALENs for its inactivation

| Name | TALEN L/R | SEQ ID # | Nucleic acid sequence |
|---|---|---|---|
| Target of T01 | | 63 | TGACTTCCAGAGAGCAATATGGCTG GTTCCCCAACATGCCTCACCCTCA |
| | L | 64 | TGACTTCCAGAGAGCAA |
| | R | 65 | AACATGCCTCACCCTCA |
| Target of T02 | | 66 | TTCCAGAGAGCAATATGGCTGGTTC CCCAACATGCCTCACCCTCATCTA |
| | L | 67 | TTCCAGAGAGCAATATG |
| | R | 68 | TGCCTCACCCTCATCTA |
| Target of T03 | | 69 | TTGACTCTATTGTCTGGACCTTCAA CACAACCCCTCTTGTCACCATACA |
| | L | 70 | TTGACTCTATTGTCTGG |
| | R | 71 | CCTCTTGTCACCATACA |

3 days after TALEn transfection, cells were transduced with a recombinant lentiviral vector driving expression of the L90-v2 CAR off an EF1a promoter. The lentiviral vector is built in a way that CAR expression is coupled with BFP expression (Blue Fluorescent Protein) through a ribosomal skip peptide. The L90-v2 CAR is constituted by an extracellular binding domain recognizing the CS1 target (scFv L90) followed by hinge and transmembrane regions derived from the hCD8α protein. The intracellular portion of the molecule contains a 41BB-derived costimulatory domain, followed by the CD3γ signaling domain (sequences displayed in previous Table 18-19-20 for individual components, scFv and CAR sequences respectively).

Transduction efficiency was assessed 6 days after transduction by flow cytometry, by following BFP expression. Cells were also stained with anti-CD8 and anti-CS1 antibodies.

Results

CAR CS1+ Expression

The results from FIG. 16 show that the transduction efficiencies are higher in mock transfected cells than in cells that have been transfected with TALEn targeting the CS1 gene. This is probably due to specific cell killing of non-transduced CS1-expressing T-cells, while this population is not affected when the cells no longer express CS1 as a consequence of TALEN-driven gene disruption.

No significant differences in CS1 levels are observed at this timepoint between TALEN or mock transfected cells (negative control-transfection without plasmid), since CS1 levels decrease over time after initial activation of T-cells. On the other hand, a significant decrease in the % of CD8+ cells is observed in mock transfected CAR expressing cells compared to TALEN transfected CAR+ cells, indicating that a high proportion of CD8+ cells has been eliminated by the CAR+ T-cells.

Cytotoxic Activity Assessment

The cytotoxic activity of these cells was evaluated 8 days after CAR transduction, by co-culturing the same amount of T-cells either with a cell line expressing CS1 (L363 cells) or a negative control cell line lacking expression of CS1 (MOLM13). The viability of the target cell lines was measured by flow cytometry 4 h after starting cell co-cultures. The results shown in FIG. 15A show reduced cell viability of CS1(+) cells when they were co-cultured with CAR+ T-cells, while no impact on CS1(−) cell viability was observed. The specific cell lysis was calculated using the flow cytometry data, and it was 2-times higher when T-cells have been transfected with TALEn targeting the CS1 gene prior to CAR transduction (FIG. 15B). It should be considered that the impact might be even higher, since the amount of CAR+ T-cells present in the co-cultures is higher when the cells were mock transfected (see flow cytometry data from FIG. 16). The results from the experiment are the following:

for the Mock/NTD sample, the % of BFP+ cells is 0.1% and the amount of CD8+ cells is 53.9%;
for the TALEn/NTD sample, the % of BFP+ cells is 0.2% and the amount of CD8+ cells is 49.5%;
for the Mock/L90-2 sample, the % of BFP+ cells is 94% and the amount of CD8+ cells is 1.8%;
for the TALEn/L90-2 sample, the % of BFP+ cells is 61% and the amount of CD8+ cells is 8.3%.

Transduction efficiencies are higher in mock transfected cells than in cells that have been transfected with TALEn targeting the CS1 gene (NTD: not transduced).

Reactivation after Transduction

In order to confirm that the CS1 gene has been disrupted in TALEn transfected T-cells, the different samples were reactivated with CD3/CD28 beads at D11 after transduction. 72 h after reactivation cells were stained with anti-CD8 and anti-CS1 antibodies and expression analyzed by flow cytometry.

FIG. 17 shows the transduction efficiencies and CD8/CS1 expression levels in each sample. As shown in the lower panel, an increase in CS1 levels upon re-activation is observed in mock transfected cells, while a low amount of cells are able to express CS1 in the TALEn transfected populations.

The results from the experiment are the following:

for the Mock/NTD sample, the % of BFP+ cells is 0.01%, CS1 is expressed in 65.2% of cells, and the amount of CD8+ cells is 80.7%;
for the TALEn/NTD sample, the % of BFP+ cells is 0.2%, the CS1 is expressed in 9.7% of cells and the amount of CD8+ cells is 78.8%;
for the Mock/L90-2 sample, the % of BFP+ cells is 94%, the CS1 is expressed in 37.5% of cells and the amount of CD8+ cells is 16%.
for the TALEn/L90-2 sample, the BFP intensity is 61%, the CS1 expression is 8.5% and the CD8 expression is 68.5%.

An increase in CS1 levels upon re-activation is observed in mock transfected cells, while a low amount of cells are able to express CS1 in the TALEn transfected populations.

Altogether, these results indicate that the CS1 gene is disrupted in TALEn transfected T-cells, and that this enhances the cytotoxic activity of anti-CS1 CAR+ cells, mainly by preserving the cytotoxic CD8+ T-cells.

Example 3: CD70 Target

Presentation of CD70 Target

The CD70 is a cytokine that binds to CD27 and is part of the TNF family (Goodwin R. G. et al, 1993, Cell 73:447-456). This protein has a role in adaptive T cell responses, induces the proliferation of costimulated T-cells and enhances the generation of cytolytic T-cells. Its accession number is P32970 (Uniprot). Some studies such as in Schürch, C. et al. (J. Clin. Invest., 2012; doi:10.1172/JCI45977) suggest that blocking CD27-CD70 interactions could help treat chronic myelogenous leukemia (CML).

Strategy for CD70 KO

The same strategy for the KO of CD70 gene will be performed such as in Example 1 and Example 2. Heterodimeric TALE-nuclease targeting two 49-pb long sequences separated by a 15pb spacer within the CD70 gene and one TALE-nuclease targeting a 57-pb long sequence separated by a 23pb spacer were designed and produced. Each half target is recognized by repeats of the half TALE-nucleases listed in the following Table 22.

TABLE 22

Sequences of the CD70 target and TALENs for its inactivation

| Name | TALEN L/R | SEQ ID # | Nucleic acid sequence |
|---|---|---|---|
| Target 1 | | 72 | TGGTCTTTTCTTCCAGTgggacgta gctgagcTGCAGCTGAATCACACA |
| TALEN 1 | L | 73 | TGGTCTTTTCTTCCAGT |
| | R | 74 | TGCAGCTGAATCACACA |
| Target 2 | | 75 | TGGTGATCTGCCTCGTGgtgtgcat ccagcgcTTCGCACAGGCTCAGCA |
| TALEN 2 | L | 76 | TGGTGATCTGCCTCGTG |
| | R | 77 | TTCGCACAGGCTCAGCA |
| Target 3 | | 78 | TGCGGGCTGCTTTGGTCccat-tggtcgcg ggcttggtgatCTGCCTCGTGGTGTGCA |
| TALEN 3 | L | 79 | TGCGGGCTGCTTTGGTC |
| | R | 80 | CTGCCTCGTGGTGTGCA |

Strategy for the Expression of Anti-CD70 CAR

The same strategy for expressing a CAR anti-CD70 will be performed such as in Example 1 and in Example 2.

The same structures V1, V2 and V3 are designed such as in the Example 1-2 with the same components in terms of signal peptide, linker between the VH and VL chains, transmembrane domain, co-activation and transduction domains (general architectures shown in FIG. 11A, and sequences for individual components shown in Table 18). Only the hinge differs between the 3 versions V1, V2 and V3, wherein respectively the short FcERγ hinge, the medium hinge CD8a hinge and the long IgG1 hinge are used.

In Table 23 are presented VH and VL chain of scFv anti-CD70. SEQ ID NO:81-82, 85-86, 89-90 and SEQ ID NO:83-84, 87-88, 91-92 correspond to respectively the VH chain and the VL chain of the scFv Ab4, Ab8 from AMGEN and 1F6 from Seattle Genetics.

In Table 24 are presented the anti-CD70 CARs with the above scFv; these CARs being based on the versions V1, V2 and V3 according to FIG. 11A, wherein respectively a short FcEγ hinge, a medium hinge CD8 and a long IgG1 hinge are used.

TABLE 23

Polynucleotide and nucleic acid sequences of VH and VL chains for the scFv anti-CD70 Ab4, Ab8 and 1F6 antibodies

| Name | VH or VL chain | SEQ ID # | Polypeptide and nucleic acid sequence |
|---|---|---|---|
| Ab4 | VH | 81 | QVQLVESGGGVVQPGRSLRLSCAASGFTFSNYGIHWVRQAPGKGLE WVAVIWYDGSNKYYADSVKGRFTISRDNSKNTLYLQMNSLRAEDTAV YYCARDGGYSGYDSGFDYWGQGTLVTVSS |
|  |  | 82 | caggtgcagctggtggagtctgggggaggcgtggtccagcctggggaggtccctgagactctcctgt gcagcgtctggattcaccttcagtaactatggcatacactgggtccgccaggctccaggcaaggg gctggagtgggtggcagttatatggtatgatggaagtaataaatactatgcagactccgtgaagg gccgattcaccatctccagagacaattccaagaacacgctgtatctgcaaatgaacagcctgaga gccgaggacacggctgtgtattactgtgcgagagatggaggatatagtggctacgattcggggttt gactactggggccagggaacccctggtcaccgtctcctcagctagcaccaagggcccatccgtcttc cccctggcaccctcctccaagagcacctctgggggcacagcggccctgggctgcctggtcaagga ctacttccccgaaccggtgacggtgtcgtggaactcaggcgccctgaccagcggcgtgcacacctt cccggctgtcctacagtcctcaggactctactccctcagcagcgtggtgaccgtgccctccagcag cttgggcacccagacctacatctgcaacgtgaatcacaagcccagcaacaccaaggtggacaag aaagttgagcccaaatcttgtgacaaaactcacacatgcccaccgtgcccagcacctgaactcct ggggggaccgtcagtcttcctcttccccccaaaacccaaggacaccctcatgatctcccggacccc tgaggtcacatgcgtggtggtggacgtgagccacgaagaccctgaggtcaagttcaactggtacg tggacggcgtggaggtgcataatgccaagacaaagccgcgggaggagcagtacaacagcacgt accgtgtggtcagcgtcctcaccgtcctgcaccaggactggctgaatggcaaggagtacaagtgc aaggtctccaacaaagccctcccagcccccatcgagaaaaccatctccaaagccaaagggcagc cccgagaaccacaggtgtaccccctgcccccatcccgggaggagatgaccaagaaccaggtcag cctgacctgcctggtcaaaggcttctatcccagcgacatcgccgtggagtgggagagcaatgggc agccggagaacaactacaagaccacgcctcccgtgctggactccgacggctccttcttcctctata gcaagctcaccgtggacaagagcaggtggcagcaggggaacgtcttctcatgctccgtgatgcat gaggctctgcacaaccactacacgcagaagagcctctccctgtctccgggtaaatga |
|  | VL | 83 | DIVMTQSPLSLPVTPGEPASISCRSSQSLLNSNGYNYLDWYLQKPGQS PQFLIYLGSYRASGVPDRFSGSGSGTDFTLRISRVEAEDVGVYYCIQTLQ TPFTFGPGTKVDIK |
|  |  | 84 | Gatattgtgatgactcagtctccactctccctgcccgtcacccctggagagccggcctccatctcct gcaggtctagtcagagcctcctgaatagtaatggatacaactatttggattggtacctgcagaagc cagggcagtctccacagttcctgatctatttgggttcttatcgggcctccggggtccctgacaggttc agtggcagtggatcaggcacagattttacactgagaatcagcagagtggaggctgaggatgttgg ggttttattactgtatacaaactctacaaactccattcacttttcggccctgggaccaaagtggatatc aaacgtacggtggctgcaccatctgtcttcatcttcccgccatctgatgagcagttgaaatctggaa ctgcctctgttgtgtgcctgctgaataacttctatcccagagaggccaaagtacagtggaaggtgg ataacgccctccaatcgggtaactcccaggagagtgtcacagagcaggacagcaaggacagcac ctacagcctcagcagcaccctgacgctgagcaaagcagactacgagaaacacaaagtctacgcc tgcgaagtcacccatcagggcctgagctcgcccgtcacaaagagcttcaacaggggagagtgtta gtcctca53ggactctactccctcagcagcgtggtgaccgtgccctccagcagcttgggcacccag acctacatctgcaacgtgaatcacaagcccagcaacaccaaggtggacaagaaagttgagccca aatcttgtgacaaaactcacacatgcccaccgtgcccagcacctgaactcctggggggaccgtca gtcttcctcttccccccaaaacccaaggacaccctcatgatctcccggacccctgaggtcacatgc gtggtggtggacgtgagccacgaagaccctgaggtcaagttcaactggtacgtggacggcgtgga ggtgcataatgccaagacaaagccgcgggaggagcagtacaacagcacgtaccgtgtggtcagc gtcctcaccgtcctgcaccaggactggctgaatggcaaggagtacaagtgcaaggtctccaacaa agccctcccagcccccatcgagaaaaccatctccaaagccaaagggcagccccgagaaccacag gtgtacaccctgcccccatcccgggaggagatgaccaagaaccaggtcagcctgacctgcctggt caaaggcttctatcccagcgacatcgccgtggagtgggagagcaatgggcagccggagaacaac tacaagaccacgcctcccgtgctggactccgacggctccttcttcctctatagcaagctcaccgtgg acaagagcaggtggcagcaggggaacgtcttctcatgctccgtgatgcatgaggctctgcacaac cactacacgcagaagagcctctccctgtctccgggtaaa |
| Ab8 | VH | 85 | QVQLVESGGGVVQPGRSLRLSCAASGFTFSSYGMHWVRQAPGKGLE WVAVIWYDGSDKYFADSVKGRFTISRDNSKNTLYLQMNSLRAEDTAV YYCARDGIAGARYVYFDYWGQGTLVTVSS |
|  |  | 86 | caggtgcagctggtggagtctgggggaggcgtggtccagcctggggaggtccctgagactctcctgt gcagcgtctggattcaccttcagtagctatggcatgcactgggtccgccaggctccaggcaaggg gctggagtgggtggcagttatatggtatgatggaagtgataaatactttgcagactccgtgaaggg ccgattcaccatctccagagacaattccaagaacacgctgtatctgcaaatgaacagcctgagag |

TABLE 23-continued

Polynucleotide and nucleic acid sequences of VH and VL chains for the scFv anti-CD70 Ab4, Ab8 and 1F6 antibodies

| Name | VH or VL chain | SEQ ID # | Polypeptide and nucleic acid sequence |
|---|---|---|---|
| | | | ccgaggacacggctgtgtattactgtgcgagagatgggatagcaggagctcgctacgtctactttg<br>actactggggccagggaaccctggtcaccgtctcctcagctagcaccaagggcccatccgtcttcc<br>ccctggcaccctcctccaagagcacctctgggggcacagcggccctgggctgcctggtcaaggac<br>tacttccccgaaccggtgacggtgtcgtggaactcaggcgccctgaccagcggcgtgcacaccttc<br>ccggctgtcctacagtcctcaggactctactccct |
| | VL | 87 | DIQMTQSPSSLSASVGDRVTITCRASQGISNYLAWFQQKPGKAPKSLIY<br>AASSLQGGVPSKFSGSGSGTDFTLTISSLQPEDFATYYCQQYYNYPFTF<br>GPGTTVDIK |
| | | 88 | gacatccagatgacccagtctccatcctccctgtctgcatctgtaggagacagagtcaccatcactt<br>gtcgggcgagtcagggcattagcaatttatttagcctggtttcagcagaaaccagggaaagcccct<br>aagtccctgatctatgctgcatccagtttgcaaggtggggtcccatcaaagtttcagcggcagtgga<br>tctgggacagatttcactctcaccatcagcagcctgcagcctgaagattttgcaacttattactgcc<br>aacaatattataattacccattcactttcggccctgggaccacagtggatatcaaacgtacggtgg<br>ctgcaccatctgtcttcatcttcccgccatctgatgagcagttgaaatctggaactgcctctgttgtg<br>tgcctgctgaataacttctatcccagagaggccaaagtacagtggaaggtggataacgccctcca<br>atcgggtaactcccaggagagtgtcacagagcaggacacaaggacagcacctacagcctcagc<br>agcaccctgacgctgagcaaagcagactacgagaaacacaaagtctacgcctgcgaagtcaccc<br>atcagggcctgagctcgcccgtcacaaagagcttcaacaggggagagtgttag |
| 1F6 | VH | 89 | QIQLVQSGPEVKKPGETVKISCKASGYTFTNYGMNWVKQAPGKGLK<br>WMGINTYTGEPTYADAFKGRFAFSLETSASTAYLQINNLKNEDTATYF<br>CARDYGDYGMDYWGQGTSVTVSS |
| | | 90 | atggcttgggtgtggaccttgctattcctgatggcagctgcccaaagtgcccaagcacagatccag<br>ttggtgcagtctggagacctgaggtgaagaagcctggagagacagtcaagatctcctgcaaggcttc<br>tgggtataccttcacaaactatggaatgaactgggtgaagcaggctccaggaaagggtttaaagt<br>ggatgggctggataaacacctacactggagagccaacatatgctgatgccttcaagggacggttt<br>gccttctctttgaaacctctgccagcactgcctatttgcagatcaacaacctcaaaaatgaggac<br>acggctacatatttctgtgcaagagactacggcgactatggtatggactactggggtcaaggaac<br>ctcagtcaccgtctcctca |
| | VL | 91 | DIVLTQSPASLAVSLGQRATISCRASKSVSTSGYSFMHWYQQKPGQPP<br>KLLIYLASNLESGVPARFSGSGSGTDFTLNIHPVEEEDAATYYCQHSREV<br>PWTFGGGTKLEIKR |
| | | 92 | atggagacagacacactcctgttatgggtactgctgctctggttccaggttccactggtgacattg<br>tgctgacacagtctcctgcttccttagctgtatctctggggcagagggccaccatctcatgcaggc<br>cagcaaaagtgtcagtacatctggctatagttttatgcactggtatcaacagaaaccaggacagc<br>cacccaaactcctcatctatcttgcatccaacctagaatctggggtccctgccaggttcagtggcag<br>tgggtctgggacagacttcaccctcaacatccatcctgtggaggaggaggatgctgcaacctatta<br>ctgtcagcacagtagggaggttccgtggacgttcggtggaggcaccaagctggaaatcaaacgg |

TABLE 24

Polypeptide sequences of anti-CD70 CARs based on the V1, V2 and V3 versions according to FIG. 11A

| Name of CAR | SEQ ID NO: | Polypeptide sequence |
|---|---|---|
| Ab4-V1 CAR | 93 | MALPVTALLLPLALLLHAARPQVQLVESGGGVVQPGRSLRLSCAASGFTFSNYGIHWVR<br>QAPGKGLEWVAVIWYDGSNKYYADSVKGRFTISRDNSKNTLYLQMNSLRAEDTAVY<br>YCARDGGYSYDSGFDYWGQGTLVTVSSGGGGSGGGGSGGGGSDIVMTQSPLSLPVT<br>PGEPASISCRSSQSLLNSNGYNYLDWYLQKPGQSPQFLIYLGSYRASGVPDRFSGSGS<br>GTDFTLRISRVEAEDVGVYYCIQTLQTPFTFGPGTKVDIK<u>GLAVSTISSFFPPGYQIYIWAPL<br>AGTCGVLLLSLVITLYCKRGRKKLLYIFKQPFMRPVQTTQEEDGCSCRFPEEEEGGCELRVKFSRS<br>ADAPAYQQGQNQLYNELNLGRREEYDVLDKRRGRDPEMGGKPPRKNPQEGLYNELQKDKM<br>AEAYSEIGMKGERRRGKGHDGLYQGLSTATKDTYDALHMQALPPR</u> |
| Ab4-V2 CAR | 94 | MALPVTALLLPLALLLHAARPQVQLVESGGGVVQPGRSLRLSCAASGFTFSNYGIHWVR<br>QAPGKGLEWVAVIWYDGSNKYYADSVKGRFTISRDNSKNTLYLQMNSLRAEDTAVY<br>YCARDGGYSYDSGFDYWGQGTLVTVSSGGGGSGGGGSGGGGSDIVMTQSPLSLPVT<br>PGEPASISCRSSQSLLNSNGYNYLDWYLQKPGQSPQFLIYLGSYRASGVPDRFSGSGS<br>GTDFTLRISRVEAEDVGVYYCIQTLQTPFTFGPGTKVDI<u>KTTTPAPRPPTPAPTIASQPLSL<br>RPEACRPAAGGAVHTRGLDFACD</u>IYIWAPLAGTCGVLLLSLVITLYCKRGRKKLLYIFKQPFMRP<br>VCITTQEEDGCSCRFPEEEEGGCELRVKFSRSADAPAYQQGQNQLYNELNLGRREEYDVLDKR<br>RGRDPEMGGKPRRKNMEGLYNELQKDKMAEAYSEIGMKGERRRGKGHDGLYQGLSTATK<br>DTYDALHMQALPPR |
| Ab4-V3 CAR | 95 | MALPVTALLLPLALLLHAARPQVQLVESGGGVVQPGRSLRLSCAASGFTFSNYGIHWVR<br>QAPGKGLEWVAVIWYDGSNKYYADSVKGRFTISRDNSKNTLYLQMNSLRAEDTAVY<br>YCARDGGYSYDSGFDYWGQGTLVTVSSGGGGSGGGGSGGGGSDIVMTQSPLSLPVT<br>PGEPASISCRSSQSLLNSNGYNYLDWYLQKPGQSPQFLIYLGSYRASGVPDRFSGSGS<br>GTDFTLRISRVEAEDVGVYYCIQTLQTPFTFGPGTKVDI<u>KEPKSPDKTHTCPPCPAPPVAG</u> |

TABLE 24-continued

Polypeptide sequences of anti-CD70 CARs based on the V1, V2 and V3 versions according to FIG. 11A

| Name of CAR | SEQ ID NO: | Polypeptide sequence |
|---|---|---|
| | | PSVFLFPPKPKDTLMIARTPEVTCVVVDVSHEDPEVKFNWYVDGVEVHNAKTKPREEQYNSTY RVVSVLTVLHQDWLNGKEYKCKVSNKALPAPIEKTISKAKGQPREPQVYTLPPSRDELTKNQVS LTCLVKGFYPSDIAVEWESNGQPENNYKTTPPVLDSDGSFFLYSKLTVDKSRWQQGNVFSCSV MHEALHNHYTQKSLSLSPGKIYIWAPLAGTCGVLLLSLVITLYCKRGRKKLLYIFKQPFMRPVQT TQEEDGCSCRFPEEEEGGCELRVKFSRSADAPAYQQGQNQLYNELNLGRREEYDVLDKRRGR DPEMGGKPRRKNPQEGLYNELQKDKMAEAYSEIGMKGERRRGKHDGLYQGLSTATKDTYD ALHMQALPPR |
| Ab8-V1 CAR | 96 | MALPVTALLLPLALLLHAARPQVQLVESGGGVVQPGRSLRLSCAASGFTFSSYGMHWV RQAPGKGLEWVAVIWYDGSDKYFADSVKGRFTISRDNSKNTLYLQMNSLRAEDTAV YYCARDGIAGARYVYFDYWGQGTLVTVSSGGGGSGGGGSGGGGSDIQMTQSPSSLSA SVGDRVTITCRASQGISNYLAWFQQKPGKAPKSLIYAASSLQGGVPSKFSGSGSGTDF TLTISSLCIPEDFATYYCQQYYNYPFTFGPGTTVDIKGLAVSTISSFFPPGYQIYIWAPLAGTC GVLLLSLVITLYCKRGRKKLLYIFKQPFMRPVCIT- TQEEDGCSCRFPEEEEGGCELRVKFSRSADAP AYQQGQNCILYNELNLGRREEYDVLDKRRGRDPEMGGKPRRKNPCIEGLYNELQKDKMAEAY SEIGMKGERRRGKHDGLYQGLSTATKDTYDALHMCIALPPR |
| Ab8-V2 CAR | 97 | MALPVTALLLPLALLLHAARPQVQLVESGGGVVQPGRSLRLSCAASGFTFSSYGMHWV RQAPGKGLEWVAVIWYDGSDKYFADSVKGRFTISRDNSKNTLYLQMNSLRAEDTAV YYCARDGIAGARYVYFDYWGQGTLVTVSSGGGGSGGGGSGGGGSDIQMTQSPSSLSA SVGDRVTITCRASQGISNYLAWFQQKPGKAPKSLIYAASSLQGGVPSKFSGSGSGTDF TLTISSLQPEDFATYYCQQYYNYPFTFGPGTTVDIKTTTTPAPRPPTPAPTIASQPLSRPEAC RPAAGGAVHTRGLDFACDIYIWAPLAGTCGVLLLSLVITLYCKRGRKKLLYIFKQPFMRPVQTTQ EEDGCSCRFPEEEEGGCELRVKFSRSADAPAYQQGQNQLYNELNLGRREEYDVLDKRRGRDPE MGGKPRRKNPQEGLYNELQKDKMAEAYSEIGMKGERRRGKHDGLYQGLSTATKDTYDALH MQALPPR |
| Ab8-V3 CAR | 98 | MALPVTALLLPLALLLHAARPQVQLVESGGGVVQPGRSLRLSCAASGFTFSSYGMHWV RQAPGKGLEWVAVIWYDGSDKYFADSVKGRFTISRDNSKNTLYLQMNSLRAEDTAV YYCARDGIAGARYVYFDYWGQGTLVTVSSGGGGSGGGGSGGGGSDIQMTQSPSSLSA SVGDRVTITCRASQGISNYLAWFQQKPGKAPKSLIYAASSLQGGVPSKFSGSGSGTDF TLTISSLQPEDFATYYCQQYYNYPFTFGPGTTVDIKEPKSPDKTHTCPPCPAPPVAGPSVFL FPPKPKDTLMIARTPEVTCVVVDVSHEDPEVKFNWYVDGVEVHNAKTKPREEQYNSTYRVVS VLTVLHQDWLNGKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGNVFSCSVMHE ALHNHYTQKSLSLSPGKIYIWAPLAGTCGVLLLSLVITLYCKRGRKKLLYIFKQPFMRPVQTTQEE DGCSCRFPEEEEGGCELRVKFSRSADAPAYQQGQNQLYNELNLGRREEYDVLDKRRGRDPEM GGKPRRKNPQEGLYNELQKDKMAEAYSEIGMKGERRRGKHDGLYQGLSTATKDTYDALHM QALPPR |
| 1F6 V1 CAR | 99 | MALPVTALLLPLALLLHAARPQIQLVQSGPEVKKPGETVKISCKASGYTFTNYGMNWVK QAPGKGLKWMGINTYTGEPTYADAFKGRFAFSLETSASTAYLQINNLKNEDTATYFC ARDYGDYGMDYWGQGTSVTVSSGGGGSGGGGSGGGGSDIVLTQSPASLAVSLGQRA TISCRASKSVSTSGYSFMHWYQQKPGQPPKLLIYLASNLESGVPARFSGSGSGTDFTL NIHPVEEEDAATYYCQHSREVPWTFGGGTKLEIKRGLAVSTISSFFPPGYQIYIWAPLAGT CGVLLLSLVITLYCKRGRKKLLYIFKQPFMRPVQTTQEEDGCSCRFPEEEEGGCELRVKFSRSADA PAYQQGQNQLYNELNLGRREEYDVLDKRRGRDPEMGGKPRRKNPQEGLYNELQKDKMAEA YSEIGMKGERRRGKHDGLYQGLSTATKDTYDALHMQALPPR |
| 1F6 V2 CAR | 100 | MALPVTALLLPLALLLHAARPQIQLVQSGPEVKKPGETVKISCKASGYTFTNYGMNWVK QAPGKGLKWMGINTYTGEPTYADAFKGRFAFSLETSASTAYLQINNLKNEDTATYFC ARDYGDYGMDYWGQGTSVTVSSGGGGSGGGGSGGGGSDIVLTQSPASLAVSLGQRA TISCRASKSVSTSGYSFMHWYQQKPGQPPKLLIYLASNLESGVPARFSGSGSGTDFTL NIHPVEEEDAATYYCQHSREVPWTFGGGTKLEIKRTTTTPAPRPPTPAPTIASQPLSRPEA CRPAAGGAVHTRGLDFACDIYIWAPLAGTCGVLLLSLVITLYCKRGRKKLLYIFKQPFMRPVQTT QEEDGCSCRFPEEEEGGCELRVKFSRSADAPAYQQGQNQLYNELNLGRREEYDVLDKRRGRD PEMGGKPRRKNPQEGLYNELQKDKMAEAYSEIGMKGERRRGKHDGLYQGLSTATKDTYDA LHMQALPPR |
| 1F6 V3 CAR | 101 | MALPVTALLLPLALLLHAARPQIQLVQSGPEVKKPGETVKISCKASGYTFTNYGMNWVK QAPGKGLKWMGINTYTGEPTYADAFKGRFAFSLETSASTAYLQINNLKNEDTATYFC ARDYGDYGMDYWGQGTSVTVSSGGGGSGGGGSGGGGSDIVLTQSPASLAVSLGQRA TISCRASKSVSTSGYSFMHWYQQKPGQPPKLLIYLASNLESGVPARFSGSGSGTDFTL NIHPVEEEDAATYYCQHSREVPWTFGGGTKLEIKREPKSPDKTHTCPPCPAPPVAGPSVF LFPPKPKDTLMIARTPEVTCVVVDVSHEDPEVKFNWYVDGVEVHNAKTKPREEQYNSTYRVV SVLTVLHQDWLNGKEYKCKVSNKALPAPIEKTISKAKGQPREPQVYTLPPSRDELTKNQVSLTCL VKGFYPSDIAVEWESNGQPENNYKTTPPVLDSDGSFFLYSKLTVDKSRWQQGNVFSCSVMHE ALHNHYTQKSLSLSPGKIYIWAPLAGTCGVLLLSLVITLYCKRGRKKLLYIFKQPFMRPVQTTQEE DGCSCRFPEEEEGGCELRVKFSRSADAPAYQQGQNQLYNELNLGRREEYDVLDKRRGRDPEM GGKPRRKNPQEGLYNELQKDKMAEAYSEIGMKGERRRGKHDGLYQGLSTATKDTYDALHM QALPPR |

REFERENCES

Bardenheuer, W., K. Lehmberg, et al. (2005). "Resistance to cytarabine and gemcitabine and in vitro selection of transduced cells after retroviral expression of cytidine deaminase in human hematopoietic progenitor cells." *Leukemia* 19(12): 2281-8.

Betts, M. R., J. M. Brenchley, et al. (2003). "Sensitive and viable identification of antigen-specific CD8+ T cells by a flow cytometric assay for degranulation." *J Immunol Methods* 281(1-2): 65-78.

Boch, J., H. Scholze, et al. (2009). "Breaking the code of DNA binding specificity of TAL-type III effectors." *Science* 326(5959): 1509-12.

Brewin, J., C. Mancao, et al. (2009). "Generation of EBV-specific cytotoxic T cells that are resistant to calcineurin inhibitors for the treatment of posttransplantation lymphoproliferative disease." *Blood* 114(23): 4792-803.

Cambier, J. C. (1995) "Antigen and Fc Receptor Signaling: The Awesome Power of the Immunoreceptor Tyrosine-I Based Activation Motif (ITAM)" *The Journal of Immunology* 155 (7) 3281-3285.

Cong, L., F. A. Ran, et al. (2013). "Multiplex genome engineering using CRISPR/Cas systems." *Science* 339 (6121): 819-23.

Critchlow, S. E. and S. P. Jackson (1998). "DNA end-joining: from yeast to man." *Trends Biochem Sci* 23(10): 394-8.

Dalgaard, J. Z., A. J. Klar, et al. (1997). "Statistical modeling and analysis of the LAGLIDADG family of site-specific endonucleases and identification of an intein that encodes a site-specific endonuclease of the HNH family." *Nucleic Acids Res* 25(22): 4626-38.

Deltcheva, E., K. Chylinski, et al. (2011). "CRISPR RNA maturation by trans-encoded small RNA and host factor RNase III." *Nature* 471(7340): 602-7.

Garneau, J. E., M. E. Dupuis, et al. (2010). "The CRISPR/Cas bacterial immune system cleaves bacteriophage and plasmid DNA." *Nature* 468(7320): 67-71.

Gasiunas, G., R. Barrangou, et al. (2012). "Cas9-crRNA ribonucleoprotein complex mediates specific DNA cleavage for adaptive immunity in bacteria." *Proc Natl Acad Sci USA* 109(39): E2579-86.

Hacke, K., J. A. Treger, et al. (2013). "Genetic modification of mouse bone marrow by lentiviral vector-mediated delivery of hypoxanthine-Guanine phosphoribosyltransferase short hairpin RNA confers chemoprotection against 6-thioguanine cytotoxicity." *Transplant Proc* 45(5): 2040-4.

Jena, B., G. Dotti, et al. (2010). "Redirecting T-cell specificity by introducing a tumor-specific chimeric antigen receptor." *Blood* 116(7): 1035-44.

Jinek, M., K. Chylinski, et al. (2012). "A programmable dual-RNA-guided DNA endonuclease in adaptive bacterial immunity." *Science* 337(6096): 816-21.

Jonnalagadda, M., C. E. Brown, et al. (2013). "Engineering human T cells for resistance to methotrexate and mycophenolate mofetil as an in vivo cell selection strategy." *PLoS One* 8(6): e65519.

Kushman, M. E., S. L. Kabler, et al. (2007). "Expression of human glutathione S-transferase P1 confers resistance to benzo[a]pyrene or benzo[a]pyrene-7,8-dihydrodiol mutagenesis, macromolecular alkylation and formation of stable N2-Gua-BPDE adducts in stably transfected V79MZ cells co-expressing hCYP1A1." *Carcinogenesis* 28(1): 207-14.

Lackner, G., N. Moebius, et al. (2011). "Complete genome sequence of *Burkholderia rhizoxinica*, an Endosymbiont of *Rhizopus microsporus*." *J Bacteriol* 193(3): 783-4.

Ma, J. L., E. M. Kim, et al. (2003). "Yeast Mre11 and Rad1 proteins define a Ku-independent mechanism to repair double-strand breaks lacking overlapping end sequences." *Mol Cell Biol* 23(23): 8820-8.

Mak, A. N., P. Bradley, et al. (2012). "The crystal structure of TAL effector PthXo1 bound to its DNA target." *Science* 335(6069): 716-9.

Mali, P., L. Yang, et al. (2013). "RNA-guided human genome engineering via Cas9." *Science* 339(6121): 823-6.

Metzger, H. et al. (1986) "The Receptor with High Affinity for Immunoglobulin E" *Annual Review of Immunology*. 4: 419-470

Moscou, M. J. and A. J. Bogdanove (2009). "A simple cipher governs DNA recognition by TAL effectors." *Science* 326(5959): 1501.

Nivens, M. C., T. Felder, et al. (2004). "Engineered resistance to camptothecin and antifolates by retroviral coexpression of tyrosyl DNA phosphodiesterase-I and thymidylate synthase." *Cancer Chemother Pharmacol* 53(2): 107-15.

Park, T. S., S. A. Rosenberg, et al. (2011). "Treating cancer with genetically engineered T cells." *Trends Biotechnol* 29(11): 550-7.

Sangiolo, D., M. Lesnikova, et al. (2007). "Lentiviral vector conferring resistance to mycophenolate mofetil and sensitivity to ganciclovir for in vivo T-cell selection." *Gene Ther* 14(21): 1549-54.

Schweitzer, B. I., A. P. Dicker, et al. (1990). "Dihydrofolate reductase as a therapeutic target." *Faseb J* 4(8): 2441-52.

Sugimoto, Y., S. Tsukahara, et al. (2003). "Drug-selected co-expression of P-glycoprotein and gp91 in vivo from an MDR1-bicistronic retrovirus vector Ha-MDR-IRES-gp91." *J Gene Med* 5(5): 366-76.

Takebe, N., S. C. Zhao, et al. (2001). "Generation of dual resistance to 4-hydroperoxycyclophosphamide and methotrexate by retroviral transfer of the human aldehyde dehydrogenase class 1 gene and a mutated dihydrofolate reductase gene." *Mol Ther* 3(1): 88-96.

Waldmann H. and Hale G. (2005) "CAMPATH: from concept to clinic". *Phil. Trans. R. Soc. B* 360: 1707-1711.

Yam, P., M. Jensen, et al. (2006). "Ex vivo selection and expansion of cells based on expression of a mutated inosine monophosphate dehydrogenase 2 after HIV vector transduction: effects on lymphocytes, monocytes, and CD34+ stem cells." *Mol Ther* 14(2): 236-44.

Zielske, S. P., J. S. Reese, et al. (2003). "In vivo selection of MGMT(P140K) lentivirus-transduced human NOD/SCID repopulating cells without pretransplant irradiation conditioning." J Clin Invest 112(10): 1561-70.

The invention claimed is:

1. A method of preparing an immune cell for immunotherapy comprising:
    (a) inactivating or mutating a gene encoding a CD38 antigen marker in an immune cell; and
    (b) expressing in said immune cell a transgene encoding a chimeric antigen receptor (CAR) directed against said CD38 antigen marker.

2. The method according to claim 1, further comprising activating and expanding the immune cell.

3. The method according to claim 1, further comprising purifying the resulting immune cell by excluding the cells presenting said CD38 antigen marker at their surface.

4. The method according to claim 1, wherein said immune cell is obtained from a donor.

5. The method according to claim 1, wherein inactivating or mutating the gene is performed using a rare-cutting endonuclease.

6. The method according to claim 5, wherein the rare-cutting endonuclease is a TAL-nuclease.

7. The method according to claim 5, wherein said endonuclease is expressed from transfected mRNA.

8. The method according to claim 1, wherein said immune cell is a natural killer cell.

9. An engineered immune cell obtainable according to the method of claim 1.

10. A method of preparing an immune cell for immunotherapy comprising inactivating or mutating a gene encoding a CD38 antigen marker in an immune cell using a rare-cutting endonuclease.

11. The method according to claim 10, further comprising expressing in said immune cell a transgene encoding a chimeric antigen receptor (CAR) directed against said CD38 antigen marker.

12. The method according to claim 10, further comprising activating and expanding the immune cell.

13. The method according to claim 10, further comprising purifying the resulting immune cell by excluding the cells presenting said CD38 antigen marker at their surface.

14. The method according to claim 10, wherein said immune cell is obtained from a donor.

15. The method according to claim 10, wherein the rare-cutting endonuclease is a TAL-nuclease.

16. The method according to claim 10, wherein said endonuclease is expressed from transfected mRNA.

17. The method according to claim 10, wherein said immune cell is a natural killer cell.

18. An engineered immune cell comprising,
    an inactivated or mutated gene encoding a CD38 antigen marker, wherein said CD38 antigen marker is inactivated or mutated by cleavage with a rare-cutting endonuclease and
    a transgene encoding a chimeric antigen receptor (CAR).

* * * * *

SEQUENCE LISTING

<160> NUMBER OF SEQ ID NOS: 148

<210> SEQ ID NO 1

```
<211> LENGTH: 47
<212> TYPE: DNA
<213> ORGANISM: homo sapiens
<220> FEATURE:
<223> OTHER INFORMATION: CD38 target

<400> SEQUENCE: 1
tgaggtgggt tggcgactaa ggcgcaccgg tgggcactgc ggggaca                    47

<210> SEQ ID NO 2
<211> LENGTH: 936
<212> TYPE: PRT
<213> ORGANISM: artificial sequence
<220> FEATURE:
<223> OTHER INFORMATION: CD38ex1_T2-L1 TALEN

<400> SEQUENCE: 2
```

Met Gly Asp Pro Lys Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
            20                  25                  30

Ser Gln Gln Gln Glu Lys Ile Lys Pro Lys Val Arg Ser Thr Val
        35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
            100                 105                 110

Leu Leu Thr Val Ala Gly Glu Leu Arg Gly Pro Pro Leu Gln Leu Asp
        115                 120                 125

Thr Gly Gln Leu Leu Lys Ile Ala Lys Arg Gly Gly Val Thr Ala Val
    130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Asn Gly Gly Lys
                165                 170                 175

Gln Ala Leu Glu Thr Val Gln Arg Leu Leu Pro Val Leu Cys Gln Ala
            180                 185                 190

His Gly Leu Thr Pro Glu Gln Val Val Ala Ile Ala Ser Asn Ile Gly
        195                 200                 205

Gly Lys Gln Ala Leu Glu Thr Val Gln Ala Leu Leu Pro Val Leu Cys
    210                 215                 220

Gln Ala His Gly Leu Thr Pro Gln Gln Val Val Ala Ile Ala Ser Asn
225                 230                 235                 240

Asn Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
            260                 265                 270

Ser Asn Asn Gly Gly Lys Gln Ala Leu Glu Thr Val Gln Arg Leu Leu
        275                 280                 285

Pro Val Leu Cys Gln Ala His Gly Leu Thr Pro Gln Gln Val Val Ala
    290                 295                 300

Ile Ala Ser Asn Gly Gly Gly Lys Gln Ala Leu Glu Thr Val Gln Arg
305                 310                 315                 320

-continued

```
Leu Leu Pro Val Leu Cys Gln Ala His Gly Leu Thr Pro Gln Gln Val
                325                 330                 335
Val Ala Ile Ala Ser Asn Asn Gly Gly Lys Gln Ala Leu Glu Thr Val
            340                 345                 350
Gln Arg Leu Leu Pro Val Leu Cys Gln Ala His Gly Leu Thr Pro Gln
        355                 360                 365
Gln Val Val Ala Ile Ala Ser Asn Asn Gly Gly Lys Gln Ala Leu Glu
    370                 375                 380
Thr Val Gln Arg Leu Leu Pro Val Leu Cys Gln Ala His Gly Leu Thr
385                 390                 395                 400
Pro Gln Gln Val Val Ala Ile Ala Ser Asn Asn Gly Gly Lys Gln Ala
                405                 410                 415
Leu Glu Thr Val Gln Arg Leu Leu Pro Val Leu Cys Gln Ala His Gly
            420                 425                 430
Leu Thr Pro Gln Gln Val Val Ala Ile Ala Ser Asn Gly Gly Gly Lys
        435                 440                 445
Gln Ala Leu Glu Thr Val Gln Arg Leu Leu Pro Val Leu Cys Gln Ala
    450                 455                 460
His Gly Leu Thr Pro Gln Gln Val Val Ala Ile Ala Ser Asn Gly Gly
465                 470                 475                 480
Gly Lys Gln Ala Leu Glu Thr Val Gln Arg Leu Leu Pro Val Leu Cys
                485                 490                 495
Gln Ala His Gly Leu Thr Pro Gln Gln Val Val Ala Ile Ala Ser Asn
            500                 505                 510
Asn Gly Gly Lys Gln Ala Leu Glu Thr Val Gln Arg Leu Leu Pro Val
        515                 520                 525
Leu Cys Gln Ala His Gly Leu Thr Pro Gln Gln Val Val Ala Ile Ala
    530                 535                 540
Ser Asn Asn Gly Gly Lys Gln Ala Leu Glu Thr Val Gln Arg Leu Leu
545                 550                 555                 560
Pro Val Leu Cys Gln Ala His Gly Leu Thr Pro Glu Gln Val Val Ala
                565                 570                 575
Ile Ala Ser His Asp Gly Gly Lys Gln Ala Leu Glu Thr Val Gln Arg
            580                 585                 590
Leu Leu Pro Val Leu Cys Gln Ala His Gly Leu Thr Pro Gln Gln Val
        595                 600                 605
Val Ala Ile Ala Ser Asn Asn Gly Gly Lys Gln Ala Leu Glu Thr Val
    610                 615                 620
Gln Arg Leu Leu Pro Val Leu Cys Gln Ala His Gly Leu Thr Pro Glu
625                 630                 635                 640
Gln Val Val Ala Ile Ala Ser Asn Ile Gly Gly Lys Gln Ala Leu Glu
                645                 650                 655
Thr Val Gln Ala Leu Leu Pro Val Leu Cys Gln Ala His Gly Leu Thr
            660                 665                 670
Pro Gln Gln Val Val Ala Ile Ala Ser Asn Gly Gly Gly Arg Pro Ala
        675                 680                 685
Leu Glu Ser Ile Val Ala Gln Leu Ser Arg Pro Asp Pro Ala Leu Ala
    690                 695                 700
Ala Leu Thr Asn Asp His Leu Val Ala Leu Ala Cys Leu Gly Gly Arg
705                 710                 715                 720
Pro Ala Leu Asp Ala Val Lys Lys Gly Leu Gly Asp Pro Ile Ser Arg
                725                 730                 735
```

```
Ser Gln Leu Val Lys Ser Glu Leu Glu Lys Lys Ser Glu Leu Arg
            740                 745                 750

His Lys Leu Lys Tyr Val Pro His Glu Tyr Ile Glu Leu Ile Glu Ile
            755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
                805                 810                 815

Gly Val Ile Val Asp Thr Lys Ala Tyr Ser Gly Gly Tyr Asn Leu Pro
            820                 825                 830

Ile Gly Gln Ala Asp Glu Met Gln Arg Tyr Val Glu Glu Asn Gln Thr
            835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
                885                 890                 895

Gly Ala Val Leu Ser Val Glu Glu Leu Leu Ile Gly Gly Glu Met Ile
            900                 905                 910

Lys Ala Gly Thr Leu Thr Leu Glu Glu Val Arg Arg Lys Phe Asn Asn
            915                 920                 925

Gly Glu Ile Asn Phe Ala Ala Asp
930                 935

<210> SEQ ID NO 3
<211> LENGTH: 942
<212> TYPE: PRT
<213> ORGANISM: artificial sequence
<220> FEATURE:
<223> OTHER INFORMATION: CD38ex1_T2-R1 TALEN

<400> SEQUENCE: 3

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
                20                  25                  30

Leu Arg Thr Leu Gly Tyr Ser Gln Gln Gln Gln Glu Lys Ile Lys Pro
            35                  40                  45

Lys Val Arg Ser Thr Val Ala Gln His His Glu Ala Leu Val Gly His
        50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
            100                 105                 110

Ala Arg Ala Leu Glu Ala Leu Leu Thr Val Ala Gly Glu Leu Arg Gly
        115                 120                 125

Pro Pro Leu Gln Leu Asp Thr Gly Gln Leu Leu Lys Ile Ala Lys Arg
130                 135                 140

Gly Gly Val Thr Ala Val Glu Ala Val His Ala Trp Arg Asn Ala Leu
145                 150                 155                 160
```

```
Thr Gly Ala Pro Leu Asn Leu Thr Pro Gln Gln Val Val Ala Ile Ala
                165                 170                 175

Ser Asn Asn Gly Gly Lys Gln Ala Leu Glu Thr Val Gln Arg Leu Leu
            180                 185                 190

Pro Val Leu Cys Gln Ala His Gly Leu Thr Pro Gln Gln Val Val Ala
            195                 200                 205

Ile Ala Ser Asn Gly Gly Lys Gln Ala Leu Glu Thr Val Gln Arg
210                 215                 220

Leu Leu Pro Val Leu Cys Gln Ala His Gly Leu Thr Pro Glu Gln Val
225                 230                 235                 240

Val Ala Ile Ala Ser His Asp Gly Gly Lys Gln Ala Leu Glu Thr Val
                245                 250                 255

Gln Arg Leu Leu Pro Val Leu Cys Gln Ala His Gly Leu Thr Pro Glu
            260                 265                 270

Gln Val Val Ala Ile Ala Ser His Asp Gly Gly Lys Gln Ala Leu Glu
            275                 280                 285

Thr Val Gln Arg Leu Leu Pro Val Leu Cys Gln Ala His Gly Leu Thr
            290                 295                 300

Pro Glu Gln Val Val Ala Ile Ala Ser His Asp Gly Gly Lys Gln Ala
305                 310                 315                 320

Leu Glu Thr Val Gln Arg Leu Leu Pro Val Leu Cys Gln Ala His Gly
                325                 330                 335

Leu Thr Pro Glu Gln Val Val Ala Ile Ala Ser His Asp Gly Gly Lys
            340                 345                 350

Gln Ala Leu Glu Thr Val Gln Arg Leu Leu Pro Val Leu Cys Gln Ala
            355                 360                 365

His Gly Leu Thr Pro Gln Gln Val Val Ala Ile Ala Ser Asn Asn Gly
            370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser His
                405                 410                 415

Asp Gly Gly Lys Gln Ala Leu Glu Thr Val Gln Arg Leu Leu Pro Val
            420                 425                 430

Leu Cys Gln Ala His Gly Leu Thr Pro Glu Gln Val Val Ala Ile Ala
            435                 440                 445

Ser Asn Ile Gly Gly Lys Gln Ala Leu Glu Thr Val Gln Ala Leu Leu
            450                 455                 460

Pro Val Leu Cys Gln Ala His Gly Leu Thr Pro Gln Gln Val Val Ala
465                 470                 475                 480

Ile Ala Ser Asn Asn Gly Gly Lys Gln Ala Leu Glu Thr Val Gln Arg
                485                 490                 495

Leu Leu Pro Val Leu Cys Gln Ala His Gly Leu Thr Pro Gln Gln Val
            500                 505                 510

Val Ala Ile Ala Ser Asn Gly Gly Gly Lys Gln Ala Leu Glu Thr Val
            515                 520                 525

Gln Arg Leu Leu Pro Val Leu Cys Gln Ala His Gly Leu Thr Pro Gln
530                 535                 540

Gln Val Val Ala Ile Ala Ser Asn Asn Gly Gly Lys Gln Ala Leu Glu
545                 550                 555                 560

Thr Val Gln Arg Leu Leu Pro Val Leu Cys Gln Ala His Gly Leu Thr
                565                 570                 575

Pro Glu Gln Val Val Ala Ile Ala Ser His Asp Gly Gly Lys Gln Ala
```

```
                    580                 585                 590
Leu Glu Thr Val Gln Arg Leu Leu Pro Val Leu Cys Gln Ala His Gly
                595                 600                 605

Leu Thr Pro Glu Gln Val Val Ala Ile Ala Ser His Asp Gly Gly Lys
            610                 615                 620

Gln Ala Leu Glu Thr Val Gln Arg Leu Leu Pro Val Leu Cys Gln Ala
625                 630                 635                 640

His Gly Leu Thr Pro Glu Gln Val Val Ala Ile Ala Ser His Asp Gly
                645                 650                 655

Gly Lys Gln Ala Leu Glu Thr Val Gln Arg Leu Leu Pro Val Leu Cys
            660                 665                 670

Gln Ala His Gly Leu Thr Pro Gln Gln Val Val Ala Ile Ala Ser Asn
        675                 680                 685

Gly Gly Gly Arg Pro Ala Leu Glu Ser Ile Val Ala Gln Leu Ser Arg
    690                 695                 700

Pro Asp Pro Ala Leu Ala Ala Leu Thr Asn Asp His Leu Val Ala Leu
705                 710                 715                 720

Ala Cys Leu Gly Gly Arg Pro Ala Leu Asp Ala Val Lys Lys Gly Leu
                725                 730                 735

Gly Asp Pro Ile Ser Arg Ser Gln Leu Val Lys Ser Glu Leu Glu Glu
            740                 745                 750

Lys Lys Ser Glu Leu Arg His Lys Leu Lys Tyr Val Pro His Glu Tyr
        755                 760                 765

Ile Glu Leu Ile Glu Ile Ala Arg Asn Ser Thr Gln Asp Arg Ile Leu
    770                 775                 780

Glu Met Lys Val Met Glu Phe Phe Met Lys Val Tyr Gly Tyr Arg Gly
785                 790                 795                 800

Lys His Leu Gly Gly Ser Arg Lys Pro Asp Gly Ala Ile Tyr Thr Val
                805                 810                 815

Gly Ser Pro Ile Asp Tyr Gly Val Ile Val Asp Thr Lys Ala Tyr Ser
            820                 825                 830

Gly Gly Tyr Asn Leu Pro Ile Gly Gln Ala Asp Glu Met Gln Arg Tyr
        835                 840                 845

Val Glu Glu Asn Gln Thr Arg Asn Lys His Ile Asn Pro Asn Glu Trp
    850                 855                 860

Trp Lys Val Tyr Pro Ser Ser Val Thr Glu Phe Lys Phe Leu Phe Val
865                 870                 875                 880

Ser Gly His Phe Lys Gly Asn Tyr Lys Ala Gln Leu Thr Arg Leu Asn
                885                 890                 895

His Ile Thr Asn Cys Asn Gly Ala Val Leu Ser Val Glu Glu Leu Leu
            900                 905                 910

Ile Gly Gly Glu Met Ile Lys Ala Gly Thr Leu Thr Leu Glu Glu Val
        915                 920                 925

Arg Arg Lys Phe Asn Asn Gly Glu Ile Asn Phe Ala Ala Asp
    930                 935                 940

<210> SEQ ID NO 4
<211> LENGTH: 49
<212> TYPE: PRT
<213> ORGANISM: homo sapiens
<220> FEATURE:
<223> OTHER INFORMATION: CD38ex1_T4 target

<400> SEQUENCE: 4

Thr Gly Cys Gly Ala Gly Thr Thr Cys Ala Gly Cys Cys Cys Gly Gly
```

-continued

```
                1               5                  10                 15
Thr Gly Thr Cys Cys Gly Gly Gly Ala Cys Ala Ala Cys Cys
                20                 25                 30

Cys Thr Gly Cys Thr Gly Cys Cys Gly Gly Cys Thr Cys Thr Cys Thr
        35                 40                 45

Ala
```

<210> SEQ ID NO 5
<211> LENGTH: 970
<212> TYPE: PRT
<213> ORGANISM: artificial sequence
<220> FEATURE:
<223> OTHER INFORMATION: CD38ex1_T4-L TALEN

<400> SEQUENCE: 5

```
Met Gly Asp Pro Lys Lys Arg Lys Val Ile Asp Tyr Pro Tyr Asp
1               5                  10                 15

Val Pro Asp Tyr Ala Ile Asp Ile Ala Asp Leu Arg Thr Leu Gly Tyr
                20                 25                 30

Ser Gln Gln Gln Glu Lys Ile Lys Pro Lys Val Arg Ser Thr Val
        35                 40                 45

Ala Gln His His Glu Ala Leu Val Gly His Gly Phe Thr His Ala His
    50                 55                 60

Ile Val Ala Leu Ser Gln His Pro Ala Ala Leu Gly Thr Val Ala Val
65                  70                 75                  80

Lys Tyr Gln Asp Met Ile Ala Ala Leu Pro Glu Ala Thr His Glu Ala
                85                 90                 95

Ile Val Gly Val Gly Lys Gln Trp Ser Gly Ala Arg Ala Leu Glu Ala
                100                105                110

Leu Leu Thr Val Ala Gly Glu Leu Arg Gly Pro Pro Leu Gln Leu Asp
        115                120                125

Thr Gly Gln Leu Leu Lys Ile Ala Lys Arg Gly Gly Val Thr Ala Val
        130                135                140

Glu Ala Val His Ala Trp Arg Asn Ala Leu Thr Gly Ala Pro Leu Asn
145                150                155                160

Leu Thr Pro Gln Gln Val Val Ala Ile Ala Ser Asn Gly Gly Lys
                165                170                175

Gln Ala Leu Glu Thr Val Gln Arg Leu Leu Pro Val Leu Cys Gln Ala
        180                185                190

His Gly Leu Thr Pro Glu Gln Val Val Ala Ile Ala Ser Asn Asn Gly
        195                200                205

Gly Lys Gln Ala Leu Glu Thr Val Gln Ala Leu Leu Pro Val Leu Cys
    210                215                220

Gln Ala His Gly Leu Thr Pro Gln Gln Val Val Ala Ile Ala Ser His
225                230                235                240

Asp Gly Gly Lys Gln Ala Leu Glu Thr Val Gln Arg Leu Leu Pro Val
                245                250                255

Leu Cys Gln Ala His Gly Leu Thr Pro Gln Gln Val Val Ala Ile Ala
        260                265                270

Ser Asn Asn Gly Gly Lys Gln Ala Leu Glu Thr Val Gln Arg Leu Leu
        275                280                285

Pro Val Leu Cys Gln Ala His Gly Leu Thr Pro Gln Gln Val Val Ala
    290                295                300

Ile Ala Ser Asn Ile Gly Gly Lys Gln Ala Leu Glu Thr Val Gln Arg
305                310                315                320
```

```
Leu Leu Pro Val Leu Cys Gln Ala His Gly Leu Thr Pro Gln Gln Val
            325                 330                 335
Val Ala Ile Ala Ser Asn Asn Gly Gly Lys Gln Ala Leu Glu Thr Val
        340                 345                 350
Gln Arg Leu Leu Pro Val Leu Cys Gln Ala His Gly Leu Thr Pro Gln
    355                 360                 365
Gln Val Val Ala Ile Ala Ser Asn Gly Gly Lys Gln Ala Leu Glu
370                 375                 380
Thr Val Gln Arg Leu Leu Pro Val Leu Cys Gln Ala His Gly Leu Thr
385                 390                 395                 400
Pro Gln Gln Val Val Ala Ile Ala Ser Asn Gly Gly Lys Gln Ala
            405                 410                 415
Leu Glu Thr Val Gln Arg Leu Leu Pro Val Leu Cys Gln Ala His Gly
        420                 425                 430
Leu Thr Pro Gln Gln Val Val Ala Ile Ala Ser His Asp Gly Gly Lys
    435                 440                 445
Gln Ala Leu Glu Thr Val Gln Arg Leu Leu Pro Val Leu Cys Gln Ala
450                 455                 460
His Gly Leu Thr Pro Gln Gln Val Val Ala Ile Ala Ser Asn Ile Gly
465                 470                 475                 480
Gly Lys Gln Ala Leu Glu Thr Val Gln Arg Leu Leu Pro Val Leu Cys
            485                 490                 495
Gln Ala His Gly Leu Thr Pro Gln Gln Val Val Ala Ile Ala Ser Asn
        500                 505                 510
Asn Gly Gly Lys Gln Ala Leu Glu Thr Val Gln Arg Leu Leu Pro Val
    515                 520                 525
Leu Cys Gln Ala His Gly Leu Thr Pro Gln Gln Val Val Ala Ile Ala
530                 535                 540
Ser His Asp Gly Gly Lys Gln Ala Leu Glu Thr Val Gln Arg Leu Leu
545                 550                 555                 560
Pro Val Leu Cys Gln Ala His Gly Leu Thr Pro Glu Gln Val Val Ala
            565                 570                 575
Ile Ala Ser His Asp Gly Gly Lys Gln Ala Leu Glu Thr Val Gln Arg
        580                 585                 590
Leu Leu Pro Val Leu Cys Gln Ala His Gly Leu Thr Pro Gln Gln Val
    595                 600                 605
Val Ala Ile Ala Ser His Asp Gly Gly Lys Gln Ala Leu Glu Thr Val
610                 615                 620
Gln Arg Leu Leu Pro Val Leu Cys Gln Ala His Gly Leu Thr Pro Glu
625                 630                 635                 640
Gln Val Val Ala Ile Ala Ser Asn Asn Gly Gly Lys Gln Ala Leu Glu
            645                 650                 655
Thr Val Gln Ala Leu Leu Pro Val Leu Cys Gln Ala His Gly Leu Thr
        660                 665                 670
Pro Gln Gln Val Val Ala Ile Ala Ser Asn Asn Gly Gly Lys Gln Ala
    675                 680                 685
Leu Glu Thr Val Gln Arg Leu Leu Pro Val Leu Cys Gln Ala His Gly
690                 695                 700
Leu Thr Pro Glu Gln Val Val Ala Ile Ala Ser Asn Gly Gly Gly Arg
705                 710                 715                 720
Pro Ala Leu Glu Ser Ile Val Ala Gln Leu Ser Arg Pro Asp Pro Ala
            725                 730                 735
```

-continued

```
Leu Ala Ala Leu Thr Asn Asp His Leu Val Ala Leu Ala Cys Leu Gly
            740                 745                 750

Gly Arg Pro Ala Leu Asp Ala Val Lys Lys Gly Leu Gly Asp Pro Ile
        755                 760                 765

Ser Arg Ser Gln Leu Val Lys Ser Glu Leu Glu Glu Lys Lys Ser Glu
    770                 775                 780

Leu Arg His Lys Leu Lys Tyr Val Pro His Glu Tyr Ile Glu Leu Ile
785                 790                 795                 800

Glu Ile Ala Arg Asn Ser Thr Gln Asp Arg Ile Leu Glu Met Lys Val
                805                 810                 815

Met Glu Phe Phe Met Lys Val Tyr Gly Tyr Arg Gly Lys His Leu Gly
        820                 825                 830

Gly Ser Arg Lys Pro Asp Gly Ala Ile Tyr Thr Val Gly Ser Pro Ile
    835                 840                 845

Asp Tyr Gly Val Ile Val Asp Thr Lys Ala Tyr Ser Gly Gly Tyr Asn
850                 855                 860

Leu Pro Ile Gly Gln Ala Asp Glu Met Gln Arg Tyr Val Glu Glu Asn
865                 870                 875                 880

Gln Thr Arg Asn Lys His Ile Asn Pro Asn Glu Trp Trp Lys Val Tyr
                885                 890                 895

Pro Ser Ser Val Thr Glu Phe Lys Phe Leu Phe Val Ser Gly His Phe
        900                 905                 910

Lys Gly Asn Tyr Lys Ala Gln Leu Thr Arg Leu Asn His Ile Thr Asn
    915                 920                 925

Cys Asn Gly Ala Val Leu Ser Val Glu Glu Leu Leu Ile Gly Gly Glu
930                 935                 940

Met Ile Lys Ala Gly Thr Leu Thr Leu Glu Glu Val Arg Arg Lys Phe
945                 950                 955                 960

Asn Asn Gly Glu Ile Asn Phe Ala Ala Asp
                965                 970

<210> SEQ ID NO 6
<211> LENGTH: 942
<212> TYPE: PRT
<213> ORGANISM: artificial sequence
<220> FEATURE:
<223> OTHER INFORMATION: CD38ex1_T4-R  TALEN

<400> SEQUENCE: 6

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
            20                  25                  30

Leu Arg Thr Leu Gly Tyr Ser Gln Gln Gln Glu Lys Ile Lys Pro
        35                  40                  45

Lys Val Arg Ser Thr Val Ala Gln His His Glu Ala Leu Val Gly His
    50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
                85                  90                  95

Glu Ala Thr His Glu Ala Ile Val Gly Val Gly Lys Gln Trp Ser Gly
            100                 105                 110

Ala Arg Ala Leu Glu Ala Leu Leu Thr Val Ala Gly Glu Leu Arg Gly
        115                 120                 125
```

```
Pro Pro Leu Gln Leu Asp Thr Gly Gln Leu Leu Lys Ile Ala Lys Arg
    130                 135                 140
Gly Gly Val Thr Ala Val Glu Ala Val His Ala Trp Arg Asn Ala Leu
145                 150                 155                 160
Thr Gly Ala Pro Leu Asn Leu Thr Pro Gln Gln Val Val Ala Ile Ala
                165                 170                 175
Ser Asn Gly Gly Gly Lys Gln Ala Leu Glu Thr Val Gln Arg Leu Leu
            180                 185                 190
Pro Val Leu Cys Gln Ala His Gly Leu Thr Pro Gln Gln Val Val Ala
            195                 200                 205
Ile Ala Ser Asn Asn Gly Gly Lys Gln Ala Leu Glu Thr Val Gln Arg
    210                 215                 220
Leu Leu Pro Val Leu Cys Gln Ala His Gly Leu Thr Pro Glu Gln Val
225                 230                 235                 240
Val Ala Ile Ala Ser His Asp Gly Gly Lys Gln Ala Leu Glu Thr Val
                245                 250                 255
Gln Arg Leu Leu Pro Val Leu Cys Gln Ala His Gly Leu Thr Pro Glu
            260                 265                 270
Gln Val Val Ala Ile Ala Ser Asn Gly Gly Gly Lys Gln Ala Leu Glu
            275                 280                 285
Thr Val Gln Arg Leu Leu Pro Val Leu Cys Gln Ala His Gly Leu Thr
        290                 295                 300
Pro Glu Gln Val Val Ala Ile Ala Ser Asn Asn Gly Gly Lys Gln Ala
305                 310                 315                 320
Leu Glu Thr Val Gln Arg Leu Leu Pro Val Leu Cys Gln Ala His Gly
                325                 330                 335
Leu Thr Pro Glu Gln Val Val Ala Ile Ala Ser His Asp Gly Gly Lys
            340                 345                 350
Gln Ala Leu Glu Thr Val Gln Arg Leu Leu Pro Val Leu Cys Gln Ala
            355                 360                 365
His Gly Leu Thr Pro Gln Gln Val Val Ala Ile Ala Ser His Asp Gly
        370                 375                 380
Gly Lys Gln Ala Leu Glu Thr Val Gln Arg Leu Leu Pro Val Leu Cys
385                 390                 395                 400
Gln Ala His Gly Leu Thr Pro Glu Gln Val Val Ala Ile Ala Ser Asn
                405                 410                 415
Asn Gly Gly Lys Gln Ala Leu Glu Thr Val Gln Arg Leu Leu Pro Val
            420                 425                 430
Leu Cys Gln Ala His Gly Leu Thr Pro Glu Gln Val Val Ala Ile Ala
            435                 440                 445
Ser Asn Asn Gly Gly Lys Gln Ala Leu Glu Thr Val Gln Ala Leu Leu
        450                 455                 460
Pro Val Leu Cys Gln Ala His Gly Leu Thr Pro Gln Gln Val Val Ala
465                 470                 475                 480
Ile Ala Ser His Asp Gly Gly Lys Gln Ala Leu Glu Thr Val Gln Arg
                485                 490                 495
Leu Leu Pro Val Leu Cys Gln Ala His Gly Leu Thr Pro Gln Gln Val
            500                 505                 510
Val Ala Ile Ala Ser Asn Gly Gly Gly Lys Gln Ala Leu Glu Thr Val
            515                 520                 525
Gln Arg Leu Leu Pro Val Leu Cys Gln Ala His Gly Leu Thr Pro Gln
        530                 535                 540
Gln Val Val Ala Ile Ala Ser His Asp Gly Gly Lys Gln Ala Leu Glu
```

```
                   545                 550                 555                 560

Thr Val Gln Arg Leu Leu Pro Val Leu Cys Gln Ala His Gly Leu Thr
                           565                 570                 575

Pro Glu Gln Val Val Ala Ile Ala Ser Asn Gly Gly Lys Gln Ala
                       580                 585                 590

Leu Glu Thr Val Gln Arg Leu Leu Pro Val Leu Cys Gln Ala His Gly
                           595                 600                 605

Leu Thr Pro Glu Gln Val Val Ala Ile Ala Ser His Asp Gly Gly Lys
                       610                 615                 620

Gln Ala Leu Glu Thr Val Gln Arg Leu Leu Pro Val Leu Cys Gln Ala
        625                 630                 635                 640

His Gly Leu Thr Pro Glu Gln Val Val Ala Ile Ala Ser Asn Gly Gly
                               645                 650                 655

Gly Lys Gln Ala Leu Glu Thr Val Gln Arg Leu Leu Pro Val Leu Cys
                           660                 665                 670

Gln Ala His Gly Leu Thr Pro Gln Gln Val Val Ala Ile Ala Ser Asn
                       675                 680                 685

Ile Gly Gly Arg Pro Ala Leu Glu Ser Ile Val Ala Gln Leu Ser Arg
                   690                 695                 700

Pro Asp Pro Ala Leu Ala Ala Leu Thr Asn Asp His Leu Val Ala Leu
        705                 710                 715                 720

Ala Cys Leu Gly Gly Arg Pro Ala Leu Asp Ala Val Lys Lys Gly Leu
                           725                 730                 735

Gly Asp Pro Ile Ser Arg Ser Gln Leu Val Lys Ser Glu Leu Glu Glu
                       740                 745                 750

Lys Lys Ser Glu Leu Arg His Lys Leu Lys Tyr Val Pro His Glu Tyr
                   755                 760                 765

Ile Glu Leu Ile Glu Ile Ala Arg Asn Ser Thr Gln Asp Arg Ile Leu
                   770                 775                 780

Glu Met Lys Val Met Glu Phe Phe Met Lys Val Tyr Gly Tyr Arg Gly
        785                 790                 795                 800

Lys His Leu Gly Gly Ser Arg Lys Pro Asp Gly Ala Ile Tyr Thr Val
                           805                 810                 815

Gly Ser Pro Ile Asp Tyr Gly Val Ile Val Asp Thr Lys Ala Tyr Ser
                       820                 825                 830

Gly Gly Tyr Asn Leu Pro Ile Gly Gln Ala Asp Glu Met Gln Arg Tyr
                       835                 840                 845

Val Glu Glu Asn Gln Thr Arg Asn Lys His Ile Asn Pro Asn Glu Trp
        850                 855                 860

Trp Lys Val Tyr Pro Ser Ser Val Thr Glu Phe Lys Phe Leu Phe Val
        865                 870                 875                 880

Ser Gly His Phe Lys Gly Asn Tyr Lys Ala Gln Leu Thr Arg Leu Asn
                           885                 890                 895

His Ile Thr Asn Cys Asn Gly Ala Val Leu Ser Val Glu Glu Leu Leu
                           900                 905                 910

Ile Gly Gly Glu Met Ile Lys Ala Gly Thr Leu Thr Leu Glu Glu Val
                       915                 920                 925

Arg Arg Lys Phe Asn Asn Gly Glu Ile Asn Phe Ala Ala Asp
        930                 935                 940

<210> SEQ ID NO 7
<211> LENGTH: 49
<212> TYPE: PRT
<213> ORGANISM: homo sapiens
```

```
<220> FEATURE:
<223> OTHER INFORMATION: CD38ex1_T5

<400> SEQUENCE: 7

Thr Gly Ala Thr Cys Cys Thr Cys Gly Thr Cys Gly Thr Gly Thr
1               5                   10                  15

Gly Cys Thr Cys Gly Cys Gly Gly Thr Gly Thr Cys Gly Thr Cys
                20                  25                  30

Cys Cys Gly Ala Gly Thr Gly Gly Cys Gly Cys Ala Gly Cys
                35                  40              45

Ala

<210> SEQ ID NO 8
<211> LENGTH: 936
<212> TYPE: PRT
<213> ORGANISM: artificial sequence
<220> FEATURE:
<223> OTHER INFORMATION: CD38ex1_T5-L TALEN

<400> SEQUENCE: 8

Met Gly Asp Pro Lys Lys Arg Lys Val Ile Asp Tyr Pro Tyr Asp
1               5                   10                  15

Val Pro Asp Tyr Ala Ile Asp Ile Ala Asp Leu Arg Thr Leu Gly Tyr
                20                  25                  30

Ser Gln Gln Gln Glu Lys Ile Lys Pro Lys Val Arg Ser Thr Val
                35                  40                  45

Ala Gln His His Glu Ala Leu Val Gly His Gly Phe Thr His Ala His
    50                  55                  60

Ile Val Ala Leu Ser Gln His Pro Ala Ala Leu Gly Thr Val Ala Val
65                  70                  75                  80

Lys Tyr Gln Asp Met Ile Ala Ala Leu Pro Glu Ala Thr His Glu Ala
                85                  90                  95

Ile Val Gly Val Gly Lys Gln Trp Ser Gly Ala Arg Ala Leu Glu Ala
                100                 105                 110

Leu Leu Thr Val Ala Gly Glu Leu Arg Gly Pro Pro Leu Gln Leu Asp
                115                 120                 125

Thr Gly Gln Leu Leu Lys Ile Ala Lys Arg Gly Gly Val Thr Ala Val
                130                 135                 140

Glu Ala Val His Ala Trp Arg Asn Ala Leu Thr Gly Ala Pro Leu Asn
145                 150                 155                 160

Leu Thr Pro Gln Gln Val Val Ala Ile Ala Ser Asn Gly Gly Lys
                165                 170                 175

Gln Ala Leu Glu Thr Val Gln Arg Leu Leu Pro Val Leu Cys Gln Ala
                180                 185                 190

His Gly Leu Thr Pro Glu Gln Val Val Ala Ile Ala Ser Asn Asn Gly
                195                 200                 205

Gly Lys Gln Ala Leu Glu Thr Val Gln Ala Leu Leu Pro Val Leu Cys
                210                 215                 220

Gln Ala His Gly Leu Thr Pro Gln Gln Val Val Ala Ile Ala Ser Asn
225                 230                 235                 240

Ile Gly Gly Lys Gln Ala Leu Glu Thr Val Gln Arg Leu Leu Pro Val
                245                 250                 255

Leu Cys Gln Ala His Gly Leu Thr Pro Gln Gln Val Val Ala Ile Ala
                260                 265                 270

Ser Asn Gly Gly Gly Lys Gln Ala Leu Glu Thr Val Gln Arg Leu Leu
                275                 280                 285
```

```
Pro Val Leu Cys Gln Ala His Gly Leu Thr Pro Gln Gln Val Val Ala
    290                 295                 300
Ile Ala Ser His Asp Gly Gly Lys Gln Ala Leu Glu Thr Val Gln Arg
305                 310                 315                 320
Leu Leu Pro Val Leu Cys Gln Ala His Gly Leu Thr Pro Gln Gln Val
                325                 330                 335
Val Ala Ile Ala Ser His Asp Gly Gly Lys Gln Ala Leu Glu Thr Val
            340                 345                 350
Gln Arg Leu Leu Pro Val Leu Cys Gln Ala His Gly Leu Thr Pro Gln
        355                 360                 365
Gln Val Val Ala Ile Ala Ser Asn Gly Gly Lys Gln Ala Leu Glu
    370                 375                 380
Thr Val Gln Arg Leu Leu Pro Val Leu Cys Gln Ala His Gly Leu Thr
385                 390                 395                 400
Pro Gln Gln Val Val Ala Ile Ala Ser His Asp Gly Gly Lys Gln Ala
                405                 410                 415
Leu Glu Thr Val Gln Arg Leu Leu Pro Val Leu Cys Gln Ala His Gly
            420                 425                 430
Leu Thr Pro Gln Gln Val Val Ala Ile Ala Ser Asn Asn Gly Gly Lys
        435                 440                 445
Gln Ala Leu Glu Thr Val Gln Arg Leu Leu Pro Val Leu Cys Gln Ala
    450                 455                 460
His Gly Leu Thr Pro Gln Gln Val Val Ala Ile Ala Ser Asn Gly Gly
465                 470                 475                 480
Gly Lys Gln Ala Leu Glu Thr Val Gln Arg Leu Leu Pro Val Leu Cys
                485                 490                 495
Gln Ala His Gly Leu Thr Pro Gln Gln Val Val Ala Ile Ala Ser His
            500                 505                 510
Asp Gly Gly Lys Gln Ala Leu Glu Thr Val Gln Arg Leu Leu Pro Val
        515                 520                 525
Leu Cys Gln Ala His Gly Leu Thr Pro Gln Gln Val Val Ala Ile Ala
    530                 535                 540
Ser Asn Asn Gly Gly Lys Gln Ala Leu Glu Thr Val Gln Arg Leu Leu
545                 550                 555                 560
Pro Val Leu Cys Gln Ala His Gly Leu Thr Pro Glu Gln Val Val Ala
                565                 570                 575
Ile Ala Ser Asn Gly Gly Gly Lys Gln Ala Leu Glu Thr Val Gln Arg
            580                 585                 590
Leu Leu Pro Val Leu Cys Gln Ala His Gly Leu Thr Pro Gln Gln Val
        595                 600                 605
Val Ala Ile Ala Ser Asn Asn Gly Gly Lys Gln Ala Leu Glu Thr Val
    610                 615                 620
Gln Arg Leu Leu Pro Val Leu Cys Gln Ala His Gly Leu Thr Pro Glu
625                 630                 635                 640
Gln Val Val Ala Ile Ala Ser Asn Asn Gly Gly Lys Gln Ala Leu Glu
                645                 650                 655
Thr Val Gln Ala Leu Leu Pro Val Leu Cys Gln Ala His Gly Leu Thr
            660                 665                 670
Pro Gln Gln Val Val Ala Ile Ala Ser Asn Gly Gly Gly Arg Pro Ala
        675                 680                 685
Leu Glu Ser Ile Val Ala Gln Leu Ser Arg Pro Asp Pro Ala Leu Ala
    690                 695                 700
```

```
Ala Leu Thr Asn Asp His Leu Val Ala Leu Ala Cys Leu Gly Gly Arg
705                 710                 715                 720

Pro Ala Leu Asp Ala Val Lys Lys Gly Leu Gly Asp Pro Ile Ser Arg
            725                 730                 735

Ser Gln Leu Val Lys Ser Glu Leu Glu Glu Lys Lys Ser Glu Leu Arg
        740                 745                 750

His Lys Leu Lys Tyr Val Pro His Glu Tyr Ile Glu Leu Ile Glu Ile
    755                 760                 765

Ala Arg Asn Ser Thr Gln Asp Arg Ile Leu Glu Met Lys Val Met Glu
770                 775                 780

Phe Phe Met Lys Val Tyr Gly Tyr Arg Gly Lys His Leu Gly Gly Ser
785                 790                 795                 800

Arg Lys Pro Asp Gly Ala Ile Tyr Thr Val Gly Ser Pro Ile Asp Tyr
            805                 810                 815

Gly Val Ile Val Asp Thr Lys Ala Tyr Ser Gly Gly Tyr Asn Leu Pro
        820                 825                 830

Ile Gly Gln Ala Asp Glu Met Gln Arg Tyr Val Glu Glu Asn Gln Thr
    835                 840                 845

Arg Asn Lys His Ile Asn Pro Asn Glu Trp Trp Lys Val Tyr Pro Ser
850                 855                 860

Ser Val Thr Glu Phe Lys Phe Leu Phe Val Ser Gly His Phe Lys Gly
865                 870                 875                 880

Asn Tyr Lys Ala Gln Leu Thr Arg Leu Asn His Ile Thr Asn Cys Asn
            885                 890                 895

Gly Ala Val Leu Ser Val Glu Glu Leu Leu Ile Gly Gly Glu Met Ile
        900                 905                 910

Lys Ala Gly Thr Leu Thr Leu Glu Glu Val Arg Arg Lys Phe Asn Asn
    915                 920                 925

Gly Glu Ile Asn Phe Ala Ala Asp
930                 935

<210> SEQ ID NO 9
<211> LENGTH: 942
<212> TYPE: PRT
<213> ORGANISM: artificial sequence
<220> FEATURE:
<223> OTHER INFORMATION: CD38ex1_T5-R TALEN

<400> SEQUENCE: 9

Met Gly Asp Pro Lys Lys Lys Arg Lys Val Ile Asp Lys Glu Thr Ala
1               5                   10                  15

Ala Ala Lys Phe Glu Arg Gln His Met Asp Ser Ile Asp Ile Ala Asp
            20                  25                  30

Leu Arg Thr Leu Gly Tyr Ser Gln Gln Gln Gln Glu Lys Ile Lys Pro
        35                  40                  45

Lys Val Arg Ser Thr Val Ala Gln His His Glu Ala Leu Val Gly His
    50                  55                  60

Gly Phe Thr His Ala His Ile Val Ala Leu Ser Gln His Pro Ala Ala
65                  70                  75                  80

Leu Gly Thr Val Ala Val Lys Tyr Gln Asp Met Ile Ala Ala Leu Pro
            85                  90                  95

Glu Ala Thr His Glu Ala Ile Val Gly Val Gly Lys Gln Trp Ser Gly
        100                 105                 110

Ala Arg Ala Leu Glu Ala Leu Leu Thr Val Ala Gly Glu Leu Arg Gly
    115                 120                 125
```

```
Pro Pro Leu Gln Leu Asp Thr Gly Gln Leu Leu Lys Ile Ala Lys Arg
    130                 135                 140

Gly Gly Val Thr Ala Val Glu Ala Val His Ala Trp Arg Asn Ala Leu
145                 150                 155                 160

Thr Gly Ala Pro Leu Asn Leu Thr Pro Gln Gln Val Val Ala Ile Ala
                165                 170                 175

Ser His Asp Gly Gly Lys Gln Ala Leu Glu Thr Val Gln Arg Leu Leu
            180                 185                 190

Pro Val Leu Cys Gln Ala His Gly Leu Thr Pro Gln Gln Val Val Ala
                195                 200                 205

Ile Ala Ser Asn Asn Gly Gly Lys Gln Ala Leu Glu Thr Val Gln Arg
    210                 215                 220

Leu Leu Pro Val Leu Cys Gln Ala His Gly Leu Thr Pro Glu Gln Val
225                 230                 235                 240

Val Ala Ile Ala Ser Asn Ile Gly Gly Lys Gln Ala Leu Glu Thr Val
                245                 250                 255

Gln Arg Leu Leu Pro Val Leu Cys Gln Ala His Gly Leu Thr Pro Glu
            260                 265                 270

Gln Val Val Ala Ile Ala Ser Asn Asn Gly Gly Lys Gln Ala Leu Glu
    275                 280                 285

Thr Val Gln Arg Leu Leu Pro Val Leu Cys Gln Ala His Gly Leu Thr
290                 295                 300

Pro Glu Gln Val Val Ala Ile Ala Ser Asn Asn Gly Gly Lys Gln Ala
305                 310                 315                 320

Leu Glu Thr Val Gln Arg Leu Leu Pro Val Leu Cys Gln Ala His Gly
                325                 330                 335

Leu Thr Pro Glu Gln Val Val Ala Ile Ala Ser Asn Gly Gly Gly Lys
            340                 345                 350

Gln Ala Leu Glu Thr Val Gln Arg Leu Leu Pro Val Leu Cys Gln Ala
    355                 360                 365

His Gly Leu Thr Pro Gln Gln Val Val Ala Ile Ala Ser Asn Asn Gly
370                 375                 380

Gly Lys Gln Ala Leu Glu Thr Val Gln Arg Leu Leu Pro Val Leu Cys
385                 390                 395                 400

Gln Ala His Gly Leu Thr Pro Glu Gln Val Val Ala Ile Ala Ser Asn
                405                 410                 415

Asn Gly Gly Lys Gln Ala Leu Glu Thr Val Gln Arg Leu Leu Pro Val
            420                 425                 430

Leu Cys Gln Ala His Gly Leu Thr Pro Glu Gln Val Val Ala Ile Ala
    435                 440                 445

Ser His Asp Gly Gly Lys Gln Ala Leu Glu Thr Val Gln Ala Leu Leu
450                 455                 460

Pro Val Leu Cys Gln Ala His Gly Leu Thr Pro Gln Gln Val Val Ala
465                 470                 475                 480

Ile Ala Ser Asn Asn Gly Gly Lys Gln Ala Leu Glu Thr Val Gln Arg
                485                 490                 495

Leu Leu Pro Val Leu Cys Gln Ala His Gly Leu Thr Pro Gln Gln Val
            500                 505                 510

Val Ala Ile Ala Ser His Asp Gly Gly Lys Gln Ala Leu Glu Thr Val
    515                 520                 525

Gln Arg Leu Leu Pro Val Leu Cys Gln Ala His Gly Leu Thr Pro Gln
530                 535                 540

Gln Val Val Ala Ile Ala Ser His Asp Gly Gly Lys Gln Ala Leu Glu
```

```
              545                 550                 555                 560
          Thr Val Gln Arg Leu Leu Pro Val Leu Cys Gln Ala His Gly Leu Thr
                          565                 570                 575
          Pro Glu Gln Val Val Ala Ile Ala Ser Asn Ile Gly Gly Lys Gln Ala
                          580                 585                 590
          Leu Glu Thr Val Gln Arg Leu Leu Pro Val Leu Cys Gln Ala His Gly
                          595                 600                 605
          Leu Thr Pro Glu Gln Val Val Ala Ile Ala Ser Asn Asn Gly Gly Lys
                          610                 615                 620
          Gln Ala Leu Glu Thr Val Gln Arg Leu Leu Pro Val Leu Cys Gln Ala
          625                 630                 635                 640
          His Gly Leu Thr Pro Glu Gln Val Val Ala Ile Ala Ser His Asp Gly
                          645                 650                 655
          Gly Lys Gln Ala Leu Glu Thr Val Gln Arg Leu Leu Pro Val Leu Cys
                          660                 665                 670
          Gln Ala His Gly Leu Thr Pro Gln Gln Val Val Ala Ile Ala Ser Asn
                          675                 680                 685
          Ile Gly Gly Arg Pro Ala Leu Glu Ser Ile Val Ala Gln Leu Ser Arg
                          690                 695                 700
          Pro Asp Pro Ala Leu Ala Ala Leu Thr Asn Asp His Leu Val Ala Leu
          705                 710                 715                 720
          Ala Cys Leu Gly Gly Arg Pro Ala Leu Asp Ala Val Lys Lys Gly Leu
                          725                 730                 735
          Gly Asp Pro Ile Ser Arg Ser Gln Leu Val Lys Ser Glu Leu Glu Glu
                          740                 745                 750
          Lys Lys Ser Glu Leu Arg His Lys Leu Lys Tyr Val Pro His Glu Tyr
                          755                 760                 765
          Ile Glu Leu Ile Glu Ile Ala Arg Asn Ser Thr Gln Asp Arg Ile Leu
                          770                 775                 780
          Glu Met Lys Val Met Glu Phe Phe Met Lys Val Tyr Gly Tyr Arg Gly
          785                 790                 795                 800
          Lys His Leu Gly Gly Ser Arg Lys Pro Asp Gly Ala Ile Tyr Thr Val
                          805                 810                 815
          Gly Ser Pro Ile Asp Tyr Gly Val Ile Val Asp Thr Lys Ala Tyr Ser
                          820                 825                 830
          Gly Gly Tyr Asn Leu Pro Ile Gly Gln Ala Asp Glu Met Gln Arg Tyr
                          835                 840                 845
          Val Glu Glu Asn Gln Thr Arg Asn Lys His Ile Asn Pro Asn Glu Trp
          850                 855                 860
          Trp Lys Val Tyr Pro Ser Ser Val Thr Glu Phe Lys Phe Leu Phe Val
          865                 870                 875                 880
          Ser Gly His Phe Lys Gly Asn Tyr Lys Ala Gln Leu Thr Arg Leu Asn
                          885                 890                 895
          His Ile Thr Asn Cys Asn Gly Ala Val Leu Ser Val Glu Glu Leu Leu
                          900                 905                 910
          Ile Gly Gly Glu Met Ile Lys Ala Gly Thr Leu Thr Leu Glu Glu Val
                          915                 920                 925
          Arg Arg Lys Phe Asn Asn Gly Glu Ile Asn Phe Ala Ala Asp
          930                 935                 940

<210> SEQ ID NO 10
          <211> LENGTH: 451
          <212> TYPE: PRT
          <213> ORGANISM: artificial sequence
```

<220> FEATURE:
<223> OTHER INFORMATION: Daratumumab-VH chain

<400> SEQUENCE: 10

```
Val Gln Leu Leu Glu Ser Gly Gly Gly Leu Val Gln Pro Gly Gly Ser
 1               5                  10                  15

Leu Arg Leu Ser Cys Ala Val Ser Gly Phe Thr Phe Asn Ser Phe Ala
            20                  25                  30

Met Ser Trp Val Arg Gln Ala Pro Gly Lys Gly Leu Glu Trp Val Ser
        35                  40                  45

Ala Ile Ser Gly Ser Gly Gly Thr Tyr Tyr Ala Asp Ser Val Lys
    50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Phe Cys Ala
                85                  90                  95

Lys Asp Lys Ile Leu Trp Phe Gly Glu Pro Val Phe Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 11
<211> LENGTH: 214
<212> TYPE: PRT
<213> ORGANISM: artificial sequence
<220> FEATURE:
<223> OTHER INFORMATION: Daratumumab-VL chain

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Arg Ser Asn Trp Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 120
<212> TYPE: PRT
<213> ORGANISM: artificial sequence
<220> FEATURE:
<223> OTHER INFORMATION: MOR202-VH chain

<400> SEQUENCE: 12

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                  20                  25                  30

Tyr Met Asn Trp Val Arg Gln Ala Pro Gly Lys Gly Leu Glu Trp Val
            35                  40                  45

Ser Gly Ile Ser Gly Asp Pro Ser Asn Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asp Leu Pro Leu Val Tyr Thr Gly Phe Ala Tyr Trp Gly Gln
            100                 105                 110

Gly Thr Leu Val Thr Val Ser Ser
            115                 120

<210> SEQ ID NO 13
<211> LENGTH: 109
<212> TYPE: PRT
<213> ORGANISM: artificial sequence
<220> FEATURE:
<223> OTHER INFORMATION: MOR202-VL chain

<400> SEQUENCE: 13

Asp Ile Glu Leu Thr Gln Pro Pro Ser Val Ser Val Ala Pro Gly Gln
 1               5                  10                  15

Thr Ala Arg Ile Ser Cys Ser Gly Asp Asn Leu Arg His Tyr Tyr Val
                20                  25                  30

Tyr Trp Tyr Gln Gln Lys Pro Gly Gln Ala Pro Val Leu Val Ile Tyr
            35                  40                  45

Gly Asp Ser Lys Arg Pro Ser Gly Ile Pro Glu Arg Phe Ser Gly Ser
 50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Thr Tyr Thr Gly Gly Ala Ser Leu
                85                  90                  95

Val Phe Gly Gly Gly Thr Lys Leu Thr Val Leu Gly Gln
            100                 105

<210> SEQ ID NO 14
<211> LENGTH: 10
<212> TYPE: PRT
<213> ORGANISM: artificial sequence
<220> FEATURE:
<223> OTHER INFORMATION: HCDR1-1 - VH chain

<400> SEQUENCE: 14

Gly Phe Thr Phe Ser Ser Tyr Tyr Met Asn
 1               5                  10

<210> SEQ ID NO 15
<211> LENGTH: 5
<212> TYPE: PRT
<213> ORGANISM: artificial sequence
<220> FEATURE:
<223> OTHER INFORMATION: HCDR1-2 - VH chain

<400> SEQUENCE: 15

Ser Tyr Tyr Met Asn
 1               5

<210> SEQ ID NO 16
```

```
<211> LENGTH: 17
<212> TYPE: PRT
<213> ORGANISM: artificial sequence
<220> FEATURE:
<223> OTHER INFORMATION: HCDR2 - VH chain

<400> SEQUENCE: 16

Gly Ile Ser Gly Asp Pro Ser Asn Thr Tyr Tyr Ala Asp Ser Val Lys
1               5                   10                  15
Gly

<210> SEQ ID NO 17
<211> LENGTH: 11
<212> TYPE: PRT
<213> ORGANISM: artificial sequence
<220> FEATURE:
<223> OTHER INFORMATION: HCDR3 - VH chain

<400> SEQUENCE: 17

Asp Leu Pro Leu Val Tyr Thr Gly Phe Ala Tyr
1               5                   10

<210> SEQ ID NO 18
<211> LENGTH: 5
<212> TYPE: PRT
<213> ORGANISM: artificial sequence
<220> FEATURE:
<223> OTHER INFORMATION: HCDR4 - VH chain

<400> SEQUENCE: 18

Asp Tyr Trp Met Gln
1               5

<210> SEQ ID NO 19
<211> LENGTH: 16
<212> TYPE: PRT
<213> ORGANISM: artificial sequence
<220> FEATURE:
<223> OTHER INFORMATION: HCDR5 - VH chain

<400> SEQUENCE: 19

Thr Ile Tyr Pro Gly Asp Gly Asp Thr Gly Tyr Ala Gln Lys Phe Lys
1               5                   10                  15

<210> SEQ ID NO 20
<211> LENGTH: 11
<212> TYPE: PRT
<213> ORGANISM: artificial sequence
<220> FEATURE:
<223> OTHER INFORMATION: HCDR6 - VH chain

<400> SEQUENCE: 20

Gly Asp Tyr Tyr Gly Ser Asn Ser Leu Asp Tyr
1               5                   10

<210> SEQ ID NO 21
<211> LENGTH: 11
<212> TYPE: PRT
<213> ORGANISM: artificial sequence
<220> FEATURE:
<223> OTHER INFORMATION: LCDR1 - VH chain

<400> SEQUENCE: 21

Ser Gly Asp Asn Leu Arg His Tyr Tyr Val Tyr
1               5                   10
```

```
<210> SEQ ID NO 22
<211> LENGTH: 7
<212> TYPE: PRT
<213> ORGANISM: artificial sequence
<220> FEATURE:
<223> OTHER INFORMATION: LCDR2 - VH chain

<400> SEQUENCE: 22

Gly Asp Ser Lys Arg Pro Ser
1               5

<210> SEQ ID NO 23
<211> LENGTH: 9
<212> TYPE: PRT
<213> ORGANISM: artificial sequence
<220> FEATURE:
<223> OTHER INFORMATION: LCDR3 - VH chain

<400> SEQUENCE: 23

Gln Thr Tyr Thr Gly Gly Ala Ser Leu
1               5

<210> SEQ ID NO 24
<211> LENGTH: 11
<212> TYPE: PRT
<213> ORGANISM: artificial sequence
<220> FEATURE:
<223> OTHER INFORMATION: LCDR4 - VH chain

<400> SEQUENCE: 24

Lys Ala Ser Gln Asp Val Ser Thr Val Val Ala
1               5                   10

<210> SEQ ID NO 25
<211> LENGTH: 7
<212> TYPE: PRT
<213> ORGANISM: artificial sequence
<220> FEATURE:
<223> OTHER INFORMATION: LCDR5 - VH chain

<400> SEQUENCE: 25

Ser Ala Ser Tyr Arg Tyr Ile
1               5

<210> SEQ ID NO 26
<211> LENGTH: 8
<212> TYPE: PRT
<213> ORGANISM: artificial sequence
<220> FEATURE:
<223> OTHER INFORMATION: LCDR6 - VH chain

<400> SEQUENCE: 26

Gln Gln His Ser Pro Pro Tyr Thr
1               5

<210> SEQ ID NO 27
<211> LENGTH: 21
<212> TYPE: PRT
<213> ORGANISM: artificial sequence
<220> FEATURE:
<223> OTHER INFORMATION: CD8α-Signal peptide (SP)

<400> SEQUENCE: 27

Met Ala Leu Pro Val Thr Ala Leu Leu Leu Pro Leu Ala Leu Leu Leu
1               5                   10                  15

His Ala Ala Arg Pro
            20
```

<210> SEQ ID NO 28
<211> LENGTH: 15
<212> TYPE: PRT
<213> ORGANISM: artificial sequence
<220> FEATURE:
<223> OTHER INFORMATION: GS linker

<400> SEQUENCE: 28

Gly Gly Gly Gly Ser Gly Gly Gly Gly Ser Gly Gly Gly Gly Ser
1               5                   10                  15

<210> SEQ ID NO 29
<211> LENGTH: 16
<212> TYPE: PRT
<213> ORGANISM: homo sapiens
<220> FEATURE:
<223> OTHER INFORMATION: FCRIIα hinge

<400> SEQUENCE: 29

Gly Leu Ala Val Ser Thr Ile Ser Ser Phe Phe Pro Pro Gly Tyr Gln
1               5                   10                  15

<210> SEQ ID NO 30
<211> LENGTH: 69
<212> TYPE: PRT
<213> ORGANISM: homo sapiens
<220> FEATURE:
<223> OTHER INFORMATION: CD8α hinge

<400> SEQUENCE: 30

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys
65

<210> SEQ ID NO 31
<211> LENGTH: 231
<212> TYPE: PRT
<213> ORGANISM: homo sapiens
<220> FEATURE:
<223> OTHER INFORMATION: IgG1 hinge

<400> SEQUENCE: 31

Glu Pro Lys Ser Pro Asp Lys Thr His Thr Cys Pro Pro Cys Pro Ala
1               5                   10                  15

Pro Pro Val Ala Gly Pro Ser Val Phe Leu Phe Pro Pro Lys Pro Lys
                20                  25                  30

Asp Thr Leu Met Ile Ala Arg Thr Pro Glu Val Thr Cys Val Val Val
            35                  40                  45

Asp Val Ser His Glu Asp Pro Glu Val Lys Phe Asn Trp Tyr Val Asp
        50                  55                  60

Gly Val Glu Val His Asn Ala Lys Thr Lys Pro Arg Glu Glu Gln Tyr
65                  70                  75                  80

Asn Ser Thr Tyr Arg Val Val Ser Val Leu Thr Val Leu His Gln Asp
                85                  90                  95

```
Trp Leu Asn Gly Lys Glu Tyr Lys Cys Lys Val Ser Asn Lys Ala Leu
            100                 105                 110

Pro Ala Pro Ile Glu Lys Thr Ile Ser Lys Ala Lys Gly Gln Pro Arg
            115                 120                 125

Glu Pro Gln Val Tyr Thr Leu Pro Pro Ser Arg Asp Glu Leu Thr Lys
            130                 135                 140

Asn Gln Val Ser Leu Thr Cys Leu Val Lys Gly Phe Tyr Pro Ser Asp
145                 150                 155                 160

Ile Ala Val Glu Trp Glu Ser Asn Gly Gln Pro Glu Asn Asn Tyr Lys
            165                 170                 175

Thr Thr Pro Pro Val Leu Asp Ser Asp Gly Ser Phe Phe Leu Tyr Ser
            180                 185                 190

Lys Leu Thr Val Asp Lys Ser Arg Trp Gln Gln Gly Asn Val Phe Ser
            195                 200                 205

Cys Ser Val Met His Glu Ala Leu His Asn His Tyr Thr Gln Lys Ser
            210                 215                 220

Leu Ser Leu Ser Pro Gly Lys
225                 230

<210> SEQ ID NO 32
<211> LENGTH: 24
<212> TYPE: PRT
<213> ORGANISM: homo sapiens
<220> FEATURE:
<223> OTHER INFORMATION: TM domain

<400> SEQUENCE: 32

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 33
<211> LENGTH: 42
<212> TYPE: PRT
<213> ORGANISM: homo sapiens
<220> FEATURE:
<223> OTHER INFORMATION: 4-1 BB co-stimulatory domain

<400> SEQUENCE: 33

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 34
<211> LENGTH: 112
<212> TYPE: PRT
<213> ORGANISM: homo sapiens
<220> FEATURE:
<223> OTHER INFORMATION: CD3ζ activation domain

<400> SEQUENCE: 34

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30
```

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
 50                  55                  60

Asp Lys Met Ala Glu Ala Tyr Ser Glu Ile Gly Met Lys Gly Glu Arg
 65                  70                  75                  80

Arg Arg Gly Lys Gly His Asp Gly Leu Tyr Gln Gly Leu Ser Thr Ala
                 85                  90                  95

Thr Lys Asp Thr Tyr Asp Ala Leu His Met Gln Ala Leu Pro Pro Arg
            100                 105                 110

<210> SEQ ID NO 35
<211> LENGTH: 442
<212> TYPE: PRT
<213> ORGANISM: artificial sequence
<220> FEATURE:
<223> OTHER INFORMATION: GMB005-V1 CAR

<400> SEQUENCE: 35

Pro Leu Ala Leu Leu His Ala Ala Arg Pro Glu Val Gln Leu Leu
 1               5                  10                  15

Glu Ser Gly Gly Gly Leu Val Gln Pro Gly Gly Ser Leu Arg Leu Ser
             20                  25                  30

Cys Ala Val Ser Gly Phe Thr Phe Asn Ser Phe Ala Met Ser Trp Val
         35                  40                  45

Arg Gln Ala Pro Gly Lys Gly Leu Glu Trp Val Ser Ala Ile Ser Gly
 50                  55                  60

Ser Gly Gly Gly Thr Tyr Tyr Ala Asp Ser Val Lys Gly Arg Phe Thr
 65                  70                  75                  80

Ile Ser Arg Asp Asn Ser Lys Asn Thr Leu Tyr Leu Gln Met Asn Ser
                 85                  90                  95

Leu Arg Ala Glu Asp Thr Ala Val Tyr Phe Cys Ala Lys Asp Lys Ile
            100                 105                 110

Leu Trp Phe Gly Glu Pro Val Phe Asp Tyr Trp Gly Gln Gly Thr Leu
        115                 120                 125

Val Thr Val Ser Ser Ala Ser Gly Gly Gly Gly Ser Gly Gly Gly Gly
    130                 135                 140

Ser Gly Gly Gly Gly Ser Glu Ile Val Leu Thr Gln Ser Pro Ala Thr
145                 150                 155                 160

Leu Ser Leu Ser Pro Gly Glu Arg Ala Thr Leu Ser Cys Arg Ala Ser
                165                 170                 175

Gln Ser Val Ser Ser Tyr Leu Ala Trp Tyr Gln Gln Lys Pro Gly Gln
            180                 185                 190

Ala Pro Arg Leu Leu Ile Tyr Asp Ala Ser Asn Arg Ala Thr Gly Ile
        195                 200                 205

Pro Ala Arg Phe Ser Gly Ser Gly Ser Gly Thr Asp Phe Thr Leu Thr
    210                 215                 220

Ile Ser Ser Leu Glu Pro Glu Asp Phe Ala Val Tyr Tyr Cys Gln Gln
225                 230                 235                 240

Arg Ser Asn Trp Pro Pro Thr Phe Gly Gln Gly Thr Lys Val Glu Ile
                245                 250                 255

Lys Gly Leu Ala Val Ser Thr Ile Ser Ser Phe Phe Pro Pro Gly Tyr
            260                 265                 270

Gln Ile Tyr Ile Trp Ala Pro Leu Ala Gly Thr Cys Gly Val Leu Leu
        275                 280                 285

```
Leu Ser Leu Val Ile Thr Leu Tyr Cys Lys Arg Gly Arg Lys Lys Leu
        290                 295                 300

Leu Tyr Ile Phe Lys Gln Pro Phe Met Arg Pro Val Gln Thr Thr Gln
305                 310                 315                 320

Glu Glu Asp Gly Cys Ser Cys Arg Phe Pro Glu Glu Glu Glu Gly Gly
                325                 330                 335

Cys Glu Leu Arg Val Lys Phe Ser Arg Ser Ala Asp Ala Pro Ala Tyr
                340                 345                 350

Gln Gln Gly Gln Asn Gln Leu Tyr Asn Glu Leu Asn Leu Gly Arg Arg
            355                 360                 365

Glu Glu Tyr Asp Val Leu Asp Lys Arg Arg Gly Arg Asp Pro Glu Met
        370                 375                 380

Gly Gly Lys Pro Arg Arg Lys Asn Pro Gln Glu Gly Leu Tyr Asn Glu
385                 390                 395                 400

Leu Gln Lys Asp Lys Met Ala Glu Ala Tyr Ser Glu Ile Gly Met Lys
                405                 410                 415

Gly Glu Arg Arg Arg Gly Lys Gly His Asp Gly Leu Tyr Gln Gly Leu
                420                 425                 430

Ser Thr Ala Thr Lys Asp Thr Tyr Asp Ala
            435                 440

<210> SEQ ID NO 36
<211> LENGTH: 471
<212> TYPE: PRT
<213> ORGANISM: artificial sequence
<220> FEATURE:
<223> OTHER INFORMATION: GMB005-V2 CAR

<400> SEQUENCE: 36

Pro Leu Ala Leu Leu His Ala Ala Arg Pro Glu Val Gln Leu Leu
1               5                   10                  15

Glu Ser Gly Gly Gly Leu Val Gln Pro Gly Gly Ser Leu Arg Leu Ser
                20                  25                  30

Cys Ala Val Ser Gly Phe Thr Phe Asn Ser Phe Ala Met Ser Trp Val
            35                  40                  45

Arg Gln Ala Pro Gly Lys Gly Leu Glu Trp Val Ser Ala Ile Ser Gly
        50                  55                  60

Ser Gly Gly Gly Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

Leu Arg Ala Glu Asp Thr Ala Val Tyr Phe Cys Ala Lys Asp Lys Ile
                100                 105                 110

Leu Trp Phe Gly Glu Pro Val Phe Asp Tyr Trp Gly Gln Gly Thr Leu
            115                 120                 125

Val Thr Val Ser Ser Ala Ser Gly Gly Gly Gly Ser Gly Gly Gly Gly
        130                 135                 140

Ser Gly Gly Gly Gly Ser Glu Ile Val Leu Thr Gln Ser Pro Ala Thr
145                 150                 155                 160

Leu Ser Leu Ser Pro Gly Glu Arg Ala Thr Leu Ser Cys Arg Ala Ser
                165                 170                 175

Gln Ser Val Ser Ser Tyr Leu Ala Trp Tyr Gln Gln Lys Pro Gly Gln
            180                 185                 190

Ala Pro Arg Leu Leu Ile Tyr Asp Ala Ser Asn Arg Ala Thr Gly Ile
        195                 200                 205
```

Pro Ala Arg Phe Ser Gly Ser Gly Thr Asp Phe Thr Leu Thr
210                 215                 220

Ile Ser Ser Leu Glu Pro Glu Asp Phe Ala Val Tyr Tyr Cys Gln Gln
225                 230                 235                 240

Arg Ser Asn Trp Pro Pro Thr Phe Gly Gln Gly Thr Lys Val Glu Ile
                245                 250                 255

Lys Thr Thr Thr Pro Ala Pro Arg Pro Pro Thr Pro Ala Pro Thr Ile
                260                 265                 270

Ala Ser Gln Pro Leu Ser Leu Arg Pro Glu Ala Cys Arg Pro Ala Ala
            275                 280                 285

Gly Gly Ala Val His Thr Arg Gly Leu Asp Phe Ala Cys Asp Ile Tyr
290                 295                 300

Ile Trp Ala Pro Leu Ala Gly Thr Cys Gly Val Leu Leu Leu Ser Leu
305                 310                 315                 320

Val Ile Thr Leu Tyr Cys Lys Arg Gly Arg Lys Leu Leu Tyr Ile
                325                 330                 335

Phe Lys Gln Pro Phe Met Arg Pro Val Gln Thr Thr Gln Glu Glu Asp
                340                 345                 350

Gly Cys Ser Cys Arg Phe Pro Glu Glu Glu Glu Gly Gly Cys Glu Leu
            355                 360                 365

Arg Val Lys Phe Ser Arg Ser Ala Asp Ala Pro Ala Tyr Gln Gln Gly
370                 375                 380

Gln Asn Gln Leu Tyr Asn Glu Leu Asn Leu Gly Arg Arg Glu Glu Tyr
385                 390                 395                 400

Asp Val Leu Asp Lys Arg Arg Gly Arg Asp Pro Glu Met Gly Gly Lys
                405                 410                 415

Pro Arg Arg Lys Asn Pro Gln Glu Gly Leu Tyr Asn Glu Leu Gln Lys
                420                 425                 430

Asp Lys Met Ala Glu Ala Tyr Ser Glu Ile Gly Met Lys Gly Glu Arg
            435                 440                 445

Arg Arg Gly Lys Gly His Asp Gly Leu Tyr Gln Gly Leu Ser Thr Ala
                450                 455                 460

Thr Lys Asp Thr Tyr Asp Ala
465                 470

<210> SEQ ID NO 37
<211> LENGTH: 657
<212> TYPE: PRT
<213> ORGANISM: artificial sequence
<220> FEATURE:
<223> OTHER INFORMATION: GMB005-V3 CAR

<400> SEQUENCE: 37

Pro Leu Ala Leu Leu His Ala Ala Arg Pro Glu Val Gln Leu Leu
1               5                   10                  15

Glu Ser Gly Gly Gly Leu Val Gln Pro Gly Gly Ser Leu Arg Leu Ser
                20                  25                  30

Cys Ala Val Ser Gly Phe Thr Phe Asn Ser Phe Ala Met Ser Trp Val
            35                  40                  45

Arg Gln Ala Pro Gly Lys Gly Leu Glu Trp Val Ser Ala Ile Ser Gly
50                  55                  60

Ser Gly Gly Gly Thr Tyr Tyr Ala Asp Ser Val Lys Gly Arg Phe Thr
65                  70                  75                  80

Ile Ser Arg Asp Asn Ser Lys Asn Thr Leu Tyr Leu Gln Met Asn Ser
                85                  90                  95

```
Leu Arg Ala Glu Asp Thr Ala Val Tyr Phe Cys Ala Lys Asp Lys Ile
                100                 105                 110

Leu Trp Phe Gly Glu Pro Val Phe Asp Tyr Trp Gly Gln Gly Thr Leu
            115                 120                 125

Val Thr Val Ser Ser Ala Ser Gly Gly Gly Gly Ser Gly Gly Gly Gly
130                 135                 140

Ser Gly Gly Gly Gly Ser Glu Ile Val Leu Thr Gln Ser Pro Ala Thr
145                 150                 155                 160

Leu Ser Leu Ser Pro Gly Glu Arg Ala Thr Leu Ser Cys Arg Ala Ser
                165                 170                 175

Gln Ser Val Ser Ser Tyr Leu Ala Trp Tyr Gln Gln Lys Pro Gly Gln
            180                 185                 190

Ala Pro Arg Leu Leu Ile Tyr Asp Ala Ser Asn Arg Ala Thr Gly Ile
        195                 200                 205

Pro Ala Arg Phe Ser Gly Ser Gly Ser Gly Thr Asp Phe Thr Leu Thr
    210                 215                 220

Ile Ser Ser Leu Glu Pro Glu Asp Phe Ala Val Tyr Tyr Cys Gln Gln
225                 230                 235                 240

Arg Ser Asn Trp Pro Pro Thr Phe Gly Gln Gly Thr Lys Val Glu Ile
                245                 250                 255

Lys Glu Pro Lys Ser Pro Asp Lys Thr His Thr Cys Pro Pro Cys Pro
            260                 265                 270

Ala Pro Pro Val Ala Gly Pro Ser Val Phe Leu Phe Pro Pro Lys Pro
        275                 280                 285

Lys Asp Thr Leu Met Ile Ala Arg Thr Pro Glu Val Thr Cys Val Val
    290                 295                 300

Val Asp Val Ser His Glu Asp Pro Glu Val Lys Phe Asn Trp Tyr Val
305                 310                 315                 320

Asp Gly Val Glu Val His Asn Ala Lys Thr Lys Pro Arg Glu Glu Gln
                325                 330                 335

Tyr Asn Ser Thr Tyr Arg Val Val Ser Val Leu Thr Val Leu His Gln
            340                 345                 350

Asp Trp Leu Asn Gly Lys Glu Tyr Lys Cys Lys Val Ser Asn Lys Ala
        355                 360                 365

Leu Pro Ala Pro Ile Glu Lys Thr Ile Ser Lys Ala Lys Gly Gln Pro
    370                 375                 380

Arg Glu Pro Gln Val Tyr Thr Leu Pro Pro Ser Arg Asp Glu Leu Thr
385                 390                 395                 400

Lys Asn Gln Val Ser Leu Thr Cys Leu Val Lys Gly Phe Tyr Pro Ser
                405                 410                 415

Asp Ile Ala Val Glu Trp Glu Ser Asn Gly Gln Pro Glu Asn Asn Tyr
            420                 425                 430

Lys Thr Thr Pro Pro Val Leu Asp Ser Asp Gly Ser Phe Phe Leu Tyr
        435                 440                 445

Ser Lys Leu Thr Val Asp Lys Ser Arg Trp Gln Gln Gly Asn Val Phe
    450                 455                 460

Ser Cys Ser Val Met His Glu Ala Leu His Asn His Tyr Thr Gln Lys
465                 470                 475                 480

Ser Leu Ser Leu Ser Pro Gly Lys Ile Tyr Ile Trp Ala Pro Leu Ala
                485                 490                 495

Gly Thr Cys Gly Val Leu Leu Leu Ser Leu Val Ile Thr Leu Tyr Cys
            500                 505                 510

Lys Arg Gly Arg Lys Lys Leu Leu Tyr Ile Phe Lys Gln Pro Phe Met
```

```
                515                 520                 525
Arg Pro Val Gln Thr Thr Gln Glu Glu Asp Gly Cys Ser Cys Arg Phe
530                 535                 540

Pro Glu Glu Glu Glu Gly Gly Cys Glu Leu Arg Val Lys Phe Ser Arg
545                 550                 555                 560

Ser Ala Asp Ala Pro Ala Tyr Gln Gln Gly Gln Asn Gln Leu Tyr Asn
                565                 570                 575

Glu Leu Asn Leu Gly Arg Arg Gly Glu Tyr Asp Val Leu Asp Lys Arg
                580                 585                 590

Arg Gly Arg Asp Pro Glu Met Gly Gly Lys Pro Arg Arg Lys Asn Pro
                595                 600                 605

Gln Glu Gly Leu Tyr Asn Glu Leu Gln Lys Asp Lys Met Ala Glu Ala
                610                 615                 620

Tyr Ser Glu Ile Gly Met Lys Gly Glu Arg Arg Arg Gly Lys Gly His
625                 630                 635                 640

Asp Gly Leu Tyr Gln Gly Leu Ser Thr Ala Thr Lys Asp Thr Tyr Asp
                645                 650                 655

Ala
```

```
<210> SEQ ID NO 38
<211> LENGTH: 119
<212> TYPE: PRT
<213> ORGANISM: mus musculus
<220> FEATURE:
<223> OTHER INFORMATION: Luc63-VH chain

<400> SEQUENCE: 38

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Ser Arg Tyr
                20                  25                  30

Trp Met Ser Trp Val Arg Gln Ala Pro Gly Lys Gly Leu Glu Trp Ile
            35                  40                  45

Gly Glu Ile Asn Pro Asp Ser Ser Thr Ile Asn Tyr Thr Pro Ser Leu
50                  55                  60

Lys Asp Lys Phe Ile Ile Ser Arg Asp Asn Ala Lys Asn Thr Leu Tyr
65                  70                  75                  80

Leu Gln Met Ser Lys Val Arg Ser Glu Asp Thr Ala Leu Tyr Tyr Cys
                85                  90                  95

Ala Arg Pro Asp Gly Asn Tyr Trp Tyr Phe Asp Val Trp Gly Ala Gly
                100                 105                 110

Thr Thr Val Thr Val Ser Ser
        115
```

```
<210> SEQ ID NO 39
<211> LENGTH: 107
<212> TYPE: PRT
<213> ORGANISM: mus musculus
<220> FEATURE:
<223> OTHER INFORMATION: Luc63-VL chain

<400> SEQUENCE: 39

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Gly Ile Ala
                20                  25                  30

Val Ala Trp Tyr Gln Gln Lys Pro Gly Gln Ser Pro Lys Leu Leu Ile
```

```
                35                  40                  45
Tyr Trp Ala Ser Thr Arg His Thr Gly Val Pro Asp Arg Phe Thr Gly
     50                  55                  60
Ser Gly Ser Gly Thr Asp Phe Thr Leu Thr Ile Ser Asn Val Gln Ser
 65                  70                  75                  80
Glu Asp Leu Ala Asp Tyr Phe Cys Gln Gln Tyr Ser Ser Tyr Pro Tyr
                 85                  90                  95
Thr Phe Gly Gly Gly Thr Lys Leu Glu Ile Lys
                100                 105

<210> SEQ ID NO 40
<211> LENGTH: 120
<212> TYPE: PRT
<213> ORGANISM: mus musculus
<220> FEATURE:
<223> OTHER INFORMATION: Luc90-VH chain

<400> SEQUENCE: 40

Gln Val Gln Leu Gln Gln Pro Gly Ala Glu Leu Val Arg Pro Gly Ala
  1               5                  10                  15
Ser Val Lys Leu Ser Cys Lys Ala Ser Gly Tyr Ser Phe Thr Thr Tyr
                 20                  25                  30
Trp Met Asn Trp Val Lys Gln Arg Pro Gly Gln Gly Leu Glu Trp Ile
             35                  40                  45
Gly Met Ile His Pro Ser Asp Ser Glu Thr Arg Leu Asn Gln Lys Phe
     50                  55                  60
Lys Asp Lys Ala Thr Leu Thr Val Asp Lys Ser Ser Ser Thr Ala Tyr
 65                  70                  75                  80
Met Gln Leu Ser Ser Pro Thr Ser Glu Asp Ser Ala Val Tyr Tyr Cys
                 85                  90                  95
Ala Arg Ser Thr Met Ile Ala Thr Arg Ala Met Asp Tyr Trp Gly Gln
                100                 105                 110
Gly Thr Ser Val Thr Val Ser Ser
            115                 120

<210> SEQ ID NO 41
<211> LENGTH: 107
<212> TYPE: PRT
<213> ORGANISM: mus musculus
<220> FEATURE:
<223> OTHER INFORMATION: Luc90-VL chain

<400> SEQUENCE: 41

Asp Ile Val Met Thr Gln Ser Gln Lys Ser Met Ser Thr Ser Val Gly
  1               5                  10                  15
Asp Arg Val Ser Ile Thr Cys Lys Ala Ser Gln Asp Val Ile Thr Gly
                 20                  25                  30
Val Ala Trp Tyr Gln Gln Lys Pro Gly Gln Ser Pro Lys Leu Leu Ile
             35                  40                  45
Tyr Ser Ala Ser Tyr Arg Tyr Thr Gly Val Pro Asp Arg Phe Thr Gly
     50                  55                  60
Ser Gly Ser Gly Thr Asp Phe Thr Phe Thr Ile Ser Asn Val Gln Ala
 65                  70                  75                  80
Glu Asp Leu Ala Val Tyr Tyr Cys Gln Gln His Tyr Ser Thr Pro Leu
                 85                  90                  95
Thr Phe Gly Ala Gly Thr Lys Leu Glu Leu Lys
                100                 105
```

-continued

```
<210> SEQ ID NO 42
<211> LENGTH: 121
<212> TYPE: PRT
<213> ORGANISM: mus musculus
<220> FEATURE:
<223> OTHER INFORMATION: Luc34-VH chain

<400> SEQUENCE: 42

Gln Val Gln Leu Gln Gln Ser Gly Ala Glu Leu Ala Arg Pro Gly Ala
1               5                   10                  15

Ser Val Lys Leu Ser Cys Lys Ala Ser Gly Tyr Thr Phe Thr Ser Tyr
                20                  25                  30

Trp Met Gln Trp Val Lys Gln Arg Pro Gly Gln Gly Leu Glu Trp Ile
            35                  40                  45

Gly Ala Ile Tyr Pro Gly Asp Gly Asp Thr Arg Tyr Thr Gln Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Ala Ser Glu Asp Ser Ala Val Tyr Tyr Cys
                85                  90                  95

Ala Arg Gly Lys Val Tyr Tyr Gly Ser Asn Pro Phe Ala Tyr Trp Gly
            100                 105                 110

Gln Gly Thr Leu Val Thr Val Ser Ala
        115                 120

<210> SEQ ID NO 43
<211> LENGTH: 107
<212> TYPE: PRT
<213> ORGANISM: mus musculus
<220> FEATURE:
<223> OTHER INFORMATION: Luc34-VL chain

<400> SEQUENCE: 43

Asp Ile Gln Met Thr Gln Ser Ser Tyr Leu Ser Val Ser Leu Gly
1               5                   10                  15

Gly Arg Val Thr Ile Thr Cys Lys Ala Ser Asp His Ile Asn Asn Trp
                20                  25                  30

Leu Ala Trp Tyr Gln Gln Lys Pro Gly Asn Ala Pro Arg Leu Leu Ile
            35                  40                  45

Ser Gly Ala Thr Ser Leu Glu Thr Gly Val Pro Ser Arg Phe Ser Gly
        50                  55                  60

Ser Gly Ser Gly Lys Asp Tyr Thr Leu Ser Ile Thr Ser Leu Gln Thr
65                  70                  75                  80

Glu Asp Val Ala Thr Tyr Tyr Cys Gln Gln Tyr Trp Ser Thr Pro Trp
                85                  90                  95

Thr Phe Gly Gly Gly Thr Lys Leu Glu Ile Lys
            100                 105

<210> SEQ ID NO 44
<211> LENGTH: 120
<212> TYPE: PRT
<213> ORGANISM: mus musculus
<220> FEATURE:
<223> OTHER INFORMATION: LucX1-VH chain

<400> SEQUENCE: 44

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
```

```
                    20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Lys Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95

Ala Arg Ser Thr Met Ile Ala Thr Gly Ala Met Asp Tyr Trp Gly Gln
            100                 105                 110

Gly Thr Ser Val Thr Val Ser Ser
            115                 120

<210> SEQ ID NO 45
<211> LENGTH: 107
<212> TYPE: PRT
<213> ORGANISM: mus musculus
<220> FEATURE:
<223> OTHER INFORMATION: LucX1-VL chain

<400> SEQUENCE: 45

Glu Thr Thr Val Thr Gln Ser Pro Ala Ser Leu Ser Met Ala Ile Gly
1               5                   10                  15

Glu Lys Val Thr Ile Arg Cys Ile Thr Ser Thr Asp Ile Asp Asp Asp
                20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Leu
                85                  90                  95

Thr Phe Gly Gly Gly Thr Lys Leu Glu Ile Lys
            100                 105

<210> SEQ ID NO 46
<211> LENGTH: 120
<212> TYPE: PRT
<213> ORGANISM: mus musculus
<220> FEATURE:
<223> OTHER INFORMATION: LucX2-VH chain

<400> SEQUENCE: 46

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Ala Phe Ser Ser Ser
                20                  25                  30

Trp Met Asn Trp Val Lys Gln Arg Pro Gly Gln Gly Leu Glu Trp Ile
        35                  40                  45

Gly Arg Ile Tyr Pro Gly Asp Gly Asp Thr Lys Tyr Asn Gly Lys Phe
    50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Val Asp Ser Ala Val Tyr Phe Cys
                85                  90                  95
```

Ala Arg Ser Thr Met Ile Ala Thr Gly Ala Met Asp Tyr Trp Gly Gln
            100                 105                 110

Gly Thr Ser Val Thr Val Ser Ser
        115                 120

<210> SEQ ID NO 47
<211> LENGTH: 108
<212> TYPE: PRT
<213> ORGANISM: mus musculus
<220> FEATURE:
<223> OTHER INFORMATION: LucX2-VL chain

<400> SEQUENCE: 47

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Tyr Thr Phe Gly Gly Gly Thr Lys Leu Glu Ile Lys
            100                 105

<210> SEQ ID NO 48
<211> LENGTH: 432
<212> TYPE: PRT
<213> ORGANISM: artificial sequence
<220> FEATURE:
<223> OTHER INFORMATION: Luc63-V1 CAR

<400> SEQUENCE: 48

Met Ala Leu Pro Val Thr Ala Leu Leu Leu Pro Leu Ala Leu Leu Leu
1               5                   10                  15

His Ala Ala Arg Pro Glu Val Lys Leu Glu Ser Gly Gly Gly Leu
            20                  25                  30

Val Gln Pro Gly Gly Ser Leu Lys Leu Ser Cys Ala Ala Ser Gly Phe
        35                  40                  45

Asp Phe Ser Arg Tyr Trp Met Ser Trp Val Arg Gln Ala Pro Gly Lys
    50                  55                  60

Gly Leu Glu Trp Ile Gly Glu Ile Asn Pro Asp Ser Ser Thr Ile Asn
65                  70                  75                  80

Tyr Thr Pro Ser Leu Lys Asp Lys Phe Ile Ile Ser Arg Asp Asn Ala
                85                  90                  95

Lys Asn Thr Leu Tyr Leu Gln Met Ser Lys Val Arg Ser Glu Asp Thr
            100                 105                 110

Ala Leu Tyr Tyr Cys Ala Arg Pro Asp Gly Asn Tyr Trp Tyr Phe Asp
        115                 120                 125

Val Trp Gly Ala Gly Thr Thr Val Thr Val Ser Ser Gly Gly Gly Gly
    130                 135                 140

Ser Gly Gly Gly Gly Ser Gly Gly Gly Ser Asp Ile Val Met Thr
145                 150                 155                 160

Gln Ser His Lys Phe Met Ser Thr Ser Val Gly Asp Arg Val Ser Ile
                165                 170                 175

```
Thr Cys Lys Ala Ser Gln Asp Val Gly Ile Ala Val Ala Trp Tyr Gln
            180                 185                 190

Gln Lys Pro Gly Gln Ser Pro Lys Leu Leu Ile Tyr Trp Ala Ser Thr
        195                 200                 205

Arg His Thr Gly Val Pro Asp Arg Phe Thr Gly Ser Gly Ser Gly Thr
    210                 215                 220

Asp Phe Thr Leu Thr Ile Ser Asn Val Gln Ser Glu Asp Leu Ala Asp
225                 230                 235                 240

Tyr Phe Cys Gln Gln Tyr Ser Ser Tyr Pro Tyr Thr Phe Gly Gly Gly
                245                 250                 255

Thr Lys Leu Glu Ile Lys Gly Leu Ala Val Ser Thr Ile Ser Ser Phe
            260                 265                 270

Phe Pro Pro Gly Tyr Gln Lys Arg Gly Arg Lys Lys Leu Leu Tyr Ile
        275                 280                 285

Phe Lys Gln Pro Phe Met Arg Pro Val Gln Thr Thr Gln Glu Glu Asp
    290                 295                 300

Gly Cys Ser Cys Arg Phe Pro Glu Glu Glu Gly Gly Cys Glu Leu
305                 310                 315                 320

Arg Val Lys Phe Ser Arg Ser Ala Asp Ala Pro Ala Tyr Gln Gln Gly
                325                 330                 335

Gln Asn Gln Leu Tyr Asn Glu Leu Asn Leu Gly Arg Arg Glu Glu Tyr
            340                 345                 350

Asp Val Leu Asp Lys Arg Arg Gly Arg Asp Pro Glu Met Gly Gly Lys
        355                 360                 365

Pro Arg Arg Lys Asn Pro Gln Glu Gly Leu Tyr Asn Glu Leu Gln Lys
    370                 375                 380

Asp Lys Met Ala Glu Ala Tyr Ser Glu Ile Gly Met Lys Gly Glu Arg
385                 390                 395                 400

Arg Arg Gly Lys Gly His Asp Gly Leu Tyr Gln Gly Leu Ser Thr Ala
                405                 410                 415

Thr Lys Asp Thr Tyr Asp Ala Leu His Met Gln Ala Leu Pro Pro Arg
            420                 425                 430

<210> SEQ ID NO 49
<211> LENGTH: 485
<212> TYPE: PRT
<213> ORGANISM: artificial sequence
<220> FEATURE:
<223> OTHER INFORMATION: Luc63-V2 CAR

<400> SEQUENCE: 49

Met Ala Leu Pro Val Thr Ala Leu Leu Leu Pro Leu Ala Leu Leu Leu
1               5                   10                  15

His Ala Ala Arg Pro Glu Val Lys Leu Leu Glu Ser Gly Gly Gly Leu
            20                  25                  30

Val Gln Pro Gly Gly Ser Leu Lys Leu Ser Cys Ala Ala Ser Gly Phe
        35                  40                  45

Asp Phe Ser Arg Tyr Trp Met Ser Trp Val Arg Gln Ala Pro Gly Lys
    50                  55                  60

Gly Leu Glu Trp Ile Gly Glu Ile Asn Pro Asp Ser Ser Thr Ile Asn
65                  70                  75                  80

Tyr Thr Pro Ser Leu Lys Asp Lys Phe Ile Ile Ser Arg Asp Asn Ala
                85                  90                  95

Lys Asn Thr Leu Tyr Leu Gln Met Ser Lys Val Arg Ser Glu Asp Thr
            100                 105                 110
```

Ala Leu Tyr Tyr Cys Ala Arg Pro Asp Gly Asn Tyr Trp Tyr Phe Asp
            115                 120                 125

Val Trp Gly Ala Gly Thr Thr Val Thr Val Ser Ser Gly Gly Gly Gly
        130                 135                 140

Ser Gly Gly Gly Gly Ser Gly Gly Gly Ser Asp Ile Val Met Thr
145                 150                 155                 160

Gln Ser His Lys Phe Met Ser Thr Ser Val Gly Asp Arg Val Ser Ile
                165                 170                 175

Thr Cys Lys Ala Ser Gln Asp Val Gly Ile Ala Val Ala Trp Tyr Gln
            180                 185                 190

Gln Lys Pro Gly Gln Ser Pro Lys Leu Leu Ile Tyr Trp Ala Ser Thr
        195                 200                 205

Arg His Thr Gly Val Pro Asp Arg Phe Thr Gly Ser Gly Ser Gly Thr
    210                 215                 220

Asp Phe Thr Leu Thr Ile Ser Asn Val Gln Ser Glu Asp Leu Ala Asp
225                 230                 235                 240

Tyr Phe Cys Gln Gln Tyr Ser Ser Tyr Pro Tyr Thr Phe Gly Gly Gly
                245                 250                 255

Thr Lys Leu Glu Ile Lys Thr Thr Thr Pro Ala Pro Arg Pro Pro Thr
            260                 265                 270

Pro Ala Pro Thr Ile Ala Ser Gln Pro Leu Ser Leu Arg Pro Glu Ala
        275                 280                 285

Cys Arg Pro Ala Ala Gly Gly Ala Val His Thr Arg Gly Leu Asp Phe
    290                 295                 300

Ala Cys Asp Ile Tyr Ile Trp Ala Pro Leu Ala Gly Thr Cys Gly Val
305                 310                 315                 320

Leu Leu Leu Ser Leu Val Ile Thr Leu Tyr Cys Lys Arg Gly Arg Lys
                325                 330                 335

Lys Leu Leu Tyr Ile Phe Lys Gln Pro Phe Met Arg Pro Val Gln Thr
            340                 345                 350

Thr Gln Glu Glu Asp Gly Cys Ser Cys Arg Phe Pro Glu Glu Glu Glu
        355                 360                 365

Gly Gly Cys Glu Leu Arg Val Lys Phe Ser Arg Ser Ala Asp Ala Pro
    370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Arg Arg Lys Asn Pro Gln Glu Gly Leu Tyr
            420                 425                 430

Asn Glu Leu Gln Lys Asp Lys Met Ala Glu Ala Tyr Ser Glu Ile Gly
        435                 440                 445

Met Lys Gly Glu Arg Arg Arg Gly Lys Gly His Asp Gly Leu Tyr Gln
    450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 50
<211> LENGTH: 647
<212> TYPE: PRT
<213> ORGANISM: artificial sequence
<220> FEATURE:

<223> OTHER INFORMATION: Luc63-V3 CAR

<400> SEQUENCE: 50

```
Met Ala Leu Pro Val Thr Ala Leu Leu Leu Pro Leu Ala Leu Leu Leu
1               5                   10                  15

His Ala Ala Arg Pro Glu Val Lys Leu Leu Glu Ser Gly Gly Gly Leu
            20                  25                  30

Val Gln Pro Gly Gly Ser Leu Lys Leu Ser Cys Ala Ala Ser Gly Phe
        35                  40                  45

Asp Phe Ser Arg Tyr Trp Met Ser Trp Val Arg Gln Ala Pro Gly Lys
    50                  55                  60

Gly Leu Glu Trp Ile Gly Glu Ile Asn Pro Asp Ser Ser Thr Ile Asn
65                  70                  75                  80

Tyr Thr Pro Ser Leu Lys Asp Lys Phe Ile Ile Ser Arg Asp Asn Ala
                85                  90                  95

Lys Asn Thr Leu Tyr Leu Gln Met Ser Lys Val Arg Ser Glu Asp Thr
            100                 105                 110

Ala Leu Tyr Tyr Cys Ala Arg Pro Asp Gly Asn Tyr Trp Tyr Phe Asp
        115                 120                 125

Val Trp Gly Ala Gly Thr Thr Val Thr Val Ser Ser Gly Gly Gly Gly
    130                 135                 140

Ser Gly Gly Gly Gly Ser Gly Gly Gly Gly Ser Asp Ile Val Met Thr
145                 150                 155                 160

Gln Ser His Lys Phe Met Ser Thr Ser Val Gly Asp Arg Val Ser Ile
                165                 170                 175

Thr Cys Lys Ala Ser Gln Asp Val Gly Ile Ala Val Ala Trp Tyr Gln
            180                 185                 190

Gln Lys Pro Gly Gln Ser Pro Lys Leu Leu Ile Tyr Trp Ala Ser Thr
        195                 200                 205

Arg His Thr Gly Val Pro Asp Arg Phe Thr Gly Ser Gly Ser Gly Thr
    210                 215                 220

Asp Phe Thr Leu Thr Ile Ser Asn Val Gln Ser Glu Asp Leu Ala Asp
225                 230                 235                 240

Tyr Phe Cys Gln Gln Tyr Ser Ser Tyr Pro Tyr Thr Phe Gly Gly Gly
                245                 250                 255

Thr Lys Leu Glu Ile Lys Glu Pro Lys Ser Pro Asp Lys Thr His Thr
            260                 265                 270

Cys Pro Pro Cys Pro Ala Pro Val Ala Gly Pro Ser Val Phe Leu
        275                 280                 285

Phe Pro Pro Lys Pro Lys Asp Thr Leu Met Ile Ala Arg Thr Pro Glu
    290                 295                 300

Val Thr Cys Val Val Val Asp Val Ser His Glu Asp Pro Glu Val Lys
305                 310                 315                 320

Phe Asn Trp Tyr Val Asp Gly Val Glu Val His Asn Ala Lys Thr Lys
                325                 330                 335

Pro Arg Glu Glu Gln Tyr Asn Ser Thr Tyr Arg Val Val Ser Val Leu
            340                 345                 350

Thr Val Leu His Gln Asp Trp Leu Asn Gly Lys Glu Tyr Lys Cys Lys
        355                 360                 365

Val Ser Asn Lys Ala Leu Pro Ala Pro Ile Glu Lys Thr Ile Ser Lys
    370                 375                 380

Ala Lys Gly Gln Pro Arg Glu Pro Gln Val Tyr Thr Leu Pro Pro Ser
385                 390                 395                 400
```

-continued

Arg Asp Glu Leu Thr Lys Asn Gln Val Ser Leu Thr Cys Leu Val Lys
                405                 410                 415

Gly Phe Tyr Pro Ser Asp Ile Ala Val Glu Trp Glu Ser Asn Gly Gln
            420                 425                 430

Pro Glu Asn Asn Tyr Lys Thr Thr Pro Pro Val Leu Asp Ser Asp Gly
        435                 440                 445

Ser Phe Phe Leu Tyr Ser Lys Leu Thr Val Asp Lys Ser Arg Trp Gln
    450                 455                 460

Gln Gly Asn Val Phe Ser Cys Ser Val Met His Glu Ala Leu His Asn
465                 470                 475                 480

His Tyr Thr Gln Lys Ser Leu Ser Leu Ser Pro Gly Lys Lys Arg Gly
                485                 490                 495

Arg Lys Lys Leu Leu Tyr Ile Phe Lys Gln Pro Phe Met Arg Pro Val
            500                 505                 510

Gln Thr Thr Gln Glu Glu Asp Gly Cys Ser Cys Arg Phe Pro Glu Glu
        515                 520                 525

Glu Glu Gly Gly Cys Glu Leu Arg Val Lys Phe Ser Arg Ser Ala Asp
    530                 535                 540

Ala Pro Ala Tyr Gln Gln Gly Gln Asn Gln Leu Tyr Asn Glu Leu Asn
545                 550                 555                 560

Leu Gly Arg Arg Glu Glu Tyr Asp Val Leu Asp Lys Arg Arg Gly Arg
                565                 570                 575

Asp Pro Glu Met Gly Gly Lys Pro Arg Arg Lys Asn Pro Gln Glu Gly
            580                 585                 590

Leu Tyr Asn Glu Leu Gln Lys Asp Lys Met Ala Glu Ala Tyr Ser Glu
        595                 600                 605

Ile Gly Met Lys Gly Glu Arg Arg Arg Gly Lys Gly His Asp Gly Leu
    610                 615                 620

Tyr Gln Gly Leu Ser Thr Ala Thr Lys Asp Thr Tyr Asp Ala Leu His
625                 630                 635                 640

Met Gln Ala Leu Pro Pro Arg
                645

<210> SEQ ID NO 51
<211> LENGTH: 433
<212> TYPE: PRT
<213> ORGANISM: artificial sequence
<220> FEATURE:
<223> OTHER INFORMATION: Luc90-V1 CAR

<400> SEQUENCE: 51

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
            20                  25                  30

Val Arg Pro Gly Ala Ser Val Lys Leu Ser Cys Lys Ala Ser Gly Tyr
        35                  40                  45

Ser Phe Thr Thr Tyr Trp Met Asn Trp Val Lys Gln Arg Pro Gly Gln
    50                  55                  60

Gly Leu Glu Trp Ile Gly Met Ile His Pro Ser Asp Ser Glu Thr Arg
65                  70                  75                  80

Leu Asn Gln Lys Phe Lys Asp Lys Ala Thr Leu Thr Val Asp Lys Ser
                85                  90                  95

Ser Ser Thr Ala Tyr Met Gln Leu Ser Ser Pro Thr Ser Glu Asp Ser
            100                 105                 110

```
Ala Val Tyr Tyr Cys Ala Arg Ser Thr Met Ile Ala Thr Arg Ala Met
            115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Gln Lys Ser Met Ser Thr Ser Val Gly Asp Arg Val Ser
                165                 170                 175

Ile Thr Cys Lys Ala Ser Gln Asp Val Ile Thr Gly Val Ala Trp Tyr
            180                 185                 190

Gln Gln Lys Pro Gly Gln Ser Pro Lys Leu Leu Ile Tyr Ser Ala Ser
        195                 200                 205

Tyr Arg Tyr Thr Gly Val Pro Asp Arg Phe Thr Gly Ser Gly Ser Gly
    210                 215                 220

Thr Asp Phe Thr Phe Thr Ile Ser Asn Val Gln Ala Glu Asp Leu Ala
225                 230                 235                 240

Val Tyr Tyr Cys Gln Gln His Tyr Ser Thr Pro Leu Thr Phe Gly Ala
                245                 250                 255

Gly Thr Lys Leu Glu Leu Lys Gly Leu Ala Val Ser Thr Ile Ser Ser
            260                 265                 270

Phe Phe Pro Pro Gly Tyr Gln Lys Arg Gly Arg Lys Leu Leu Tyr
        275                 280                 285

Ile Phe Lys Gln Pro Phe Met Arg Pro Val Gln Thr Thr Gln Glu Glu
            290                 295                 300

Asp Gly Cys Ser Cys Arg Phe Pro Glu Glu Glu Gly Gly Cys Glu
305                 310                 315                 320

Leu Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
        355                 360                 365

Lys Pro Arg Arg Lys Asn Pro Gln Glu Gly Leu Tyr Asn Glu Leu Gln
370                 375                 380

Lys Asp Lys Met Ala Glu Ala Tyr Ser Glu Ile Gly Met Lys Gly Glu
385                 390                 395                 400

Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
            420                 425                 430

Arg

<210> SEQ ID NO 52
<211> LENGTH: 486
<212> TYPE: PRT
<213> ORGANISM: artificial sequence
<220> FEATURE:
<223> OTHER INFORMATION: Luc90-V2 CAR

<400> SEQUENCE: 52

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
                20                  25                  30

Val Arg Pro Gly Ala Ser Val Lys Leu Ser Cys Lys Ala Ser Gly Tyr
```

```
                35                  40                  45
Ser Phe Thr Thr Tyr Trp Met Asn Trp Val Lys Gln Arg Pro Gly Gln
 50                  55                  60

Gly Leu Glu Trp Ile Gly Met Ile His Pro Ser Asp Ser Glu Thr Arg
 65                  70                  75                  80

Leu Asn Gln Lys Phe Lys Asp Lys Ala Thr Leu Thr Val Asp Lys Ser
                 85                  90                  95

Ser Ser Thr Ala Tyr Met Gln Leu Ser Ser Pro Thr Ser Glu Asp Ser
                100                 105                 110

Ala Val Tyr Tyr Cys Ala Arg Ser Thr Met Ile Ala Thr Arg Ala Met
                115                 120                 125

Asp Tyr Trp Gly Gln Gly Thr Ser Val Thr Val Ser Ser Gly Gly Gly
                130                 135                 140

Gly Ser Gly Gly Gly Gly Ser Gly Gly Gly Gly Ser Asp Ile Val Met
145                 150                 155                 160

Thr Gln Ser Gln Lys Ser Met Ser Thr Ser Val Gly Asp Arg Val Ser
                165                 170                 175

Ile Thr Cys Lys Ala Ser Gln Asp Val Ile Thr Gly Val Ala Trp Tyr
                180                 185                 190

Gln Gln Lys Pro Gly Gln Ser Pro Lys Leu Leu Ile Tyr Ser Ala Ser
                195                 200                 205

Tyr Arg Tyr Thr Gly Val Pro Asp Arg Phe Thr Gly Ser Gly Ser Gly
                210                 215                 220

Thr Asp Phe Thr Phe Thr Ile Ser Asn Val Gln Ala Glu Asp Leu Ala
225                 230                 235                 240

Val Tyr Tyr Cys Gln Gln His Tyr Ser Thr Pro Leu Thr Phe Gly Ala
                245                 250                 255

Gly Thr Lys Leu Glu Leu Lys Thr Thr Thr Pro Ala Pro Arg Pro Pro
                260                 265                 270

Thr Pro Ala Pro Thr Ile Ala Ser Gln Pro Leu Ser Leu Arg Pro Glu
                275                 280                 285

Ala Cys Arg Pro Ala Ala Gly Gly Ala Val His Thr Arg Gly Leu Asp
290                 295                 300

Phe Ala Cys Asp Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
                340                 345                 350

Thr Thr Gln Glu Glu Asp Gly Cys Ser Cys Arg Phe Pro Glu Glu Glu
                355                 360                 365

Glu Gly Gly Cys Glu Leu Arg Val Lys Phe Ser Arg Ser Ala Asp Ala
                370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
                420                 425                 430

Tyr Asn Glu Leu Gln Lys Asp Lys Met Ala Glu Ala Tyr Ser Glu Ile
                435                 440                 445

Gly Met Lys Gly Glu Arg Arg Arg Gly Lys Gly His Asp Gly Leu Tyr
                450                 455                 460
```

-continued

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 53
<211> LENGTH: 648
<212> TYPE: PRT
<213> ORGANISM: artificial sequence
<220> FEATURE:
<223> OTHER INFORMATION: Luc90-V3 CAR

<400> SEQUENCE: 53

Met Ala Leu Pro Val Thr Ala Leu Leu Leu Pro Leu Ala Leu Leu Leu
1               5                   10                  15

His Ala Ala Arg Pro Gln Val Gln Leu Gln Gln Pro Gly Ala Glu Leu
                20                  25                  30

Val Arg Pro Gly Ala Ser Val Lys Leu Ser Cys Lys Ala Ser Gly Tyr
            35                  40                  45

Ser Phe Thr Thr Tyr Trp Met Asn Trp Val Lys Gln Arg Pro Gly Gln
        50                  55                  60

Gly Leu Glu Trp Ile Gly Met Ile His Pro Ser Asp Ser Glu Thr Arg
65                  70                  75                  80

Leu Asn Gln Lys Phe Lys Asp Lys Ala Thr Leu Thr Val Asp Lys Ser
                85                  90                  95

Ser Ser Thr Ala Tyr Met Gln Leu Ser Ser Pro Thr Ser Glu Asp Ser
            100                 105                 110

Ala Val Tyr Tyr Cys Ala Arg Ser Thr Met Ile Ala Thr Arg Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser Gln Lys Ser Met Ser Thr Ser Val Gly Asp Arg Val Ser
                165                 170                 175

Ile Thr Cys Lys Ala Ser Gln Asp Val Ile Thr Gly Val Ala Trp Tyr
            180                 185                 190

Gln Gln Lys Pro Gly Gln Ser Pro Lys Leu Leu Ile Tyr Ser Ala Ser
        195                 200                 205

Tyr Arg Tyr Thr Gly Val Pro Asp Arg Phe Thr Gly Ser Gly Ser Gly
    210                 215                 220

Thr Asp Phe Thr Phe Thr Ile Ser Asn Val Gln Ala Glu Asp Leu Ala
225                 230                 235                 240

Val Tyr Tyr Cys Gln Gln His Tyr Ser Thr Pro Leu Thr Phe Gly Ala
                245                 250                 255

Gly Thr Lys Leu Glu Leu Lys Glu Pro Lys Ser Pro Asp Lys Thr His
            260                 265                 270

Thr Cys Pro Pro Cys Pro Ala Pro Pro Val Ala Gly Pro Ser Val Phe
        275                 280                 285

Leu Phe Pro Pro Lys Pro Lys Asp Thr Leu Met Ile Ala Arg Thr Pro
    290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
                325                 330                 335

-continued

Lys Pro Arg Glu Glu Gln Tyr Asn Ser Thr Tyr Arg Val Val Ser Val
                340                 345                 350

Leu Thr Val Leu His Gln Asp Trp Leu Asn Gly Lys Glu Tyr Lys Cys
            355                 360                 365

Lys Val Ser Asn Lys Ala Leu Pro Ala Pro Ile Glu Lys Thr Ile Ser
        370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Lys Arg
                485                 490                 495

Gly Arg Lys Lys Leu Leu Tyr Ile Phe Lys Gln Pro Phe Met Arg Pro
            500                 505                 510

Val Gln Thr Thr Gln Glu Glu Asp Gly Cys Ser Cys Arg Phe Pro Glu
        515                 520                 525

Glu Glu Glu Gly Gly Cys Glu Leu Arg Val Lys Phe Ser Arg Ser Ala
        530                 535                 540

Asp Ala Pro Ala Tyr Gln Gln Gly Gln Asn Gln Leu Tyr Asn Glu Leu
545                 550                 555                 560

Asn Leu Gly Arg Arg Glu Glu Tyr Asp Val Leu Asp Lys Arg Arg Gly
                565                 570                 575

Arg Asp Pro Glu Met Gly Gly Lys Pro Arg Arg Lys Asn Pro Gln Glu
            580                 585                 590

Gly Leu Tyr Asn Glu Leu Gln Lys Asp Lys Met Ala Glu Ala Tyr Ser
        595                 600                 605

Glu Ile Gly Met Lys Gly Glu Arg Arg Arg Gly Lys Gly His Asp Gly
        610                 615                 620

Leu Tyr Gln Gly Leu Ser Thr Ala Thr Lys Asp Thr Tyr Asp Ala Leu
625                 630                 635                 640

His Met Gln Ala Leu Pro Pro Arg
                645

<210> SEQ ID NO 54
<211> LENGTH: 434
<212> TYPE: PRT
<213> ORGANISM: artificial sequence
<220> FEATURE:
<223> OTHER INFORMATION: Luc34-V1 CAR

<400> SEQUENCE: 54

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Ala Arg Pro Gly Ala Ser Val Lys Leu Ser Cys Lys Ala Ser Gly Tyr
        35                  40                  45

-continued

```
Thr Phe Thr Ser Tyr Trp Met Gln Trp Val Lys Gln Arg Pro Gly Gln
         50                  55                  60
Gly Leu Glu Trp Ile Gly Ala Ile Tyr Pro Gly Asp Gly Asp Thr Arg
 65                  70                  75                  80
Tyr Thr Gln Lys Phe Lys Gly Lys Ala Thr Leu Thr Ala Asp Lys Ser
                 85                  90                  95
Ser Ser Thr Ala Tyr Met Gln Leu Ser Ser Leu Ala Ser Glu Asp Ser
                100                 105                 110
Ala Val Tyr Tyr Cys Ala Arg Gly Lys Val Tyr Tyr Gly Ser Asn Pro
            115                 120                 125
Phe Ala Tyr Trp Gly Gln Gly Thr Leu Val Thr Val Ser Ala Gly Gly
        130                 135                 140
Gly Gly Ser Gly Gly Gly Ser Gly Gly Gly Ser Asp Ile Gln
145                 150                 155                 160
Met Thr Gln Ser Ser Ser Tyr Leu Ser Val Ser Leu Gly Gly Arg Val
                165                 170                 175
Thr Ile Thr Cys Lys Ala Ser Asp His Ile Asn Asn Trp Leu Ala Trp
            180                 185                 190
Tyr Gln Gln Lys Pro Gly Asn Ala Pro Arg Leu Leu Ile Ser Gly Ala
        195                 200                 205
Thr Ser Leu Glu Thr Gly Val Pro Ser Arg Phe Ser Gly Ser Gly Ser
210                 215                 220
Gly Lys Asp Tyr Thr Leu Ser Ile Thr Ser Leu Gln Thr Glu Asp Val
225                 230                 235                 240
Ala Thr Tyr Tyr Cys Gln Gln Tyr Trp Ser Thr Pro Trp Thr Phe Gly
                245                 250                 255
Gly Gly Thr Lys Leu Glu Ile Lys Gly Leu Ala Val Ser Thr Ile Ser
            260                 265                 270
Ser Phe Phe Pro Pro Gly Tyr Gln Lys Arg Gly Arg Lys Lys Leu Leu
        275                 280                 285
Tyr Ile Phe Lys Gln Pro Phe Met Arg Pro Val Gln Thr Thr Gln Glu
    290                 295                 300
Glu Asp Gly Cys Ser Cys Arg Phe Pro Glu Glu Glu Glu Gly Gly Cys
305                 310                 315                 320
Glu Leu Arg Val Lys Phe Ser Arg Ser Ala Asp Ala Pro Ala Tyr Gln
                325                 330                 335
Gln Gly Gln Asn Gln Leu Tyr Asn Glu Leu Asn Leu Gly Arg Arg Glu
            340                 345                 350
Glu Tyr Asp Val Leu Asp Lys Arg Arg Gly Arg Asp Pro Glu Met Gly
        355                 360                 365
Gly Lys Pro Arg Arg Lys Asn Pro Gln Glu Gly Leu Tyr Asn Glu Leu
370                 375                 380
Gln Lys Asp Lys Met Ala Glu Ala Tyr Ser Glu Ile Gly Met Lys Gly
385                 390                 395                 400
Glu Arg Arg Arg Gly Lys Gly His Asp Gly Leu Tyr Gln Gly Leu Ser
                405                 410                 415
Thr Ala Thr Lys Asp Thr Tyr Asp Ala Leu His Met Gln Ala Leu Pro
            420                 425                 430
Pro Arg
```

<210> SEQ ID NO 55
<211> LENGTH: 487
<212> TYPE: PRT

<213> ORGANISM: artificial sequence
<220> FEATURE:
<223> OTHER INFORMATION: Luc34-V2 CAR

<400> SEQUENCE: 55

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
            20                  25                  30

Ala Arg Pro Gly Ala Ser Val Lys Leu Ser Cys Lys Ala Ser Gly Tyr
        35                  40                  45

Thr Phe Thr Ser Tyr Trp Met Gln Trp Val Lys Gln Arg Pro Gly Gln
    50                  55                  60

Gly Leu Glu Trp Ile Gly Ala Ile Tyr Pro Gly Asp Gly Asp Thr Arg
65                  70                  75                  80

Tyr Thr Gln Lys Phe Lys Gly Lys Ala Thr Leu Thr Ala Asp Lys Ser
                85                  90                  95

Ser Ser Thr Ala Tyr Met Gln Leu Ser Ser Leu Ala Ser Glu Asp Ser
            100                 105                 110

Ala Val Tyr Tyr Cys Ala Arg Gly Lys Val Tyr Tyr Gly Ser Asn Pro
        115                 120                 125

Phe Ala Tyr Trp Gly Gln Gly Thr Leu Val Thr Val Ser Ala Gly Gly
    130                 135                 140

Gly Gly Ser Gly Gly Gly Gly Ser Gly Gly Gly Gly Ser Asp Ile Gln
145                 150                 155                 160

Met Thr Gln Ser Ser Ser Tyr Leu Ser Val Ser Leu Gly Gly Arg Val
                165                 170                 175

Thr Ile Thr Cys Lys Ala Ser Asp His Ile Asn Asn Trp Leu Ala Trp
            180                 185                 190

Tyr Gln Gln Lys Pro Gly Asn Ala Pro Arg Leu Leu Ile Ser Gly Ala
        195                 200                 205

Thr Ser Leu Glu Thr Gly Val Pro Ser Arg Phe Ser Gly Ser Gly Ser
    210                 215                 220

Gly Lys Asp Tyr Thr Leu Ser Ile Thr Ser Leu Gln Thr Glu Asp Val
225                 230                 235                 240

Ala Thr Tyr Tyr Cys Gln Gln Tyr Trp Ser Thr Pro Trp Thr Phe Gly
                245                 250                 255

Gly Gly Thr Lys Leu Glu Ile Lys Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
        355                 360                 365

Glu Glu Gly Gly Cys Glu Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
```

```
                385                 390                 395                 400
Leu Gly Arg Arg Glu Glu Tyr Asp Val Leu Asp Lys Arg Arg Gly Arg
                    405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
                435                 440                 445

Ile Gly Met Lys Gly Glu Arg Arg Arg Gly Lys Gly His Asp Gly Leu
        450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 56
<211> LENGTH: 649
<212> TYPE: PRT
<213> ORGANISM: artificial sequence
<220> FEATURE:
<223> OTHER INFORMATION: Luc34-V3 CAR

<400> SEQUENCE: 56

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
                20                  25                  30

Ala Arg Pro Gly Ala Ser Val Lys Leu Ser Cys Lys Ala Ser Gly Tyr
            35                  40                  45

Thr Phe Thr Ser Tyr Trp Met Gln Trp Val Lys Gln Arg Pro Gly Gln
        50                  55                  60

Gly Leu Glu Trp Ile Gly Ala Ile Tyr Pro Gly Asp Gly Asp Thr Arg
65                  70                  75                  80

Tyr Thr Gln Lys Phe Lys Gly Lys Ala Thr Leu Thr Ala Asp Lys Ser
                85                  90                  95

Ser Ser Thr Ala Tyr Met Gln Leu Ser Ser Leu Ala Ser Glu Asp Ser
            100                 105                 110

Ala Val Tyr Tyr Cys Ala Arg Gly Lys Val Tyr Tyr Gly Ser Asn Pro
        115                 120                 125

Phe Ala Tyr Trp Gly Gln Gly Thr Leu Val Thr Val Ser Ala Gly Gly
    130                 135                 140

Gly Gly Ser Gly Gly Gly Gly Ser Gly Gly Gly Gly Ser Asp Ile Gln
145                 150                 155                 160

Met Thr Gln Ser Ser Ser Tyr Leu Ser Val Ser Leu Gly Gly Arg Val
                165                 170                 175

Thr Ile Thr Cys Lys Ala Ser Asp His Ile Asn Asn Trp Leu Ala Trp
            180                 185                 190

Tyr Gln Gln Lys Pro Gly Asn Ala Pro Arg Leu Leu Ile Ser Gly Ala
        195                 200                 205

Thr Ser Leu Glu Thr Gly Val Pro Ser Arg Phe Ser Gly Ser Gly Ser
    210                 215                 220

Gly Lys Asp Tyr Thr Leu Ser Ile Thr Ser Leu Gln Thr Glu Asp Val
225                 230                 235                 240

Ala Thr Tyr Tyr Cys Gln Gln Tyr Trp Ser Thr Pro Trp Thr Phe Gly
                245                 250                 255

Gly Gly Thr Lys Leu Glu Ile Lys Glu Pro Lys Ser Pro Asp Lys Thr
```

```
                260               265                 270
His Thr Cys Pro Pro Cys Pro Ala Pro Pro Val Ala Gly Pro Ser Val
            275                 280                 285

Phe Leu Phe Pro Pro Lys Pro Lys Asp Thr Leu Met Ile Ala Arg Thr
            290                 295             300

Pro Glu Val Thr Cys Val Val Val Asp Val Ser His Glu Asp Pro Glu
305                     310                 315                 320

Val Lys Phe Asn Trp Tyr Val Asp Gly Val Glu Val His Asn Ala Lys
                    325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
            355                 360                 365

Cys Lys Val Ser Asn Lys Ala Leu Pro Ala Pro Ile Glu Lys Thr Ile
        370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                    405                 410                 415

Val Lys Gly Phe Tyr Pro Ser Asp Ile Ala Val Glu Trp Glu Ser Asn
                420                 425                 430

Gly Gln Pro Glu Asn Asn Tyr Lys Thr Thr Pro Pro Val Leu Asp Ser
            435                 440                 445

Asp Gly Ser Phe Phe Leu Tyr Ser Lys Leu Thr Val Asp Lys Ser Arg
        450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys Lys
                    485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
            515                 520                 525

Glu Glu Glu Glu Gly Gly Cys Glu Leu Arg Val Lys Phe Ser Arg Ser
        530                 535                 540

Ala Asp Ala Pro Ala Tyr Gln Gln Gly Gln Asn Gln Leu Tyr Asn Glu
545                 550                 555                 560

Leu Asn Leu Gly Arg Arg Glu Glu Tyr Asp Val Leu Asp Lys Arg Arg
                    565                 570                 575

Gly Arg Asp Pro Glu Met Gly Gly Lys Pro Arg Arg Lys Asn Pro Gln
                580                 585                 590

Glu Gly Leu Tyr Asn Glu Leu Gln Lys Asp Lys Met Ala Glu Ala Tyr
            595                 600                 605

Ser Glu Ile Gly Met Lys Gly Glu Arg Arg Arg Gly Lys Gly His Asp
        610                 615                 620

Gly Leu Tyr Gln Gly Leu Ser Thr Ala Thr Lys Asp Thr Tyr Asp Ala
625                 630                 635                 640

Leu His Met Gln Ala Leu Pro Pro Arg
                645

<210> SEQ ID NO 57
<211> LENGTH: 433
<212> TYPE: PRT
<213> ORGANISM: artificial sequence
```

<220> FEATURE:
<223> OTHER INFORMATION: LucX1-V1 CAR

<400> SEQUENCE: 57

```
Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Gln
    50                  55                  60

Gly Leu Glu Trp Ile Gly Arg Ile Tyr Pro Gly Asp Gly Asp Thr Lys
65                  70                  75                  80

Tyr Asn Gly Lys Phe Lys Gly Lys Ala Thr Leu Thr Ala Asp Lys Ser
                85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Glu Thr Thr Val
145                 150                 155                 160

Thr Gln Ser Pro Ala Ser Leu Ser Met Ala Ile Gly Glu Lys Val Thr
                165                 170                 175

Ile Arg Cys Ile Thr Ser Thr Asp Ile Asp Asp Asp Met Asn Trp Tyr
            180                 185                 190

Gln Gln Lys Pro Gly Glu Pro Pro Lys Leu Leu Ile Ser Glu Gly Asn
        195                 200                 205

Thr Leu Arg Pro Gly Val Pro Ser Arg Phe Ser Ser Ser Gly Tyr Gly
    210                 215                 220

Thr Asp Phe Val Phe Thr Ile Glu Asn Met Leu Ser Glu Asp Val Ala
225                 230                 235                 240

Asp Tyr Tyr Cys Leu Gln Ser Asp Asn Leu Pro Leu Thr Phe Gly Gly
                245                 250                 255

Gly Thr Lys Leu Glu Ile Lys Gly Leu Ala Val Ser Thr Ile Ser Ser
            260                 265                 270

Phe Phe Pro Pro Gly Tyr Gln Lys Arg Gly Arg Lys Lys Leu Leu Tyr
        275                 280                 285

Ile Phe Lys Gln Pro Phe Met Arg Pro Val Gln Thr Thr Gln Glu Glu
    290                 295                 300

Asp Gly Cys Ser Cys Arg Phe Pro Glu Glu Glu Glu Gly Gly Cys Glu
305                 310                 315                 320

Leu Arg Val Lys Phe Ser Arg Ser Ala Asp Ala Pro Ala Tyr Gln Gln
                325                 330                 335

Gly Gln Asn Gln Leu Tyr Asn Glu Leu Asn Leu Gly Arg Arg Glu Glu
            340                 345                 350

Tyr Asp Val Leu Asp Lys Arg Arg Gly Arg Asp Pro Glu Met Gly Gly
        355                 360                 365

Lys Pro Arg Arg Lys Asn Pro Gln Glu Gly Leu Tyr Asn Glu Leu Gln
    370                 375                 380

Lys Asp Lys Met Ala Glu Ala Tyr Ser Glu Ile Gly Met Lys Gly Glu
385                 390                 395                 400
```

```
Arg Arg Arg Gly Lys Gly His Asp Gly Leu Tyr Gln Gly Leu Ser Thr
                405                 410                 415

Ala Thr Lys Asp Thr Tyr Asp Ala Leu His Met Gln Ala Leu Pro Pro
            420                 425                 430

Arg

<210> SEQ ID NO 58
<211> LENGTH: 487
<212> TYPE: PRT
<213> ORGANISM: artificial sequence
<220> FEATURE:
<223> OTHER INFORMATION: LucX1-V2 CAR

<400> SEQUENCE: 58

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Ala Glu Leu
                20                  25                  30

Ala Arg Pro Gly Ala Ser Val Lys Leu Ser Cys Lys Ala Ser Gly Tyr
            35                  40                  45

Thr Phe Thr Ser Tyr Trp Met Gln Trp Val Lys Gln Arg Pro Gly Gln
    50                  55                  60

Gly Leu Glu Trp Ile Gly Ala Ile Tyr Pro Gly Asp Gly Asp Thr Arg
65                  70                  75                  80

Tyr Thr Gln Lys Phe Lys Gly Lys Ala Thr Leu Thr Ala Asp Lys Ser
                85                  90                  95

Ser Ser Thr Ala Tyr Met Gln Leu Ser Ser Leu Ala Ser Glu Asp Ser
            100                 105                 110

Ala Val Tyr Tyr Cys Ala Arg Gly Lys Val Tyr Tyr Gly Ser Asn Pro
        115                 120                 125

Phe Ala Tyr Trp Gly Gln Gly Thr Leu Val Thr Val Ser Ala Gly Gly
    130                 135                 140

Gly Gly Ser Gly Gly Gly Gly Ser Gly Gly Gly Gly Ser Asp Ile Gln
145                 150                 155                 160

Met Thr Gln Ser Ser Ser Tyr Leu Ser Val Ser Leu Gly Gly Arg Val
                165                 170                 175

Thr Ile Thr Cys Lys Ala Ser Asp His Ile Asn Asn Trp Leu Ala Trp
            180                 185                 190

Tyr Gln Gln Lys Pro Gly Asn Ala Pro Arg Leu Leu Ile Ser Gly Ala
        195                 200                 205

Thr Ser Leu Glu Thr Gly Val Pro Ser Arg Phe Ser Gly Ser Gly Ser
    210                 215                 220

Gly Lys Asp Tyr Thr Leu Ser Ile Thr Ser Leu Gln Thr Glu Asp Val
225                 230                 235                 240

Ala Thr Tyr Tyr Cys Gln Gln Tyr Trp Ser Thr Pro Trp Thr Phe Gly
                245                 250                 255

Gly Gly Thr Lys Leu Glu Ile Lys Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320
```

```
Gly Val Leu Leu Leu Ser Leu Val Ile Thr Leu Tyr Cys Lys Arg Gly
            325                 330                 335

Arg Lys Lys Leu Leu Tyr Ile Phe Lys Gln Pro Phe Met Arg Pro Val
            340                 345                 350

Gln Thr Thr Gln Glu Glu Asp Gly Cys Ser Cys Arg Phe Pro Glu Glu
            355                 360                 365

Glu Glu Gly Gly Cys Glu Leu Arg Val Lys Phe Ser Arg Ser Ala Asp
            370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
            405                 410                 415

Asp Pro Glu Met Gly Gly Lys Pro Arg Arg Lys Asn Pro Gln Glu Gly
            420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
            450                 455                 460

Tyr Gln Gly Leu Ser Thr Ala Thr Lys Asp Thr Tyr Asp Ala Leu His
465                 470                 475                 480

Met Gln Ala Leu Pro Pro Arg
            485

<210> SEQ ID NO 59
<211> LENGTH: 648
<212> TYPE: PRT
<213> ORGANISM: artificial sequence
<220> FEATURE:
<223> OTHER INFORMATION: LucX1-V3 CAR

<400> SEQUENCE: 59

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
            35                  40                  45

Ala Phe Ser Ser Ser Trp Met Asn Trp Val Lys Gln Arg Pro Gly Gln
        50                  55                  60

Gly Leu Glu Trp Ile Gly Arg Ile Tyr Pro Gly Asp Gly Asp Thr Lys
65                  70                  75                  80

Tyr Asn Gly Lys Phe Lys Gly Lys Ala Thr Leu Thr Ala Asp Lys Ser
                85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
            115                 120                 125

Asp Tyr Trp Gly Gln Gly Thr Ser Val Thr Val Ser Ser Gly Gly Gly
            130                 135                 140

Gly Ser Gly Gly Gly Gly Ser Gly Gly Gly Gly Ser Glu Thr Thr Val
145                 150                 155                 160

Thr Gln Ser Pro Ala Ser Leu Ser Met Ala Ile Gly Glu Lys Val Thr
                165                 170                 175

Ile Arg Cys Ile Thr Ser Thr Asp Ile Asp Asp Asp Met Asn Trp Tyr
            180                 185                 190
```

```
Gln Gln Lys Pro Gly Glu Pro Pro Lys Leu Leu Ile Ser Glu Gly Asn
        195                 200                 205

Thr Leu Arg Pro Gly Val Pro Ser Arg Phe Ser Ser Gly Tyr Gly
210                 215                 220

Thr Asp Phe Val Phe Thr Ile Glu Asn Met Leu Ser Glu Asp Val Ala
225                 230                 235                 240

Asp Tyr Tyr Cys Leu Gln Ser Asp Asn Leu Pro Leu Thr Phe Gly Gly
            245                 250                 255

Gly Thr Lys Leu Glu Ile Lys Glu Pro Lys Ser Pro Asp Lys Thr His
        260                 265                 270

Thr Cys Pro Pro Cys Pro Ala Pro Pro Val Ala Gly Pro Ser Val Phe
        275                 280                 285

Leu Phe Pro Pro Lys Pro Lys Asp Thr Leu Met Ile Ala Arg Thr Pro
290                 295                 300

Glu Val Thr Cys Val Val Val Asp Val Ser His Glu Asp Pro Glu Val
305                 310                 315                 320

Lys Phe Asn Trp Tyr Val Asp Gly Val Glu Val His Asn Ala Lys Thr
            325                 330                 335

Lys Pro Arg Glu Glu Gln Tyr Asn Ser Thr Tyr Arg Val Val Ser Val
        340                 345                 350

Leu Thr Val Leu His Gln Asp Trp Leu Asn Gly Lys Glu Tyr Lys Cys
        355                 360                 365

Lys Val Ser Asn Lys Ala Leu Pro Ala Pro Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Arg Asp Glu Leu Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Lys Leu Thr Val Asp Lys Ser Arg Trp
450                 455                 460

Gln Gln Gly Asn Val Phe Ser Cys Ser Val Met His Glu Ala Leu His
465                 470                 475                 480

Asn His Tyr Thr Gln Lys Ser Leu Ser Leu Ser Pro Gly Lys Lys Arg
            485                 490                 495

Gly Arg Lys Lys Leu Leu Tyr Ile Phe Lys Gln Pro Phe Met Arg Pro
        500                 505                 510

Val Gln Thr Thr Gln Glu Glu Asp Gly Cys Ser Cys Arg Phe Pro Glu
        515                 520                 525

Glu Glu Glu Gly Gly Cys Glu Leu Arg Val Lys Phe Ser Arg Ser Ala
        530                 535                 540

Asp Ala Pro Ala Tyr Gln Gln Gly Gln Asn Gln Leu Tyr Asn Glu Leu
545                 550                 555                 560

Asn Leu Gly Arg Arg Glu Glu Tyr Asp Val Leu Asp Lys Arg Arg Gly
                565                 570                 575

Arg Asp Pro Glu Met Gly Gly Lys Pro Arg Arg Lys Asn Pro Gln Glu
            580                 585                 590

Gly Leu Tyr Asn Glu Leu Gln Lys Asp Lys Met Ala Glu Ala Tyr Ser
        595                 600                 605

Glu Ile Gly Met Lys Gly Glu Arg Arg Arg Gly Lys Gly His Asp Gly
```

```
              610                 615                 620
Leu Tyr Gln Gly Leu Ser Thr Ala Thr Lys Asp Thr Tyr Asp Ala Leu
625                 630                 635                 640

His Met Gln Ala Leu Pro Pro Arg
                645

<210> SEQ ID NO 60
<211> LENGTH: 434
<212> TYPE: PRT
<213> ORGANISM: artificial sequence
<220> FEATURE:
<223> OTHER INFORMATION: LucX2-V1 CAR

<400> SEQUENCE: 60

Met Ala Leu Pro Val Thr Ala Leu Leu Leu Pro Leu Ala Leu Leu Leu
1                 5                   10                  15

His Ala Ala Arg Pro Gln Val Gln Leu Gln Gln Ser Gly Pro Glu Leu
                20                  25                  30

Val Lys Pro Gly Ala Ser Val Lys Ile Ser Cys Lys Ala Ser Gly Tyr
            35                  40                  45

Ala Phe Ser Ser Ser Trp Met Asn Trp Val Lys Gln Arg Pro Gly Gln
        50                  55                  60

Gly Leu Glu Trp Ile Gly Arg Ile Tyr Pro Gly Asp Gly Asp Thr Lys
65                  70                  75                  80

Tyr Asn Gly Lys Phe Lys Gly Lys Ala Thr Leu Thr Ala Asp Lys Ser
                85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
        115                 120                 125

Asp Tyr Trp Gly Gln Gly Thr Ser Val Thr Val Ser Ser Gly Gly Gly
130                 135                 140

Gly Ser Gly Gly Gly Gly Ser Gly Gly Gly Gly Ser Asp Ile Val Met
145                 150                 155                 160

Thr Gln Ser His Lys Phe Met Ser Thr Ser Val Gly Asp Arg Val Ser
                165                 170                 175

Ile Thr Cys Lys Ala Ser Gln Asp Val Ser Thr Ala Val Ala Trp Tyr
            180                 185                 190

Gln Gln Lys Pro Gly Gln Ser Pro Lys Leu Leu Ile Tyr Ser Ala Ser
        195                 200                 205

Tyr Arg Tyr Thr Gly Val Pro Asp Arg Phe Thr Gly Ser Gly Ser Gly
210                 215                 220

Thr Asp Phe Thr Phe Thr Ile Ser Ser Val Gln Ala Glu Asp Leu Ala
225                 230                 235                 240

Val Tyr Tyr Cys Gln Gln His Tyr Ser Thr Pro Tyr Thr Phe Gly
                245                 250                 255

Gly Gly Thr Lys Leu Glu Ile Lys Gly Leu Ala Val Ser Thr Ile Ser
            260                 265                 270

Ser Phe Phe Pro Pro Gly Tyr Gln Lys Arg Gly Arg Lys Lys Leu Leu
        275                 280                 285

Tyr Ile Phe Lys Gln Pro Phe Met Arg Pro Val Gln Thr Thr Gln Glu
290                 295                 300

Glu Asp Gly Cys Ser Cys Arg Phe Pro Glu Glu Glu Glu Gly Gly Cys
305                 310                 315                 320

Glu Leu Arg Val Lys Phe Ser Arg Ser Ala Asp Ala Pro Ala Tyr Gln
```

```
                    325                 330                 335
Gln Gly Gln Asn Gln Leu Tyr Asn Glu Leu Asn Leu Gly Arg Arg Glu
            340                 345                 350

Glu Tyr Asp Val Leu Asp Lys Arg Arg Gly Arg Asp Pro Glu Met Gly
        355                 360                 365

Gly Lys Pro Arg Arg Lys Asn Pro Gln Glu Gly Leu Tyr Asn Glu Leu
    370                 375                 380

Gln Lys Asp Lys Met Ala Glu Ala Tyr Ser Glu Ile Gly Met Lys Gly
385                 390                 395                 400

Glu Arg Arg Arg Gly Lys Gly His Asp Gly Leu Tyr Gln Gly Leu Ser
                405                 410                 415

Thr Ala Thr Lys Asp Thr Tyr Asp Ala Leu His Met Gln Ala Leu Pro
            420                 425                 430

Pro Arg

<210> SEQ ID NO 61
<211> LENGTH: 487
<212> TYPE: PRT
<213> ORGANISM: artificial sequence
<220> FEATURE:
<223> OTHER INFORMATION: LucX2-V2 CAR

<400> SEQUENCE: 61

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Gln
    50                  55                  60

Gly Leu Glu Trp Ile Gly Arg Ile Tyr Pro Gly Asp Gly Asp Thr Lys
65                  70                  75                  80

Tyr Asn Gly Lys Phe Lys Gly Lys Ala Thr Leu Thr Ala Asp Lys Ser
                85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
        115                 120                 125

Asp Tyr Trp Gly Gln Gly Thr Ser Val Thr Val Ser Ser Gly Gly Gly
    130                 135                 140

Gly Ser Gly Gly Gly Gly Ser Gly Gly Gly Gly Ser Asp Ile Val Met
145                 150                 155                 160

Thr Gln Ser His Lys Phe Met Ser Thr Ser Val Gly Asp Arg Val Ser
                165                 170                 175

Ile Thr Cys Lys Ala Ser Gln Asp Val Ser Thr Ala Val Ala Trp Tyr
            180                 185                 190

Gln Gln Lys Pro Gly Gln Ser Pro Lys Leu Leu Ile Tyr Ser Ala Ser
        195                 200                 205

Tyr Arg Tyr Thr Gly Val Pro Asp Arg Phe Thr Gly Ser Gly Ser Gly
    210                 215                 220

Thr Asp Phe Thr Phe Thr Ile Ser Ser Val Gln Ala Glu Asp Leu Ala
225                 230                 235                 240

Val Tyr Tyr Cys Gln Gln His Tyr Ser Thr Pro Pro Tyr Thr Phe Gly
                245                 250                 255
```

```
Gly Gly Thr Lys Leu Glu Ile Lys Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Lys Arg Gly
                325                 330                 335

Arg Lys Lys Leu Leu Tyr Ile Phe Lys Gln Pro Phe Met Arg Pro Val
                340                 345                 350

Gln Thr Thr Gln Glu Glu Asp Gly Cys Ser Cys Arg Phe Pro Glu Glu
            355                 360                 365

Glu Glu Gly Gly Cys Glu Leu Arg Val Lys Phe Ser Arg Ser Ala Asp
    370                 375                 380

Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
                405                 410                 415

Asp Pro Glu Met Gly Gly Lys Pro Arg Arg Lys Asn Pro Gln Glu Gly
                420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Gly Lys Gly His Asp Gly Leu
                450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485

<210> SEQ ID NO 62
<211> LENGTH: 649
<212> TYPE: PRT
<213> ORGANISM: artificial sequence
<220> FEATURE:
<223> OTHER INFORMATION: LucX2-V3 CAR

<400> SEQUENCE: 62

Met Ala Leu Pro Val Thr Ala Leu Leu Leu Pro Leu Ala Leu Leu Leu
1               5                   10                  15

His Ala Ala Arg Pro Gln Val Gln Leu Gln Gln Ser Gly Pro Glu Leu
            20                  25                  30

Val Lys Pro Gly Ala Ser Val Lys Ile Ser Cys Lys Ala Ser Gly Tyr
        35                  40                  45

Ala Phe Ser Ser Ser Trp Met Asn Trp Val Lys Gln Arg Pro Gly Gln
    50                  55                  60

Gly Leu Glu Trp Ile Gly Arg Ile Tyr Pro Gly Asp Gly Asp Thr Lys
65                  70                  75                  80

Tyr Asn Gly Lys Phe Lys Gly Lys Ala Thr Leu Thr Ala Asp Lys Ser
                85                  90                  95

Ser Ser Thr Ala Tyr Met Gln Leu Ser Ser Leu Thr Ser Val Asp Ser
            100                 105                 110

Ala Val Tyr Phe Cys Ala Arg Ser Thr Met Ile Ala Thr Gly Ala Met
        115                 120                 125
```

```
Asp Tyr Trp Gly Gln Gly Thr Ser Val Thr Val Ser Gly Gly Gly
        130                 135                 140

Gly Ser Gly Gly Gly Ser Gly Gly Gly Ser Asp Ile Val Met
145                 150                 155                 160

Thr Gln Ser His Lys Phe Met Ser Thr Ser Val Gly Asp Arg Val Ser
                165                 170                 175

Ile Thr Cys Lys Ala Ser Gln Asp Val Ser Thr Ala Val Ala Trp Tyr
            180                 185                 190

Gln Gln Lys Pro Gly Gln Ser Pro Lys Leu Leu Ile Tyr Ser Ala Ser
        195                 200                 205

Tyr Arg Tyr Thr Gly Val Pro Asp Arg Phe Thr Gly Ser Gly Ser Gly
    210                 215                 220

Thr Asp Phe Thr Phe Thr Ile Ser Ser Val Gln Ala Glu Asp Leu Ala
225                 230                 235                 240

Val Tyr Tyr Cys Gln Gln His Tyr Ser Thr Pro Pro Tyr Thr Phe Gly
                245                 250                 255

Gly Gly Thr Lys Leu Glu Ile Lys Glu Pro Lys Ser Pro Asp Lys Thr
            260                 265                 270

His Thr Cys Pro Pro Cys Pro Ala Pro Pro Val Ala Gly Pro Ser Val
        275                 280                 285

Phe Leu Phe Pro Pro Lys Pro Lys Asp Thr Leu Met Ile Ala Arg Thr
    290                 295                 300

Pro Glu Val Thr Cys Val Val Val Asp Val Ser His Glu Asp Pro Glu
305                 310                 315                 320

Val Lys Phe Asn Trp Tyr Val Asp Gly Val Glu Val His Asn Ala Lys
                325                 330                 335

Thr Lys Pro Arg Glu Glu Gln Tyr Asn Ser Thr Tyr Arg Val Val Ser
            340                 345                 350

Val Leu Thr Val Leu His Gln Asp Trp Leu Asn Gly Lys Glu Tyr Lys
        355                 360                 365

Cys Lys Val Ser Asn Lys Ala Leu Pro Ala Pro Ile Glu Lys Thr Ile
    370                 375                 380

Ser Lys Ala Lys Gly Gln Pro Arg Glu Pro Gln Val Tyr Thr Leu Pro
385                 390                 395                 400

Pro Ser Arg Asp Glu Leu Thr Lys Asn Gln Val Ser Leu Thr Cys Leu
                405                 410                 415

Val Lys Gly Phe Tyr Pro Ser Asp Ile Ala Val Glu Trp Glu Ser Asn
            420                 425                 430

Gly Gln Pro Glu Asn Asn Tyr Lys Thr Thr Pro Pro Val Leu Asp Ser
        435                 440                 445

Asp Gly Ser Phe Phe Leu Tyr Ser Lys Leu Thr Val Asp Lys Ser Arg
    450                 455                 460

Trp Gln Gln Gly Asn Val Phe Ser Cys Ser Val Met His Glu Ala Leu
465                 470                 475                 480

His Asn His Tyr Thr Gln Lys Ser Leu Ser Leu Ser Pro Gly Lys Lys
                485                 490                 495

Arg Gly Arg Lys Lys Leu Leu Tyr Ile Phe Lys Gln Pro Phe Met Arg
            500                 505                 510

Pro Val Gln Thr Thr Gln Glu Glu Asp Gly Cys Ser Cys Arg Phe Pro
        515                 520                 525

Glu Glu Glu Glu Gly Gly Cys Glu Leu Arg Val Lys Phe Ser Arg Ser
    530                 535                 540
```

Ala Asp Ala Pro Ala Tyr Gln Gln Gly Gln Asn Gln Leu Tyr Asn Glu
545                 550                 555                 560

Leu Asn Leu Gly Arg Arg Glu Glu Tyr Asp Val Leu Asp Lys Arg Arg
                565                 570                 575

Gly Arg Asp Pro Glu Met Gly Gly Lys Pro Arg Arg Lys Asn Pro Gln
            580                 585                 590

Glu Gly Leu Tyr Asn Glu Leu Gln Lys Asp Lys Met Ala Glu Ala Tyr
        595                 600                 605

Ser Glu Ile Gly Met Lys Gly Glu Arg Arg Arg Gly Lys Gly His Asp
    610                 615                 620

Gly Leu Tyr Gln Gly Leu Ser Thr Ala Thr Lys Asp Thr Tyr Asp Ala
625                 630                 635                 640

Leu His Met Gln Ala Leu Pro Pro Arg
                645

<210> SEQ ID NO 63
<211> LENGTH: 49
<212> TYPE: DNA
<213> ORGANISM: artificial sequence
<220> FEATURE:
<223> OTHER INFORMATION: CS1 T01 target

<400> SEQUENCE: 63
tgacttccag agagcaatat ggctggttcc ccaacatgcc tcaccctca        49

<210> SEQ ID NO 64
<211> LENGTH: 17
<212> TYPE: DNA
<213> ORGANISM: artificial sequence
<220> FEATURE:
<223> OTHER INFORMATION: CS1 T01 left TALE

<400> SEQUENCE: 64
tgacttccag agagcaa                                            17

<210> SEQ ID NO 65
<211> LENGTH: 17
<212> TYPE: DNA
<213> ORGANISM: artificial sequence
<220> FEATURE:
<223> OTHER INFORMATION: CS1 T01 right TALE

<400> SEQUENCE: 65
aacatgcctc accctca                                            17

<210> SEQ ID NO 66
<211> LENGTH: 49
<212> TYPE: DNA
<213> ORGANISM: homosapiens
<220> FEATURE:
<223> OTHER INFORMATION: CS1 T02 target

<400> SEQUENCE: 66
ttccagagag caatatggct ggttccccaa catgcctcac cctcatcta         49

<210> SEQ ID NO 67
<211> LENGTH: 17
<212> TYPE: DNA
<213> ORGANISM: artificial sequence
<220> FEATURE:
<223> OTHER INFORMATION: CS1 T02 left TALE

<400> SEQUENCE: 67
ttccagagag caatatg                                                    17

<210> SEQ ID NO 68
<211> LENGTH: 17
<212> TYPE: DNA
<213> ORGANISM: artificial sequence
<220> FEATURE:
<223> OTHER INFORMATION: CS1 T02 right TALE

<400> SEQUENCE: 68
tgcctcaccc tcatcta                                                    17

<210> SEQ ID NO 69
<211> LENGTH: 49
<212> TYPE: DNA
<213> ORGANISM: homo sapiens
<220> FEATURE:
<223> OTHER INFORMATION: CS1 T03 target

<400> SEQUENCE: 69
ttgactctat tgtctggacc ttcaacacaa cccctcttgt caccataca                 49

<210> SEQ ID NO 70
<211> LENGTH: 17
<212> TYPE: DNA
<213> ORGANISM: artificial sequence
<220> FEATURE:
<223> OTHER INFORMATION: CS1 T03 left TALE

<400> SEQUENCE: 70
ttgactctat tgtctgg                                                    17

<210> SEQ ID NO 71
<211> LENGTH: 17
<212> TYPE: DNA
<213> ORGANISM: artificial sequence
<220> FEATURE:
<223> OTHER INFORMATION: CS1 T03 right TALE

<400> SEQUENCE: 71
cctcttgtca ccataca                                                    17

<210> SEQ ID NO 72
<211> LENGTH: 49
<212> TYPE: DNA
<213> ORGANISM: homo sapiens
<220> FEATURE:
<223> OTHER INFORMATION: CD70 target 1

<400> SEQUENCE: 72
tggtcttttc ttccagtggg acgtagctga gctgcagctg aatcacaca                 49

<210> SEQ ID NO 73
<211> LENGTH: 17
<212> TYPE: DNA
<213> ORGANISM: artificial sequence
<220> FEATURE:
<223> OTHER INFORMATION: CD70 Target 1-left TALE

<400> SEQUENCE: 73
tggtcttttc ttccagt                                                    17

<210> SEQ ID NO 74
<211> LENGTH: 17
<212> TYPE: DNA
<213> ORGANISM: artificial sequence

```
<220> FEATURE:
<223> OTHER INFORMATION: CD70 Target 1-right TALE

<400> SEQUENCE: 74
tgcagctgaa tcacaca                                                    17

<210> SEQ ID NO 75
<211> LENGTH: 49
<212> TYPE: DNA
<213> ORGANISM: homo sapiens
<220> FEATURE:
<223> OTHER INFORMATION: CD70 target 2

<400> SEQUENCE: 75
tggtgatctg cctcgtggtg tgcatccagc gcttcgcaca ggctcagca                 49

<210> SEQ ID NO 76
<211> LENGTH: 17
<212> TYPE: DNA
<213> ORGANISM: artificial sequence
<220> FEATURE:
<223> OTHER INFORMATION: CD70 Target 2-left TALE

<400> SEQUENCE: 76
tggtgatctg cctcgtg                                                    17

<210> SEQ ID NO 77
<211> LENGTH: 17
<212> TYPE: DNA
<213> ORGANISM: artificial sequence
<220> FEATURE:
<223> OTHER INFORMATION: CD70 Target 2-right TALE

<400> SEQUENCE: 77
ttcgcacagg ctcagca                                                    17

<210> SEQ ID NO 78
<211> LENGTH: 57
<212> TYPE: DNA
<213> ORGANISM: homo sapiens
<220> FEATURE:
<223> OTHER INFORMATION: CD70 target 3

<400> SEQUENCE: 78
tgcgggctgc tttggtccca ttggtcgcgg gcttggtgat ctgcctcgtg gtgtgca        57

<210> SEQ ID NO 79
<211> LENGTH: 17
<212> TYPE: DNA
<213> ORGANISM: artificial sequence
<220> FEATURE:
<223> OTHER INFORMATION: CD70 Target 3-left TALE

<400> SEQUENCE: 79
tgcgggctgc tttggtc                                                    17

<210> SEQ ID NO 80
<211> LENGTH: 17
<212> TYPE: DNA
<213> ORGANISM: artificial sequence
<220> FEATURE:
<223> OTHER INFORMATION: CD70 Target 3-right TALE

<400> SEQUENCE: 80
ctgcctcgtg gtgtgca                                                    17
```

<210> SEQ ID NO 81
<211> LENGTH: 122
<212> TYPE: PRT
<213> ORGANISM: artificial sequence
<220> FEATURE:
<223> OTHER INFORMATION: anti-CD70 Ab4-VH chain

<400> SEQUENCE: 81

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Ala Val Ile Trp Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Gly Tyr Ser Gly Tyr Asp Ser Gly Phe Asp Tyr Trp
            100                 105                 110

Gly Gln Gly Thr Leu Val Thr Val Ser Ser
        115                 120
```

<210> SEQ ID NO 82
<211> LENGTH: 1358
<212> TYPE: DNA
<213> ORGANISM: artificial sequence
<220> FEATURE:
<223> OTHER INFORMATION: anti-CD70 Ab4-VH chain

<400> SEQUENCE: 82

```
aggtgcagct ggtggagtct ggggggaggcg tggtccagcc tgggaggtcc ctgagactct    60
cctgtgcagc gtctggattc accttcagta actatggcat acactgggtc cgccaggctc   120
caggcaaggg gctggagtgg gtggcagtta tatggtatga tggaagtaat aaatactatg   180
cagactccgt gaagggccga ttcaccatct ccagagacaa ttccaagaac acgctgtatc   240
tgcaaatgaa cagcctgaga gccgaggaca cggctgtgta ttactgtgcg agagatggag   300
gatatagtgg ctacgattcg gggtttgact actggggcca gggaaccctg gtcaccgtct   360
cctcagctag caccaagggc ccatccgtct tccccctggc accctcctcc aagagcacct   420
ctgggggcac agcggccctg gctgcctggt caaggactac ttccccgaa ccggtgacgg   480
tgtcgtggaa ctcaggcgcc ctgaccagcg gcgtgcacac cttcccggct gtcctacagt   540
cctcaggact ctactccctc agcagcgtgg tgaccgtgcc ctccagcagc ttgggcaccc   600
agacctacat ctgcaacgtg aatcacaagc ccagcaacac caaggtggac aagaaagttg   660
agcccaaatc ttgtgacaaa actcacacat gcccaccgtg cccagcacct gaactcctgg   720
ggggaccgtc agtcttcctc ttccccccaa aacccaagga caccctcatg atctcccgga   780
cccctgaggt cacatgcgtg gtggtggacg tgagccacga agaccctgag gtcaagttca   840
actggtacgt ggacggcgtg gaggtgcata atgccaagac aaagccgcgg gaggagcagt   900
acaacagcac gtaccgtgtg gtcagcgtcc tcaccgtcct gcaccaggac tggctgaatg   960
gcaaggagta caagtgcaag gtctccaaca aagcccctcccagccccatc gagaaaacca  1020
tctccaaagc caaagggcag ccccgagaac cacaggtgta caccctgccc ccatcccggg  1080
```

```
aggagatgac caagaaccag gtcagcctga cctgcctggt caaaggcttc tatcccagcg    1140
acatcgccgt ggagtgggag agcaatgggc agccggagaa caactacaag accacgcctc    1200
ccgtgctgga ctccgacggc tccttcttcc tctatagcaa gctcaccgtg gacaagagca    1260
ggtggcagca ggggaacgtc ttctcatgct ccgtgatgca tgaggctctg cacaaccact    1320
acacgcagaa gagcctctcc ctgtctccgg gtaaatga                            1358
```

```
<210> SEQ ID NO 83
<211> LENGTH: 112
<212> TYPE: PRT
<213> ORGANISM: artificial sequence
<220> FEATURE:
<223> OTHER INFORMATION: anti-CD70 Ab4-VL chain

<400> SEQUENCE: 83

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu Asn Ser
            20                  25                  30

Asn Gly Tyr Asn Tyr Leu Asp Trp Tyr Leu Gln Lys Pro Gly Gln Ser
        35                  40                  45

Pro Gln Phe Leu Ile Tyr Leu Gly Ser Tyr Arg Ala Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Val Gly Val Tyr Tyr Cys Ile Gln Thr
                85                  90                  95

Leu Gln Thr Pro Phe Thr Phe Gly Pro Gly Thr Lys Val Asp Ile Lys
            100                 105                 110
```

```
<210> SEQ ID NO 84
<211> LENGTH: 1476
<212> TYPE: DNA
<213> ORGANISM: artificial sequence
<220> FEATURE:
<223> OTHER INFORMATION: anti-CD70 Ab4-VL chain

<400> SEQUENCE: 84
gatattgtga tgactcagtc tccactctcc ctgcccgtca cccctggaga gccggcctcc      60
atctcctgca ggtctagtca gagcctcctg aatagtaatg gatacaacta tttggattgg    120
tacctgcaga agccagggca gtctccacag ttcctgatct atttgggttc ttatcgggcc    180
tccggggtcc ctgacaggtt cagtggcagt ggatcaggca cagattttac actgagaatc    240
agcagagtgg aggctgagga tgttggggtt tattactgta tacaaactct acaaactcca    300
ttcactttcg gccctgggac caaagtggat atcaaacgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgttag    660
tcctcaggac tctactccct cagcagcgtg gtgaccgtgc cctccagcag cttgggcacc    720
cagacctaca tctgcaacgt gaatcacaag cccagcaaca ccaaggtgga caagaaagtt    780
gagcccaaat cttgtgacaa aactcacaca tgcccaccgt gcccagcacc tgaactcctg    840
```

```
ggggaccgt cagtcttcct cttccccca aacccaagg acaccctcat gatctcccgg    900
acccctgagg tcacatgcgt ggtggtggac gtgagccacg aagaccctga ggtcaagttc    960
aactggtacg tggacggcgt ggaggtgcat aatgccaaga caaagccgcg ggaggagcag   1020
tacaacagca cgtaccgtgt ggtcagcgtc ctcaccgtcc tgcaccagga ctggctgaat   1080
ggcaaggagt acaagtgcaa ggtctccaac aaagccctcc cagcccccat cgagaaaacc   1140
atctccaaag ccaaagggca gccccgagaa ccacaggtgt acaccctgcc cccatcccgg   1200
gaggagatga ccaagaacca ggtcagcctg acctgcctgg tcaaaggctt ctatcccagc   1260
gacatcgccg tggagtggga gagcaatggg cagccggaga acaactacaa gaccacgcct   1320
cccgtgctgg actccgacgg ctccttcttc ctctatagca agctcaccgt ggacaagagc   1380
aggtggcagc aggggaacgt cttctcatgc tccgtgatgc atgaggctct gcacaaccac   1440
tacacgcaga agagcctctc cctgtctccg ggtaaa                             1476
```

<210> SEQ ID NO 85
<211> LENGTH: 122
<212> TYPE: PRT
<213> ORGANISM: artificial sequence
<220> FEATURE:
<223> OTHER INFORMATION: anti-CD70 Ab8-VH chain

<400> SEQUENCE: 85

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asp Lys Tyr Phe Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Gly Ile Ala Gly Ala Arg Tyr Val Tyr Phe Asp Tyr Trp
            100                 105                 110

Gly Gln Gly Thr Leu Val Thr Val Ser Ser
        115                 120

<210> SEQ ID NO 86
<211> LENGTH: 560
<212> TYPE: DNA
<213> ORGANISM: artificial sequence
<220> FEATURE:
<223> OTHER INFORMATION: anti-CD70 Ab8-VH chain

<400> SEQUENCE: 86

```
caggtgcagc tggtggagtc tgggggaggc gtggtccagc ctggaggtc cctgagactc     60 tcctgtgcag cgtctggatt caccttcagt agctatggca tgcactgggt ccgccaggct    120
ccaggcaagg ggctggagtg ggtggcagtt atatggtatg atggaagtga taaatacttt    180
gcagactccg tgaagggccg attcaccatc tccagagaca attccaagaa cacgctgtat    240
ctgcaaatga acagcctgag agccgaggac acggctgtgt attactgtgc gagagatggg    300
atagcaggag ctcgctacgt ctactttgac tactggggcc agggaaccct ggtcaccgtc    360
```

```
tcctcagcta gcaccaaggg cccatccgtc ttccccctgg caccctcctc caagagcacc      420
tctgggggca gcgcggccct gggctgcctg gtcaaggact acttccccga accggtgacg      480
gtgtcgtgga actcaggcgc cctgaccagc ggcgtgcaca ccttcccggc tgtcctacag      540
tcctcaggac tctactccct                                                  560
```

<210> SEQ ID NO 87
<211> LENGTH: 107
<212> TYPE: PRT
<213> ORGANISM: artificial sequence
<220> FEATURE:
<223> OTHER INFORMATION: anti-CD70 Ab8-VL chain

<400> SEQUENCE: 87

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Tyr
            20                  25                  30

Leu Ala Trp Phe Gln Gln Lys Pro Gly Lys Ala Pro Lys Ser Leu Ile
        35                  40                  45

Tyr Ala Ala Ser Ser Leu Gln Gly Gly Val Pro Ser Lys Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asn Tyr Pro Phe
                85                  90                  95

Thr Phe Gly Pro Gly Thr Thr Val Asp Ile Lys
            100                 105
```

<210> SEQ ID NO 88
<211> LENGTH: 645
<212> TYPE: DNA
<213> ORGANISM: artificial sequence
<220> FEATURE:
<223> OTHER INFORMATION: anti-CD70 Ab8-VL chain

<400> SEQUENCE: 88

```
gacatccaga tgacccagtc tccatcctcc ctgtctgcat ctgtaggaga cagagtcacc       60
atcacttgtc gggcgagtca gggcattagc aattatttag cctggtttca gcagaaacca      120
gggaaagccc ctaagtccct gatctatgct gcatccagtt tgcaaggtgg gtcccatca       180 aagttcagcg gcagtggatc tgggacagat ttcactctca ccatcagcag cctgcagcct      240
gaagattttg caacttatta ctgccaacaa tattataatt acccattcac tttcggccct      300
gggaccacag tggatatcaa acgtacggtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gttag                      645
```

<210> SEQ ID NO 89
<211> LENGTH: 117
<212> TYPE: PRT
<213> ORGANISM: artificial sequence
<220> FEATURE:
<223> OTHER INFORMATION: anti-CD70 1F6-VH chain

<400> SEQUENCE: 89

```
Gln Ile Gln Leu Val Gln Ser Gly Pro Glu Val Lys Lys Pro Gly Glu
1               5                   10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Ile Asn Thr Tyr Thr Gly Glu Pro Thr Tyr Ala Asp Ala Phe Lys
    50                  55                  60

Gly Arg Phe Ala Phe Ser Leu Glu Thr Ser Ala Ser Thr Ala Tyr Leu
65                  70                  75                  80

Gln Ile Asn Asn Leu Lys Asn Glu Asp Thr Ala Thr Tyr Phe Cys Ala
                85                  90                  95

Arg Asp Tyr Gly Asp Tyr Gly Met Asp Tyr Trp Gly Gln Gly Thr Ser
            100                 105                 110

Val Thr Val Ser Ser
        115
```

<210> SEQ ID NO 90
<211> LENGTH: 411
<212> TYPE: DNA
<213> ORGANISM: artificial sequence
<220> FEATURE:
<223> OTHER INFORMATION: anti-CD70 1F6-VH chain

<400> SEQUENCE: 90

```
atggcttggg tgtggacctt gctattcctg atggcagctg cccaaagtgc ccaagcacag      60
atccagttgg tgcagtctgg acctgaggtg aagaagcctg gagagacagt caagatctcc     120
tgcaaggctt ctgggtatac cttcacaaac tatggaatga actgggtgaa gcaggctcca     180
ggaaagggtt taaagtggat gggctggata acacctaca ctggagagcc aacatatgct      240
gatgccttca aggacggtt tgccttctct ttggaaacct ctgccagcac tgcctatttg      300
cagatcaaca acctcaaaaa tgaggacacg gctacatatt tctgtgcaag agactacggc     360
gactatggta tggactactg gggtcaagga acctcagtca ccgtctcctc a              411
```

<210> SEQ ID NO 91
<211> LENGTH: 112
<212> TYPE: PRT
<213> ORGANISM: artificial sequence
<220> FEATURE:
<223> OTHER INFORMATION: anti-CD70 1F6-VL chain

<400> SEQUENCE: 91

```
Asp Ile Val Leu Thr Gln Ser Pro Ala Ser Leu Ala Val Ser Leu Gly
1               5                   10                  15

Gln Arg Ala Thr Ile Ser Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Glu Val Pro Trp Thr Phe Gly Gly Gly Thr Lys Leu Glu Ile Lys Arg
```

<210> SEQ ID NO 92
<211> LENGTH: 396
<212> TYPE: DNA
<213> ORGANISM: artificial sequence
<220> FEATURE:
<223> OTHER INFORMATION: anti-CD70 1F6-VL chain

<400> SEQUENCE: 92

```
atggagacag acacactcct gttatgggta ctgctgctct gggttccagg ttccactggt    60
gacattgtgc tgacacagtc tcctgcttcc ttagctgtat ctctggggca gagggccacc   120
atctcatgca gggccagcaa aagtgtcagt acatctggct atagttttat gcactggtat   180
caacagaaac caggacagcc acccaaactc ctcatctatc ttgcatccaa cctagaatct   240
ggggtccctg ccaggttcag tggcagtggg tctgggacag acttcaccct caacatccat   300
cctgtggagg aggaggatgc tgcaacctat tactgtcagc acagtaggga ggttccgtgg   360
acgttcggtg gaggcaccaa gctggaaatc aaacgg                             396
```

<210> SEQ ID NO 93
<211> LENGTH: 464
<212> TYPE: PRT
<213> ORGANISM: artificial sequence
<220> FEATURE:
<223> OTHER INFORMATION: anti-CD70 Ab4-V1 CAR

<400> SEQUENCE: 93

Met Ala Leu Pro Val Thr Ala Leu Leu Leu Pro Leu Ala Leu Leu Leu
1               5                   10                  15
His Ala Ala Arg Pro Gln Val Gln Leu Val Glu Ser Gly Gly Gly Val
                20                  25                  30
Val Gln Pro Gly Arg Ser Leu Arg Leu Ser Cys Ala Ala Ser Gly Phe
            35                  40                  45
Thr Phe Ser Asn Tyr Gly Ile His Trp Val Arg Gln Ala Pro Gly Lys
        50                  55                  60
Gly Leu Glu Trp Val Ala Val Ile Trp Tyr Asp Gly Ser Asn Lys Tyr
65                  70                  75                  80
Tyr Ala Asp Ser Val Lys Gly Arg Phe Thr Ile Ser Arg Asp Asn Ser
                85                  90                  95
Lys Asn Thr Leu Tyr Leu Gln Met Asn Ser Leu Arg Ala Glu Asp Thr
            100                 105                 110
Ala Val Tyr Tyr Cys Ala Arg Asp Gly Gly Tyr Ser Gly Tyr Asp Ser
        115                 120                 125
Gly Phe Asp Tyr Trp Gly Gln Gly Thr Leu Val Thr Val Ser Ser Gly
    130                 135                 140
Gly Gly Gly Ser Gly Gly Gly Gly Ser Gly Gly Gly Gly Ser Asp Ile
145                 150                 155                 160
Val Met Thr Gln Ser Pro Leu Ser Leu Pro Val Thr Pro Gly Glu Pro
                165                 170                 175
Ala Ser Ile Ser Cys Arg Ser Ser Gln Ser Leu Leu Asn Ser Asn Gly
            180                 185                 190
Tyr Asn Tyr Leu Asp Trp Tyr Leu Gln Lys Pro Gly Gln Ser Pro Gln
        195                 200                 205
Phe Leu Ile Tyr Leu Gly Ser Tyr Arg Ala Ser Gly Val Pro Asp Arg
    210                 215                 220
Phe Ser Gly Ser Gly Ser Gly Thr Asp Phe Thr Leu Arg Ile Ser Arg

```
            225                 230                 235                 240
Val Glu Ala Glu Asp Val Gly Val Tyr Tyr Cys Ile Gln Thr Leu Gln
                    245                 250                 255
Thr Pro Phe Thr Phe Gly Pro Gly Thr Lys Val Asp Ile Lys Gly Leu
                260                 265                 270
Ala Val Ser Thr Ile Ser Ser Phe Phe Pro Gly Tyr Gln Ile Tyr
            275                 280                 285
Ile Trp Ala Pro Leu Ala Gly Thr Cys Gly Val Leu Leu Leu Ser Leu
        290                 295                 300
Val Ile Thr Leu Tyr Cys Lys Arg Gly Arg Lys Lys Leu Leu Tyr Ile
305                 310                 315                 320
Phe Lys Gln Pro Phe Met Arg Pro Val Gln Thr Thr Gln Glu Glu Asp
                    325                 330                 335
Gly Cys Ser Cys Arg Phe Pro Glu Glu Glu Glu Gly Gly Cys Glu Leu
                340                 345                 350
Arg Val Lys Phe Ser Arg Ser Ala Asp Ala Pro Ala Tyr Gln Gln Gly
            355                 360                 365
Gln Asn Gln Leu Tyr Asn Glu Leu Asn Leu Gly Arg Arg Glu Glu Tyr
        370                 375                 380
Asp Val Leu Asp Lys Arg Arg Gly Arg Asp Pro Glu Met Gly Gly Lys
385                 390                 395                 400
Pro Arg Arg Lys Asn Pro Gln Glu Gly Leu Tyr Asn Glu Leu Gln Lys
                    405                 410                 415
Asp Lys Met Ala Glu Ala Tyr Ser Glu Ile Gly Met Lys Gly Glu Arg
                420                 425                 430
Arg Arg Gly Lys Gly His Asp Gly Leu Tyr Gln Gly Leu Ser Thr Ala
            435                 440                 445
Thr Lys Asp Thr Tyr Asp Ala Leu His Met Gln Ala Leu Pro Pro Arg
        450                 455                 460

<210> SEQ ID NO 94
<211> LENGTH: 493
<212> TYPE: PRT
<213> ORGANISM: artificial sequence
<220> FEATURE:
<223> OTHER INFORMATION: anti-CD70 Ab4-V2 CAR

<400> SEQUENCE: 94

Met Ala Leu Pro Val Thr Ala Leu Leu Leu Pro Leu Ala Leu Leu Leu
1               5                   10                  15
His Ala Ala Arg Pro Gln Val Gln Leu Val Glu Ser Gly Gly Gly Val
                20                  25                  30
Val Gln Pro Gly Arg Ser Leu Arg Leu Ser Cys Ala Ala Ser Gly Phe
            35                  40                  45
Thr Phe Ser Asn Tyr Gly Ile His Trp Val Arg Gln Ala Pro Gly Lys
        50                  55                  60
Gly Leu Glu Trp Val Ala Val Ile Trp Tyr Asp Gly Ser Asn Lys Tyr
65                  70                  75                  80
Tyr Ala Asp Ser Val Lys Gly Arg Phe Thr Ile Ser Arg Asp Asn Ser
                85                  90                  95
Lys Asn Thr Leu Tyr Leu Gln Met Asn Ser Leu Arg Ala Glu Asp Thr
                100                 105                 110
Ala Val Tyr Tyr Cys Ala Arg Asp Gly Gly Tyr Ser Gly Tyr Asp Ser
            115                 120                 125
Gly Phe Asp Tyr Trp Gly Gln Gly Thr Leu Val Thr Val Ser Ser Gly
```

```
            130                 135                 140
Gly Gly Ser Gly Gly Gly Ser Gly Gly Gly Ser Asp Ile
145                 150                 155             160

Val Met Thr Gln Ser Pro Leu Ser Leu Pro Val Thr Pro Gly Glu Pro
                165                 170                 175

Ala Ser Ile Ser Cys Arg Ser Ser Gln Ser Leu Leu Asn Ser Asn Gly
            180                 185                 190

Tyr Asn Tyr Leu Asp Trp Tyr Leu Gln Lys Pro Gly Gln Ser Pro Gln
        195                 200                 205

Phe Leu Ile Tyr Leu Gly Ser Tyr Arg Ala Ser Gly Val Pro Asp Arg
    210                 215                 220

Phe Ser Gly Ser Gly Ser Gly Thr Asp Phe Thr Leu Arg Ile Ser Arg
225                 230                 235                 240

Val Glu Ala Glu Asp Val Gly Val Tyr Tyr Cys Ile Gln Thr Leu Gln
                245                 250                 255

Thr Pro Phe Thr Phe Gly Pro Gly Thr Lys Val Asp Ile Lys Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
        435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 95
<211> LENGTH: 584
<212> TYPE: PRT
<213> ORGANISM: artificial sequence
<220> FEATURE:
<223> OTHER INFORMATION: anti-CD70 Ab4-V3 CAR

<400> SEQUENCE: 95

Met Ala Leu Pro Val Thr Ala Leu Leu Leu Pro Leu Ala Leu Leu Leu
```

-continued

```
1               5                   10                  15
His Ala Ala Arg Pro Gln Val Gln Leu Val Glu Ser Gly Gly Val
            20                  25                  30
Val Gln Pro Gly Arg Ser Leu Arg Leu Ser Cys Ala Ala Ser Gly Phe
            35                  40                  45
Thr Phe Ser Asn Tyr Gly Ile His Trp Val Arg Gln Ala Pro Gly Lys
        50                  55                  60
Gly Leu Glu Trp Val Ala Val Ile Trp Tyr Asp Gly Ser Asn Lys Tyr
65                  70                  75                  80
Tyr Ala Asp Ser Val Lys Gly Arg Phe Thr Ile Ser Arg Asp Asn Ser
                85                  90                  95
Lys Asn Thr Leu Tyr Leu Gln Met Asn Ser Leu Arg Ala Glu Asp Thr
            100                 105                 110
Ala Val Tyr Tyr Cys Ala Arg Asp Gly Gly Tyr Ser Tyr Asp Ser
            115                 120                 125
Gly Phe Asp Tyr Trp Gly Gln Gly Thr Leu Val Thr Val Ser Ser Gly
    130                 135                 140
Gly Gly Gly Ser Gly Gly Gly Gly Ser Gly Gly Gly Gly Ser Asp Ile
145                 150                 155                 160
Val Met Thr Gln Ser Pro Leu Ser Leu Pro Val Thr Pro Gly Glu Pro
                165                 170                 175
Ala Ser Ile Ser Cys Arg Ser Ser Gln Ser Leu Leu Asn Ser Asn Gly
            180                 185                 190
Tyr Asn Tyr Leu Asp Trp Tyr Leu Gln Lys Pro Gly Gln Ser Pro Gln
            195                 200                 205
Phe Leu Ile Tyr Leu Gly Ser Tyr Arg Ala Ser Gly Val Pro Asp Arg
    210                 215                 220
Phe Ser Gly Ser Gly Ser Gly Thr Asp Phe Thr Leu Arg Ile Ser Arg
225                 230                 235                 240
Val Glu Ala Glu Asp Val Gly Val Tyr Tyr Cys Ile Gln Thr Leu Gln
                245                 250                 255
Thr Pro Phe Thr Phe Gly Pro Gly Thr Lys Val Asp Ile Lys Glu Pro
            260                 265                 270
Lys Ser Pro Asp Lys Thr His Thr Cys Pro Pro Cys Pro Ala Pro Pro
            275                 280                 285
Val Ala Gly Pro Ser Val Phe Leu Phe Pro Pro Lys Pro Lys Asp Thr
    290                 295                 300
Leu Met Ile Ala Arg Thr Pro Glu Val Thr Cys Val Val Val Asp Val
305                 310                 315                 320
Ser His Glu Asp Pro Glu Val Lys Phe Asn Trp Tyr Val Asp Gly Val
                325                 330                 335
Glu Val His Asn Ala Lys Thr Lys Pro Arg Glu Glu Gln Tyr Asn Ser
            340                 345                 350
Thr Tyr Arg Val Val Ser Val Leu Thr Val Leu His Gln Asp Trp Leu
            355                 360                 365
Asn Gly Lys Glu Tyr Lys Cys Lys Val Ser Asn Lys Ala Leu Pro Ala
    370                 375                 380
Pro Ile Glu Lys Thr Ile Ser Lys Ala Lys Gly Gln Pro Arg Glu Pro
385                 390                 395                 400
Gln Val Tyr Thr Leu Pro Pro Ser Arg Asp Glu Leu Thr Lys Asn Gln
                405                 410                 415
Val Ser Leu Thr Cys Leu Val Lys Gly Phe Tyr Pro Ser Asp Ile Ala
            420                 425                 430
```

-continued

```
Val Glu Trp Glu Ser Asn Gly Gln Pro Glu Asn Asn Tyr Lys Thr Thr
            435                 440                 445

Pro Pro Val Leu Asp Ser Asp Gly Ser Phe Phe Leu Tyr Ser Lys Leu
450                 455                 460

Thr Val Asp Lys Ser Arg Trp Gln Gln Gly Asn Val Phe Ser Cys Ser
465                 470                 475                 480

Val Met His Glu Ala Leu His Asn His Tyr Thr Gln Lys Ser Leu Ser
            485                 490                 495

Leu Ser Pro Gly Lys Ile Tyr Ile Trp Ala Pro Leu Ala Gly Thr Cys
            500                 505                 510

Gly Val Leu Leu Leu Ser Leu Val Ile Thr Leu Tyr Cys Lys Arg Gly
            515                 520                 525

Arg Lys Lys Leu Leu Tyr Ile Phe Lys Gln Pro Phe Met Arg Pro Val
            530                 535                 540

Gln Thr Thr Gln Glu Glu Asp Gly Cys Ser Cys Arg Phe Pro Glu Glu
545                 550                 555                 560

Glu Glu Gly Gly Cys Glu Leu Arg Val Lys Phe Ser Arg Ser Ala Asp
            565                 570                 575

Ala Pro Ala Tyr Gln Gln Gly Gln
            580
```

<210> SEQ ID NO 96
<211> LENGTH: 459
<212> TYPE: PRT
<213> ORGANISM: artificial sequence
<220> FEATURE:
<223> OTHER INFORMATION: anti-CD70 Ab8-V1 CAR

<400> SEQUENCE: 96

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Trp Tyr Asp Gly Ser Asp Lys Tyr
65                  70                  75                  80

Phe Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Gly Ile Ala Gly Ala Arg Tyr Val
        115                 120                 125

Tyr Phe Asp Tyr Trp Gly Gln Gly Thr Leu Val Thr Val Ser Ser Gly
    130                 135                 140

Gly Gly Gly Ser Gly Gly Gly Gly Ser Gly Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Arg Ala Ser Gln Gly Ile Ser Asn Tyr Leu Ala
            180                 185                 190

Trp Phe Gln Gln Lys Pro Gly Lys Ala Pro Lys Ser Leu Ile Tyr Ala
        195                 200                 205
```

```
Ala Ser Ser Leu Gln Gly Gly Val Pro Ser Lys Phe Ser Gly Ser Gly
    210                 215                 220

Ser Gly Thr Asp Phe Thr Leu Thr Ile Ser Ser Leu Gln Pro Glu Asp
225                 230                 235                 240

Phe Ala Thr Tyr Tyr Cys Gln Gln Tyr Tyr Asn Tyr Pro Phe Thr Phe
                245                 250                 255

Gly Pro Gly Thr Thr Val Asp Ile Lys Gly Leu Ala Val Ser Thr Ile
            260                 265                 270

Ser Ser Phe Phe Pro Pro Gly Tyr Gln Ile Tyr Ile Trp Ala Pro Leu
        275                 280                 285

Ala Gly Thr Cys Gly Val Leu Leu Leu Ser Leu Val Ile Thr Leu Tyr
    290                 295                 300

Cys Lys Arg Gly Arg Lys Lys Leu Leu Tyr Ile Phe Lys Gln Pro Phe
305                 310                 315                 320

Met Arg Pro Val Gln Thr Thr Gln Glu Glu Asp Gly Cys Ser Cys Arg
                325                 330                 335

Phe Pro Glu Glu Glu Glu Gly Gly Cys Glu Leu Arg Val Lys Phe Ser
            340                 345                 350

Arg Ser Ala Asp Ala Pro Ala Tyr Gln Gln Gly Gln Asn Gln Leu Tyr
        355                 360                 365

Asn Glu Leu Asn Leu Gly Arg Arg Glu Glu Tyr Asp Val Leu Asp Lys
    370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
                405                 410                 415

Ala Tyr Ser Glu Ile Gly Met Lys Gly Glu Arg Arg Arg Gly Lys Gly
            420                 425                 430

His Asp Gly Leu Tyr Gln Gly Leu Ser Thr Ala Thr Lys Asp Thr Tyr
        435                 440                 445

Asp Ala Leu His Met Gln Ala Leu Pro Pro Arg
    450                 455

<210> SEQ ID NO 97
<211> LENGTH: 488
<212> TYPE: PRT
<213> ORGANISM: artificial sequence
<220> FEATURE:
<223> OTHER INFORMATION: anti-CD70 Ab8-V2 CAR

<400> SEQUENCE: 97

Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
                20                  25                  30

Val Gln Pro Gly Arg Ser Leu Arg Leu Ser Cys Ala Ala Ser Gly Phe
            35                  40                  45

Thr Phe Ser Ser Tyr Gly Met His Trp Val Arg Gln Ala Pro Gly Lys
    50                  55                  60

Gly Leu Glu Trp Val Ala Val Ile Trp Tyr Asp Gly Ser Asp Lys Tyr
65                  70                  75                  80

Phe Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110
```

Ala Val Tyr Tyr Cys Ala Arg Asp Gly Ile Ala Gly Ala Arg Tyr Val
            115                 120                 125

Tyr Phe Asp Tyr Trp Gly Gln Gly Thr Leu Val Thr Val Ser Ser Gly
        130                 135                 140

Gly Gly Gly Ser Gly Gly Gly Ser Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Arg Ala Ser Gln Gly Ile Ser Asn Tyr Leu Ala
            180                 185                 190

Trp Phe Gln Gln Lys Pro Gly Lys Ala Pro Lys Ser Leu Ile Tyr Ala
        195                 200                 205

Ala Ser Ser Leu Gln Gly Gly Val Pro Ser Lys Phe Ser Gly Ser Gly
    210                 215                 220

Ser Gly Thr Asp Phe Thr Leu Thr Ile Ser Ser Leu Gln Pro Glu Asp
225                 230                 235                 240

Phe Ala Thr Tyr Tyr Cys Gln Gln Tyr Tyr Asn Tyr Pro Phe Thr Phe
                245                 250                 255

Gly Pro Gly Thr Thr Val Asp Ile Lys Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415

Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
        435                 440                 445

Glu Ile Gly Met Lys Gly Glu Arg Arg Arg Gly Lys Gly His Asp Gly
    450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 98
<211> LENGTH: 674
<212> TYPE: PRT
<213> ORGANISM: artificial sequence
<220> FEATURE:

<223> OTHER INFORMATION: anti-CD70 Ab8-V3 CAR

<400> SEQUENCE: 98

```
Met Ala Leu Pro Val Thr Ala Leu Leu Leu Pro Leu Ala Leu Leu Leu
1               5                   10                  15

His Ala Ala Arg Pro Gln Val Gln Leu Val Glu Ser Gly Gly Gly Val
            20                  25                  30

Val Gln Pro Gly Arg Ser Leu Arg Leu Ser Cys Ala Ala Ser Gly Phe
        35                  40                  45

Thr Phe Ser Ser Tyr Gly Met His Trp Val Arg Gln Ala Pro Gly Lys
    50                  55                  60

Gly Leu Glu Trp Val Ala Val Ile Trp Tyr Asp Gly Ser Asp Lys Tyr
65                  70                  75                  80

Phe Ala Asp Ser Val Lys Gly Arg Phe Thr Ile Ser Arg Asp Asn Ser
                85                  90                  95

Lys Asn Thr Leu Tyr Leu Gln Met Asn Ser Leu Arg Ala Glu Asp Thr
            100                 105                 110

Ala Val Tyr Tyr Cys Ala Arg Asp Gly Ile Ala Gly Ala Arg Tyr Val
        115                 120                 125

Tyr Phe Asp Tyr Trp Gly Gln Gly Thr Leu Val Thr Val Ser Ser Gly
    130                 135                 140

Gly Gly Gly Ser Gly Gly Gly Ser Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Arg Ala Ser Gln Gly Ile Ser Asn Tyr Leu Ala
            180                 185                 190

Trp Phe Gln Gln Lys Pro Gly Lys Ala Pro Lys Ser Leu Ile Tyr Ala
        195                 200                 205

Ala Ser Ser Leu Gln Gly Gly Val Pro Ser Lys Phe Ser Gly Ser Gly
    210                 215                 220

Ser Gly Thr Asp Phe Thr Leu Thr Ile Ser Ser Leu Gln Pro Glu Asp
225                 230                 235                 240

Phe Ala Thr Tyr Tyr Cys Gln Gln Tyr Asn Tyr Pro Phe Thr Phe
                245                 250                 255

Gly Pro Gly Thr Thr Val Asp Ile Lys Glu Pro Lys Ser Pro Asp Lys
            260                 265                 270

Thr His Thr Cys Pro Pro Cys Pro Ala Pro Pro Val Ala Gly Pro Ser
        275                 280                 285

Val Phe Leu Phe Pro Pro Lys Pro Lys Asp Thr Leu Met Ile Ala Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
                325                 330                 335

Lys Thr Lys Pro Arg Glu Glu Gln Tyr Asn Ser Thr Tyr Arg Val Val
            340                 345                 350

Ser Val Leu Thr Val Leu His Gln Asp Trp Leu Asn Gly Lys Glu Tyr
        355                 360                 365

Lys Cys Lys Val Ser Asn Lys Ala Leu Pro Ala Pro Ile Glu Lys Thr
    370                 375                 380

Ile Ser Lys Ala Lys Gly Gln Pro Arg Glu Pro Gln Val Tyr Thr Leu
385                 390                 395                 400
```

```
Pro Pro Ser Arg Asp Glu Leu Thr Lys Asn Gln Val Ser Leu Thr Cys
                405                 410                 415
Leu Val Lys Gly Phe Tyr Pro Ser Asp Ile Ala Val Glu Trp Glu Ser
            420                 425                 430
Asn Gly Gln Pro Glu Asn Asn Tyr Lys Thr Thr Pro Pro Val Leu Asp
        435                 440                 445
Ser Asp Gly Ser Phe Phe Leu Tyr Ser Lys Leu Thr Val Asp Lys Ser
    450                 455                 460
Arg Trp Gln Gln Gly Asn Val Phe Ser Cys Ser Val Met His Glu Ala
465                 470                 475                 480
Leu His Asn His Tyr Thr Gln Lys Ser Leu Ser Leu Ser Pro Gly Lys
                485                 490                 495
Ile Tyr Ile Trp Ala Pro Leu Ala Gly Thr Cys Gly Val Leu Leu Leu
            500                 505                 510
Ser Leu Val Ile Thr Leu Tyr Cys Lys Arg Gly Arg Lys Lys Leu Leu
        515                 520                 525
Tyr Ile Phe Lys Gln Pro Phe Met Arg Pro Val Gln Thr Thr Gln Glu
    530                 535                 540
Glu Asp Gly Cys Ser Cys Arg Phe Pro Glu Glu Glu Glu Gly Gly Cys
545                 550                 555                 560
Glu Leu Arg Val Lys Phe Ser Arg Ser Ala Asp Ala Pro Ala Tyr Gln
                565                 570                 575
Gln Gly Gln Asn Gln Leu Tyr Asn Glu Leu Asn Leu Gly Arg Arg Glu
            580                 585                 590
Glu Tyr Asp Val Leu Asp Lys Arg Arg Gly Arg Asp Pro Glu Met Gly
        595                 600                 605
Gly Lys Pro Arg Arg Lys Asn Pro Gln Glu Gly Leu Tyr Asn Glu Leu
    610                 615                 620
Gln Lys Asp Lys Met Ala Glu Ala Tyr Ser Glu Ile Gly Met Lys Gly
625                 630                 635                 640
Glu Arg Arg Arg Gly Lys Gly His Asp Gly Leu Tyr Gln Gly Leu Ser
                645                 650                 655
Thr Ala Thr Lys Asp Thr Tyr Asp Ala Leu His Met Gln Ala Leu Pro
            660                 665                 670
Pro Arg

<210> SEQ ID NO 99
<211> LENGTH: 459
<212> TYPE: PRT
<213> ORGANISM: artificial sequence
<220> FEATURE:
<223> OTHER INFORMATION: anti-CD70 1F6-V1 CAR

<400> SEQUENCE: 99

Met Ala Leu Pro Val Thr Ala Leu Leu Leu Pro Leu Ala Leu Leu Leu
1               5                   10                  15
His Ala Ala Arg Pro Gln Ile Gln Leu Val Gln Ser Gly Pro Glu Val
                20                  25                  30
Lys Lys Pro Gly Glu Thr Val Lys Ile Ser Cys Lys Ala Ser Gly Tyr
            35                  40                  45
Thr Phe Thr Asn Tyr Gly Met Asn Trp Val Lys Gln Ala Pro Gly Lys
        50                  55                  60
Gly Leu Lys Trp Met Gly Ile Asn Thr Tyr Thr Gly Glu Pro Thr Tyr
65                  70                  75                  80
Ala Asp Ala Phe Lys Gly Arg Phe Ala Phe Ser Leu Glu Thr Ser Ala
```

85                  90                  95

Ser Thr Ala Tyr Leu Gln Ile Asn Asn Leu Lys Asn Glu Asp Thr Ala
            100                 105                 110

Thr Tyr Phe Cys Ala Arg Asp Tyr Gly Asp Tyr Gly Met Asp Tyr Trp
            115                 120                 125

Gly Gln Gly Thr Ser Val Thr Val Ser Ser Gly Gly Gly Gly Ser Gly
            130                 135                 140

Gly Gly Ser Gly Gly Gly Ser Asp Ile Val Leu Thr Gln Ser
145                 150                 155                 160

Pro Ala Ser Leu Ala Val Ser Leu Gly Gln Arg Ala Thr Ile Ser Cys
            165                 170                 175

Arg Ala Ser Lys Ser Val Ser Thr Ser Gly Tyr Ser Phe Met His Trp
            180                 185                 190

Tyr Gln Gln Lys Pro Gly Gln Pro Pro Lys Leu Leu Ile Tyr Leu Ala
            195                 200                 205

Ser Asn Leu Glu Ser Gly Val Pro Ala Arg Phe Ser Gly Ser Gly Ser
            210                 215                 220

Gly Thr Asp Phe Thr Leu Asn Ile His Pro Val Glu Glu Asp Ala
225                 230                 235                 240

Ala Thr Tyr Tyr Cys Gln His Ser Arg Glu Val Pro Trp Thr Phe Gly
            245                 250                 255

Gly Gly Thr Lys Leu Glu Ile Lys Arg Gly Leu Ala Val Ser Thr Ile
            260                 265                 270

Ser Ser Phe Phe Pro Pro Gly Tyr Gln Ile Tyr Ile Trp Ala Pro Leu
            275                 280                 285

Ala Gly Thr Cys Gly Val Leu Leu Leu Ser Leu Val Ile Thr Leu Tyr
            290                 295                 300

Cys Lys Arg Gly Arg Lys Lys Leu Leu Tyr Ile Phe Lys Gln Pro Phe
305                 310                 315                 320

Met Arg Pro Val Gln Thr Thr Gln Glu Glu Asp Gly Cys Ser Cys Arg
            325                 330                 335

Phe Pro Glu Glu Glu Glu Gly Gly Cys Glu Leu Arg Val Lys Phe Ser
            340                 345                 350

Arg Ser Ala Asp Ala Pro Ala Tyr Gln Gln Gly Gln Asn Gln Leu Tyr
            355                 360                 365

Asn Glu Leu Asn Leu Gly Arg Arg Glu Glu Tyr Asp Val Leu Asp Lys
            370                 375                 380

Arg Arg Gly Arg Asp Pro Glu Met Gly Gly Lys Pro Arg Arg Lys Asn
385                 390                 395                 400

Pro Gln Glu Gly Leu Tyr Asn Glu Leu Gln Lys Asp Lys Met Ala Glu
            405                 410                 415

Ala Tyr Ser Glu Ile Gly Met Lys Gly Glu Arg Arg Arg Gly Lys Gly
            420                 425                 430

His Asp Gly Leu Tyr Gln Gly Leu Ser Thr Ala Thr Lys Asp Thr Tyr
            435                 440                 445

Asp Ala Leu His Met Gln Ala Leu Pro Pro Arg
450                 455

<210> SEQ ID NO 100
<211> LENGTH: 488
<212> TYPE: PRT
<213> ORGANISM: artificial sequence
<220> FEATURE:
<223> OTHER INFORMATION: anti-CD70 1F6-V2 CAR

```
<400> SEQUENCE: 100

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Val
            20                  25                  30

Lys Lys Pro Gly Glu Thr Val Lys Ile Ser Cys Lys Ala Ser Gly Tyr
        35                  40                  45

Thr Phe Thr Asn Tyr Gly Met Asn Trp Val Lys Gln Ala Pro Gly Lys
    50                  55                  60

Gly Leu Lys Trp Met Gly Ile Asn Thr Tyr Thr Gly Glu Pro Thr Tyr
65                  70                  75                  80

Ala Asp Ala Phe Lys Gly Arg Phe Ala Phe Ser Leu Glu Thr Ser Ala
                85                  90                  95

Ser Thr Ala Tyr Leu Gln Ile Asn Asn Leu Lys Asn Glu Asp Thr Ala
            100                 105                 110

Thr Tyr Phe Cys Ala Arg Asp Tyr Gly Asp Tyr Gly Met Asp Tyr Trp
        115                 120                 125

Gly Gln Gly Thr Ser Val Thr Val Ser Ser Gly Gly Gly Gly Ser Gly
    130                 135                 140

Gly Gly Gly Ser Gly Gly Gly Gly Ser Asp Ile Val Leu Thr Gln Ser
145                 150                 155                 160

Pro Ala Ser Leu Ala Val Ser Leu Gly Gln Arg Ala Thr Ile Ser Cys
                165                 170                 175

Arg Ala Ser Lys Ser Val Ser Thr Ser Gly Tyr Ser Phe Met His Trp
            180                 185                 190

Tyr Gln Gln Lys Pro Gly Gln Pro Pro Lys Leu Leu Ile Tyr Leu Ala
        195                 200                 205

Ser Asn Leu Glu Ser Gly Val Pro Ala Arg Phe Ser Gly Ser Gly Ser
    210                 215                 220

Gly Thr Asp Phe Thr Leu Asn Ile His Pro Val Glu Glu Glu Asp Ala
225                 230                 235                 240

Ala Thr Tyr Tyr Cys Gln His Ser Arg Glu Val Pro Trp Thr Phe Gly
                245                 250                 255

Gly Gly Thr Lys Leu Glu Ile Lys Arg Thr Thr Thr Pro Ala Pro Arg
            260                 265                 270

Pro Pro Thr Pro Ala Pro Thr Ile Ala Ser Gln Pro Leu Ser Leu Arg
        275                 280                 285

Pro Glu Ala Cys Arg Pro Ala Ala Gly Gly Ala Val His Thr Arg Gly
    290                 295                 300

Leu Asp Phe Ala Cys Asp Ile Tyr Ile Trp Ala Pro Leu Ala Gly Thr
305                 310                 315                 320

Cys Gly Val Leu Leu Leu Ser Leu Val Ile Thr Leu Tyr Cys Lys Arg
                325                 330                 335

Gly Arg Lys Lys Leu Leu Tyr Ile Phe Lys Gln Pro Phe Met Arg Pro
            340                 345                 350

Val Gln Thr Thr Gln Glu Glu Asp Gly Cys Ser Cys Arg Phe Pro Glu
        355                 360                 365

Glu Glu Glu Gly Gly Cys Glu Leu Arg Val Lys Phe Ser Arg Ser Ala
    370                 375                 380

Asp Ala Pro Ala Tyr Gln Gln Gly Gln Asn Gln Leu Tyr Asn Glu Leu
385                 390                 395                 400

Asn Leu Gly Arg Arg Glu Glu Tyr Asp Val Leu Asp Lys Arg Arg Gly
                405                 410                 415
```

```
Arg Asp Pro Glu Met Gly Gly Lys Pro Arg Arg Lys Asn Pro Gln Glu
            420                 425                 430

Gly Leu Tyr Asn Glu Leu Gln Lys Asp Lys Met Ala Glu Ala Tyr Ser
            435                 440                 445

Glu Ile Gly Met Lys Gly Glu Arg Arg Arg Gly Lys Gly His Asp Gly
450                 455                 460

Leu Tyr Gln Gly Leu Ser Thr Ala Thr Lys Asp Thr Tyr Asp Ala Leu
465                 470                 475                 480

His Met Gln Ala Leu Pro Pro Arg
                485

<210> SEQ ID NO 101
<211> LENGTH: 674
<212> TYPE: PRT
<213> ORGANISM: artificial sequence
<220> FEATURE:
<223> OTHER INFORMATION: anti-CD70 1F6-V3 CAR

<400> SEQUENCE: 101

Met Ala Leu Pro Val Thr Ala Leu Leu Leu Pro Leu Ala Leu Leu Leu
1               5                   10                  15

His Ala Ala Arg Pro Gln Ile Gln Leu Val Gln Ser Gly Pro Glu Val
            20                  25                  30

Lys Lys Pro Gly Glu Thr Val Lys Ile Ser Cys Lys Ala Ser Gly Tyr
        35                  40                  45

Thr Phe Thr Asn Tyr Gly Met Asn Trp Val Lys Gln Ala Pro Gly Lys
    50                  55                  60

Gly Leu Lys Trp Met Gly Ile Asn Thr Tyr Thr Gly Glu Pro Thr Tyr
65                  70                  75                  80

Ala Asp Ala Phe Lys Gly Arg Phe Ala Phe Ser Leu Glu Thr Ser Ala
                85                  90                  95

Ser Thr Ala Tyr Leu Gln Ile Asn Asn Leu Lys Asn Glu Asp Thr Ala
            100                 105                 110

Thr Tyr Phe Cys Ala Arg Asp Tyr Gly Asp Tyr Gly Met Asp Tyr Trp
        115                 120                 125

Gly Gln Gly Thr Ser Val Thr Val Ser Ser Gly Gly Gly Gly Ser Gly
    130                 135                 140

Gly Gly Gly Ser Gly Gly Gly Gly Ser Asp Ile Val Leu Thr Gln Ser
145                 150                 155                 160

Pro Ala Ser Leu Ala Val Ser Leu Gly Gln Arg Ala Thr Ile Ser Cys
                165                 170                 175

Arg Ala Ser Lys Ser Val Ser Thr Ser Gly Tyr Ser Phe Met His Trp
            180                 185                 190

Tyr Gln Gln Lys Pro Gly Gln Pro Pro Lys Leu Leu Ile Tyr Leu Ala
        195                 200                 205

Ser Asn Leu Glu Ser Gly Val Pro Ala Arg Phe Ser Gly Ser Gly Ser
    210                 215                 220

Gly Thr Asp Phe Thr Leu Asn Ile His Pro Val Glu Glu Glu Asp Ala
225                 230                 235                 240

Ala Thr Tyr Tyr Cys Gln His Ser Arg Glu Val Pro Trp Thr Phe Gly
                245                 250                 255

Gly Gly Thr Lys Leu Glu Ile Lys Arg Glu Pro Lys Ser Pro Asp Lys
            260                 265                 270

Thr His Thr Cys Pro Pro Cys Pro Ala Pro Pro Val Ala Gly Pro Ser
        275                 280                 285
```

Val Phe Leu Phe Pro Pro Lys Pro Lys Asp Thr Leu Met Ile Ala Arg
    290                 295                 300

Thr Pro Glu Val Thr Cys Val Val Val Asp Val Ser His Glu Asp Pro
305                 310                 315                 320

Glu Val Lys Phe Asn Trp Tyr Val Asp Gly Val Glu Val His Asn Ala
            325                 330                 335

Lys Thr Lys Pro Arg Glu Glu Gln Tyr Asn Ser Thr Tyr Arg Val Val
        340                 345                 350

Ser Val Leu Thr Val Leu His Gln Asp Trp Leu Asn Gly Lys Glu Tyr
    355                 360                 365

Lys Cys Lys Val Ser Asn Lys Ala Leu Pro Ala Pro Ile Glu Lys Thr
370                 375                 380

Ile Ser Lys Ala Lys Gly Gln Pro Arg Glu Pro Gln Val Tyr Thr Leu
385                 390                 395                 400

Pro Pro Ser Arg Asp Glu Leu Thr Lys Asn Gln Val Ser Leu Thr Cys
            405                 410                 415

Leu Val Lys Gly Phe Tyr Pro Ser Asp Ile Ala Val Glu Trp Glu Ser
        420                 425                 430

Asn Gly Gln Pro Glu Asn Asn Tyr Lys Thr Thr Pro Pro Val Leu Asp
    435                 440                 445

Ser Asp Gly Ser Phe Phe Leu Tyr Ser Lys Leu Thr Val Asp Lys Ser
450                 455                 460

Arg Trp Gln Gln Gly Asn Val Phe Ser Cys Ser Val Met His Glu Ala
465                 470                 475                 480

Leu His Asn His Tyr Thr Gln Lys Ser Leu Ser Leu Ser Pro Gly Lys
            485                 490                 495

Ile Tyr Ile Trp Ala Pro Leu Ala Gly Thr Cys Gly Val Leu Leu Leu
        500                 505                 510

Ser Leu Val Ile Thr Leu Tyr Cys Lys Arg Gly Arg Lys Lys Leu Leu
    515                 520                 525

Tyr Ile Phe Lys Gln Pro Phe Met Arg Pro Val Gln Thr Thr Gln Glu
530                 535                 540

Glu Asp Gly Cys Ser Cys Arg Phe Pro Glu Glu Glu Glu Gly Gly Cys
545                 550                 555                 560

Glu Leu Arg Val Lys Phe Ser Arg Ser Ala Asp Ala Pro Ala Tyr Gln
            565                 570                 575

Gln Gly Gln Asn Gln Leu Tyr Asn Glu Leu Asn Leu Gly Arg Arg Glu
        580                 585                 590

Glu Tyr Asp Val Leu Asp Lys Arg Arg Gly Arg Asp Pro Glu Met Gly
    595                 600                 605

Gly Lys Pro Arg Arg Lys Asn Pro Gln Glu Gly Leu Tyr Asn Glu Leu
610                 615                 620

Gln Lys Asp Lys Met Ala Glu Ala Tyr Ser Glu Ile Gly Met Lys Gly
625                 630                 635                 640

Glu Arg Arg Arg Gly Lys Gly His Asp Gly Leu Tyr Gln Gly Leu Ser
            645                 650                 655

Thr Ala Thr Lys Asp Thr Tyr Asp Ala Leu His Met Gln Ala Leu Pro
        660                 665                 670

Pro Arg

<210> SEQ ID NO 102
<211> LENGTH: 23
<212> TYPE: DNA

```
<213> ORGANISM: artificial sequence
<220> FEATURE:
<223> OTHER INFORMATION: Cas9 TCR Ex1 78 -1

<400> SEQUENCE: 102
gagaatcaaa atcggtgaat agg                                              23

<210> SEQ ID NO 103
<211> LENGTH: 23
<212> TYPE: DNA
<213> ORGANISM: artificial sequence
<220> FEATURE:
<223> OTHER INFORMATION: Cas9 TCR Ex3 26 1

<400> SEQUENCE: 103
ttcaaaacct gtcagtgatt ggg                                              23

<210> SEQ ID NO 104
<211> LENGTH: 23
<212> TYPE: DNA
<213> ORGANISM: artificial sequence
<220> FEATURE:
<223> OTHER INFORMATION: Cas9 TCR Ex1 153 1

<400> SEQUENCE: 104
tgtgctagac atgaggtcta tgg                                              23

<210> SEQ ID NO 105
<211> LENGTH: 23
<212> TYPE: DNA
<213> ORGANISM: artificial sequence
<220> FEATURE:
<223> OTHER INFORMATION: Cas9 TCR Ex3 74 -1

<400> SEQUENCE: 105
cgtcatgagc agattaaacc cgg                                              23

<210> SEQ ID NO 106
<211> LENGTH: 23
<212> TYPE: DNA
<213> ORGANISM: artificial sequence
<220> FEATURE:
<223> OTHER INFORMATION: Cas9 TCR Ex1 4 -1

<400> SEQUENCE: 106
tcagggttct ggatatctgt ggg                                              23

<210> SEQ ID NO 107
<211> LENGTH: 23
<212> TYPE: DNA
<213> ORGANISM: artificial sequence
<220> FEATURE:
<223> OTHER INFORMATION: Cas9 TCR Ex1 5 -1

<400> SEQUENCE: 107
gtcagggttc tggatatctg tgg                                              23

<210> SEQ ID NO 108
<211> LENGTH: 23
<212> TYPE: DNA
<213> ORGANISM: artificial sequence
<220> FEATURE:
<223> OTHER INFORMATION: Cas9 TCR Ex3 33 -1

<400> SEQUENCE: 108
ttcggaaccc aatcactgac agg                                              23
```

```
<210> SEQ ID NO 109
<211> LENGTH: 23
<212> TYPE: DNA
<213> ORGANISM: artificial sequence
<220> FEATURE:
<223> OTHER INFORMATION: Cas9 TCR Ex3 60 -1

<400> SEQUENCE: 109
taaacccggc cactttcagg agg                                              23

<210> SEQ ID NO 110
<211> LENGTH: 23
<212> TYPE: DNA
<213> ORGANISM: artificial sequence
<220> FEATURE:
<223> OTHER INFORMATION: Cas9 TCR Ex1 200 -1

<400> SEQUENCE: 110
aaagtcagat tgttgctcc agg                                               23

<210> SEQ ID NO 111
<211> LENGTH: 23
<212> TYPE: DNA
<213> ORGANISM: artificial sequence
<220> FEATURE:
<223> OTHER INFORMATION: Cas9 TCR Ex1 102 1

<400> SEQUENCE: 111
aacaaatgtg tcacaaagta agg                                              23

<210> SEQ ID NO 112
<211> LENGTH: 23
<212> TYPE: DNA
<213> ORGANISM: artificial sequence
<220> FEATURE:
<223> OTHER INFORMATION: Cas9 TCR Ex1 39 -1

<400> SEQUENCE: 112
tggatttaga gtctctcagc tgg                                              23

<210> SEQ ID NO 113
<211> LENGTH: 23
<212> TYPE: DNA
<213> ORGANISM: artificial sequence
<220> FEATURE:
<223> OTHER INFORMATION: Cas9 TCR Ex1 59 -1

<400> SEQUENCE: 113
taggcagaca gacttgtcac tgg                                              23

<210> SEQ ID NO 114
<211> LENGTH: 23
<212> TYPE: DNA
<213> ORGANISM: artificial sequence
<220> FEATURE:
<223> OTHER INFORMATION: Cas9 TCR Ex1 22 -1

<400> SEQUENCE: 114
agctggtaca cggcagggtc agg                                              23

<210> SEQ ID NO 115
<211> LENGTH: 23
<212> TYPE: DNA
<213> ORGANISM: artificial sequence
<220> FEATURE:
```

<223> OTHER INFORMATION: Cas9 TCR Ex1 21 -1

<400> SEQUENCE: 115
gctggtacac ggcagggtca ggg                                            23

<210> SEQ ID NO 116
<211> LENGTH: 23
<212> TYPE: DNA
<213> ORGANISM: artificial sequence
<220> FEATURE:
<223> OTHER INFORMATION: Cas9 TCR Ex1 28 -1

<400> SEQUENCE: 116
tctctcagct ggtacacggc agg                                            23

<210> SEQ ID NO 117
<211> LENGTH: 23
<212> TYPE: DNA
<213> ORGANISM: artificial sequence
<220> FEATURE:
<223> OTHER INFORMATION: Cas9 TCR Ex3 25 1

<400> SEQUENCE: 117
tttcaaaacc tgtcagtgat tgg                                            23

<210> SEQ ID NO 118
<211> LENGTH: 23
<212> TYPE: DNA
<213> ORGANISM: artificial sequence
<220> FEATURE:
<223> OTHER INFORMATION: Cas9 TCR Ex3 63 -1

<400> SEQUENCE: 118
gattaaaccc ggccactttc agg                                            23

<210> SEQ ID NO 119
<211> LENGTH: 23
<212> TYPE: DNA
<213> ORGANISM: artificial sequence
<220> FEATURE:
<223> OTHER INFORMATION: Cas9 TCR Ex2 17 -1

<400> SEQUENCE: 119
ctcgaccagc ttgacatcac agg                                            23

<210> SEQ ID NO 120
<211> LENGTH: 23
<212> TYPE: DNA
<213> ORGANISM: artificial sequence
<220> FEATURE:
<223> OTHER INFORMATION: Cas9 TCR Ex1 32 -1

<400> SEQUENCE: 120
agagtctctc agctggtaca cgg                                            23

<210> SEQ ID NO 121
<211> LENGTH: 23
<212> TYPE: DNA
<213> ORGANISM: artificial sequence
<220> FEATURE:
<223> OTHER INFORMATION: Cas9 TCR Ex1 27 -1

<400> SEQUENCE: 121
ctctcagctg gtacacggca ggg                                            23

```
<210> SEQ ID NO 122
<211> LENGTH: 23
<212> TYPE: DNA
<213> ORGANISM: artificial sequence
<220> FEATURE:
<223> OTHER INFORMATION: Cas9 TCR Ex2 12 1

<400> SEQUENCE: 122
aagttcctgt gatgtcaagc tgg                                              23

<210> SEQ ID NO 123
<211> LENGTH: 23
<212> TYPE: DNA
<213> ORGANISM: artificial sequence
<220> FEATURE:
<223> OTHER INFORMATION: Cas9 TCR Ex3 55 1

<400> SEQUENCE: 123
atcctcctcc tgaaagtggc cgg                                              23

<210> SEQ ID NO 124
<211> LENGTH: 23
<212> TYPE: DNA
<213> ORGANISM: artificial sequence
<220> FEATURE:
<223> OTHER INFORMATION: Cas9 TCR Ex3 86 1

<400> SEQUENCE: 124
tgctcatgac gctgcggctg tgg                                              23

<210> SEQ ID NO 125
<211> LENGTH: 23
<212> TYPE: DNA
<213> ORGANISM: artificial sequence
<220> FEATURE:
<223> OTHER INFORMATION: Cas9 TCR Ex1 146 1

<400> SEQUENCE: 125
acaaaactgt gctagacatg agg                                              23

<210> SEQ ID NO 126
<211> LENGTH: 23
<212> TYPE: DNA
<213> ORGANISM: artificial sequence
<220> FEATURE:
<223> OTHER INFORMATION: Cas9 TCR Ex1 86 -1

<400> SEQUENCE: 126
atttgtttga gaatcaaaat cgg                                              23

<210> SEQ ID NO 127
<211> LENGTH: 23
<212> TYPE: DNA
<213> ORGANISM: artificial sequence
<220> FEATURE:
<223> OTHER INFORMATION: Cas9 TCR Ex2 3 -1

<400> SEQUENCE: 127
catcacagga actttctaaa agg                                              23

<210> SEQ ID NO 128
<211> LENGTH: 23
<212> TYPE: DNA
<213> ORGANISM: artificial sequence
<220> FEATURE:
<223> OTHER INFORMATION: Cas9 TCR Ex2 34 1
```

```
<400> SEQUENCE: 128
gtcgagaaaa gctttgaaac agg                                              23

<210> SEQ ID NO 129
<211> LENGTH: 23
<212> TYPE: DNA
<213> ORGANISM: artificial sequence
<220> FEATURE:
<223> OTHER INFORMATION: Cas9 TCR Ex3 51 -1

<400> SEQUENCE: 129
ccactttcag gaggaggatt cgg                                              23

<210> SEQ ID NO 130
<211> LENGTH: 23
<212> TYPE: DNA
<213> ORGANISM: artificial sequence
<220> FEATURE:
<223> OTHER INFORMATION: Cas9 TCR Ex3 18 -1

<400> SEQUENCE: 130
ctgacaggtt ttgaaagttt agg                                              23

<210> SEQ ID NO 131
<211> LENGTH: 23
<212> TYPE: DNA
<213> ORGANISM: artificial sequence
<220> FEATURE:
<223> OTHER INFORMATION: Cas9 TCR Ex2 43 1

<400> SEQUENCE: 131
agctttgaaa caggtaagac agg                                              23

<210> SEQ ID NO 132
<211> LENGTH: 23
<212> TYPE: DNA
<213> ORGANISM: artificial sequence
<220> FEATURE:
<223> OTHER INFORMATION: Cas9 TCR Ex1 236 -1

<400> SEQUENCE: 132
tggaataatg ctgttgttga agg                                              23

<210> SEQ ID NO 133
<211> LENGTH: 23
<212> TYPE: DNA
<213> ORGANISM: artificial sequence
<220> FEATURE:
<223> OTHER INFORMATION: Cas9 TCR Ex1 182 1

<400> SEQUENCE: 133
agagcaacag tgctgtggcc tgg                                              23

<210> SEQ ID NO 134
<211> LENGTH: 23
<212> TYPE: DNA
<213> ORGANISM: artificial sequence
<220> FEATURE:
<223> OTHER INFORMATION: Cas9 TCR Ex3 103 1

<400> SEQUENCE: 134
ctgtggtcca gctgaggtga ggg                                              23

<210> SEQ ID NO 135
<211> LENGTH: 23
```

```
<212> TYPE: DNA
<213> ORGANISM: artificial sequence
<220> FEATURE:
<223> OTHER INFORMATION: Cas9 TCR Ex3 97 1

<400> SEQUENCE: 135
ctgcggctgt ggtccagctg agg                                              23

<210> SEQ ID NO 136
<211> LENGTH: 23
<212> TYPE: DNA
<213> ORGANISM: artificial sequence
<220> FEATURE:
<223> OTHER INFORMATION: Cas9 TCR Ex3 104 1

<400> SEQUENCE: 136
tgtggtccag ctgaggtgag ggg                                              23

<210> SEQ ID NO 137
<211> LENGTH: 23
<212> TYPE: DNA
<213> ORGANISM: artificial sequence
<220> FEATURE:
<223> OTHER INFORMATION: Cas9 TCR Ex1 267 1

<400> SEQUENCE: 137
cttcttcccc agcccaggta agg                                              23

<210> SEQ ID NO 138
<211> LENGTH: 23
<212> TYPE: DNA
<213> ORGANISM: artificial sequence
<220> FEATURE:
<223> OTHER INFORMATION: Cas9 TCR Ex1 15 -1

<400> SEQUENCE: 138
acacggcagg gtcagggttc tgg                                              23

<210> SEQ ID NO 139
<211> LENGTH: 23
<212> TYPE: DNA
<213> ORGANISM: artificial sequence
<220> FEATURE:
<223> OTHER INFORMATION: Cas9 TCR Ex1 177 1

<400> SEQUENCE: 139
cttcaagagc aacagtgctg tgg                                              23

<210> SEQ ID NO 140
<211> LENGTH: 23
<212> TYPE: DNA
<213> ORGANISM: artificial sequence
<220> FEATURE:
<223> OTHER INFORMATION: Cas9 TCR Ex1 256 -1

<400> SEQUENCE: 140
ctggggaaga aggtgtcttc tgg                                              23

<210> SEQ ID NO 141
<211> LENGTH: 23
<212> TYPE: DNA
<213> ORGANISM: artificial sequence
<220> FEATURE:
<223> OTHER INFORMATION: Cas9 TCR Ex3 56 1

<400> SEQUENCE: 141
```
tcctcctcct gaaagtggcc ggg                                                     23

<210> SEQ ID NO 142
<211> LENGTH: 23
<212> TYPE: DNA
<213> ORGANISM: artificial sequence
<220> FEATURE:
<223> OTHER INFORMATION: Cas9 TCR Ex3 80 1

<400> SEQUENCE: 142
ttaatctgct catgacgctg cgg                                                     23

<210> SEQ ID NO 143
<211> LENGTH: 23
<212> TYPE: DNA
<213> ORGANISM: artificial sequence
<220> FEATURE:
<223> OTHER INFORMATION: Cas9 TCR Ex3 57 -1

<400> SEQUENCE: 143
acccggccac tttcaggagg agg                                                     23

<210> SEQ ID NO 144
<211> LENGTH: 23
<212> TYPE: DNA
<213> ORGANISM: artificial sequence
<220> FEATURE:
<223> OTHER INFORMATION: Cas9 TCR Ex1 268 1

<400> SEQUENCE: 144
ttcttcccca gcccaggtaa ggg                                                     23

<210> SEQ ID NO 145
<211> LENGTH: 23
<212> TYPE: DNA
<213> ORGANISM: artificial sequence
<220> FEATURE:
<223> OTHER INFORMATION: Cas9 TCR Ex1 266 -1

<400> SEQUENCE: 145
cttacctggg ctggggaaga agg                                                     23

<210> SEQ ID NO 146
<211> LENGTH: 23
<212> TYPE: DNA
<213> ORGANISM: artificial sequence
<220> FEATURE:
<223> OTHER INFORMATION: Cas9 TCR Ex1 262 1

<400> SEQUENCE: 146
gacaccttct tccccagccc agg                                                     23

<210> SEQ ID NO 147
<211> LENGTH: 23
<212> TYPE: DNA
<213> ORGANISM: artificial sequence
<220> FEATURE:
<223> OTHER INFORMATION: Cas9 TCR Ex3 102 1

<400> SEQUENCE: 147
gctgtggtcc agctgaggtg agg                                                     23

<210> SEQ ID NO 148
<211> LENGTH: 23
<212> TYPE: DNA
<213> ORGANISM: artificial sequence

```
<220> FEATURE:
<223> OTHER INFORMATION: Cas9 TCR Ex3 51 1

<400> SEQUENCE: 148
ccgaatcctc ctcctgaaag tgg                                              23
```